US008710081B2

(12) United States Patent
Hutchinson et al.

(10) Patent No.: US 8,710,081 B2
(45) Date of Patent: Apr. 29, 2014

(54) 5-LIPOXYGENASE-ACTIVATING PROTEIN (FLAP) INHIBITORS

(71) Applicant: Panmira Pharmaceuticals, LLC, San Diego, CA (US)

(72) Inventors: John H. Hutchinson, La Jolla, CA (US); Petpiboon Peppi Prasit, Rancho Sante Fe, CA (US); Mark Moran, Orinda, CA (US); Jillian F. Evans, San Diego, CA (US); Jasmine Eleanor Zunic, San Diego, CA (US); Nicholas Simon Stock, San Diego, CA (US)

(73) Assignee: Panmira Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 13/942,934

(22) Filed: Jul. 16, 2013

(65) Prior Publication Data

US 2014/0018394 A1 Jan. 16, 2014

Related U.S. Application Data

(60) Continuation of application No. 13/012,045, filed on Jan. 24, 2011, now abandoned, and a division of application No. 11/553,946, filed on Oct. 27, 2006, now Pat. No. 7,977,359.

(60) Provisional application No. 60/734,030, filed on Nov. 4, 2005, provisional application No. 60/747,174, filed on May 12, 2006, provisional application No. 60/823,344, filed on Aug. 23, 2006.

(51) Int. Cl.
*A61K 31/4439* (2006.01)
*C07D 401/14* (2006.01)

(52) U.S. Cl.
USPC .......................... 514/333; 546/256

(58) Field of Classification Search
USPC .......................... 514/333; 546/256
See application file for complete search history.

(56) References Cited

U.S. PATENT DOCUMENTS

| | | | |
|---|---|---|---|
| 4,273,782 A | 6/1981 | Cross et al. |
| 4,616,009 A | 10/1986 | Tahara et al. |
| 4,826,987 A | 5/1989 | Nielsen et al. |
| 5,081,138 A | 1/1992 | Gillard et al. |
| 5,081,145 A | 1/1992 | Guindon et al. |
| 5,093,356 A | 3/1992 | Girard et al. |
| 5,095,031 A | 3/1992 | Brooks et al. |
| 5,109,009 A | 4/1992 | Nielsen et al. |
| 5,157,039 A | 10/1992 | Nielsen et al. |
| 5,182,367 A | 1/1993 | Gillard et al. |
| 5,190,968 A | 3/1993 | Gillard et al. |
| 5,202,321 A | 4/1993 | Hutchinson et al. |
| 5,204,344 A | 4/1993 | Prasit et al. |
| 5,225,421 A | 7/1993 | Gillard et al. |
| 5,229,516 A | 7/1993 | Musser et al. |
| 5,232,916 A | 8/1993 | Zamboni et al. |
| 5,252,585 A | 10/1993 | Frenette et al. |
| 5,254,567 A | 10/1993 | Down et al. |
| 5,272,145 A | 12/1993 | Prasit et al. |
| 5,273,980 A | 12/1993 | Frenette et al. |
| 5,288,743 A | 2/1994 | Brooks et al. |
| 5,290,788 A | 3/1994 | Stevens et al. |
| 5,290,798 A | 3/1994 | Gillard et al. |
| 5,308,850 A | 5/1994 | Gillard et al. |
| 5,314,898 A | 5/1994 | Chung et al. |
| 5,334,719 A | 8/1994 | Frenette |
| 5,374,635 A | 12/1994 | Leger et al. |
| 5,380,850 A | 1/1995 | Prasit et al. |
| 5,389,650 A | 2/1995 | Frenette et al. |
| 5,399,699 A | 3/1995 | Kolasa et al. |
| 5,420,282 A | 5/1995 | Brooks et al. |
| 5,420,289 A | 5/1995 | Musser et al. |
| 5,459,150 A | 10/1995 | Brooks et al. |
| 5,578,634 A | 11/1996 | Bach et al. |
| 5,635,516 A | 6/1997 | Caubere et al. |
| 5,750,558 A | 5/1998 | Brooks et al. |
| 5,877,329 A | 3/1999 | Chen et al. |
| 5,972,241 A | 10/1999 | Johnson et al. |
| 6,246,452 B1 | 6/2001 | Sekine et al. |
| 6,500,853 B1 | 12/2002 | Seehra et al. |
| 6,627,646 B2 | 9/2003 | Bakale et al. |
| 6,699,883 B1 | 3/2004 | Doemling |
| 6,855,722 B2 | 2/2005 | Lu et al. |
| 6,867,209 B1 | 3/2005 | Mavunkel et al. |
| 7,118,869 B2 | 10/2006 | Blumenfeld et al. |
| 7,405,302 B2 | 7/2008 | Hutchinson et al. |
| 7,572,797 B2 | 8/2009 | Denton et al. |
| 7,795,274 B2 | 9/2010 | Hutchinson et al. |

(Continued)

FOREIGN PATENT DOCUMENTS

| CA | 2032253 C | 6/1991 |
|---|---|---|
| CA | 1337427 A | 10/1995 |

(Continued)

OTHER PUBLICATIONS

U.S. Appl. No. 12/681,636, filed Jul. 22, 2010.

(Continued)

*Primary Examiner* — Jennifer M Kim

(74) *Attorney, Agent, or Firm* — Wilson Sonsini Goodrich & Rosati

(57) ABSTRACT

Described herein are compounds and pharmaceutical compositions containing such compounds, which modulate the activity of 5-lipoxygenase-activating protein (FLAP). Also described herein are methods of using such FLAP modulators, alone and in combination with other compounds, for treating respiratory, cardiovascular, and other leukotriene-dependent or leukotriene mediated conditions or diseases.

15 Claims, 14 Drawing Sheets

(56) References Cited

U.S. PATENT DOCUMENTS

| | | |
|---|---|---|
| 7,834,037 B2 | 11/2010 | Hutchinson et al. |
| 7,977,359 B2 | 7/2011 | Hutchinson et al. |
| 8,399,666 B2 | 3/2013 | Hutchinson et al. |
| 2001/0039037 A1 | 11/2001 | Harland |
| 2003/0203833 A1 | 10/2003 | Ignar et al. |
| 2004/0014759 A1 | 1/2004 | Picard et al. |
| 2004/0086952 A1 | 5/2004 | Gentz et al. |
| 2004/0198800 A1 | 10/2004 | Allan et al. |
| 2005/0245515 A1 | 11/2005 | Dehmlow et al. |
| 2006/0211677 A1 | 9/2006 | Chu et al. |
| 2007/0003971 A1 | 1/2007 | Blumenfeld et al. |
| 2007/0047207 A1 | 3/2007 | McPhee |
| 2007/0105866 A1 | 5/2007 | Hutchinson et al. |
| 2007/0123522 A1 | 5/2007 | Hutchinson et al. |
| 2007/0219206 A1 | 9/2007 | Hutchinson et al. |
| 2007/0225285 A1 | 9/2007 | Hutchinson et al. |
| 2007/0244128 A1 | 10/2007 | Hutchinson et al. |
| 2008/0227807 A1 | 9/2008 | Hutchinson et al. |
| 2008/0293739 A1 | 11/2008 | Trede |
| 2009/0018170 A1 | 1/2009 | Hutchinson et al. |
| 2011/0118315 A1 | 5/2011 | Hutchinson et al. |
| 2013/0102636 A1 | 4/2013 | Hutchinson et al. |

FOREIGN PATENT DOCUMENTS

| | | | |
|---|---|---|---|
| DE | 4338770 A1 | 5/1995 |
| EP | 0275667 B1 | 3/1992 |
| EP | 0510398 A2 | 10/1992 |
| EP | 0337767 B1 | 1/1993 |
| EP | 0535924 A1 | 4/1993 |
| EP | 0540051 B1 | 5/1993 |
| EP | 0597112 A1 | 5/1994 |
| EP | 0290145 B1 | 10/1994 |
| EP | 04190949 B1 | 4/1995 |
| EP | 0937459 A2 | 8/1999 |
| EP | 1749829 A1 | 2/2007 |
| EP | 1943219 | 10/2011 |
| FR | 2431491 A1 | 2/1980 |
| GB | 2280181 A | 1/1995 |
| JP | 6058881 A | 3/1994 |
| JP | 06100551 A | 4/1994 |
| JP | 7005651 A | 1/1995 |
| JP | 08020532 A | 1/1996 |
| JP | 09002977 A | 1/1997 |
| JP | 11080032 A | 3/1999 |
| JP | 11189531 A | 7/1999 |
| JP | 11193265 A | 7/1999 |
| JP | 2000007590 A | 1/2000 |
| JP | 2000302671 A | 10/2000 |
| JP | 2001139462 A | 5/2001 |
| JP | 2002226429 A | 8/2002 |
| JP | 3457694 A | 8/2003 |
| JP | 2004262933 A | 9/2004 |
| JP | 2005002346 A | 1/2005 |
| JP | 2005082701 A | 3/2005 |
| JP | 2005170939 A | 6/2005 |
| JP | 2005194250 A | 7/2005 |
| JP | 2009023986 A | 2/2009 |
| NZ | 234883 | 8/1990 |
| NZ | 248177 | 7/1993 |
| WO | 8802364 A | 4/1988 |
| WO | 9106537 A2 | 5/1991 |
| WO | 9203132 A1 | 3/1992 |
| WO | 9316069 A1 | 8/1993 |
| WO | 9320065 A1 | 10/1993 |
| WO | 9323391 A1 | 11/1993 |
| WO | 9325546 A1 | 12/1993 |
| WO | 9400446 A1 | 1/1994 |
| WO | 9411378 A1 | 5/1994 |
| WO | 9412179 A1 | 6/1994 |
| WO | 9413293 A1 | 6/1994 |
| WO | 9413662 A1 | 6/1994 |
| WO | 9414434 A1 | 7/1994 |
| WO | 9429290 A1 | 12/1994 |
| WO | 9506637 A1 | 3/1995 |
| WO | 9535372 A1 | 12/1995 |
| WO | 9603377 A1 | 2/1996 |
| WO | 9615118 A1 | 5/1996 |
| WO | 9618393 A1 | 6/1996 |
| WO | 9632379 A1 | 10/1996 |
| WO | 9635670 A1 | 11/1996 |
| WO | 9727190 A1 | 7/1997 |
| WO | 9728105 A1 | 8/1997 |
| WO | 9741100 A1 | 11/1997 |
| WO | 9749703 A1 | 12/1997 |
| WO | 9803202 A1 | 1/1998 |
| WO | 9821184 A1 | 5/1998 |
| WO | 9852943 A1 | 11/1998 |
| WO | 9856757 A1 | 12/1998 |
| WO | 9907351 A1 | 2/1999 |
| WO | 9933458 A1 | 7/1999 |
| WO | 9933800 A1 | 7/1999 |
| WO | 9943651 A1 | 9/1999 |
| WO | 9943672 A1 | 9/1999 |
| WO | 9952942 A1 | 10/1999 |
| WO | 9961426 A1 | 12/1999 |
| WO | 0029574 A1 | 5/2000 |
| WO | 0043384 A1 | 7/2000 |
| WO | 0071535 A1 | 11/2000 |
| WO | 0200621 A1 | 1/2001 |
| WO | 0121594 A1 | 3/2001 |
| WO | 0132621 A1 | 5/2001 |
| WO | 0136403 A1 | 5/2001 |
| WO | 0141807 A1 | 6/2001 |
| WO | 0144184 A1 | 6/2001 |
| WO | 0158869 A1 | 8/2001 |
| WO | 0159105 A1 | 8/2001 |
| WO | 0164639 A1 | 9/2001 |
| WO | 0166520 A1 | 9/2001 |
| WO | 0170211 A1 | 9/2001 |
| WO | 0177149 A1 | 10/2001 |
| WO | 0210152 A2 | 2/2002 |
| WO | 0228835 A1 | 4/2002 |
| WO | 02051397 A1 | 7/2002 |
| WO | 02051837 A2 | 7/2002 |
| WO | 03022813 A1 | 3/2003 |
| WO | 03022814 A1 | 3/2003 |
| WO | 03028719 A1 | 4/2003 |
| WO | 03035625 A1 | 5/2003 |
| WO | 03044014 A1 | 5/2003 |
| WO | 03050174 A1 | 6/2003 |
| WO | 03094889 A1 | 11/2003 |
| WO | 03099771 A1 | 12/2003 |
| WO | 2004000795 A1 | 12/2003 |
| WO | 2004000831 A1 | 12/2003 |
| WO | 2004017917 A2 | 3/2004 |
| WO | 2004017920 A1 | 3/2004 |
| WO | 2004020409 A1 | 3/2004 |
| WO | 2004043392 A3 | 5/2004 |
| WO | 2004048331 A1 | 6/2004 |
| WO | 2004050643 A1 | 6/2004 |
| WO | 2004065388 A1 | 8/2004 |
| WO | 2004078719 A1 | 9/2004 |
| WO | 2004101554 A1 | 11/2004 |
| WO | 2004108671 A1 | 12/2004 |
| WO | 2005009951 A1 | 2/2005 |
| WO | 2005019381 A1 | 3/2005 |
| WO | 2005023246 A1 | 3/2005 |
| WO | 2005023806 A1 | 3/2005 |
| WO | 2005030717 A1 | 4/2005 |
| WO | 2005042542 A1 | 5/2005 |
| WO | 2005054176 A1 | 6/2005 |
| WO | 2005054193 A1 | 6/2005 |
| WO | 2005054213 A1 | 6/2005 |
| WO | 2005065266 A1 | 7/2005 |
| WO | 2005065266 A2 | 7/2005 |
| WO | 2005066151 A2 | 7/2005 |
| WO | 2005066157 A1 | 7/2005 |
| WO | 2005082346 A1 | 9/2005 |
| WO | 2005097203 A2 | 10/2005 |
| WO | 2005112921 A1 | 12/2005 |
| WO | 2005123674 A1 | 12/2005 |
| WO | 2006014262 A2 | 2/2006 |

(56) References Cited

FOREIGN PATENT DOCUMENTS

| | | |
|---|---|---|
| WO | 2006023843 A2 | 3/2006 |
| WO | 2006030031 A1 | 3/2006 |
| WO | 2006041961 A1 | 4/2006 |
| WO | 2006044602 A1 | 4/2006 |
| WO | 2006074984 A1 | 7/2006 |
| WO | 2006077364 A1 | 7/2006 |
| WO | 2006077365 A1 | 7/2006 |
| WO | 2006077366 A1 | 7/2006 |
| WO | 2006077367 A1 | 7/2006 |
| WO | 2006098912 A1 | 9/2006 |
| WO | 2006105439 A1 | 10/2006 |
| WO | 2006111560 A2 | 10/2006 |
| WO | 2006131737 A1 | 12/2006 |
| WO | 2007022427 A2 | 2/2007 |
| WO | 2007047204 A1 | 4/2007 |
| WO | 2007047207 A2 | 4/2007 |
| WO | 2007048042 A2 | 4/2007 |
| WO | 2007052123 A2 | 5/2007 |
| WO | 2007053094 A1 | 5/2007 |
| WO | 2007053095 A1 | 5/2007 |
| WO | 2007056021 A2 | 5/2007 |
| WO | 2007056220 A2 | 5/2007 |
| WO | 2007056228 A2 | 5/2007 |
| WO | 2007109279 A2 | 9/2007 |
| WO | 2007123225 A1 | 11/2007 |
| WO | 2008058341 A1 | 5/2008 |
| WO | 2008067566 A1 | 6/2008 |
| WO | 2008097930 A1 | 8/2008 |
| WO | 2008127728 A1 | 10/2008 |
| WO | 2008137609 A1 | 11/2008 |
| WO | 2008137805 A1 | 11/2008 |
| WO | 2008141011 A1 | 11/2008 |
| WO | 2009002746 A1 | 12/2008 |
| WO | 2009009041 A2 | 1/2009 |
| WO | 2009045700 A2 | 4/2009 |
| WO | 2009055721 A2 | 4/2009 |
| WO | 2009114865 A2 | 9/2009 |
| WO | 2010068311 A1 | 6/2010 |

OTHER PUBLICATIONS

Brideau, et al., "Pharmacoiogy of MK-0591 (3-[1-(4-chlorobenzyl)-3-(t-butylthio)-5-(quinolin-2-ylmethoxy)-indol-2-yl)-2,2-dimethylpropanoic acid), a Potent, Orally Active Leukotriene Biosynthesis Inhibitor" 1992; Can J. Physiol. Pharmacol.; vol. 70; pp. 799-807.

Chapman, et al., "The efficacy of an oral inhibitor of leukotriene synthesis (MK-0591) in asthmatics treated with inhaled steroids" 1994; Am. J. Respir. Crit. Care Med.; vol. 149; pp. A215.

Depre, et al., Pharmakokinetics and pharmadynamics of multiple oral dose of MK-0591, a lipoxygenase-activating protein inhibitor 1994; Clin. Pharmacol. Ther.; vol. 56; pp. 22-30.

Bhovi, et al., "Synthesis and antimicrobial activity of some 1,5-dioxadiazolyl/ditriazolyi and dipyrrolylindole derivatives" 2005; Asian J. Chem; vol. 17(1); pp. 518-524.

Jawein, et al., "Inhibition of five lipoxygenase activating protein (FLAP) by MK-886 decreases artherosclerosis in apoE/LDLR-double knockout mice," 2006; European Journal of Clinical Investigation; vol. 36(3); pp. 141-146.

Leff, et al., "Discovery of leukotrienes and development of antileukotrierie agents" 2001; Ann. Allergy Asthma Immunol.; vol. 86(1); pp. 4-8.

O'Byrne, "Leukotrienes in the Pathogenesis of Asthma" 1997; Chest; vol. 111(Suppl 2); pp. 27S-34S.

Riccioni, et al., "Brief Review. Advances in Therapy with Antileukotriene Drugs" 2004; Ann. Clin. Lab Sci.; vol. 34(4); pp. 379-387.

ScienceIP Search Report Jun. 2, 2006.

ScienceIP Search Report Jun. 15, 2007.

Uematsu, et al., Pharmacokinetics and pharmacodynamic analysis of a novel leukotriene biosynthesis inhibitor MK-0591, (1995).

Brooks, et al., "Modulators of Leukotriene Biosynthesis and Receptor Activation" 1996; J. Med. Chem.; vol. 39(14); pp. 2629-2654.

Ford-Hutchinson, et al., "5-Lipoxygenase" 1994; Annu. Rev. Biochem.; vol. 63; pp. 383-417.

Gadaginamath, "Chemoselective reaction of bisherterocycle dicarboxylate towards hydrazine hydrate: Synthesis and antimicrobial activity of some new trisheterocycles: 5-pyrrolyalaminocarbonyl/oxadiazolyl/mercaptooxadiazolylmethoxy-1-furfurly-2 methylindones" 2003; Indian J. Chem; vol. 42B; pp. 3108-3112.

Young, "Inhibitors of 5-Lipoxygeriese: a therapeutic potential yet to be fully realized?" 1999; Eur, J. Med. Chem.; vol. 34; pp. 671-685.

Miller, et al., "Identification and Isolation of a Membrane Protein Necessary for Leukotriene Production." Jan. 1990; Nature; vol. 343; pp. 278-281.

Drazen, "Clinical Pharmacology and Leukotriene Receptor Agonists and 5-Lipoxygenase Inhibitors" Jun. 1998; Respiratory and Critical Care Medicine; vol. 157(6) Part 2; pp. S233-S237.

Rouzer, et al., "MK-886, a Potent and Specific Leukotriene Biosynthesis Inhibitor Blocks and Reverses the Membrane Association of 5-Lipoxygenase in Ionophore-Challenged Leukocytes" 1990 The Journal of Biological Chemistry; vol. 265 (3); pp. 1436-1442.

Hui, et al., "Effects of a 5-Lipoxygenase Inhibitor on Leukotriene Generation and Airway Responses after Allergen Challenge in Asthmatic Patients" Mar. 1991; Thorax; vol. 46(3); pp. 184-189.

Hamilton, et al., Attenuation of early and late phase allergen-induced bronchoconstriction in asthmatic subjects by a 5-Lipoxygenase activating protein antagonist, BAYx 1005; 1997; Thorax; vol. 52; pp. 348-354.

Nasser, et al., "Effect of the 5-lipoxygenase inhibitor ZD2138 on allergen-induced early and late asthmatic responses." 1994; Thorax; vol. 49; pp. 743-748.

U.S. Appl. No. 11/925,841, filed Oct. 27, 2007.
U.S. Appl. No. 11/744,555, filed May 4, 2007.
U.S. Appl. No. 11/746,010, filed May 8, 2007.
U.S. Appl. No. 11/745,387, filed May 7, 2007.
U.S. Appl. No. 11/538,762, filed Oct. 4, 2006.
U.S. Appl. No. 12/131,828, filed Jun. 2, 2008.
U.S. Appl. No. 12/257,876, filed Oct. 24, 2008.
U.S. Appl. No. 12/525,676, filed Aug. 4, 2009.
U.S. Appl. No. 12/471,106, filed May 22, 2009.

Valasinas, et al., 1978; Journal of Labelled Compounds and Radiopharmaceuticals; 15 (Suppl. Vol.): pp. 549-554.

Battersby, et al., (1972-1999) (1973); Journal of the Chemical Society, Perkin Transactions 1: Organic and Bio-Organic Chemistry; vol. 15; pp. 1546-1556.

Frydman, et al., (1969); Journal of the American Chemical Society; vol. 91(9); pp. 2338-2426.

Frydman, et al., (1968); Journal of Organic Chemistry; vol. 33 (10); pp. 3762-3766.

U.S. Appl. No. 12/089,706, filed Apr. 9, 2008.
U.S. Appl. No. 12/092,570, filed May 2, 2008.
U.S. Appl. No. 12/089,707, filed Oct. 1, 2008.

Gadaginamath, et al., "Chemoselective reaction of bisheterocycle dicarboxylate towards hydrazine hydrate: Synthesis and antimicrobial activity of some new trisheterocycles: 5-Pyrrolyaminocarbonyl/oxadiazoyl/mercaptooxadiazolylmethoxy-1-1furfuryl-2-methylindoles" Indian Journal of Chemistry; 2003: vol. 42B; pp. 3108-3112.

Chemical Abstracts, Abstract No. 141:54149 (2007).
Chemical Abstracts, Abstract No. 143:286345 (2007).

Bellot, et al., "Concomitant Treatment with a 5-Lipoxygenase Inhibitor Improves the Anti-Inflammatory Effect of the inhibition of Nitric Oxide Synthase during the Early Phase of Endotoxin-induced Uveitis in the Rabbit" Ophthalmic Research; 1997; vol. 29(4); Abstract.

Jain, et al., "Polymorphism in Pharmacy" Indian Drugs; 1986; vol. 23(6); pp. 315-329.

Kwon; Handbook of Essential Pharmacokinetics, Pharmacodynamics and Drug Metabolism for Industrial Scientists; 2001; p. 213; paragraph 3.

(56) References Cited

OTHER PUBLICATIONS

Lorrain, et al., "Pharmacology of AM803, a novel selective five-lipoxygenase-activating protein (FLAP) inhibitor in rodent models of acute inflammation." European Journal of Pharmacology; 2010; vol. 640; pp. 211-218.
Morrisette, et al., "High-throughout crystallization: polymorphs, salts, co-crystals and solvates of pharmaceutical solids." Advanced Drug Delivery; 2004; vol. 56; pp. 275-300.
Muzaffar, et al., "Polymorphism and Drug Availability" 1979; Journal of Pharmacy; vol. 1(1): pp. 59-66.
Otsuka, et al., "Effect of Polymorphic Forms of Bulk Powders on Pharmaceutical Porperties of Carbamazepine Granules" Chem. Pharm. Bull.; 1999; vol. 47(6); pp. 852-856.
Rautio, et al., "Prodrugs; Design and Clinical Applications" Nat. Rev. Drug. Dis: 2008; vol. 7; pp. 255-270.
Silverman; The Organic Chemistry of Drug Design and Drug Action; 1993; NY Academic Press; pp. 72-76.
Singhal, et al., "Drug polymorphism and dosage form design; a practical perspective" 2004; Advanced Drug Delivery Reviews; vol. 56; pp. 334-347.
Taday, et al., "Using Terahertz Pulse Spectroscopy to Study the Crystalline Structure of a Drug; A Case Study of the Polymorphs of Ranitidine Hydrochloride" Journal of Pharm. Sci.; 2003; vol. 92(4); pp. 831-838.
Valasinas, et al., "Synthesis of Porphobilinogen-9-14C" Journal of Labelled Compounds and Radiopharmaceuticals: 1978;15 (Suppl. Vol.); pp. 549-554.
Vippagunta, et al., "Crystalline Solids" Advanced Drug Delivery Reviews; 2001; vol. 48; pp. 3-26.
Young, et al., "Inhibitors of 5-lipoxygenase; a therapeutic potential yet to be fully realized?" Eur. J. Med. Chem.: 1999; vol. 34; pp. 671-685.
US Pharmacopia #23; National Formulary #18; 1995; pp. 1843-1844.
PCT/US08/42690 Search Report dated May 24, 2007.
PCT/US06/43108 Search Report dated Sep. 5, 2007.
PCT/US06/43095 Search Report dated Feb. 25, 2008.
U.S. Appl. No. 11/553,946, filed Oct. 27, 2006.
U.S. Appl. No. 11/553,946, Preliminary Amendment dated Apr. 2, 2008.
U.S. Appl. No. 11/553946, Amendment filed with Request for Continued Examination dated Jun. 15, 2010.
U.S. Appl. No. 12/993,319, filed Jan. 14, 2011.
U.S. Appl. No. 12/906,325, filed Oct. 18, 2010.
U.S. Appl. No. 12/517,166, filed Jul. 14, 2009.
Friedman, et al., "Oral Leukotriene Inhibitor (MK-886) Blocks Allergen-Induced Airway Responses" American Review of Respiratory Disease, Apr. 1993, vol. 147(4), pp. 839-844.
Prasit, et al., "A New Class of Leuktriene Biosynthesis Inhibtors: The Discovery of MK0591"; Bioorganic & Medicinal Chemistry Letters, 1992, vol. 2, No. 11, pp. 1395-1398.
Hutchinson, et al., "Development of L-689,065; The Prototype of a New Class of Potent 5-Lipoxgenase Inhibitors" Bioorganic & Medicinal Chemistry Letters: 1992; vol. 2, No. 12; 1699-1702.
Gillard, et al., "L-663-536 (MK-886) (3-[1-(4-chlorobenzyl)-3-t-butyl-thio-5-isopropylindol-2-yl]-2,2-dimethylpropanoic acid), a novel, orally active leukotriene biosynthesis inhibitor"; Canadian Journal of Physiol. Pharmac., 1989, vol. 67, pp. 456-465: Abstract.
Larraya, et al., "Preparation of 4-Azaindole and 7-Azaindole Dimers with a BisalkoxyEilkyl Spacer in order to Preferentially Target Melatonin MT1 Receptors over Melatonin MT2 Receptors"; European Journal of Medicinal Chemistry; 2004; vol. 39; No. 6; pp. 515-526.
Gardiner, et al., "Inhibition of antigen-induced contraction of guinea-pig airways by a leukotriene synthesis inhibitor, BAY x1005"; European Journal of Pharmacology; 1994; vol. 258; No. 1/2; pp. 95-102.

Hutchinson, et al., "Substituted Thiopyranol [2,3,4-c,d] indoles as Potent, Selective, and Orally Active Inhibitors of 5-Lipoxygenase Synthesis and Biological Evalutation of L-691, 816." Journal of Medicinal Chemistry; vol. 36; pp. 2771-2787, (1993).
Hutchinson, et al., "5-Lipoxygenase-Activating Protein Inhibitors: Development of 3[3-tert-Butylsulfanyl-1-[4-(6-methoxy-pyridin-3-yl)-benzyl]-5-(pyridin-2-ylmethoxy-1H-indol-2-yl]-2,2-dimethyl-propionic Acid (AM103)." Journal of Medicinal Chemistry; 2009; vol. 52; pp. 5803-5815.
Guasch, et al., "MK-591 acutely restores glomerular size selectively and reduces proteinuria in human glomerulonephritis." Kidney International; 1999; vol. 56; pp. 261-267.
Rainsford, "Inhibition of Leukotriene Inhibitors, and Calcium and Platelet-activating Factor Antagonists, of acute gastric and intestinal damage in arthritic rats and in cholinomimetic-treated mice." Journal of Pharmacy and Pharmacology; 1999; vol. 51 (3); pp. 331-339.
Lorrain, D.S., et al., "Pharmacological Characterization of 3-[3-tert-Butylsulfanyl-1-[4-(6-methoxy-pyridin-3-yl)-benzyl]-5-(pyridin-2-ylmethoxy)-1HIndol-2-yl]-2,2-dimethyl-propionic Acid (AM103), a Novel Selective 5-Lipoxygenase-Activating Protein Inhibitor That Reduces Acute and Chronic Inflammation." The Journal of Pharmacology and Experimental Therapeutics; 2009; vol. 331(3); pp. 1042-1050.
Evans, J.F., et al. "What's all the FLAP about?; 5-Lipoxygenase-activating protein inhibitors for inflammatory diseases." Trends in Pharmacological Science; 2008; vol. 29(2); pp. 72-78.
Whittle, "Gastrointestinal Effects of Non-Steroidal Anti-inflammatory Drugs" Fundamental and Clinical Pharmacology; 2003; vol. 17 (3); pp. 301-315.
Guillard, et al., "Synthesis of New Melatonin Analogues from dimers of Azairidole and indole by use of Suzuki Homocoupling " Heterocycles; 2003; vol. 60 (4); pp. 865-877.
Vaananen, et al., "Pharmacological Investigation of the Role of Leukotrienes in the Pathogenesis of Experimental NSAID Gastropathy," Inflammation; 1992; vol. 16(3); pp. 227-240.
Birnberg, et al, "The Synthesis of 5-Arylpyrrolo[3, 2-b]pyridines and 7-Aryl-pyrrolo[3,2b]pyridines: ADdition of 3-Aminopyrroles to Aryl Enaminones"; Journal of Heterocyclic Chemistry; 1995; vol. 32(4); pp. 1293-1298.
Suzuki, et al., "Sodium Telluride in N-Methyl-2-pyrrolidone. Reduction of Aromatic carbonyl Compounds to Alcohols and Formation of Pyrrolo [2,3-d]pyrimidines (7-deaza-9H-purines) from Aromatic Nitriles." Journal of Organic Chemistry; 1993; vol. 58(1); pp. 241-244.
Hakonarson, et al., "Effects of a 5-Lipoxygenase-Activating Protein Inhibtor on Biomarkers Associated with Risk of Myocardial Infarction." The Journal of the American Medical Association; 2005; vol. 293(18); pp. 2245-2256.
Frenette, et al., "Substituted Indoles as Potent and Orally Active 5-Lipoxygenase. Activating Protein (FLAP) Inhibitors" Bioorganic & Medicinal Chemistry Letters; 1999; vol. 9(16); pp. 2391-2396.
Woods, et al., "O-Alkylcarboxylate Oxime and N-Hydroxyures Analogs of Substituted Indole Leukotriene Biosynthesis Inhibitors" Bioorganic & Medicinal Chemistry Letters; 1996; vol. 6(13); pp. 1547-1552.
Kemp, "Leukotriene receptor antagonists for the treatment of asthma"; IDrugs; 2000; vol. 3(4); pp. 430-441; Abstract only.
Diamant, et al., "The Effect of MK-0591, a novel 5-lipoxygenase activating protein inhibitor, on leukotriene biosynthesis and allergen-induced airway response in asthmatic subjects in vivo" Journal of Allergy and Chemical Immunology; Jan. 1995; 95(1); pp, 42-51.
U.S. Appl. No. 11/553,946, Response to Office Action of Jan. 14, 2010, filed Jun. 15, 2010.
U.S. Appl. No. 12/089,707, Preliminary Amendment filed Apr. 9, 2008.
U.S. Appl. No. 12/089,707, Response to Office Action of Aug. 3, 2011, filed Jan. 3, 2012.

Scheme I

Scheme II

Scheme III

Batcho-Leimgruber Indole Synthesis

Reissert Indole Synthesis

Hegedus Indole Synthesis

Fukuyama Indole Synthesis

Sugasawa Indole Synthesis

Bischler Indole Synthesis

Gassman Indole Synthesis

Japp-Klingemann Indole Synthesis

Buchwald Indole Synthesis

Larock Indole Synthesis

Bartoli Indole Synthesis

Castro Indole Synthesis

Heck Indole Synthesis

Hemetsberger Indole Synthesis

Mori-Ban Indole Synthesis

Madelung Indole Synthesis

McMurray Indole Synthesis

Nenitzescu Indole Synthesis

Other Syntheses

X = TMS, Boc

Using Palladium

Photochemical

Acid Catalyzed Cyclization

X = TFA, alkyl, sulfonyl

5-LIPOXYGENASE-ACTIVATING PROTEIN (FLAP) INHIBITORS

CROSS-REFERENCE TO RELATED APPLICATIONS

This application is a continuation application of Ser. No. 13/012,045 filed Jan. 24, 2011, which is a divisional application of U.S. Ser. No. 11/553,946 filed Oct. 27, 2006, which claims the benefit of U.S. Provisional Application No. 60/734,030, entitled "5-LIPDXYGENASE-ACTIVATING PROTEIN (FLAP) INHIBITORS" filed on Nov. 4, 2005; U.S. Provisional Application No. 60/747,174, entitled "5-LIPDXYGENASE-ACTIVATING PROTEIN (FLAP) INHIBITORS", filed on May 12, 2006; and U.S. Provisional Application No. 60/823,344, entitled "5-LIPDXYGENASE-ACTIVATING PROTEIN (FLAP) INHIBITORS", filed on Aug. 23, 2006, all of which are herein incorporated by reference.

FIELD OF THE INVENTION

Described herein are compounds, methods of making such compounds, pharmaceutical compositions and medicaments comprising such compounds, and methods of using such compounds to treat or prevent diseases or conditions associated with 5-lipoxygenase-activating protein (FLAP) activity.

BACKGROUND OF THE INVENTION

The protein 5-lipoxygenase-activating protein (FLAP) is associated with the pathway of leukotriene synthesis. In particular, 5-lipoxygenase-activating protein (FLAP) is responsible for binding arachidonic acid and transferring it to 5-lipoxygenase. See, e.g., Abramovitz, M. et al., *Eur. J. Biochem.* 215:105-111 (1993).

5-lipoxygenase can then catalyze the two-step oxygenation and dehydration of arachidonic acid, converting it into the intermediate compound 5-HPETE (5-hydroperoxyeicosatetraenoic acid), and in the presence of FLAP convert the 5-HPETE to Leukotriene $A_4$ ($LTA_4$).

Leukotrienes are biological compounds formed from arachidonic acid in the leukotriene synthesis pathway (Samuelsson et al, *Science,* 220, 568-575, 1983; Cooper, The Cell, A Molecular Approach, 2nd Ed. Sinauer Associates, Inc., Sunderland (MA), 2000). They are synthesized primarily by eosinophils, neutrophils, mast cells, basophils, dendritic cells, macrophages and monocytes. Leukotrienes have been implicated in biological actions including, by way of example only, smooth muscle contraction, leukocyte activation, cytokine secretion, mucous secretion, and vascular function.

SUMMARY OF THE INVENTION

Presented herein are methods, compounds, pharmaceutical compositions, and medicaments for (a) diagnosing, preventing, or treating allergic and non-allergic inflammation, (b) controlling signs and symptoms that are associated with inflammation, and/or (c) controlling proliferative or metabolic disorders. These disorders may arise from genetic, iatrogeic, immunological, infectious, metabolic, oncologic, toxic, and/or traumatic etiology. In one aspect, the methods, compounds, pharmaceutical compositions, and medicaments described herein comprise 5-lipoxygenase-activating protein (FLAP) inhibitors described herein.

In one aspect provided herein are compounds of Formula (G), pharmaceutically acceptable salts, pharmaceutically acceptable N-oxides, pharmaceutically active metabolites, pharmaceutically acceptable prodrugs, and pharmaceutically acceptable solvates thereof, which antagonize or inhibit FLAP and may be used to treat patients suffering from leukotriene-dependent conditions or diseases, including, but not limited to, asthma, chronic obstructive pulmonary disease, pulmonary hypertension, interstitial lung fibrosis, rhinitis, arthritis, allergy, psoriasis, inflammatory bowel disease, adult respiratory distress syndrome, myocardial infarction, aneurysm, stroke, cancer, endotoxic shock, proliferative disorders and inflammatory conditions.

Formula (G) is as follows:

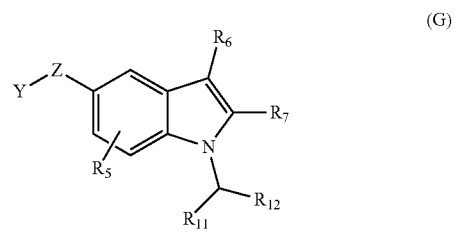

(G)

wherein,

Z is selected from $[C(R_1)_2]_m[C(R_2)_2]_n$, $[C(R_2)_2]_n[C(R_1)_2]_mO$, $O[C(R_1)]_m[C(R_2)_2]_n$, $[C(R_2)_2]_nO[C(R_1)_2]_n$, or $[C(R_1)_2]_nO[C(R_2)_2]_m$, wherein each $R_1$ is independently H, $CF_3$, or an optionally substituted lower alkyl and two $R_1$ on the same carbon may join to form a carbonyl (=O); and each $R_2$ is independently H, OH, OMe, $CF_3$, or an optionally substituted lower alkyl and two $R_2$ on the same carbon may join to form a carbonyl (=O); m is 0, 1 or 2; each n is independently 0, 1, 2, or 3;

Y is H or -(substituted or unsubstituted aryl); or -(substituted or unsubstituted heteroaryl);

where each substituent on Y or Z is $(L_sR_s)$, wherein each $L_s$ is independently selected from a bond, —O—, —C(=O)—, —S—, —S(=O)—, —S(=O)$_2$—, —NHC(O)—, —C(O)NH—, S(=O)$_2$NH—, —NHS(=O)$_2$, —OC(O)NH—, —NHC(O)O—, —OC(O)O—, —NHC(O)NH—, —C(O)O—, —OC(O)—, substituted or unsubstituted $C_1$-$C_6$ alkyl, $C_2$-$C_6$ alkenyl, —$C_1$-$C_6$ fluoroalkyl, substituted or unsubstituted heteroaryl, substituted or unsubstituted aryl, or substituted or unsubstituted heterocycle; and each $R_s$ is independently selected from H, halogen, —N(R$_4$)$_2$, —CN, —NO$_2$, N$_3$, —S(=O)$_2$NH$_2$, substituted or unsubstituted lower alkyl, substituted or unsubstituted lower cycloalkyl, —$C_1$-$C_6$ fluoroalkyl, substituted or unsubstituted aryl, substituted or unsubstituted heteroaryl, or substituted or unsubstituted heteroalkyl; where j is 0, 1, 2, 3, or 4;

$R_6$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(O), —CH(OH), -(substituted or unsubstituted $C_1$-$C_6$ alkyl), or -(substituted or unsubstituted $C_2$-$C_6$ alkenyl);

$R_7$ is $L_3$-X-$L_4$-$G_1$, wherein, $L_3$ is a substituted or unsubstituted alkyl;

X is a bond, O, —C(=O), —CR$_9$(OR$_9$), S, —S(=O), —S(=O)$_2$, —NR$_9$, —NR$_9$C(O), —C(O)NR$_9$, —NR$_9$C(O)NR$_9$—;

$L_4$ is a bond, or a substituted or unsubstituted alkyl;

$G_1$ is H, tetrazolyl, —NHS(=O)$_2$R$_8$, S(=O)$_2$N(R$_9$)$_2$, —OR$_9$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, —S(=O)$_2$R$_8$, -L$_5$-(substituted or unsubstituted alkyl), -L$_5$-(substituted or unsubstituted alkenyl), -L$_5$-(substituted or unsubstituted heteroaryl), or -L$_5$-(substituted or unsubstituted aryl), wherein L$_5$ is —OC(O)O—, —NHC(O)NH—, —NHC(O)O, —O(O)CNH—, —NHC(O), —C(O)NH, —C(O)O, or —OC(O);

or $G_1$ is W-G$_5$, where W is a substituted or unsubstituted aryl, substituted or unsubstituted heterocycle or substituted or unsubstituted heteroaryl and G$_5$ is H, tetrazolyl, —NHS(=O)$_2$R$_8$, S(=O)$_2$N(R$_9$)$_2$, OH, —OR$_8$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, or —S(=O)$_2$R$_8$;

each $R_8$ is independently selected from substituted or unsubstituted lower alkyl, substituted or unsubstituted lower cycloalkyl, substituted or unsubstituted phenyl or substituted or unsubstituted benzyl;

each $R_9$ is independently selected from H, substituted or unsubstituted lower alkyl, substituted or unsubstituted lower cycloalkyl, substituted or unsubstituted phenyl or substituted or unsubstituted benzyl; or two R$_9$ groups can together form a 5-, 6-, 7-, or 8-membered heterocyclic ring; or R$_8$ and R$_9$ can together form a 5-, 6-, 7-, or 8-membered heterocyclic ring and each $R_{10}$ is independently selected from H, —S(=O)$_2$R$_8$, —S(=O)$_2$NH$_2$—C(O)R$_8$, —CN, —NO$_2$, heteroaryl, or heteroalkyl;

$R_5$ is H, halogen, substituted or unsubstituted C$_1$-C$_6$ alkyl, substituted or unsubstituted O—C$_1$-C$_6$ alkyl;

$R_{11}$ is L$_7$-L$_{10}$-G$_6$, wherein L$_7$ is a bond, —C(O), —C(O)NH—, —NHC(O), or (substituted or unsubstituted C$_1$-C$_6$ alkyl); L$_{10}$ is a bond, (substituted or unsubstituted alkyl), (substituted or unsubstituted cycloalkyl), (substituted or unsubstituted heteroaryl), (substituted or unsubstituted aryl), or (substituted or unsubstituted heterocycle);

$G_6$ is OR$_9$, —C(=O)R$_9$, —C(=O)OR$_9$, —SR$_8$, —S(=O)R$_8$, —S(=O)$_2$R$_8$, N(R$_9$)$_2$, tetrazolyl, —NHS(=O)$_2$R$_8$, —S(=O)$_2$N(R$_9$)$_2$, —C(O)NHS(=O)$_2$R$_8$, —S(=O)$_2$NHC(O)R$_9$, —C(=O)N(R$_9$)$_2$, NR$_9$C(O)R$_9$, C(R$_9$)$_2$C(=O)N(R$_9$)$_2$—C(=NR$_{10}$)N(R$_9$)$_2$, —NR$_9$C(=NR$_{10}$)N(R$_9$)$_2$, —NR$_9$C(=CR$_{10}$)N(R$_9$)$_2$, -L$_5$-(substituted or unsubstituted alkyl), -L$_5$-(substituted or unsubstituted alkenyl), -L$_5$-(substituted or unsubstituted heteroaryl), or -L$_5$-(substituted or unsubstituted aryl), wherein L$_5$ is —O—, C(=O), S, S(=O), S(=O)$_2$, —NH, —NHC(O)O, —NHC(O)NH—, —OC(O)O—, —OC(O)NH—, —NHC(O), —C(O)NH, —C(O)O, or —OC(O)

or $G_6$ is W-G$_7$, wherein W is (substituted or unsubstituted heterocycle), (substituted or unsubstituted aryl) or a (substituted or unsubstituted heteroaryl) and G$_7$ is H, halogen, CN, NO$_2$, N$_3$, CF$_3$, OCF$_3$, C$_1$-C$_6$ alkyl, C$_3$-C$_6$ cycloalkyl, —C$_1$-C$_6$ fluoroalkyl, tetrazolyl, —NHS(=O)$_2$R$_8$, S(=O)$_2$N(R$_9$)$_2$, OH, —OR$_8$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, or —S(=O)$_2$R$_8$, -L$_5$-(substituted or unsubstituted alkyl), -L$_5$-(substituted or unsubstituted alkenyl), -L$_5$-(substituted or unsubstituted heteroalkyl), -L$_5$-(substituted or unsubstituted heteroaryl), -L$_5$-(substituted or unsubstituted heterocycle), or -L$_5$-(substituted or unsubstituted aryl), wherein L$_5$ is a bond, —O—, C(=O), S, S(=O), S(=O)$_2$, —NH, —NHC(O)O, —NHC(O)NH—, —OC(O)O—, —OC(O)NH—, —NHC(O), —C(O)NH, —C(O)O, or —OC(O);

provided that R$_{11}$ comprises at least one (unsubstituted or substituted) aromatic moiety and at least one (unsubstituted or substituted) cyclic moiety, wherein the (unsubstituted or substituted) cyclic moiety is a (unsubstituted or substituted) heterocyclic group or a (unsubstituted or substituted) heteroaryl group and R$_{11}$ is not a thienyl-phenyl group;

$R_{12}$ is H, (substituted or unsubstituted C$_1$-C$_6$ alkyl), (substituted or unsubstituted C$_3$-C$_6$ cycloalkyl); or active metabolite, or solvate, or pharmaceutically acceptable salt, or a pharmaceutically acceptable prodrug thereof.

For any and all of the embodiments (such as, e.g. Formula (G), Formula (G-I), and Formula (G-II)), substituents can be selected from among from a subset of the listed alternatives. For example, in some embodiments, Z is [C(R$_2$)$_2$]$_n$C(R$_1$)$_2$O.

In further or alternative embodiments, Y is -(substituted or unsubstituted heteroaryl) or -(substituted or unsubstituted aryl) and G$_6$ is W-G$_7$.

In further or alternative embodiments, Y is -(substituted or unsubstituted heteroaryl).

In further or alternative embodiments, Y is selected from the group consisting of pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, imidazo[1,2-a]pyridinyl and furopyridinyl, wherein Y is substituted or unsubstituted.

In further or alternative embodiments, Y is selected from the group consisting of pyridinyl or quinolinyl, wherein Y is substituted or unsubstituted.

In further or alternative embodiments, R$_6$ is L$_2$-(substituted or unsubstituted alkyl), or L$_2$-(substituted or unsubstituted cycloalkyl), L$_2$-(substituted or unsubstituted aryl), where L$_2$ is a bond, O, S, —S(O)$_2$, —C(O), or substituted or unsubstituted alkyl.

In further or alternative embodiments, X is a bond, O, —C(=O), —CR$_9$(OR$_9$), S, —S(=O), —S(=O)$_2$, —NR$_9$, —NR$_9$C(O), —C(O)NR$_9$.

In further or alternative embodiments, G$_1$ is tetrazolyl, —NHS(=O)$_2$R$_8$, S(=O)$_2$N(R$_9$)$_2$, —OR$_9$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, or —S(=O)$_2$R$_8$.

In further or alternative embodiments, $L_3$ is unsubstituted alkyl; X is a bond; $L_4$ is a bond; and $G_1$ is —C(O)OR$_9$.

In further or alternative embodiments, $R_9$ is H or unsubstituted alkyl.

In further or alternative embodiments, $L_{10}$ is a substituted or unsubstituted aryl substituted or unsubstituted heteroaryl and $G_6$ is W-G$_7$ wherein W is substituted or unsubstituted heteroaryl, substituted or unsubstituted heterocycle.

In further or alternative embodiments, $L_{10}$ is a substituted or unsubstituted aryl.

In further or alternative embodiments, $L_3$ is unsubstituted alkyl; X is a bond; $L_4$ is a bond; and $G_1$ is —OR$_9$.

In further or alternative embodiments, $G_1$ is W-G$_5$, where W is a substituted or unsubstituted heterocycle or substituted or unsubstituted heteroaryl.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In one aspect, provided herein is a compound selected from among: 3-[3-tert-butylsulfanyl-1-(4-pyridin-2-yl-benzyl)-5-(pyridin-2-ylmethoxy)-1H-indol-2-yl]-2,2-dimethyl-propionamide (Compound 1-1); 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid ethyl ester (Compound 1-2); 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid 6-hydroxy-hexyl ester (Compound 1-3); 1-[3-tert-butylsulfanyl-1-(4-pyridin-2-yl-benzyl)-5-(pyridin-2-ylmethoxy)-1H-indol-2-yl]-2-methyl-propan-2-ol (Compound 1-4); 1-[3-tert-butylsulfanyl-1-(4-pyridin-3-yl-benzyl)-5-(pyridin-2-ylmethoxy)-1H-indol-2-yl]-2-methyl-propan-2-ol (Compound 1-5); 1-[3-tert-butylsulfanyl-5-(pyridin-2-ylmethoxy)-1-(4-thiazol-2-yl-benzyl)-1H-indol-2-yl]-2-methyl-propan-2-ol (Compound 1-6); 1-[3-tert-butylsulfanyl-1-(4-[1,3,4]oxadiazol-2-yl-benzyl)-5-(pyridin-2-ylmethoxy)-1H-indol-2-yl]-2-methyl-propan-2-ol (Compound 1-7); 3-tert-butylsulfanyl-1-[4-(6-methoxy-pyridin-3-yl)-benzyl]-2-(2-methyl-2-[1,3,4]oxadiazol-2-yl-propyl)-5-(pyridin-2-ylmethoxy)-1H-indole (Compound 1-8); 5-{2-[3-tert-butylsulfanyl-1-[4-(6-methoxy-pyridin-3-yl)-benzyl]-5-(pyridin-2-ylmethoxy)-1H-indol-2-yl]-1,1-dimethyl-ethyl}-[1,3,4]oxadiazol-2-ylamine (Compound 1-9); 3-[3-tert-butylsulfanyl-1-[4-(6-methoxy-pyridin-3-yl)-benzyl]-5-(pyridin-2-ylmethoxy)-1H-indol-2-yl]-2,2-dimethyl-N-pyrazin-2-yl-propionamide (Compound 1-10); 3-[3-tert-butylsulfanyl-1-[4-(6-methoxy-pyridin-3-yl)-benzyl]-5-(pyridin-2-ylmethoxy)-1H-indol-2-yl]-2,2-dimethyl-N-thiazol-2-yl-propionamide (Compound 1-11); 3-[3-tert-butylsulfanyl-1-[4-(6-methoxy-pyridin-3-yl)-benzyl]-5-(pyridin-2-ylmethoxy)-1H-indol-2-yl]-2,2-dimethyl-N-pyridin-3-yl-propionamide (Compound 1-12); 3-[3-tert-butylsulfanyl-1-[4-(6-methoxy-pyridin-3-yl)-benzyl]-5-(pyridin-2-ylmethoxy)-1H-indol-2-yl]-N-(2-dimethylamino-ethyl)-2,2-dimethyl-propionamide (Compound 1-13); 5-{4-[3-tert-butylsulfanyl-2-(2,2-dimethyl-propyl)-5-(pyridin-2-ylmethoxy)-indol-1-ylmethyl]-phenyl}-[1,3,4]oxadiazol-2-ylamine (Compound 1-14); 3-[3-tert-butylsulfanyl-1-[4-(5-fluoro-pyridin-2-yl)-benzyl]-5-(quinolin-2-ylmethoxy)-1H-indol-2-yl]-N-(2-dimethylamino-ethyl)-2,2-dimethyl-propanoylguanidine (Compound 1-15); 3-[3-tert-butylsulfanyl-5-(pyridin-2-ylmethoxy)-1-(4-thiazol-2-yl-benzyl)-1H-indol-2-yl]-2,2-dimethyl-propionic acid (Compound 2-1); 3-[3-tert-butylsulfanyl-5-(pyridin-2-ylmethoxy)-1-(4-pyrimidin-2-yl-benzyl)-1H-indol-2-yl]-2,2-dimethyl-propionic acid (Compound 2-2); -[3-tert-butylsulfanyl-1-(4-pyridin-3-yl-benzyl)-5-(pyridin-2-ylmethoxy)-1H-indol-2-yl]-2,2-dimethyl-propionic acid (Compound 2-3); 3-[3-tert-butylsulfanyl-5-(pyridin-2-ylmethoxy)-1-(4-pyrimidin-5-yl-benzyl)-1H-indol-2-yl]-2,2-dimethyl-propionic acid (Compound 2-4); 3-[3-tert-butylsulfanyl-1-(4-pyrazin-2-yl-benzyl)-5-(pyridin-2-ylmethoxy)-1H-indol-2-yl]-2,2-dimethyl-propionic acid (Compound 2-5); 3-[3-tert-butylsulfanyl-1-[4-(6-methoxy-pyridazin-3-yl)-benzyl]-5-(pyridin-2-ylmethoxy)-1H-indol-2-yl]-2,2-dimethyl-propionic acid (Compound 2-6); 3-[1-[4-(5-amino-pyrazin-2-yl)-benzyl]-3-tert-butylsulfanyl-5-(pyridin-2-ylmethoxy)-1H-indol-2-yl]-2,2-dimethyl-propionic acid (Compound 2-7); 3-[3-(3,3-dimethyl-butyryl)-5-(pyridin-2-ylmethoxy)-1-(4-thiazol-2-yl-benzyl)-1H-indol-2-yl]-2,2-dimethyl-propionic acid (Compound 2-8); 2,2-dimethyl-3-[5-(pyridin-2-ylmethoxy)-1-(4-thiazol-2-yl-benzyl)-1H-indol-2-yl]-propionic acid (Compound 2-9); 3-[3-acetyl-5-(pyridin-2-ylmethoxy)-1-(4-thiazol-2-yl-benzyl)-1H-indol-2-yl]-2,2-dimethyl-propionic acid (Compound 2-10); 3-[1-[4-(6-methoxy-pyridazin-3-yl)-benzyl]-5-(pyridin-2-ylmethoxy)-1H-indol-2-yl]-2,2-dimethyl-propionic acid (Compound 2-11); 3-[3-acetyl-1-[4-(6-methoxy-pyridazin-3-yl)-benzyl]-5-(pyridin-2-ylmethoxy)-1H-indol-2-yl]-2,2-dimethyl-propionic acid (Compound 2-12); 3-[3-ethyl-1-[4-(6-methoxy-pyridazin-3-yl)-benzyl]-5-(pyridin-2-ylmethoxy)-1H-indol-2-yl]-2,2-dimethyl-propionic acid (Compound 2-13); 3-[3-(3,3-dimethyl-butyl)-5-(pyridin-2-ylmethoxy)-1-(4-thiazol-2-yl-benzyl)-1H-indol-2-yl]-2,2-dimethyl-propionic acid (Compound 2-14); 3-[3-cyclopropanecarbonyl-5-(pyridin-2-ylmethoxy)-1-(4-thiazol-2-yl-benzyl)-1H-indol-2-yl]-2,2-dimethyl-propionic acid (Compound 2-15); 3-[3-cyclobutanecarbonyl-5-(pyridin-2-ylmethoxy)-1-(4-thiazol-2-yl-benzyl)-1H-indol-2-yl]-2,2-dimethyl-propionic acid (Compound 2-16); 3-[3-tert-butylsulfanyl-1-[4-(6-hydroxy-pyridazin-3-yl)-benzyl]-5-(pyridin-2-ylmethoxy)-1H-indol-2-yl]-2,2-dimethyl-propionic acid (Compound 2-17); 3-[3-tert-butylsulfanyl-1-(4-pyridin-4-yl-benzyl)-5-(pyridin-2-ylmethoxy)-1H-indol-2-yl]-2,2-dimethyl-propionic acid (Compound 2-18); 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid (Compound 2-19); 3-[3-tert-butylsulfanyl-1-[4-(6-methyl-pyridazin-3-yl)-benzyl]-5-(pyridin-2-ylmethoxy)-1H-indol-2-yl]-2,2-dimethyl-propionic acid (Compound 2-20); 3-[3-tert-butylsulfanyl-1-[4-(5-methyl-thiazol-2-yl)-benzyl]-5-(pyridin-2-ylmethoxy)-1H-indol-2-yl]-2,2-dimethyl-propionic acid (Compound 2-21); 3-[3-cyclobutylmethyl-5-(pyridin-2-ylmethoxy)-1-(4-thiazol-2-yl-benzyl)-1H-indol-2-yl]-2,2-dimethyl-propionic acid (Compound 2-22); 3-[3-tert-butylsulfanyl-1-[4-(6-methoxy-pyridazin-3-yl)-benzyl]-5-(2-methyl-thiazol-4-ylmethoxy)-1H-indol-2-yl]-2,2-dimethyl-propionic acid (Compound 2-23); 3-[3-tert-butylsulfanyl-5-(2-methyl-thiazol-4-ylmethoxy)-1-(4-thiazol-2-yl-benzyl)-1H-indol-2-yl]-2,2-dimethyl-propionic acid (Compound 2-24); 2,2-dimethyl-3-[5-(2-methyl-thiazol-4-ylmethoxy)-1-(4-thiazol-2-yl-benzyl)-1H-indol-2-yl]-propionic acid (Compound 2-25); 3-[3-(3,3-dimethyl-butyryl)-5-(2-methyl-thiazol-4-ylmethoxy)-1-(4-thiazol-2-yl-benzyl)-1H-indol-2-yl]-2,2-dimethyl-propionic acid (Compound 2-26); 3-[1-[4-(6-methoxy-pyridazin-3-yl)-benzyl]-5-(2-methyl-thiazol-4-ylmethoxy)-1H-indol-2-yl]-2,2-dimethyl-propionic acid (Compound 2-27); 3-[3-(3,3-dimethyl-butyryl)-1-[4-(6-methoxy-pyridazin-3-yl)-benzyl]-5-(2-methyl-thiazol-4-ylmethoxy)-1H-indol-2-yl]-2,2-dimethyl-propionic acid (Compound 2-28); 3-[3-ethyl-5-(pyridin-2-ylmethoxy)-1-(4-thiazol-2-yl-benzyl)-1H-indol-2-yl]-2,2-dimethyl-propionic acid (Compound 2-29); 3-{5-(benzothiazol-2-ylmethoxy)-3-tert-butylsulfanyl-1-[4-(6-methoxy-pyridazin-3-yl)-benzyl]-1H-indol-2-yl}-2,2-dimethyl-propionic acid (Compound 2-30); 3-[3-tert-butylsulfanyl-5-(2-methyl-thiazol-4-yl-methoxy)-1-(4-pyrimidin-2-yl-benzyl)-1H-indol-2-yl]-2,2-dimethyl-propionic acid (Compound 2-31); 3-[5-(benzothiazol-2-ylmethoxy)-3-tert-butylsulfanyl-1-(4-pyrimidin-2-yl-benzyl)-1H-indol-2-yl]-2,2-dimethyl-propionic acid (Compound 2-32); 3-[3-tert-butylsulfanyl-1-[4-(2-methyl-3-pyridin-2-ylmethyl-3H-imidazol-4-yl)-benzyl]-5-(pyridin-2-ylmethoxy)-1H-indol-2-yl]-2,2-dimethyl-propionic acid (Compound 2-33); 3-[3-tert-butylsulfanyl-1-[4-(2,4-dimethyl-thiazol-5-yl)-benzyl]-5-(pyridin-2-ylmethoxy)-1H-indol-2-yl]-2,2-dimethyl-propionic acid (Compound 2-34); 3-[3-tert-butylsulfanyl-1-[4-(5-fluoro-thiazol-2-yl)-benzyl]-5-(pyridin-2-ylmethoxy)-1H-indol-2-yl]-2,2-dimethyl-propionic acid (Compound 2-35); 3-[3-tert-butylsulfanyl-1-[4-(4-methyl-thiazol-2-yl)-benzyl]-5-(pyridin-2-ylmethoxy)-1H-indol-2-yl]-2,2-dimethyl-propionic acid (Compound 2-39); 3-[3-tert-butylsulfanyl-1-[4-(3,5-dimethyl-isoxazol-4-yl)-benzyl]-5-(pyridin-2-ylmethoxy)-1H-indol-2-yl]-2,2-dimethyl-propionic acid (Compound 2-41); 3-[3-tert-butyl-sulfanyl-1-[4-(3-methyl-3H-imidazol-4-yl)-benzyl]-5-(pyridin-2-ylmethoxy)-1H-indol-2-yl]-2,2-dimethyl-propionic acid (Compound 2-43); 3-[3-tert-butylsulfanyl-1-[4-(5-methoxy-pyridin-2-yl)-benzyl]-5-(pyridin-2-ylmethoxy)-1H-indol-2-yl]-2,2-dimethyl-propionic acid (Compound 2-47); 3-[3-tert-butylsulfanyl-5-(pyridin-2-ylmethoxy)-1-(4-[1,3,4]thiadiazol-2-yl-benzyl)-1H-indol-2-yl]-2,2-dimethyl-propionic acid (Compound 2-55); 3-[3-tert-butylsulfanyl-1-[4-(6-hydroxy-pyridin-3-yl)-benzyl]-5-(pyridin-2-ylmethoxy)-1H-indol-2-yl]-2,2-dimethyl-propionic acid (Compound 2-62); 3-[3-tert-butylsulfanyl-1-[4-(6-cyano-pyridin-3-yl)-benzyl]-5-(pyridin-2-ylmethoxy)-1H-indol-2-yl]-2,2-dimethyl-propionic acid (Compound 2-64); 3-{3-tert-butylsulfanyl-5-(pyridin-2-ylmethoxy)-1-[4-(6-trifluoromethyl-pyridin-3-yl)-benzyl]-1H-indol-2-yl}-2,2-dimethyl-propionic acid (Compound 2-65); 3-[3-tert-butylsulfanyl-1-[4-(2-methoxy-pyrimidin-5-yl)-benzyl]-5-(pyridin-2-ylmethoxy)-1H-indol-2-yl]-2,2-dimethyl-propionic acid (Compound 2-67); 3-[3-tert-butyl-sulfanyl-1-[4-(2-methoxy-thiazol-4-yl)-benzyl]-5-(pyridin-2-ylmethoxy)-1H-indol-2-yl]-2,2-dimethyl-propionic acid (Compound 2-68); 3-[3-tert-butylsulfanyl-1-[4-(6-methoxy-pyridin-3-yl)-benzyl]-5-(5-methyl-pyridin-2-ylmethoxy)-1H-indol-2-yl]-2,2-dimethyl-propionic acid (Compound 2-73); 3-{3-tert-butylsulfanyl-5-(5-ethyl-pyridin-2-yl-methoxy)-1-[4-(4-methoxy-pyridin-2-yl)-benzyl]-1H-indol-2-yl}-2,2-dimethyl-propionic acid (Compound 2-76); 3-[3-tert-butylsulfanyl-1-[4-(4-methoxy-pyridin-2-yl)-benzyl]-5-(quinolin-2-ylmethoxy)-1H-indol-2-yl]-2,2-dimethyl-propionic acid (Compound 2-77); 3-{3-tert-butylsulfanyl-5-(6-fluoro-quinolin-2-ylmethoxy)-1-[4-(4-methoxy-pyridin-2-yl)-benzyl]-1H-indol-2-yl}-2,2-dimethyl-propionic acid (Compound 2-78); 3-[3-tert-butylsulfanyl-1-[4-(3-fluoro-pyridin-2-yl)-benzyl]-5-(5-methyl-pyridin-2-ylmethoxy)-1H-indol-2-yl]-2,2-dimethyl-propionic acid (Compound 2-82); 3-{3-tert-butylsulfanyl-5-(5-ethyl-pyridin-2-yl-methoxy)-1-[4-(3-fluoro-pyridin-2-yl)-benzyl]-1H-indol-2-yl}-2,2-dimethyl-propionic acid (Compound 2-84); 3-[3-tert-butylsulfanyl-1-[4-(3-fluoro-pyridin-2-yl)-benzyl]-5-(quinolin-2-ylmethoxy)-1H-indol-2-yl]-2,2-dimethyl-propionic acid (Compound 2-85); 3-[3-tert-butylsulfanyl-1-[4-(5-carbamoyl-pyridin-2-yl)-benzyl]-5-(pyridin-2-ylmethoxy)-1H-indol-2-yl]-2,2-dimethyl-propionic acid (Compound 2-87); 3-[3-tert-butylsulfanyl-1-[4-(5-cyano-pyridin-2-yl)-benzyl]-5-(pyridin-2-ylmethoxy)-1H-indol-2-yl]-2,2-dimethyl-propionic acid (Compound 2-88); 3-[3-tert-butylsulfanyl-1-[4-(5-methoxy-thiazol-2-yl)-benzyl]-5-(pyridin-2-ylmethoxy)-1H-indol-2-yl]-2,2-dimethyl-propionic acid (Compound 2-89); 3-[3-tert-butylsulfanyl-1-[4-(6-methyl-pyridin-3-yl)-benzyl]-5-(pyridin-2-ylmethoxy)-1H-indol-2-yl]-2,2-dimethyl-propionic acid (Compound 2-90); 3-{3-tert-butylsulfanyl-5-(pyridin-2-ylmethoxy)-1-[4-(5-trifluoromethyl-pyridin-2-yl)-benzyl]-1H-indol-2-yl}-2,2-dimethyl-propionic acid (Compound 2-91); 3-[3-tert-butylsulfanyl-1-[4-(2-ethoxy-thiazol-4-yl)-benzyl]-5-(pyridin-2-ylmethoxy)-1H-indol-2-yl]-2,2-dimethyl-propionic acid (Compound 2-92); 3-[3-tert-butylsulfanyl-1-[4-(4-methyl-1H-imidazol-2-yl)-benzyl]-5-(pyridin-2-ylmethoxy)-1H-indol-2-yl]-2,2-dimethyl-propionic acid (Compound 2-93); 3-[3-tert-butylsulfanyl-1-[4-(6-ethoxy-pyridin-3-yl)-benzyl]-5-(pyridin-2-ylmethoxy)-1H-indol-2-yl]-2,2-dimethyl-propionic acid (Compound 2-94); 3-[3-tert-butylsulfanyl-1-[4-(6-methoxy-pyridin-2-yl)-benzyl]-5-(pyridin-2-ylmethoxy)-1H-indol-2-yl]-2,2-dimethyl-propionic acid (Compound 2-95); 3-[3-tert-butylsulfanyl-1-[4-(5-methoxy-pyridin-3-yl)-benzyl]-5-(pyridin-2-ylmethoxy)-1H-indol-2-yl]-2,2-dimethyl-propionic acid (Compound 2-96); 3-[3-tert-butylsulfanyl-1-[4-(6-carbamoyl-pyridin-3-yl)-benzyl]-5-(pyridin-2-ylmethoxy)-1H-indol-2-yl]-2,2-dimethyl-propionic acid (Compound 2-97); 3-[3-tert-butylsulfanyl-1-[4-(5-methyl-pyridin-2-yl)-benzyl]-5-(pyridin-2-ylmethoxy)-1H-indol-2-yl]-2,2-dimethyl-propionic acid (Compound 2-98); 3-{3-tert-butylsulfanyl-5-(6-fluoro-pyridin-2-ylmethoxy)-1-[4-(6-methoxy-pyridin-3-yl)-benzyl]-1H-indol-2-yl}-2,2-dimethyl-propionic acid (Compound 2-99); 3-[3-tert-butylsulfanyl-1-[4-(6-methoxy-pyridin-3-yl)-benzyl]-5-(6-methoxy-pyridin-2-ylmethoxy)-1H-indol-2-yl]-2,2-dimethyl-propionic acid (Compound 2-100); 3-[3-tert-butylsulfanyl-1-[4-(6-methoxy-pyridin-3-yl)-benzyl]-5-(6-methyl-pyridin-2-ylmethoxy)-1H-indol-2-yl]-2,2-dimethyl-propionic acid (Compound 2-101); 3-{3-tert-butylsulfanyl-5-(5-methyl-pyridin-2-ylmethoxy)-1-[4-(6-trifluoromethyl-pyridin-3-yl)-benzyl]-1H-indol-2-yl}-2,2-dimethyl-propionic acid (Compound 2-102); 3-{3-tert-butylsulfanyl-5-(5-methyl-pyridin-2-ylmethoxy)-1-[4-(5-trifluoromethyl-pyridin-2-yl)-benzyl]-1H-indol-2-yl}-2,2-dimethyl-propionic acid (Compound 2-103); 3-{3-tert-butylsulfanyl-5-(6-cyclopropyl-pyridin-2-ylmethoxy)-1-[4-(6-methoxy-pyridin-3-yl)-benzyl]-1H-indol-2-yl}-2,2-dimethyl-propionic acid (Compound 2-104); 3-[3-tert-butylsulfanyl-1-[4-(5-methyl-pyridin-2-yl)-benzyl]-5-(5-methyl-pyridin-2-ylmethoxy)-1H-indol-2-yl]-2,2-dimethyl-propionic acid (Compound 2-105); 3-[3-tert-butylsulfanyl-1-[4-(6-methoxy-pyridazin-3-yl)-benzyl]-5-(5-methyl-pyridin-2-ylmethoxy)-1H-indol-2-yl]-2,2-dimethyl-propionic acid (Compound 2-106); 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid (Compound 2-107); 3-{3-tert-butylsulfanyl-5-(5-chloro-pyridin-2-ylmethoxy)-1-[4-(6-methoxy-pyridin-3-yl)-benzyl]-1H-indol-2-yl}-2,2-dimethyl-propionic acid (Compound 2-108); 3-{3-tert-butylsulfanyl-5-((S)-1-pyridin-2-yl-ethoxy)-1-[4-(5-trifluoromethyl-pyridin-2-yl)-benzyl]-1H-indol-2-yl}-2,2-dimethyl-propionic acid (Compound 2-109); 3-{3-tert-butylsulfanyl-5-((R)-1-pyridin-2-yl-ethoxy)-1-[4-(5-trifluoromethyl-pyridin-2-yl)-benzyl]-1H-indol-2-yl}-2,2-dimethyl-propionic acid (Compound 2-110); 3-[3-tert-butylsulfanyl-1-[4-(6-methoxy-pyridin-3-yl)-benzyl]-5-((S)-1-pyridin-2-yl-ethoxy)-1H-indol-2-yl]-2,2-dimethyl-propionic acid (Compound 2-111); 3-[3-tert-butylsulfanyl-1-

[4-(6-methoxy-pyridin-3-yl)-benzyl]-5-((R)-1-pyridin-2-yl-ethoxy)-1H-indol-2-yl]-2,2-dimethyl-propionic acid (Compound 2-112); 3-[3-tert-butylsulfanyl-1-[4-(6-methoxy-pyridin-2-yl)-benzyl]-5-((S)-1-pyridin-2-yl-ethoxy)-1H-indol-2-yl]-2,2-dimethyl-propionic acid (Compound 2-113); 3-[3-tert-butylsulfanyl-1-[4-(6-methoxy-pyridin-2-yl)-benzyl]-5-((R)-1-pyridin-2-yl-ethoxy)-1H-indol-2-yl]-2,2-dimethyl-propionic acid (Compound 2-114); 3-[3-tert-butylsulfanyl-1-[4-(2-ethoxy-thiazol-4-yl)-benzyl]-5-((S)-1-pyridin-2-yl-ethoxy)-1H-indol-2-yl]-2,2-dimethyl-propionic acid (Compound 2-115); 3-[3-tert-butylsulfanyl-1-[4-(2-ethoxy-thiazol-4-yl)-benzyl]-5-((R)-1-pyridin-2-yl-ethoxy)-1H-indol-2-yl]-2,2-dimethyl-propionic acid (Compound 2-116); 3-[3-tert-butylsulfanyl-1-[4-(6-methoxy-pyridin-3-yl)-benzyl]-5-(3-methyl-pyridin-2-ylmethoxy)-1H-indol-2-yl]-2,2-dimethyl-propionic acid (Compound 2-117); 3-{3-tert-butylsulfanyl-5-(3-methyl-pyridin-2-ylmethoxy)-1-[4-(5-trifluoromethyl-pyridin-2-yl)-benzyl]-1H-indol-2-yl}-2,2-dimethyl-propionic acid (Compound 2-118); 3-{3-tert-butylsulfanyl-5-(3,5-dimethyl-pyridin-2-ylmethoxy)-1-[4-(6-methoxy-pyridin-3-yl)-benzyl]-1H-indol-2-yl}-2,2-dimethyl-propionic acid (Compound 2-119); 3-{3-tert-butylsulfanyl-5-(3,5-dimethyl-pyridin-2-ylmethoxy)-1-[4-(5-trifluoromethyl-pyridin-2-yl)-benzyl]-1H-indol-2-yl}-2,2-dimethyl-propionic acid (Compound 2-120); 3-{5-(benzothiazol-2-ylmethoxy)-3-tert-butylsulfanyl-1-[4-(6-methoxy-pyridin-3-yl)-benzyl]-1H-indol-2-yl}-2,2-dimethyl-propionic acid (Compound 2-121); 3-{5-(benzothiazol-2-ylmethoxy)-3-tert-butylsulfanyl-1-[4-(5-methoxy-pyridin-2-yl)-benzyl]-1H-indol-2-yl}-2,2-dimethyl-propionic acid (Compound 2-122); 3-{5-(benzothiazol-2-ylmethoxy)-3-cyclobutanecarbonyl-1-[4-(6-methoxy-pyridin-3-yl)-benzyl]-1H-indol-2-yl}-2,2-dimethyl-propionic acid (Compound 2-123); 3-{5-(benzothiazol-2-ylmethoxy)-3-cyclobutylmethyl-1-[4-(6-methoxy-pyridin-3-yl)-benzyl]-1H-indol-2-yl}-2,2-dimethyl-propionic acid (Compound 2-124); 3-{3-tert-butylsulfanyl-5-(5-ethyl-pyridin-2-ylmethoxy)-1-[4-(6-methoxy-pyridin-3-yl)-benzyl]-1H-indol-2-yl}-2,2-dimethyl-propionic acid (Compound 2-125); 3-[3-tert-butylsulfanyl-1-[4-(6-ethoxy-pyridin-3-yl)-benzyl]-5-(5-ethyl-pyridin-2-ylmethoxy)-1H-indol-2-yl]-2,2-dimethyl-propionic acid (Compound 2-126); 3-{3-tert-butylsulfanyl-5-(5-ethyl-pyridin-2-ylmethoxy)-1-[4-(6-trifluoromethyl-pyridin-3-yl)-benzyl]-1H-indol-2-yl}-2,2-dimethyl-propionic acid (Compound 2-127); 3-{3-tert-butylsulfanyl-5-(5-ethyl-pyridin-2-ylmethoxy)-1-[4-(5-trifluoromethyl-pyridin-2-yl)-benzyl]-1H-indol-2-yl}-2,2-dimethyl-propionic acid (Compound 2-128); 3-[3-tert-butylsulfanyl-1-[4-(2-ethoxy-thiazol-4-yl)-benzyl]-5-(5-methyl-pyridin-2-ylmethoxy)-1H-indol-2-yl]-2,2-dimethyl-propionic acid (Compound 2-129); 3-[3-tert-butylsulfanyl-1-[4-(2-methoxy-thiazol-4-yl)-benzyl]-5-(5-methyl-pyridin-2-ylmethoxy)-1H-indol-2-yl]-2,2-dimethyl-propionic acid (Compound 2-130); 3-[3-tert-butylsulfanyl-1-[4-(6-methoxy-pyridin-2-yl)-benzyl]-5-(5-methyl-pyridin-2-ylmethoxy)-1H-indol-2-yl]-2,2-dimethyl-propionic acid (Compound 2-131); 3-[3-cyclobutylmethyl-1-[4-(6-methoxy-pyridin-3-yl)-benzyl]-5-(pyridin-2-ylmethoxy)-1H-indol-2-yl]-2,2-dimethyl-propionic acid (Compound 2-132); 3-[3-cyclobutylmethyl-1-[4-(6-methoxy-pyridin-3-yl)-benzyl]-5-(5-methyl-pyridin-2-ylmethoxy)-1H-indol-2-yl]-2,2-dimethyl-propionic acid (Compound 2-133); 3-[3-isobutyl-1-[4-(6-methoxy-pyridin-3-yl)-benzyl]-5-(5-methyl-pyridin-2-ylmethoxy)-1H-indol-2-yl]-2,2-dimethyl-propionic acid (Compound 2-134); 3-[3-tert-butylsulfanyl-1-[4-(6-methoxy-pyridin-3-yl)-benzyl]-5-(quinolin-2-ylmethoxy)-1H-indol-2-yl]-2,2-dimethyl-propionic acid (Compound 2-135); 3-{3-tert-butylsulfanyl-5-(quinolin-2-ylmethoxy)-1-[4-(6-trifluoromethyl-pyridin-3-yl)-benzyl]-1H-indol-2-yl}-2,2-dimethyl-propionic acid (Compound 2-136); 3-{3-tert-butylsulfanyl-5-(quinolin-2-ylmethoxy)-1-[4-(5-trifluoromethyl-pyridin-2-yl)-benzyl]-1H-indol-2-yl}-2,2-dimethyl-propionic acid (Compound 2-137); 3-[3-tert-butylsulfanyl-1-[4-(6-methoxy-pyridazin-3-yl)-benzyl]-5-(quinolin-2-ylmethoxy)-1H-indol-2-yl]-2,2-dimethyl-propionic acid (Compound 2-138); 3-[3-tert-butylsulfanyl-1-[4-(6-ethoxy-pyridin-3-yl)-benzyl]-5-(quinolin-2-ylmethoxy)-1H-indol-2-yl]-2,2-dimethyl-propionic acid (Compound 2-139); 3-{3-tert-butylsulfanyl-5-(6-fluoro-quinolin-2-ylmethoxy)-1-[4-(6-methoxy-pyridin-2-yl)-benzyl]-1H-indol-2-yl}-2,2-dimethyl-propionic acid (Compound 2-140); 3-{3-tert-butylsulfanyl-5-(6-fluoro-quinolin-2-ylmethoxy)-1-[4-(6-methoxy-pyridin-3-yl)-benzyl]-1H-indol-2-yl}-2,2-dimethyl-propionic acid (Compound 2-141); 3-[3-tert-butylsulfanyl-1-[4-(2-ethoxy-thiazol-4-yl)-benzyl]-5-(6-fluoro-quinolin-2-ylmethoxy)-1H-indol-2-yl]-2,2-dimethyl-propionic acid (Compound 2-142); 3-{3-tert-butylsulfanyl-5-(6-fluoro-quinolin-2-ylmethoxy)-1-[4-(5-trifluoromethyl-pyridin-2-yl)-benzyl]-1H-indol-2-yl}-2,2-dimethyl-propionic acid (Compound 2-143); 3-{3-tert-butylsulfanyl-5-(7-fluoro-quinolin-2-ylmethoxy)-1-[4-(6-trifluoromethyl-pyridin-3-yl)-benzyl]-1H-indol-2-yl}-2,2-dimethyl-propionic acid (Compound 2-144); 3-{3-tert-butylsulfanyl-5-(7-fluoro-quinolin-2-ylmethoxy)-1-[4-(5-trifluoromethyl-pyridin-2-yl)-benzyl]-1H-indol-2-yl}-2,2-dimethyl-propionic acid (Compound 2-145); 3-{3-tert-butylsulfanyl-5-(7-fluoro-quinolin-2-ylmethoxy)-1-[4-(6-methoxy-pyridin-3-yl)-benzyl]-1H-indol-2-yl}-2,2-dimethyl-propionic acid (Compound 2-146); 3-[3-tert-butylsulfanyl-1-[4-(6-ethoxy-pyridin-3-yl)-benzyl]-5-(7-fluoro-quinolin-2-ylmethoxy)-1H-indol-2-yl]-2,2-dimethyl-propionic acid (Compound 2-147); 3-[3-tert-butylsulfanyl-1-[4-(3-fluoro-pyridin-2-yl)-benzyl]-5-(6-fluoro-quinolin-2-ylmethoxy)-1H-indol-2-yl]-2,2-dimethyl-propionic acid (Compound 2-148); 3-{3-tert-butylsulfanyl-5-(5-methyl-pyridin-2-ylmethoxy)-1-[4-(3-trifluoromethyl-pyridin-2-yl)-benzyl]-1H-indol-2-yl}-2,2-dimethyl-propionic acid (Compound 2-149); 3-{3-tert-butylsulfanyl-5-(5-ethyl-pyridin-2-ylmethoxy)-1-[4-(3-trifluoromethyl-pyridin-2-yl)-benzyl]-1H-indol-2-yl}-2,2-dimethyl-propionic acid (Compound 2-150); 3-{3-tert-butylsulfanyl-5-(quinolin-2-ylmethoxy)-1-[4-(3-trifluoromethyl-pyridin-2-yl)-benzyl]-1H-indol-2-yl}-2,2-dimethyl-propionic acid (Compound 2-151); 3-{3-tert-butylsulfanyl-5-(6-fluoro-quinolin-2-ylmethoxy)-1-[4-(3-trifluoromethyl-pyridin-2-yl)-benzyl]-1H-indol-2-yl}-2,2-dimethyl-propionic acid (Compound 2-156); 3-[3-tert-butylsulfanyl-1-[4-(6-ethoxy-pyridin-3-yl)-benzyl]-5-(3-methyl-pyridin-2-ylmethoxy)-1H-indol-2-yl]-2,2-dimethyl-propionic acid (Compound 2-157); 3-{3-tert-butylsulfanyl-5-(3-methyl-pyridin-2-ylmethoxy)-1-[4-(6-trifluoromethyl-pyridin-3-yl)-benzyl]-1H-indol-2-yl}-2,2-dimethyl-propionic acid (Compound 2-158); 3-{3-tert-butylsulfanyl-5-(3,5-dimethyl-pyridin-2-ylmethoxy)-1-[4-(6-ethoxy-pyridin-3-yl)-benzyl]-1H-indol-2-yl}-2,2-dimethyl-propionic acid (Compound 2-159); 3-[3-tert-butylsulfanyl-1-[4-(6-methoxy-pyridin-3-yl)-benzyl]-5-(4-methyl-pyridin-2-ylmethoxy)-1H-indol-2-yl]-2,2-dimethyl-propionic acid (Compound 2-160); 3-[3-tert-butylsulfanyl-1-[4-(6-ethoxy-pyridin-3-yl)-benzyl]-5-(4-methyl-pyridin-2-ylmethoxy)-1H-indol-2-yl]-2,2-dimethyl-propionic acid (Compound 2-161); 3-{3-tert-butylsulfanyl-5-(4-methyl-pyridin-2-ylmethoxy)-1-[4-(5-trifluoromethyl-pyridin-2-yl)-benzyl]-1H-indol-2-yl}-2,2-dimethyl-propionic acid (Compound 2-162); 3-{3-cyclobutylmethyl-5-(5-methyl-pyridin-2-yl-methoxy)-1-[4-(5-trifluoromethyl-pyridin-2-yl)-benzyl]-1H-indol-2-yl}-2,2-dimethyl-propionic acid (Compound 2-163); 3-[3-tert-butylsulfanyl-1-[4-(6-ethoxy-pyridin-2-yl)-benzyl]-5-(6-fluoro-quinolin-2-ylmethoxy)-1H-indol-2-yl]-2,2-dimethyl-propionic acid (Compound 2-164); 3-{3-tert-butylsulfanyl-5-(6-fluoro-quinolin-2-ylmethoxy)-1-[4-(6-trifluoromethyl-pyridin-3-yl)-benzyl]-1H-indol-2-yl}-2,2-dimethyl-propionic acid (Compound 2-165); 3-[3-tert-butylsulfanyl-1-[4-(6-methoxy-pyridin-3-yl)-benzyl]-5-(6-methyl-quinolin-2-ylmethoxy)-1H-indol-2-yl]-2,2-dimethyl-propionic acid (Compound 2-166); 3-{3-tert-butylsulfanyl-5-(6-methyl-quinolin-2-ylmethoxy)-1-[4-(5-trifluoromethyl-pyridin-2-yl)-benzyl]-1H-indol-2-yl}-2,2-dimethyl-propionic acid (Compound 2-167); 3-[3-tert-butylsulfanyl-1-[4-(6-methyl-pyridazin-3-yl)-benzyl]-5-(quinolin-2-ylmethoxy)-1H-indol-2-yl]-2,2-dimethyl-propionic acid (Compound 2-168); 3-[3-tert-butylsulfanyl-1-[4-(6-ethoxy-pyridazin-3-yl)-benzyl]-5-(quinolin-2-ylmethoxy)-1H-indol-2-yl]-2,2-dimethyl-propionic acid (Compound 2-169); 3-[3-isobutyl-1-[4-(6-methoxy-pyridin-3-yl)-benzyl]-5-(quinolin-2-ylmethoxy)-1H-indol-2-yl]-2,2-dimethyl-propionic acid (Compound 2-170); 3-{3-tert-butylsulfanyl-5-(6-fluoro-quinolin-2-ylmethoxy)-1-[4-(6-methoxy-pyridazin-3-yl)-benzyl]-1H-indol-2-yl}-2,2-dimethyl-propionic acid (Compound 2-171); 3-[1-[4-(6-methoxy-pyridin-3-yl)-benzyl]-3-(2-methyl-propane-2-sulfonyl)-5-(pyridin-2-ylmethoxy)-1H-indol-2-yl]-2,2-dimethyl-propionic acid (Compound 2-172); 3-[1-[4-(6-methoxy-pyridin-3-yl)-benzyl]-3-(2-methyl-propane-2-sulfinyl)-5-(pyridin-2-ylmethoxy)-1H-indol-2-yl]-2,2-dimethyl-propionic acid (Compound 2-173); 3-[3-tert-butylsulfanyl-1-[4-(6-methoxy-pyridin-3-yl)-benzyl]-5-(1-oxy-pyridin-2-ylmethoxy)-1H-indol-2-yl]-2,2-dimethyl-propionic acid (Compound 2-174); 3-{3-tert-butylsulfanyl-5-(imidazo[1,2-c]pyridin-2-ylmethoxy)-1-[4-(6-methoxy-pyridin-3-yl)-benzyl]-1H-indol-2-yl}-2,2-dimethyl-propionic acid (Compound 2-175); 3-[3-tert-butylsulfanyl-1-[4-(6-ethoxy-pyridin-3-yl)-benzyl]-5-(imidazo[1,2-c]pyridin-2-ylmethoxy)-1H-indol-2-yl]-2,2-dimethyl-propionic acid (Compound 2-176); 3-{3-tert-butylsulfanyl-5-(imidazo[1,2-c]pyridin-2-ylmethoxy)-1-[4-(5-trifluoromethyl-pyridin-2-yl)-benzyl]-1H-indol-2-yl}-2,2-dimethyl-propionic acid (Compound 2-177); 3-[3-tert-butylsulfanyl-1-[4-(6-ethoxy-pyridin-3-yl)-benzyl]-5-((R)-1-pyridin-2-yl-ethoxy)-1H-indol-2-yl]-2,2-dimethyl-propionic acid (Compound 2-178); 3-{3-tert-butylsulfanyl-5-(6-fluoro-quinolin-2-ylmethoxy)-1-[4-(6-methyl-pyridazin-3-yl)-benzyl]-1H-indol-2-yl}-2,2-dimethyl-propionic acid (Compound 2-179); 3-[3-tert-butylsulfanyl-1-[4-(6-methoxy-pyridin-3-yl)-benzyl]-5-(5-methyl-isoxazol-3-ylmethoxy)-1H-indol-2-yl]-2,2-dimethyl-propionic acid (Compound 2-180); 3-[3-tert-butylsulfanyl-1-[4-(6-ethoxy-pyridin-3-yl)-benzyl]-5-(5-methyl-isoxazol-3-ylmethoxy)-1H-indol-2-yl]-2,2-dimethyl-propionic acid (Compound 2-181); 3-{3-tert-butylsulfanyl-5-(5-methyl-isoxazol-3-ylmethoxy)-1-[4-(5-trifluoromethyl-pyridin-2-yl)-benzyl]-1H-indol-2-yl}-2,2-dimethyl-propionic acid (Compound 2-182); 3-{3-tert-Butylsulfanyl-5-(2,5-dimethyl-2H-pyrazol-3-ylmethoxy)-1-[4-(6-methoxy-pyridin-3-yl)-benzyl]-1H-indol-2-yl}-2,2-dimethyl-propionic acid (Compound 2-183); 3-{3-tert-butylsulfanyl-5-(1,5-dimethyl-1H-pyrazol-3-ylmethoxy)-1-[4-(6-methoxy-pyridin-3-yl)-benzyl]-1H-indol-2-yl}-2,2-dimethyl-propionic acid (Compound 2-184); 3-[3-tert-butylsulfanyl-1-[4-(6-ethoxy-pyridazin-3-yl)-benzyl]-5-(6-fluoro-quinolin-2-ylmethoxy)-1H-indol-2-yl]-2,2-dimethyl-propionic acid (Compound 2-185); 3-[3-tert-butylsulfanyl-1-[4-(6-ethoxy-pyridazin-3-yl)-benzyl]-5-(5-ethyl-pyridin-2-ylmethoxy)-1H-indol-2-yl]-2,2-dimethyl-propionic acid (Compound 2-186); 3-{3-tert-butylsulfanyl-5-(5-ethyl-pyridin-2-ylmethoxy)-1-[4-(6-methoxy-pyridazin-3-yl)-benzyl]-1H-indol-2-yl}-2,2-dimethyl-propionic acid (Compound 2-187); 3-[3-tert-butylsulfanyl-1-[4-(5-fluoro-pyridin-2-yl)-benzyl]-5-(6-fluoro-quinolin-2-ylmethoxy)-1H-indol-2-yl]-2,2-dimethyl-propionic acid (Compound 2-188); 3-[3-tert-butylsulfanyl-1-[4-(5-fluoro-pyridin-2-yl)-benzyl]-5-((R)-1-pyridin-2-yl-ethoxy)-1H-indol-2-yl]-2,2-dimethyl-propionic acid (Compound 2-189); 3-[3-tert-butylsulfanyl-1-[4-(6-ethoxy-pyridin-2-yl)-benzyl]-5-(6-fluoro-quinolin-2-ylmethoxy)-1H-indol-2-yl]-2,2-dimethyl-propionic acid (Compound 2-190); 3-[3-tert-butyl-sulfanyl-1-[4-(6-ethoxy-pyridin-2-yl)-benzyl]-5-((R)-1-pyridin-2-yl-ethoxy)-1H-indol-2-yl]-2,2-dimethyl-propionic acid (Compound 2-191); 3-[3-tert-butylsulfanyl-1-[4-(5-fluoro-pyridin-2-yl)-benzyl]-5-(5-methyl-pyridin-2-ylmethoxy)-1H-indol-2-yl]-2,2-dimethyl-propionic acid (Compound 2-192); 3-[3-tert-butysulfanyl-1-[4-(6-ethoxy-pyridin-2-yl)-benzyl]-5-(5-methyl-pyridin-2-ylmethoxy)-1H-indol-2-yl]-2,2-dimethyl-propionic acid (Compound 2-193); 3-{5-(6-fluoro-quinolin-2-ylmethoxy)-3-isobutyl-1-[4-(6-trifluoromethyl-pyridin-3-yl)-benzyl]-1H-indol-2-yl}-2,2-dimethyl-propionic acid (Compound 2-194); 3-{3-tert-butylsulfanyl-5-(pyridin-2-ylmethoxy)-1-[3-(5-trifluoromethyl-pyridin-2-yl)-benzyl]-1H-indol-2-yl}-2,2-dimethyl-propionic acid (Compound 2-195); 3-[3-tert-butylsulfanyl-1-[3-(6-methoxy-pyridin-3-yl)-benzyl]-5-(pyridin-2-ylmethoxy)-1H-indol-2-yl]-2,2-dimethyl-propionic acid (Compound 2-196); 3-[3-tert-butylsulfanyl-1-[4-(5-fluoro-pyridin-2-yl)-benzyl]-5-(quinolin-2-ylmethoxy)-1H-indol-2-yl]-2,2-dimethyl-propionic acid (Compound 2-197); 3-[3-tert-butylsulfanyl-1-[4-(6-ethoxy-pyridin-2-yl)-benzyl]-5-(quinolin-2-ylmethoxy)-1H-indol-2-yl]-2,2-dimethyl-propionic acid (Compound 2-198); 3-[3-tert-butylsulfanyl-1-[4-(6-ethoxy-pyridin-2-yl)-benzyl]-5-(pyridin-2-ylmethoxy)-1H-indol-2-yl]-2,2-dimethyl-propionic acid (Compound 2-199); 3-{3-tert-butylsulfanyl-5-(6-fluoro-quinolin-2-ylmethoxy)-1-[4-(6-trifluoromethyl-pyridin-2-yl)-benzyl]-1H-indol-2-yl}-2,2-dimethyl-propionic acid (Compound 2-200); 3-[3-tert-butylsulfanyl-1-[4-(5-fluoro-pyridin-2-yl)-benzyl]-5-(pyridin-2-ylmethoxy)-1H-indol-2-yl]-2,2-dimethyl-propionic acid (Compound 2-201); 3-{3-tert-butylsulfanyl-5-(5-methyl-pyridin-2-ylmethoxy)-1-[4-(6-trifluoromethyl-pyridin-2-yl)-benzyl]-1H-indol-2-yl}-2,2-dimethyl-propionic acid (Compound 2-202); 3-{3-tert-butylsulfanyl-5-(quinolin-2-ylmethoxy)-1-[4-(6-trifluoromethyl-pyridin-2-yl)-benzyl]-1H-indol-2-yl}-2,2-dimethyl-propionic acid (Compound 2-203); 3-{3-tert-butylsulfanyl-5-(pyridin-2-ylmethoxy)-1-[4-(6-trifluoromethyl-pyridin-2-yl)-benzyl]-1H-indol-2-yl}-2,2-dimethyl-propionic acid (Compound 2-204); 3-[3-tert-butylsulfanyl-5-(quinolin-2-ylmethoxy)-1-(4-thiazol-2-yl-benzyl)-1H-indol-2-yl]-2,2-dimethyl-propionic acid (Compound 2-205); 3-[3-tert-butylsulfanyl-1-[3-(4-methoxy-tetrahydro-pyran-4-yl)-benzyl]-5-(pyridin-2-ylmethoxy)-1H-indol-2-yl]-2,2-dimethyl-propionic acid (Compound 2-206); 3-[3-tert-butylsulfanyl-5-(6-fluoro-quinolin-2-ylmethoxy)-1-(4-pyridin-2-yl-benzyl)-1H-indol-2-yl]-2,2-dimethyl-propionic acid (Compound 2-207); 3-[3-tert-butylsulfanyl-5-(5-ethyl-pyridin-2-ylmethoxy)-1-(4-pyridin-3-yl-benzyl)-1H-indol-2-yl]-2,2-dimethyl-propionic acid (Compound 2-208); 3-[3-tert-butylsulfanyl-1-(4-pyridin-3-yl-benzyl)-5-(quinolin-2-ylmethoxy)-1H-indol-2-yl]-2,2-dimethyl-propionic acid (Compound 2-209); 3-[3-tert-butylsulfanyl-5-(6-fluoro-quinolin-2-ylmethoxy)-

1-(4-pyridin-3-yl-benzyl)-1H-indol-2-yl]-2,2-dimethyl-propionic acid (Compound 2-210); 3-[3-tert-butylsulfanyl-5-(5-methyl-pyridin-2-ylmethoxy)-1-(4-pyridin-2-yl-benzyl)-1H-indol-2-yl]-2,2-dimethyl-propionic acid (Compound 2-211); 3-[3-tert-butylsulfanyl-5-(5-ethyl-pyridin-2-ylmethoxy)-1-(4-pyridin-2-yl-benzyl)-1H-indol-2-yl]-2,2-dimethyl-propionic acid (Compound 2-212); 3-[3-tert-butylsulfanyl-1-(4-pyridin-2-yl-benzyl)-5-(quinolin-2-ylmethoxy)-1H-indol-2-yl]-2,2-dimethyl-propionic acid (Compound 2-213); 3-[3-tert-butylsulfanyl-5-(5-methyl-pyridin-2-ylmethoxy)-1-(4-pyridin-3-yl-benzyl)-1H-indol-2-yl]-2,2-dimethyl-propionic acid (Compound 2-214); 3-[3-tert-butylsulfanyl-1-[4-(4-methoxy-pyridin-2-yl)-benzyl]-5-(5-methyl-pyridin-2-ylmethoxy)-1H-indol-2-yl]-2,2-dimethyl-propionic acid (Compound 2-215); 3-[3-tert-butylsulfanyl-5-(quinolin-2-ylmethoxy)-1-(4-(3-methyoxypyridin-2-yl)-benzyl)-1H-indol-2-yl]-2,2-dimethyl-propionic acid (Compound 2-216); 3-[3-tert-butylsulfanyl-5-(5-methyl-pyridin-2-ylmethoxy)-1-(4-(3-methyoxypyridin-2-yl)-benzyl)-1H-indol-2-yl]-2,2-dimethyl-propionic acid (Compound 2-217); 3-[3-tert-butylsulfanyl-5-(5-ethyl-pyridin-2-ylmethoxy)-1-(4-(3-methyoxypyridin-2-yl)-benzyl)-1H-indol-2-yl]-2,2-dimethyl-propionic acid (Compound 2-218); 3-[3-tert-butylsulfanyl-5-(5-methyl-pyridin-2-ylmethoxy)-1-(4-(4-trifluoromethypyridin-2-yl)-benzyl)-1H-indol-2-yl]-2,2-dimethyl-propionic acid (Compound 2-219); 3-[3-tert-butylsulfanyl-5-(5-ethyl-pyridin-2-ylmethoxy)-1-(4-(4-trifluoromethypyridin-2-yl)-benzyl)-1H-indol-2-yl]-2,2-dimethyl-propionic acid (Compound 2-220); 3-[3-tert-butylsulfanyl-5-(quinolin-2-ylmethoxy)-1-(4-(4-trifluoromethypyridin-2-yl)-benzyl)-1H-indol-2-yl]-2,2-dimethyl-propionic acid (Compound 2-221); 3-[3-tert-butylsulfanyl-5-(5-methyl-pyridin-2-ylmethoxy)-1-(4-(5-fluoropyridin-3-yl)-benzyl)-1H-indol-2-yl]-2,2-dimethyl-propionic acid (Compound 2-222); 3-[3-tert-butylsulfanyl-5-(5-ethyl-pyridin-2-ylmethoxy)-1-(4-(5-fluoropyridin-3-yl)-benzyl)-1H-indol-2-yl]-2,2-dimethyl-propionic acid (Compound 2-223); 3-[3-tert-butylsulfanyl-5-(quinolin-2-ylmethoxy)-1-(4-(5-fluoropyridin-3-yl)-benzyl)-1H-indol-2-yl]-2,2-dimethyl-propionic acid (Compound 2-224); 3-[3-tert-butylsulfanyl-5-(2,3-dimethyl-pyridin-6-ylmethoxy)-1-(4-(2-methoxypyridin-5-yl)-benzyl)-1H-indol-2-yl]-2,2-dimethyl-propionic acid (Compound 2-225); 3-[3-tert-butylsulfanyl-5-(2,3-dimethyl-pyridin-6-ylmethoxy)-1-(4-(3-trifluoromethylpyridin-2-yl)-benzyl)-1H-indol-2-yl]-2,2-dimethyl-propionic acid (Compound 2-226); 3-[3-tert-butylsulfanyl-5-(2,3-dimethyl-pyridin-6-ylmethoxy)-1-(4-(4-trifluoromethylpyridin-2-yl)-benzyl)-1H-indol-2-yl]-2,2-dimethyl-propionic acid (Compound 2-227); 3-[3-tert-butylsulfanyl-5-(2,3-dimethyl-pyridin-6-ylmethoxy)-1-(4-(3-fluoropyridin-2-yl)-benzyl)-1H-indol-2-yl]-2,2-dimethyl-propionic acid (Compound 2-228); 3-[3-tert-butylsulfanyl-5-(2,3-dimethyl-pyridin-6-ylmethoxy)-1-(4-(5-fluoropyridin-3-yl)-benzyl)-1H-indol-2-yl]-2,2-dimethyl-propionic acid (Compound 2-229); 3-[3-tert-butylsulfanyl-5-(2,3-dimethyl-pyridin-6-ylmethoxy)-1-(4-(4-methoxypyridin-2-yl)-benzyl)-1H-indol-2-yl]-2,2-dimethyl-propionic acid (Compound 2-230); 3-[3-tert-butylsulfanyl-5-(2,3-dimethyl-pyridin-6-ylmethoxy)-1-(4-(pyridin-2-yl)-benzyl)-1H-indol-2-yl]-2,2-dimethyl-propionic acid (Compound 2-231); 3-[3-tert-butylsulfanyl-5-(5-methyl-pyridin-2-ylmethoxy)-1-(4-(2-methoxy-pyridin-3-yl)-benzyl)-1H-indol-2-yl]-2,2-dimethyl-propionic acid (Compound 2-232); 3-[3-tert-butylsulfanyl-5-(5-ethyl-pyridin-2-ylmethoxy)-1-(4-(2-methoxy-pyridin-3-yl)-benzyl)-1H-indol-2-yl]-2,2-dimethyl-propionic acid (Compound 2-233); 3-[3-tert-butylsulfanyl-5-(quinolin-2-ylmethoxy)-1-(4-(2-methoxy-pyridin-3-yl)-benzyl)-1H-indol-2-yl]-2,2-dimethyl-propionic acid (Compound 2-234); 3-[3-tert-butylsulfanyl-1-(6'-methoxy-[2,3]bipyridinyl-5-ylmethyl)-5-(pyridin-2-ylmethoxy)-1H-indol-2-yl]-2,2-dimethyl-propionic acid (Compound 3-1); 3-[3-tert-butylsulfanyl-1-[6-(4-methoxy-phenyl)-pyridin-3-ylmethyl]-5-(pyridin-2-ylmethoxy)-1H-indol-2-yl]-2,2-dimethyl-propionic acid (Compound 3-2); 3-{3-tert-butylsulfanyl-5-(pyridin-2-ylmethoxy)-1-[6-(4-trifluoromethoxy-phenyl)-pyridin-3-ylmethyl]-1H-indol-2-yl}-2,2-dimethyl-propionic acid (Compound 3-3); 3-[3-tert-butylsulfanyl-1-[5-(4-methoxy-phenyl)-pyridin-2-ylmethyl]-5-(pyridin-2-ylmethoxy)-1H-indol-2-yl]-2,2-dimethyl-propionic acid (Compound 3-4); 3-{3-tert-butylsulfanyl-5-(pyridin-2-ylmethoxy)-1-[5-(4-trifluoromethoxy-phenyl)-pyridin-2-ylmethyl]-1H-indol-2-yl}-2,2-dimethyl-propionic acid (Compound 3-5); 3-{3-tert-butylsulfanyl-5-isopropyl-1-[4-(6-methoxy-pyridin-3-yl)-benzyl]-1H-indol-2-yl}-2,2-dimethyl-propionic acid (Compound 4-1); and 3-{3-tert-butylsulfanyl-5-hydroxy-1-[4-(6-methoxy-pyridin-3-yl)-benzyl]-1H-indol-2-yl}-2,2-dimethyl-propionic acid (Compound 4-2).

In one aspect, provided herein is a pharmaceutical composition comprising an effective amount of a compound provided herein, and a pharmaceutically acceptable excipient.

In another aspect, provided herein is a method for treating inflammation in a mammal comprising administering a therapeutically effective amount of a compound provided herein to the mammal in need.

In yet another aspect, provided herein is a method for treating asthma in a mammal comprising administering a therapeutically effective amount of a compound provided herein to the mammal in need. In a further or alternative embodiment, provided herein is a method for treating asthma in a mammal comprising administering a therapeutically effective amount of a compound provided herein, such as, for example, a compound of any of Formula (G), Formula (G-I), or Formula (G-II), wherein Z is $[C(R_2)_2]_nC(R_1)_2O$, to the mammal in need.

In another aspect are compounds presented in any of FIG. 8, 9, 10, or 11, or pharmaceutically acceptable salts, pharmaceutically acceptable N-oxides, pharmaceutically active metabolites, pharmaceutically acceptable prodrugs, and pharmaceutically acceptable solvates thereof, which antagonize or inhibit FLAP and may be used to treat patients suffering from leukotriene-dependent conditions or diseases, including, but not limited to, asthma, chronic obstructive pulmonary disease, pulmonary hypertension, interstitial lung fibrosis, rhinitis, arthritis, allergy, psoriasis, inflammatory bowel disease, adult respiratory distress syndrome, myocardial infarction, aneurysm, stroke, cancer, endotoxic shock, proliferative disorders and inflammatory conditions.

In another aspect are compounds presented in any of Tables 1, 2, 3, or 4, or pharmaceutically acceptable salts, pharmaceutically acceptable N-oxides, pharmaceutically active metabolites, pharmaceutically acceptable prodrugs, and pharmaceutically acceptable solvates thereof, which antagonize or inhibit FLAP and may be used to treat patients suffering from leukotriene-dependent conditions or diseases, including, but not limited to, asthma, chronic obstructive pulmonary disease, pulmonary hypertension, interstitial lung fibrosis, rhinitis, arthritis, allergy, psoriasis, inflammatory bowel disease, adult respiratory distress syndrome, myocardial infarction, aneurysm, stroke, cancer, endotoxic shock, proliferative disorders and inflammatory conditions.

In further or alternative embodiments, the compounds of any of Formula (G), Formula (G-I), or Formula (G-II), may be inhibitors of 5-lipoxygenase-activating protein (FLAP), while in still further or alternative embodiments, such inhibitors are selective for FLAP. In even further or alternative embodiments, such inhibitors have an $IC_{50}$ below 50 microM in the FLAP binding assay.

In further or alternative embodiments, the compounds of any of Formula (G), Formula (G-I), or Formula (G-II), may be included into pharmaceutical compositions or medicaments used for treating a leukotriene-dependent or leukotriene mediated condition or disease in a patient.

In another aspect the inflammatory conditions include, but are not limited to, asthma, chronic obstructive pulmonary disease, pulmonary hypertension, interstitial lung fibrosis, rhinitis, aortic aneurysm, myocardial infarction, and stroke. In other aspects the proliferative disorders include, but are not limited to, cancer and noncancerous disorders, including, but not limited to, those involving the skin or lymphatic tissues. In other aspects the metabolic disorders include, but are not limited to, bone remodeling, loss or gain. In additional aspects, such conditions are iatrogenic and increases in, or abnormal localization of, leukotrienes may be induced by other therapies or medical or surgical procedures.

In other aspects, the methods, compounds, pharmaceutical compositions, and medicaments described herein may be used to prevent the cellular activation of 5-lipoxygenase, while in other aspects the methods, compounds, pharmaceutical compositions, and medicaments described herein may be used to limit the formation of leukotrienes. In other aspects, such methods, compounds, pharmaceutical compositions, and medicaments may comprise FLAP inhibitors disclosed herein for the treatment of asthma by (a) lowering the concentrations of leukotrienes in certain tissue(s) of the body or in the entire body of a patient, (b) modulating the activity of enzymes or proteins in a patient wherein such enzymes or proteins are involved in the leukotriene pathway such as, by way of example, 5-lipoxygenase-activating protein or 5-lipoxygenase, or (c) combining the effects of (a) and (b). In yet other aspects, the methods, compounds, pharmaceutical compositions, and medicaments described herein may be used in combination with other medical treatments or surgical modalities.

In one aspect are methods for reducing/inhibiting the leukotriene synthetic activity of 5-lipoxygenase-activating protein (FLAP) in a mammal comprising administering to the mammal at least once an effective amount of a compound having the structure of any of Formula (G), Formula (G-I), or Formula (G-II).

In a further or alternative embodiment, the "G" group (e.g. $G_1$, $G_5$, $G_6$, $G_7$) of any of Formula (G), Formula (G-I), or Formula (G-II), is any group that is used to tailor the physical and biological properties of the molecule. Such tailoring/modifications are achieved using groups which modulate acidity, basicity, lipophilicity, solubility and other physical properties of the molecule. The physical and biological properties modulated by such modifications to "G" include, by way of example only, solubility, in vivo absorption, and in vivo metabolism. In addition, in vivo metabolism may include, by way of example only, controlling in vivo PK properties, off-target activities, potential toxicities associated with cypP450 interactions, drug-drug interactions, and the like. Further, modifications to "G" allow for the tailoring of the in vivo efficacy of the compound through the modulation of, by way of example, specific and non-specific protein binding to plasma proteins and lipids and tissue distribution in vivo. Additionally, such tailoring/modifications to "G" allow for the design of compounds selective for 5-lipoxygenase-activating protein over other proteins. In further or alternative embodiments, "G" is $L_{20}$-Q, wherein $L_{20}$ is an enzymatically cleavable linker and Q is a drug, or an affinity moiety. In further or alternative embodiments, the drug includes, by way of example only, leukotriene receptor antagonists and anti-inflammatory agents. In further or alternative embodiments, the leukotriene receptor antagonists include, but are not limited to, CysLT1/CysLT2 dual antagonists and CysLT1 antagonists. In further or alternative embodiments, the affinity moiety allows for site specific binding and include, but are not limited to, antibodies, antibody fragments, DNA, RNA, siRNA, and ligands.

In another aspect are methods for modulating, including reducing and/or inhibiting the activity of 5-lipoxygenase activating protein, directly or indirectly, in a mammal comprising administering to the mammal at least once an effective amount of at least one compound having the structure of any of Formula (G), Formula (G-I), or Formula (G-II).

In another aspect are methods for modulating, including reducing and/or inhibiting, the activity of leukotrienes in a mammal, directly or indirectly, comprising administering to the mammal at least once an effective amount of at least one compound having the structure of any of Formula (G), Formula (G-I), or Formula (G-II).

In another aspect are methods for treating leukotriene-dependent or leukotriene mediated conditions or diseases, comprising administering to the mammal at least once an effective amount of at least one compound having the structure of any of Formula (G), Formula (G-I), or Formula (G-II).

In another aspect are methods for treating inflammation comprising administering to the mammal at least once an effective amount of at least one compound having the structure of any of Formula (G), Formula (G-I), or Formula (G-II).

In another aspect are methods for treating respiratory diseases comprising administering to the mammal at least once an effective amount of at least one compound having the structure of any of Formula (G), Formula (G-I), or Formula (G-II). In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, In another aspect are methods for treating chronic obstructive pulmonary disease comprising administering to the mammal at least once an effective amount of at least one compound having the structure of any of Formula (G), Formula (G-I), or Formula (G-II). In a further embodiment of this aspect, chronic obstructive pulmonary disease includes, but is not limited to, chronic bronchitis or emphysema, pulmonary hypertension, interstitial lung fibrosis and/or airway inflammation and cystic fibrosis.

In another aspect are methods for preventing increased mucosal secretion and/or edema in a disease or condition comprising administering to the mammal at least once an effective amount of at least one compound having the structure of any of Formula (G), Formula (G-I), or Formula (G-II).

In another aspect are methods for treating vasoconstriction, atherosclerosis and its sequelae myocardial ischemia, myocardial infarction, aortic aneurysm, vasculitis and stroke comprising administering to the mammal an effective amount of a compound having the structure of any of Formula (G), Formula (G-I), or Formula (G-II).

In another aspect are methods for treating organ reperfusion injury following organ ischemia and/or endotoxic shock comprising administering to the mammal at least once an effective amount of at least one compound having the structure of any of Formula (G), Formula (G-I), or Formula (G-II).

In another aspect are methods for reducing the constriction of blood vessels in a mammal comprising administering to the mammal at least once an effective amount of at least one compound having the structure of any of Formula (G), Formula (G-I), or Formula (G-II).

In another aspect are methods for lowering or preventing an increase in blood pressure of a mammal comprising administering to the mammal at least once an effective amount of at least one compound having the structure of any of Formula (G), Formula (G-I), or Formula (G-II).

In another aspect are methods for preventing eosinophil and/or basophil and/or dendritic cell and/or neutrophil and/or monocyte recruitment comprising administering to the mammal at least once an effective amount of at least one compound having the structure of any of Formula (G), Formula (G-I), or Formula (G-II).

A further aspect are methods for the prevention or treatment of abnormal bone remodeling, loss or gain, including diseases or conditions as, by way of example, osteopenia, osteoporosis, Paget's disease, cancer and other diseases comprising administering to the mammal at least once an effective amount of at least one compound having the structure of any of Formula (G), Formula (G-I), or Formula (G-II).

In another aspect are methods for preventing ocular inflammation and allergic conjunctivitis, vernal keratoconjunctivitis, and papillary conjunctivitis comprising administering to the mammal at least once an effective amount of at least one having the structure of any of Formula (G), Formula (G-I), or Formula (G-II).

In another aspect are methods for treating CNS disorders comprising administering to the mammal at least once an effective amount of at least one compound having the structure of any of Formula (G), Formula (G-I), or Formula (G-II). CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

A further aspect are methods for the treatment of cancer comprising administering to the mammal at least once an effective amount of at least one compound having the structure of any of Formula (G), Formula (G-I), or Formula (G-II). The type of cancer may include, but is not limited to, pancreatic cancer and other solid or hematological tumors.

In another aspect are methods for treating endotoxic shock and septic shock comprising administering to the mammal at least once an effective amount of at least one compound having the structure of any of Formula (G), Formula (G-I), or Formula (G-II).

In another aspect are methods for treating rheumatoid arthritis and osteoarthritis comprising administering to the mammal at least once an effective amount of at least one compound having the structure of any of Formula (G), Formula (G-I), or Formula (G-II).

In another aspect are methods for preventing increased GI diseases comprising administering to the mammal at least once an effective amount of at least one compound having the structure of any of Formula (G), Formula (G-I), or Formula (G-II). Such diseases include, by way of example only, chronic gastritis, eosinophilic gastroenteritis, and gastric motor dysfunction.

A further aspect are methods for treating kidney diseases comprising administering to the mammal at least once an effective amount of at least one compound having the structure of any of Formula (G), Formula (G-I), or Formula (G-II). Such diseases include, by way of example only, glomerulonephritis, cyclosporine nephrotoxicity renal ischemia reperfusion.

In another aspect are methods for preventing or treating acute or chronic renal insufficiency comprising administering to the mammal at least once an effective amount of at least one compound having the structure of any of Formula (G), Formula (G-I), or Formula (G-II).

In another aspect are methods for treating type II diabetes comprising administering to the mammal at least once an effective amount of at least one compound having the structure of any of Formula (G), Formula (G-I), or Formula (G-II).

In another aspect are methods to diminish the inflammatory aspects of acute infections within one or more solid organs or tissues such as the kidney with acute pyelonephritis.

In another aspect are methods for preventing or treating acute or chronic disorders involving recruitment or activation of eosinophils comprising administering to the mammal at least once an effective amount of at least one compound having the structure of any of Formula (G), Formula (G-I), or Formula (G-II).

In another aspect are methods for preventing or treating acute or chronic erosive disease or motor dysfunction of the gastrointestinal tract caused by non-steroidal anti-inflammatory drugs (including selective or non-selective cyclooxygenase-1 or -2 inhibitors) comprising administering to the mammal at least once an effective amount of at least one compound having the structure of any of Formula (G), Formula (G-I), or Formula (G-II).

A further aspect are methods for the prevention or treatment of rejection or dysfunction in a transplanted organ or tissue comprising administering to the mammal at least once an effective amount of at least one compound having the structure of any of Formula (G), Formula (G-I), or Formula (G-II).

In another aspect are methods for treating inflammatory responses of the skin comprising administering to the mammal at least once an effective amount of at least one compound having the structure of any of Formula (G), Formula (G-I), or Formula (G-II). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a first compound having the structure of any of Formula (G), Formula (G-I), or Formula (G-II).

A further aspect are methods for the treatment of cystitis, including, by way of example only, interstitial cystitis, comprising administering to the mammal at least once an effective amount of at least one compound having the structure of any of Formula (G), Formula (G-I), or Formula (G-II).

A further aspect are methods for the treatment of metabolic syndromes such as Familial Mediterranean Fever comprising administering to the mammal at least once an effective amount of at least one compound having the structure of any of Formula (G), Formula (G-I), or Formula (G-II).

In a further aspect are methods to treat hepatorenal syndrome comprising administering to the mammal at least once an effective amount of at least one compound having the structure of any of Formula (G), Formula (G-I), or Formula (G-II).

In another aspect is the use of a compound of any of Formula (G), Formula (G-I), or Formula (G-II), in the manufacture of a medicament for treating an inflammatory disease or condition in an animal in which the activity of at least one leukotriene protein contributes to the pathology and/or symptoms of the disease or condition. In one embodiment of this aspect, the leukotriene pathway protein is 5-lipoxygenase-activating protein (FLAP). In another or further embodiment of this aspect, the inflammatory disease or conditions are respiratory, cardiovascular, or proliferative diseases.

In any of the aforementioned aspects are further embodiments in which administration is enteral, parenteral, or both, and wherein (a) the effective amount of the compound is systemically administered to the mammal; and/or (b) the effective amount of the compound is administered orally to the mammal; and/or (c) the effective amount of the compound is intravenously administered to the mammal; and/or (d) the effective amount of the compound administered by inhalation; and/or (e) the effective amount of the compound is administered by nasal administration; or and/or (f) the effective amount of the compound is administered by injection to the mammal; and/or (g) the effective amount of the compound is administered topically (dermal) to the mammal; and/or (h) the effective amount of the compound is administered by ophthalmic administration; and/or (i) the effective amount of the compound is administered rectally to the mammal In any of the aforementioned aspects are further embodiments in which the mammal is a human, including embodiments wherein (a) the human has an asthmatic condition or one or more other condition(s) selected from the group consisting of allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, or seasonal asthma, or chronic obstructive pulmonary disease, or pulmonary hypertension or interstitial lung fibrosis. In any of the aforementioned aspects are further embodiments in which the mammal is an animal model for pulmonary inflammation, examples of which are provided herein.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered in a single dose; (ii) the time between multiple administrations is every 6 hours; (iii) the compound is administered to the mammal every 8 hours;. In further or alternative embodiments, the method comprises a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In any of the aforementioned aspects involving the treatment of leukotriene dependent diseases or conditions are further embodiments comprising administering at least one additional agent, each agent may be administered in any order, including, by way of example, an anti-inflammatory agent, a different compound having the structure of any of Formula (G), Formula (G-I), or Formula (G-II), a $CysLT_1$ receptor antagonist, or a $CysLT_1/CysLT_2$ dual receptor antagonist. In further or alternative embodiments, the $CysLT_1$ antagonist is selected from montelukast (Singulair™: [1-[[1-[3-[2-[(7-chloro-2-quinolyl)]vinyl]phenyl]-3-[2-(1-hydroxy-1-methyl-ethyl)phenyl]-propyl]sulfanylmethyl]cyclopropyl]acetic acid), zafirlukast (Accolate™: 3-[[2-methoxy-4-(o-tolylsulfonylcarbamoyl)phenyl]methyl]-1-methyl-1H-indol-5-yl]amino formic acid cyclopentyl ester) or pranlukast (Onon™: 4-oxo-8-[p-(4-phenylbutyloxy)benzoylamino]-2-tetrazol-5-yl)-4H-1-benzopyran)

In further or alternative embodiments, the anti-inflammatory agent includes, but is not limited to, non-steroidal anti-inflammatory drugs such as a cyclooxygenase inhibitor (COX-1 and/or COX-2), lipoxygenase inhibitors and steroids such as prednisone or dexamethasone. In further or alternative embodiments, the anti-inflammatory agent is selected from the group consisting of Arthrotec®, Asacol, Auralgan®, Azulfidine, Daypro, etodolac, Ponstan, Salofalk, Solu-Medrol, aspirin, indomethacin (Indocin™), rofecoxib (Vioxx™) celecoxib (Celebrex™), valdecoxib (Bextra™), diclofenac, etodolac, ketoprofen, Lodine, Mobic, nabumetone, naproxen, piroxicam, Celestone, prednisone, Deltasone, or any generic equivalent thereof.

In any of the aforementioned aspects involving the treatment of proliferative disorders, including cancer, are further embodiments comprising administering at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In any of the aforementioned aspects involving the therapy of transplanted organs or tissues or cells are further embodiments comprising administering at least one additional agent selected from the group consisting of azathioprine, a corticosteroid, cyclophosphamide, cyclosporin, dacluzimab, mycophenolate mofetil, OKT3, rapamycin, tacrolimus, or thymoglobulin.

In any of the aforementioned aspects involving the therapy of interstitial cystitis are further embodiments comprising administering at least one additional agent selected from dimethylsulfoxide, omalizumab, and pentosan polysulfate.

In any of the aforementioned aspects involving the therapy of disorders of bone are further embodiments comprising administering at least one additional agent selected from the group consisting of minerals, vitamins, bisphosphonates, anabolic steroids, parathyroid hormone or analogs, and cathepsin K inhibitors dronabinol.

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal; (e) measuring levels of $LTB_4$ in the calcium ionophore-challenged blood of a mammal; (f) measuring levels of $LTE_4$ in the urinary excretion of a mammal; or (g) identifying a patient by measuring leukotriene-driven inflammatory biomarkers such as $LTB_4$, $LTC_4$, Il-6, CRP, SAA, MPO, EPO, MCP-1, MIP-α, sICAMs, Il-4, Il-13.

In any of the aforementioned aspects involving the prevention or treatment of leukotriene-dependent or leukotriene mediated diseases or conditions are further embodiments comprising identifying patients by screening for a leukotriene gene haplotype. In further or alternative embodiments the leukotriene gene haplotype is a leukotriene pathway gene, while in still further or alternative embodiments, the leukotriene gene haplotype is a 5-lipoxygenase-activating protein (FLAP) haplotype.

In any of the aforementioned aspects involving the prevention or treatment of leukotriene-dependent or leukotriene mediated diseases or conditions are further embodiments comprising identifying patients by monitoring the patient for either:
  i) at least one leukotriene related inflammatory biomarker; or
  ii) at least one functional marker response to a leukotriene modifying agent; or
  iii) at least one leukotriene related inflammatory biomarker and at least one functional marker response to a leukotriene modifying agent.

In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1).

In any of the aforementioned aspects involving the prevention or treatment of leukotriene-dependent or leukotriene mediated diseases or conditions are further embodiments comprising identifying patients by either:
  i) screening the patient for at least one leukotriene gene SNP and/or haplotype including SNP's in intronic or exonic locations; or
  ii) monitoring the patient for at least one leukotriene related inflammatory biomarker; or
  ii) monitoring the patient for at least one functional marker response to a leukotriene modifying agent In further or alternative embodiments, the leukotriene gene SNP or haplotype is a leukotriene pathway gene. In still further or alternative embodiments, the leukotriene gene SNP or haplotype is a 5-lipoxygenase-activating protein (FLAP) SNP or haplotype. In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1).

In any of the aforementioned aspects involving the prevention or treatment of leukotriene-dependent or leukotriene mediated diseases or conditions are further embodiments comprising identifying patients by at least two of the following:
  i) screening the patient for at least one leukotriene gene SNP or haplotype;
  ii) monitoring the patient for at least one leukotriene related inflammatory biomarker;
  ii) monitoring the patient for at least one functional marker response to a leukotriene modifying agent.

In further or alternative embodiments, the leukotriene gene SNP or haplotype is a leukotriene pathway gene. In still further or alternative embodiments, the leukotriene gene SNP or haplotype is a 5-lipoxygenase-activating protein (FLAP) SNP or haplotype. In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1).

In any of the aforementioned aspects involving the prevention or treatment of leukotriene-dependent or leukotriene mediated diseases or conditions are further embodiments comprising identifying patients by:
  i) screening the patient for at least one leukotriene gene SNP or haplotype; and
  ii) monitoring the patient for at least one leukotriene related inflammatory biomarker; and
  ii) monitoring the patient for at least one functional marker response to a leukotriene modifying agent.

In further or alternative embodiments, the leukotriene gene SNP or haplotype is a leukotriene pathway gene. In still further or alternative embodiments, the leukotriene gene SNP or haplotype is a 5-lipoxygenase-activating protein (FLAP) SNP or haplotype. In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1).

In another aspect is the prevention or treatment of leukotriene-dependent or leukotriene mediated diseases or conditions comprising administering to a patient an effective amount of a FLAP modulator, wherein the patients has been identified using information obtained by:
  i) screening the patient for at least one leukotriene gene SNP or haplotype; and
  ii) monitoring the patient for at least one leukotriene related inflammatory biomarker; and
  ii) monitoring the patient for at least one functional marker response to a leukotriene modifying agent.

In further or alternative embodiments, the FLAP modulator is a FLAP inhibitor. In further or alternative embodiments, the leukotriene gene SNP or haplotype is a leukotriene pathway gene. In still further or alternative embodiments, the leukotriene gene SNP or haplotype is a 5-lipoxygenase-activating protein (FLAP) SNP or haplotype. In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1). In further or alternative embodiments, the information obtained from the three diagnostic methods may be used in an algorithm in which the information is analyzed to identify patients in need of treatment with a FLAP modulator, the treatment regimen, and the type of FLAP modulator used.

In any of the aforementioned aspects the leukotriene-dependent or leukotriene mediated diseases or conditions include, but are not limited to, asthma, chronic obstructive pulmonary disease, pulmonary hypertension, interstitial lung fibrosis, rhinitis, arthritis, allergy, inflammatory bowel disease, adult respiratory distress syndrome, myocardial infarction, aneurysm, stroke, cancer, and endotoxic shock.

CERTAIN CHEMICAL TERMINOLOGY

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. In this application, the use of "or" means "and/or" unless stated otherwise. Furthermore, use of the term "including" as well as other forms, such as "include", "includes," and "included," is not limiting.

An "alkoxy" group refers to a (alkyl)O— group, where alkyl is as defined herein.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 5 carbon atoms. The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkylamine" refers to the —N(alkyl)$_x$H$_y$ group, where x and y are selected from the group x=1, y=1 and x=2, y=0. When x=2, the alkyl groups, taken together, can optionally form a cyclic ring system.

The term "alkenyl" refers to a type of alkyl group in which the first two atoms of the alkyl group form a double bond that is not part of an aromatic group. That is, an alkenyl group begins with the atoms —C(R)=C—R, wherein R refers to the remaining portions of the alkenyl group, which may be the same or different. Non-limiting examples of an alkenyl group include —CH=CH, —C(CH$_3$)=CH, —CH=CCH$_3$ and —C(CH$_3$)=CCH$_3$. The alkenyl moiety may be branched, straight chain, or cyclic (in which case, it would also be known as a "cycloalkenyl" group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. Non-limiting examples of an alkynyl group include —C≡CH, —C≡CCH$_3$ and —C≡CCH$_2$CH$_3$. The "R" portion of the alkynyl moiety may be branched, straight chain, or cyclic.

An "amide" is a chemical moiety with formula —C(O)NHR or —NHC(O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound of any of Formula (G), Formula (G-I), or Formula (G-II), thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{th}$ Ed., John Wiley & Sons, New York, N.Y., 1999, which is incorporated herein by reference in its entirety.

The term "aromatic" or "aryl" refers to an aromatic group which has at least one ring having a conjugated pi electron system and includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon.

The term "bond" or "single bond" refers to a chemical bond between two atoms, or two moieties when the atoms joined by the bond are considered to be part of larger substructure.

A "cyano" group refers to a —CN group.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

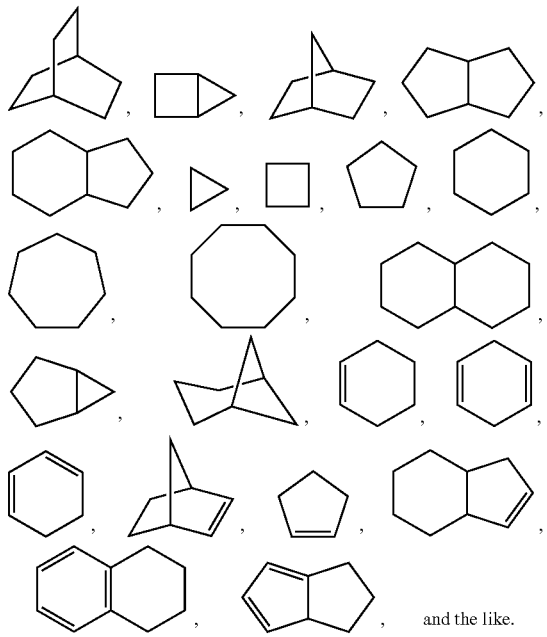

and the like.

The term "ester" refers to a chemical moiety with formula —COOR, where R is selected from the group consisting of alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety. The term "halo" or, alternatively, "halogen" means fluoro, chloro, bromo or iodo.

The terms "haloalkyl," "haloalkenyl," "haloalkynyl" and "haloalkoxy" include alkyl, alkenyl, alkynyl and alkoxy structures that are substituted with one or more halo groups or with combinations thereof. The terms "fluoroalkyl" and "fluoroalkoxy" include haloalkyl and haloalkoxy groups, respectively, in which the halo is fluorine.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Illustrative examples of heteroaryl groups include the following moieties:

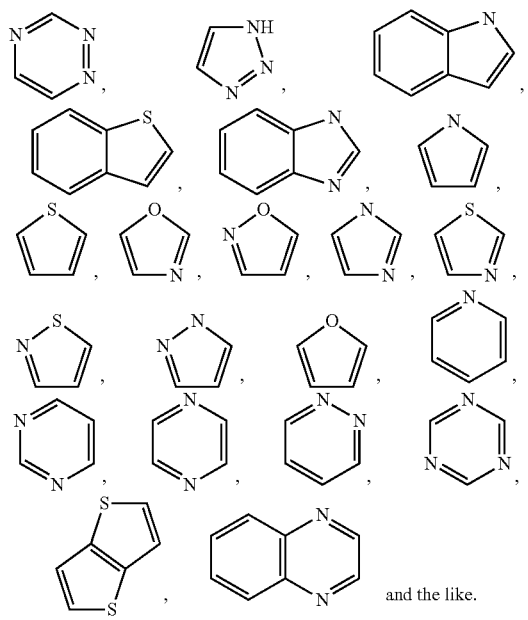

and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one.

A "heteroalicyclic" group refers to a cycloalkyl group that includes at least one heteroatom selected from nitrogen, oxygen and sulfur. The radicals may be fused with an aryl or heteroaryl. Illustrative examples of heterocycloalkyl groups, also referred to as non-aromatic heterocycles, include:

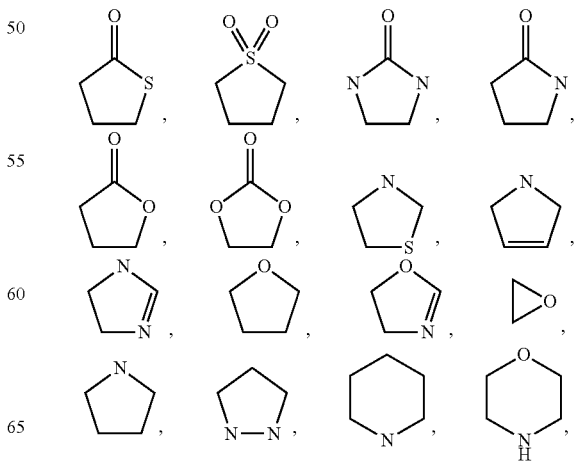

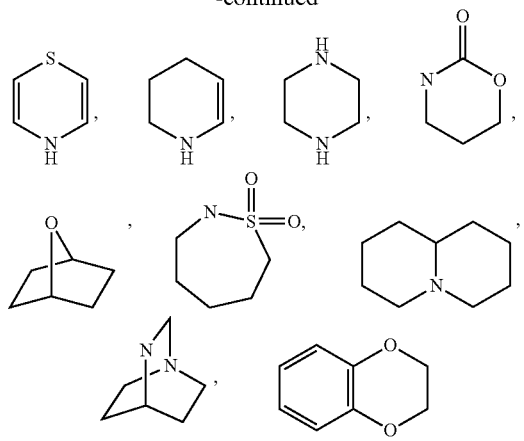

and the like. The term heteroalicyclic also includes all ring forms of the carbohydrates, including but not limited to the monosaccharides, the disaccharides and the oligosaccharides.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

An "isocyanato" group refers to a —NCO group.

An "isothiocyanato" group refers to a —NCS group.

A "mercaptyl" group refers to a (alkyl)S— group.

The term "moiety" refers to a specific segment or functional group of a molecule. Chemical moieties are often recognized chemical entities embedded in or appended to a molecule.

A "sulfinyl" group refers to a —S(=O)—R, where R is selected from the group consisting of alkyl, cycloalkyl, aryl, heteroaryl (bonded through a ring carbon) and heteroalicyclic (bonded through a ring carbon)

A "sulfonyl" group refers to a —S(=O)$_2$—R, where R is selected from the group consisting of alkyl, cycloalkyl, aryl, heteroaryl (bonded through a ring carbon) and heteroalicyclic (bonded through a ring carbon)

A "thiocyanato" group refers to a —CNS group.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof. By way of example an optional substituents may may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted lower alkyl), (substituted or unsubstituted lower cycloalkyl), heteroaryl, or heteroalkyl. The protecting groups that may form the protective derivatives of the above substituents are known to those of skill in the art and may be found in references such as Greene and Wuts, above.

The compounds presented herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

The methods and formulations described herein include the use of N-oxides, crystalline forms (also known as polymorphs), or pharmaceutically acceptable salts of compounds having the structure of any of Formula (G), Formula (G-I), or Formula (G-II), as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

CERTAIN PHARMACEUTICAL TERMINOLOGY

The term "acceptable" with respect to a formulation, composition or ingredient, as used herein, means having no persistent detrimental effect on the general health of the subject being treated.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

The term "bone disease," as used herein, refers to a disease or condition of the bone, including, but not limited to, inappropriate bone remodeling, loss or gain, osteopenia, osteomalacia, osteofibrosis, and Paget's disease [Garcia, "Leukotriene B4 stimulates osteoclastic bone resorption both in intro and in vivo", *J Bone Miner Res.* 1996; 11:1619-27].

The term "cardiovascular disease," as used herein refers to diseases affecting the heart or blood vessels or both, including but not limited to: arrhythmia; atherosclerosis and its sequelae; angina; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumaticshock; hypertension, valvular heart disease, heart failure, abnormal blood pressure; shock; vasoconstriction (including that associated with migraines); vascular abnormality, inflammation, insufficiency limited to a single organ or tissue. [Lotzer K et al., "The 5-lipoxygenase pathway in arterial wall biology and atherosclerosis", *Biochim Biophys Acta* 2005; 1736:30-7; Helgadottir A et al., "The gene encoding 5-lipoxygenase activating protein confers risk of myocardial infarction and stroke", *Nat Genet.* 2004 March; 36(3):233-9. Epub 2004

Feb. 8; [Heise C E, Evans J F et al., "Characterization of the human cysteinyl leukotriene 2 receptor", *J Biol Chem.* 2000 Sep. 29; 275(39):30531-6].

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias) [Ding X Z et al., "A novel anti-pancreatic cancer agent, LY293111", *Anticancer Drugs.* 2005 June; 16(5):467-73. Review; Chen X et al., "Overexpression of 5-lipoxygenase in rat and human esophageal adenocarcinoma and inhibitory effects of zileuton and celecoxib on carcinogenesis", *Clin Cancer Res.* 2004 Oct. 1; 10(19):6703-9].

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, urticaria [Wedi B et al., "Pathophysiological role of leukotrienes in dermatological diseases: potential therapeutic implications", *BioDrugs.* 2001; 15(11):729-43].

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "enzymatically cleavable linker," as used herein refers to unstable or degradable linkages which may be degraded by one or more enzymes.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis [Charbeneau R P et al., "Eicosanoids: mediators and therapeutic targets in fibrotic lung disease", *Clin Sci* (Lond). 2005 June; 108(6): 479-91].

The term "iatrogenic" means a leukotriene-dependent or leukotriene-mediated condition, disorder, or disease created or worsened by medical or surgical therapy.

The term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract (Disease,); skin (dermatitis); or multiple organs and tissues (systemic lupus erythematosus) [Harrison's Principles of Internal Medicine, 16$^{th}$ Edition, Kasper D L, et al, Editors; McGraw-Hill, publishers].

The term "interstitial cystitis" refers to a disorder characterized by lower abdominal discomfort, frequent and sometimes painful urination that is not caused by anatomical abnormalites, infection, toxins, trauma or tumors [Bouchelouche K et al., "The cysteinyl leukotrine D4 receptor antagonst montelukast for the treatment of interstitial cystitis", *J Urol* 2001; 166:1734].

The term "leukotriene-driven mediators," as used herein, refers to molecules able to be produced in a patient that may result from excessive production of leukotriene stimulation of cells, such as, by way of example only, $LTB_4$, $LTC_4$, $LTE_4$, cysteinyl leuktorienes, monocyte inflammatory protein (MIP-1α), interleukin-8 (IL-8), interleukin-4 (IL-4), interleukin-13 (IL-13), monocyte chemoattractant protein (MCP-1), soluble intracellular adhesion molecule (sICAM; soluble ICAM), myeloperoxidase (MPO), eosinophil peroxidase (EPO), and general inflammation molecules such as interleukin-6 (Il-6), C-reactive protein (CRP), and serum amyloid A protein (SAA).

The term "leukotriene-related mediators," as used herein, refers to molecules able to be produced in a patient that may result from excessive production of leukotriene stimulation of cells, such as, by way of example only, $LTB_4$, $LTC_4$, $LTE_4$, cysteinyl leuktorienes, monocyte inflammatory protein (MIP-1α), interleukin-8 (IL-8), interleukin-4 (IL-4), interleukin-13 (IL-13), monocyte chemoattractant protein (MCP-1), soluble intracellular adhesion molecule (sICAM; soluble ICAM), myeloperoxidase (MPO), eosinophil peroxidase (EPO), and general inflammation molecules such as interleukin-6 (Il-6), C-reactive protein (CRP), and serum amyloid A protein (SAA).

The term "leukotriene-dependent", as used herein, refers to conditions or disorders that would not occur, or would not occur to the same extent, in the absence of one or more leukotrienes.

The term "leukotriene-mediated", as used herein, refers to refers to conditions or disorders that might occur in the absence of leukotrienes but can occur in the presence of one or more leukotrienes.

The term "leukotriene-responsive patient," as used herein, refers to a patient who has been identified by either genotyping of FLAP haplotypes, or genotyping of one or more other genes in the leukotriene pathway and/or, by phenotyping of patients either by previous positive clinical response to another leukotriene modulator, including, by way of example only, zileuton (Zyflo™), montelukast (Singulair™), pranlukast (Onon™), zafirlukast (Accolate™), and/or by their profile of leukotriene-driven mediators that indicate excessive leukotriene stimulation of inflammatory cells, as likely to respond favorably to leukotriene modulator therapy.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system, i.e., brain and spinal cord [Sugaya K, et al., "New anti-inflammatory treatment strategy in Alzheimer's disease", *Jpn J Pharmacol.* 2000 February; 82(2):85-94; Yu G L, et al., "Montelukast, a cysteinyl leukotriene receptor-1 antagonist, dose- and time-dependently protects against focal cerebral ischemia in mice", *Pharmacology.* 2005 January; 73(1):31-40. Epub 2004 Sep. 27; [Zhang W P, et al., "Neuroprotective effect of ONO-1078, a leukotriene receptor antagonist, on focal cerebral ischemia in rats", *Acta Pharmacol Sin.* 2002 October; 23(10):871-7].

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjuctivitis, vernal conjunctivitis, pappillary conjunctivitis [Toriyama S., "Effects of leukotriene B4 receptor antagonist on experimental autoimmune uveoretinitis in rats", *Nippon Ganka Gakkai Zasshi.* 2000 June; 104(6):396-40; [Chen F, et al., "Treatment of S antigen uveoretinitis with lipoxygenase and cyclo-oxygenase inhibitors", *Ophthalmic Res.* 1991; 23(2):84-91].

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. Pharmaceutically acceptable salts may be obtained by reacting a compound of any of Formula (G), Formula (G-I), or Formula (G-II), with acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts may also be obtained by reacting a compound of any of Formula (G), Formula (G-I), or Formula (G-II), with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods known in the art The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of any of Formula (G), Formula (G-I), or Formula (G-II), and a co-agent, are both administered to a patient simultaneously in the form of a single entity or dosage. The term "non-fixed combination" means that the active ingredients, e.g. a compound of any of Formula (G), Formula (G-I), or Formula (G-II), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of any of Formula (G), Formula (G-I), or Formula (G-II), with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of any of Formula (G), Formula (G-I), or Formula (G-II), which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia [Evans J F, "The Cysteinyl Leukotriene (CysLT) Pathway in Allergic Rhinitis", *Allergology International* 2005; 54:187-90); Kemp J P., "Leukotriene receptor antagonists for the treatment of asthma", *IDrugs*. 2000 April; 3(4): 430-41; Riccioni G, et al., "Effect of the two different leukotriene receptor antagonists, montelukast and zafirlukast, on quality of life: a 12-week randomized study", *Allergy Asthma Proc*. 2004 November-December; 25(6):445-8].

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description. All references cited herein, including patents, patent applications, and publications, are hereby incorporated by reference in their entirety.

DETAILED DESCRIPTION OF THE INVENTION

Illustrative Biological Activity

Figure 1:
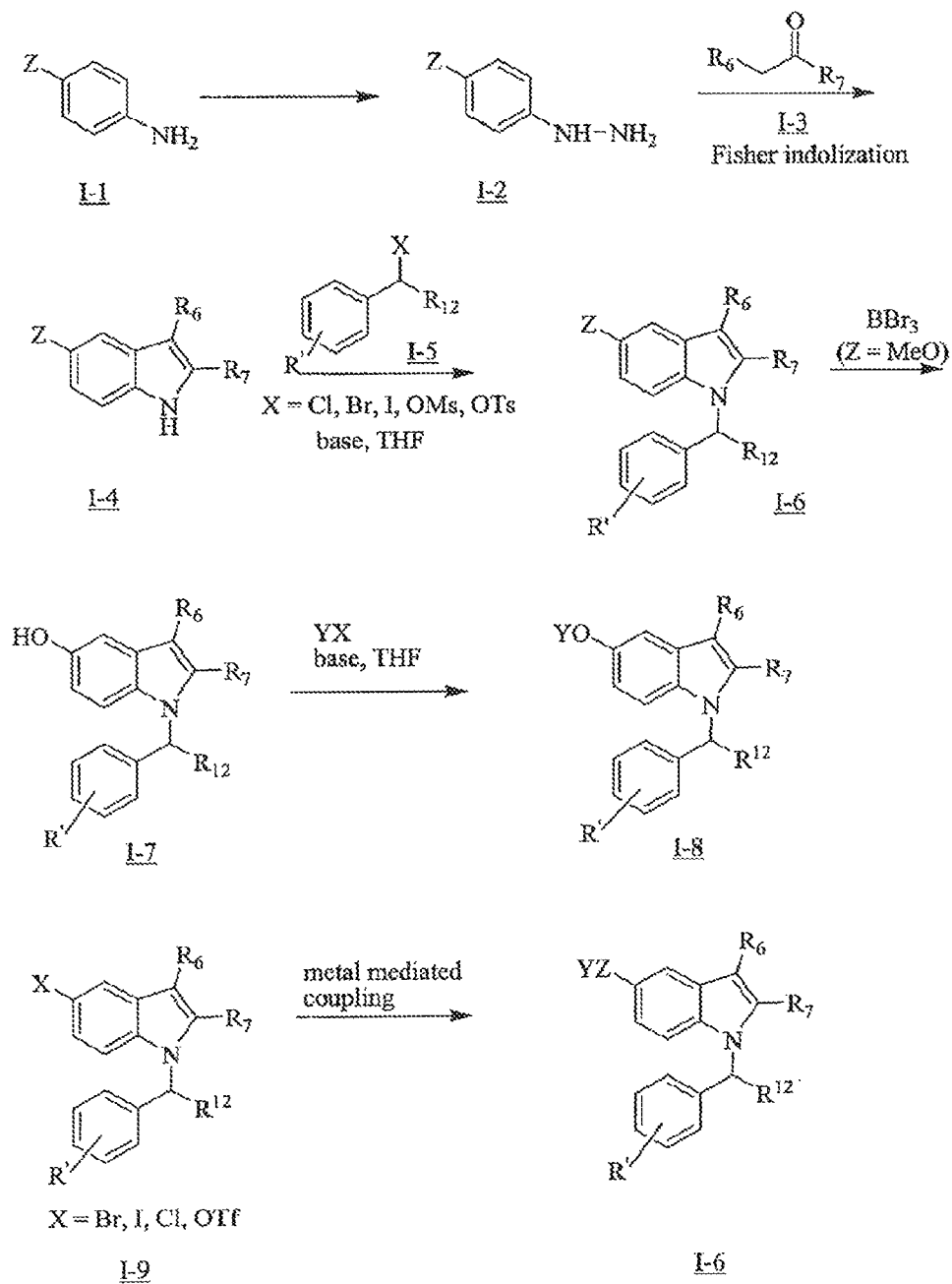
FIG. 1 presents illustrative schemes for the syntheses of compounds described herein.

Leukotrienes (LTs) are potent contractile and inflammatory mediators produced by release of arachidonic acid from cell membranes and conversion to leukotrienes by the action of 5-lipoxygenase, 5-lipoxygenase-activating protein, $LTA_4$ hydrolase and $LTC_4$ synthase. The leukotriene synthesis pathway, or 5-lipoxygenase pathway, involves a series of enzymatic reactions in which arachidonic acid is converted to leukotriene $LTB_4$, or the cysteinyl leukotrienes, $LTC_4$, $LTD_4$, and $LTE_4$. The pathway occurs mainly at the nuclear envelope and has been described. See, e.g., Wood, J W et al, *J. Exp. Med.*, 178: 1935-1946, 1993; Peters-Golden, *Am. J. Respir. Crit. Care Med.* 157:S227-S232, 1998; Drazen, et al., ed. Five-Lipoxygenase Products in Asthma, Lung Biology in Health and Disease Series, Vol. 120, Chs. 1, 2, and 7, Marcel Dekker, Inc. NY, 1998. Protein components dedicated to the leukotriene synthesis pathway include a 5-lipoxygenase (5-LO), a 5-lipoxygenase-activating protein, a $LTA_4$ hydrolase, and a $LTC_4$ synthase. The synthesis of leukotrienes has been described in the literature, e.g., by Samuelsson et al, *Science*, 220, 568-575, 1983; Peters-Golden, "Cell Biology of the 5-Lipoxygenase Pathway" *Am J Respir Crit Care Med* 157:S227-S232 (1998). Leukotrienes are synthesized directly from arachidonic acid by different cells including eosinophils, neutrophils, basophils, lymphocytes, macrophages, monocytes and mast cells. Excess $LTA_4$, for example from an activated neutrophil, may enter a cell by a transcellular pathway. Most cells in the body have $LTA_4$ hydrolase so can produce $LTB_4$. Platelets and endothelial cells have $LTC_4$ synthase, so can make $LTC_4$ when presented with $LTA_4$ by a transcellular pathway.

Arachidonic acid is a polyunsaturated fatty acid and is present mainly in the membranes of the body's cells. Upon presentation of inflammatory stimuli from the exterior of the cell, calcium is released and binds to phospholipase $A_2$ (PLA2) and 5-LO. Cell activation results in the translocation of $PLA_2$ and 5-LO from the cytoplasm to the endoplasmic reticulum and/or nuclear membranes, where in the presence of FLAP, the released arachidonic acid is converted via a 5-HPETE intermediate to the epoxide $LTA_4$. Depending on the cell type, the $LTA_4$ may be immediately converted to $LTC_4$ by the nuclear-bound $LTC_4$ synthase or to $LTB_4$ by the action of cytosolic $LTA_4$ hydrolase. $LTB_4$ is exported from cells by an as yet uncharacterized transporter and may activate other cells, or the cell it was made in, via high affinity binding to one of two G protein-coupled receptors (GPCRs), namely $BLT_1R$ or $BLT_2R$. $LTC_4$ is exported to the blood via the MRP-1 anion pump and rapidly converted to $LTD_4$ by the action of γ-glutamyl transpeptidase and $LTD_4$ is then converted to $LTE_4$ by the action of dipeptidases. $LTC_4$, $LTD_4$ and $LTE_4$ are collectively referred to as the cysteinyl leukotrienes (or previously as slow reacting substance of anaphylaxis, SRS-A). The cysteinyl leukotrienes activate other cells, or the cells they are made in, via high affinity binding to one of two GPCRs, namely $CysLT_1R$ or $CysLT_2R$. $CysLT_1$ receptors are found in the human airway eosinophils, neutrophils, macrophages, mast cells, B-lymphocytes and smooth muscle and induce bronchoconstriction. Zhu et al, *Am J Respir Cell Mol Biol Epub Aug* 25 (2005). $CysLT_2$ receptors are located in human airway eosinophils, macrophages, mast cells the human pulmonary vasculature Figueroa et al, *Clin Exp Allergy* 33:1380-1388 (2003).

Involvement of Leukotrienes in Diseases or Conditions

The involvement of leukotrienes in disease is described in detail in the literature. See e.g., by Busse, *Clin. Exp. Allergy* 26:868-79, 1996; O'Byrne, Chest 111(Supp. 2): 27S-34S, 1977; Sheftell, F. D., et al., *Headache*, 40:158-163, 2000; Klickstein et al., *J. Clin. Invest.*, 66:1166-1170, 1950; Davidson et al., *Ann. Rheum. Dis.*, 42:677-679, 1983 Leukotrienes produce marked inflammatory responses in human skin. Evidence for the involvement of leukotrienes in a human disease is found in psoriasis, in which leukotrienes have been detected in psoriatic lesions (Kragballe et al., *Arch. Dermatol.*, 119:548-552, 1983).

For example, inflammatory responses have been suggested to reflect three types of changes in the local blood vessels. The primary change is an increase in vascular diameter, which results in an increase in local blood flow and leads to an increased temperature, redness and a reduction in the velocity of blood flow, especially along the surfaces of small blood vessels. The second change is the activation of endothelial cells lining the blood vessel to express adhesion molecules that promote the binding of circulating leukocytes. The combination of slowed blood flow and induced adhesion molecules allows leukocytes to attach to the endothelium and migrate into the tissues, a process known as extravasation. These changes are initiated by cytokines and leukotrienes produced by activated macrophages. Once inflammation has begun, the first cells attracted to the site of infection are generally neutrophils. They are followed by monocytes, which differentiate into more tissue macrophages. In the latter stages of inflammation, other leukocytes, such as eosinophils and lymphocytes also enter the infected site. The third major change in the local blood vessels is an increase in vascular permeability. Instead of being tightly joined together, the endothelial cells lining the blood vessel walls become separated, leading to exit of fluid and proteins from the blood and their local accumulation in the tissue. (See Janeway, et al., Immunobiology: the immune system in health and disease, 5th ed., Garland Publishing, New York, 2001)

$LTB_4$ produces relatively weak contractions of isolated trachea and lung parenchyma, and these contractions are blocked in part by inhibitors of cyclooxygenase, suggesting that the contraction are secondary to the release of prostaglandins. However, $LTB_4$ has been shown to be a potent chemotactic agent for eosinophils and progenitors of mast cells and the $LTB_4$ receptor BLT1−/− knockout mouse is protected from eosinophilic inflammation and T-cell mediated allergic airway hyperreactivity. Miyahara et al. *J Immunol* 174:4979-4784; (Weller et al. *J Exp Med* 201:1961-1971 (2005).

Leukotrienes $C_4$ and $D_4$ are potent smooth muscle contractile agents, promoting bronchoconstriction in a variety of species, including humans (Dahlen et al., *Nature*, 288:484-486, 1980). These compounds have profound hemodynamic effects, constricting coronary blood vessels, and resulting in a reduction of cardiac output efficiency (Marone et al., in *Biology of Leukotrienes*, ed. By R. Levi and R. D. Krell, Ann. New York Acad. Sci. 524:321-333, 1988). Leukotrienes also act as vasoconstrictors, however, marked differences exist for different vascular beds. There are reports suggesting that leukotrienes contribute to cardiac reperfusion injury following myocardial ischemia (Barst and Mullane, *Eur. J. Pharmacol.*, 114: 383-387, 1985; Sasaki et al., *Cardiovasc. Res.*, 22: 142-148, 1988). $LTC_4$ and $LTD_4$ directly increase vascular permeability probably by promoting retraction of capillary endothelial cells via activation of the $CysLT_2$ receptor and possibly other as yet undefined CysLT receptors [Lotzer et al. *Arterioscler Thromb Vasc Biol* 23: e32-36. (2003)]. $LTB_4$ enhances atherosclerotic progression in two atherosclerotic mouse models, namely low density receptor lipoprotein receptor deficient (LDLr−/−) and apolipoprotein E-deficient (ApoE−/−) mice (Aiello et al, *Arterioscler Thromb Vasc Biol* 22:443-449 (2002); Subbarao et al, *Arterioscler Thromb Vasc Biol* 24:369-375 (2004); Heller et al. *Circulation* 112:578-586 (2005). $LTB_4$ has also been shown to increase human monocyte chemoattractant protein (MCP-1) a known enhancer of atherosclerotic progression (Huang et al. *Arterioscler Thromb Vasc Biol* 24:1783-1788 (2004).

The role of FLAP in the leukotriene synthesis pathway is significant because FLAP in concert with 5-lipoxygenase performs the first step in the pathway for the synthesis of leukotrienes. Therefore the leukotriene synthesis pathway provides a number of targets for compounds useful in the treatment of leukotriene-dependent or leukotriene mediated diseases or conditions, including, by way of example, vascular and inflammatory disorders, proliferative diseases, and non-cancerous disorders.

Leukotriene-dependent or leukotriene mediated conditions treated using the methods, compounds, pharmaceutical compositions and medicaments described herein, include, but are not limited to, bone diseases and disorder, cardiovascular diseases and disorders, inflammatory diseases and disorders, dermatological diseases and disorders, ocular diseases and disorders, cancer and other proliferative diseases and disorders, respiratory diseases and disorder, and non-cancerous disorders.

Treatment Options

Leukotrienes are known to contribute to the inflammation of the airways of patients with asthma. $CysLT_1$ receptor antagonists such as montelukast (Singulair™) have been shown to be efficacious in asthma and allergic rhinitis [Reiss et al. *Arch Intern Med* 158:1213-1220 (1998); Phillip et al. *Clin Exp Allergy* 32:1020-1028 (2002)]. $CysLT_1R$ antagonists pranlukast (Onon™) and zafirlukast (Accolate™) have also been shown to be efficacious in asthma.

A number of drugs have been designed to inhibit leukotriene formation, including the 5-lipoxygenase inhibitor zileuton (Zyflo™) that has shown efficacy in asthma, Israel et al. *Ann Intern Med* 119:1059-1066 (1993). The 5-lipoxygenase inhibitor ZD2138 showed efficacy in inhibiting the fall of FEV1 resulting from aspirin-induced asthma, Nasser et al, *Thorax*, 49; 749-756 (1994). The following leukotriene synthesis inhibitors have shown efficacy in asthma: MK-0591, a specific inhibitor of 5-lipoxygenase-activating protein (FLAP), Brideau, et al., *Ca. J. Physiol. Pharmacol.* 70:799-807 (1992)., MK-886, a specific inhibitor of 5-lipoxygenase-activating protein (FLAP), Friedman et al. *Am Rev Respir Dis.*, 147: 839-844 (1993), and BAY X1005, a specific inhibitor of 5-lipoxygenase-activating protein (FLAP), Fructmann et al, Agents Actions 38: 188-195 (1993).

FLAP inhibition will decrease $LTB_4$ from monocytes, neutrophils and other cells involved in vascular inflammation and thereby decrease atherosclerotic progression. The FLAP inhibitor MK-886 has been shown to to decrease the postangioplasty vasoconstrictive response in a porcine carotid injury model Provost et al. *Brit J Pharmacol* 123: 251-258 (1998). MK-886 has also been shown to suppress femoral artery intimal hyperplasia in a rat photochemical model of endothelial injury Kondo et al. *Thromb Haemost* 79:635-639 (1998). The 5-lipoxygenase inhibitor zileuton has been shown to reduce renal ischemia in a mouse model, Nimesh et al. *Mol Pharm* 66:220-227 (2004).

FLAP modulators have been used for the treatment of a variety of diseases or conditions, including, by way of example only, (i) inflammation (see e.g. Leff A R et al., "Discovery of leukotrienes and the development of antileukotriene agents", *Ann Allergy Asthma Immunol* 2001; 86 (Suppl 1)$_{4-8}$; Riccioni G, et al., "Advances in therapy with antileukotriene drugs", *Ann Clin Lab Sci.* 2004, 34(4):379-870; (ii) respiratory diseases including asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma (see e.g. Riccioni et al, *Ann. Clin. Lab. Sci.*, v34, 379-387 (2004)); (iii) chronic obstructive pulmonary disease, including chronic bronchitis or emphysema, pulmonary hypertension, interstitial lung fibrosis and/or airway inflammation and cystic fibrosis (see e.g. Kostikas K et al., "Leukotriene V4 in exhaled breath condensate and sputum supernatant in patients with COPD and asthma", *Chest* 2004; 127:1553-9); (iv) increased mucosal secretion and/or edema in a disease or condition (see e.g. Shahab R et al., "Prostaglandins, leukotrienes, and perennial rhinitis", *J Laryngol Otol.*, 2004; 118; 500-7); (v) vasoconstriction, atherosclerosis and its sequelae myocardial ischemia, myocardial infarction, aortic aneurysm, vasculitis and stroke (see e.g. Jala et al, *Trends in Immunol.*, v25, 315-322 (2004) and Mehrabian et al, *Curr. Opin. Lipidol.*, v14, 447-457 (2003)); (vi) reducing organ reperfusion injury following organ ischemia and/or endotoxic shock (see e.g. Matsui N, et al., "Protective effect of the 5-lipoxygenase inhibitor ardisiaquinone A on hepatic ischemia-reperfusion injury in rats", *Planta Med.* 2005 August; 71(8):717-20); (vii) reducing the constriction of blood vessels (see e.g. Stanke-Labesque F et al., "Inhibition of leukotriene synthesis with MK-886 prevents a rise in blood pressure and reduces noradrenaline-evoked contraction in L-NAME-treated rats", *Br J Pharmacol.* 2003 September; 140(1):186-94); (viii) lowering or preventing an increase in blood pressure (see e.g. Stanke-Labesque F et al., "Inhibition of leukotriene synthesis with MK-886 prevents a rise in blood pressure and reduces noradrenaline-evoked contraction in L-NAME-treated rats", *Br J Pharmacol.* 2003 September; 140(1):186-94, and Walch L, et al., "Pharmacological evidence for a novel cysteinyl-leukotriene receptor subtype in human pulmonary artery smooth muscle", *Br J Pharmacol.* 2002 December; 137(8):1339-45); (ix) preventing eosinophil and/or basophil and/or dendritic cell and/or neutrophil and/or monocyte recruitment (see e.g. Miyahara N, et al., "Leukotriene B4 receptor-1 is essential for allergen-mediated recruitment of CD8+ T cells and airway hyperresponsiveness", *Immunol.* 2005 Apr. 15; 174(8):4979-84); (x) abnormal bone remodeling, loss or gain, including osteopenia, osteoporosis, Paget's disease, cancer and other diseases (see e.g. Anderson G I, et al., "Inhibition of leukotriene function can modulate particulate-induced changes in bone cell differentiation and activity", *Biomed Mater Res.* 2001; 58(4):406-140; (xi) ocular inflammation and allergic conjunctivitis, vernal keratoconjunctivitis, and papillary conjunctivitis (see e.g. Lambiase et al, *Arch. Opthalmol.*, v121, 615-620 (2003)); (xii) CNS disorders, including, but are not limited to, multiple sclerosis, Parkinson's disease, Alzheimer's disease, stroke, cerebral ischemia, retinal ischemia, post-surgical cognitive dysfunction, migraine (see e.g. de Souza Carvalho D, et al., "Asthma plus migraine in childhood and adolescence: prophylactic benefits with leukotriene receptor antagonist", *Headache.* 2002 November-December; 42(10):1044-7; Sheftell F, et al., "Montelukast in the prophylaxis of migraine: a potential role for leukotriene modifiers", *Headache.* 2000 February; 40(2):158-63); (xiii) peripheral neuropathy/neuropathic pain, spinal cord injury (see e.g. Akpek E A, et al., "A study of adenosine treatment in experimental acute spinal cord injury. Effect on arachidonic acid metabolites", *Spine.* 1999 Jan. 15; 24(2):128-32), cerebral edema and head injury; (xiv) cancer, including, but is not limited to, pancreatic cancer and other solid or hematological tumors, (see e.g. Poff and Balazy, *Curr. Drug Targets Inflamm. Allergy*, v3, 19-33 (2004) and Steele et al, *Cancer Epidemiology & Prevention*, v8, 467-483 (1999); (xv) endotoxic shock and septic shock (see e.g. Leite M S, et al., "Mechanisms of increased survival after lipopolysaccharide-induced endotoxic shock in mice consuming olive oil-enriched diet", *Shock.* 2005 February; 23(2):173-8); (xvi) rheumatoid arthritis and osteoarthritis (see e.g. Alten R, et al., "Inhibition of leukotriene $B_4$-induced CD11B/CD18 (Mac-1) expression by BIIL 284, a new long acting $LTB_4$ receptor antagonist, in patients with rheumatoid arthritis", *Ann Rheum Dis.* 2004 February; 63(2):170-6); (xvii) preventing increased GI diseases, including, by way of example only, chronic gastritis, eosinophilic gastroenteritis, and gastric motor dysfunction, (see e.g. Gyomber et al, *J Gastroenterol Hepatol.*, v11, 922-927 (1996); Quack I et al *BMC Gastroenterol* v18,24 (2005); Cuzzocrea S, et al., "5-Lipoxygenase modulates colitis through the regulation of adhesion molecule expression and neutrophil migration", *Lab Invest.* 2005

June; 85(6):808-22); (xviii) kidney diseases, including, by way of example only, glomerulonephritis, cyclosporine nephrotoxicity renal ischemia reperfusion. (see e.g. Guasch et al Kidney Int., v56, 261-267; Butterly et al, v 57, 2586-2593 (2000); Guasch A et al. "MK-591 acutely restores glomerular size selectivity and reduces proteinuria in human glomerulonephritis", Kidney Int. 1999; 56:261-7; Butterly D W et al. "A role for leukotrienes in cyclosporine nephrotoxicity", Kidney Int. 2000; 57:2586-93); (xix) preventing or treating acute or chronic renal insufficiency (see e.g. Maccarrone M, et al., "Activation of 5-lipoxygenase and related cell membrane lipoperoxidation in hemodialysis patients", J Am Soc Nephrol. 1999; 10:1991-6); (xx) type II diabetes (see e.g. Valdivielso et al, v16, 85-94 (2003); (xxi) dimnish the inflammatory aspects of acute infections within one or more solid organs or tissues such as the kidney with acute pyelonephritis (see e.g. Tardif M, et al., L-651,392, "A potent leukotriene inhibitor, controls inflammatory process in Escherichia coli pyelonephritis", Antimicrob Agents Chemother. 1994 July; 38(7):1555-60); (xxii) preventing or treating acute or chronic disorders involving recruitment or activation of eosinophils (see e.g. Quack I, et al. "Eosinophilic gastroenteritis in a young girl -long term remission under montelukast", BMC Gastroenterol., 2005; 5:24; (xxiii) preventing or treating acute or chronic erosive disease or motor dysfunction of the gastrointestinal tract caused by non-steroidal anti-inflammatory drugs (including selective or non-selective cyclooxygenase-1 or -2 inhibitors) (see e.g. Marusova I B, et al., "Potential gastroprotective effect of a CysLT1 receptor blocker sodium montelukast in aspirin-induced lesions of the rat stomach mucosa", Eksp Klin Farmakol, 2002; 65:16-8 and Gyomber E, et al., "Effect of lipoxygenase inhibitors and leukotriene antagonists on acute and chronic gastric haemorrhagic mucosal lesions in ulcer models in the rat", J. Gastroenterol. Hepatol., 1996, 11, 922-7) and Martin St et al., "Gastric motor dysfunction: is eosinophilic mural gastritis a causative factor?", Eur J Gastroenterol. Hepatol., 2005, 17:983-6; (xxiv) treating type II diabetes (see e.g. Valdivielso J M, et al., "Inhibition of 5-lipoxygenase activating protein decreases proteinuria in diabetic rats", J Nephrol. 2003 January-February;16(1):85-94; Parlapiano C, et al., "The relationship between glycated hemoglobin and polymorphonuclear leukocyte leukotriene B4 release in people with diabetes mellitus", Diabetes Res Clin Pract. 1999 October; 46(1):43-5; (xxv) treatment of metabolic syndromes, including, by way of example only, Familial Mediterranean Fever (see e.g. Bentancur A G, et al., "Urine leukotriene B4 in familial Mediterranean fever", Clin Exp Rheumatol. 2004 July-August; 22(4 Suppl 34):556-8; and (xxvi) treat hepatorenal syndrome (see e.g. Capella G L., "Anti-leukotriene drugs in the prevention and treatment of hepatorenal syndrome", Prostaglandins Leukot Essent Fatty Acids. 2003 April; 68(4):263-5].

Several inhibitors of FLAP have been described (Gillard et al, Can. J. Physiol. Pharmacol., 67, 456-464, 1989; Evans et al, Molecular Pharmacol., 40, 22-27, 1991; Brideau et al, Can. J. Physiol. Pharmacol., Musser et al, J. Med. Chem., 35, 2501-2524, 1992; Steinhilber, Curr. Med. Chem. 6(1):71-85, 1999; Riendeau, Bioorg Med Chem Lett., 15(14):3352-5, 2005; Flamand, et al., Mol. Pharmacol. 62(2):250-6, 2002; Folco, et al., Am. J. Respir. Crit. Care Med. 161(2 Pt 2):S112-6, 2000; Hakonarson, JAMA, 293(18):2245-56, 2005).

Identification of Leukotriene Synthesis Pathway Inhibitors

The development and testing of novel FLAP inhibitors which are effective either alone or in combination with other drugs, and which result in minimal negative side effects would be beneficial for treating leukotriene-dependent or leukotriene mediated diseases or conditions. Inhibitors of the leukotriene synthesis pathway described herein may target any step of the pathway to prevent or reduce the formation of leukotrienes. Such leukotriene synthesis inhibitors can, by way of example, inhibit at the level of FLAP, or 5-LO, thus minimizing the formation of various products in the leukotriene pathway, thereby decreasing the amounts of such compounds available in the cell. Leukotriene synthesis inhibitors can be identified based on their ability to bind to proteins in the leukotriene synthesis pathway. For example, FLAP inhibitors can be identified based on their binding to FLAP.

Compounds

Compounds of Formula (G), Formula (G-I) and Formula (G-II):

Compounds of Formula (G), Formula (G-I), and Formula (G-II), pharmaceutically acceptable salts, pharmaceutically acceptable N-oxides, pharmaceutically active metabolites, pharmaceutically acceptable prodrugs, and pharmaceutically acceptable solvates thereof, antagonize or inhibit FLAP and may be used to treat patients suffering from leukotriene-dependent or leukotriene mediated conditions or diseases, including, but not limited to, asthma, myocardial infarction, cancer, and inflammatory conditions.

Formula (G-I) is as follows:

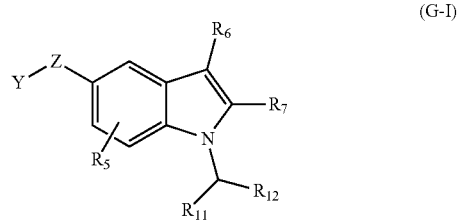

(G-I)

wherein,

Z is selected from $N(R_1)$, $S(O)_m$, $CR_1=CR_1$, $C\equiv C$—, $C(R_1)_2[C(R_2)_2]_n$, $[C(R_2)_2]_nC(R_1)_2O$, $OC(R_1)_2[C(R_2)_2]_n$, $[C(R_2)_2]_nC(R_1)_2S(O)_m$, $S(O)_mC(R_1)_2[C(R_2)_2]_n$, $[C(R_2)_2]_nC(R_1)_2NR_1$, $NR_1C(R_1)_2[C(R_2)_2]_n$, $[C(R_2)_2]_nO[C(R_1)_2]_n$, $[C(R_1)_2]_nO[C(R_2)_2]_n$, —C(O)NR_2—, —NR_2C(O)—, —NR_2C(O)O—, —OC(O)NR_2—, —S(O)_2NR_2—, —CR_1=N—N—, NR_2C(O)NR_2—, —OC(O)O—, $S(O)_2NR_2$, or —NR_2S(O)_2—, wherein each $R_1$ is independently H, $CF_3$, or an optionally substituted lower alkyl and two $R_1$ on the same carbon may join to form a carbonyl (=O); and each $R_2$ is independently H, OH, OMe, $CF_3$, or an optionally substituted lower alkyl and two $R_2$ on the same carbon may join to form a carbonyl (=O); m is 0, 1 or 2; each n is independently 0, 1, 2, or 3;

Y is -$L_1$-(substituted or unsubstituted aryl); -$L_1$-(substituted or unsubstituted heteroaryl); -$L_1$-(substituted or unsubstituted non-aromatic heterocycle), provided that when the heteroatom is directly bound to Z, the non-aromatic heterocycle is substituted; where $L_1$ is a bond, a substituted or unsubstituted alkyl, substituted or unsubstituted alkenyl, substituted or unsubstituted alkynyl, a substituted or unsubstituted heterocycle, a substituted or unsubstituted heteroaryl, a substituted or unsubstituted cycloalkyl, or substituted or unsubstituted aryl, —C(O), $C(R_8)(OH)$, $C(R_8)(OMe)$, C(=NOH), C(=NOR_{4b}), C(=O)NH, C(=O)NR_{4b}, —NHC(=O), $NR_{4b}C(=O)$, S, S(=O), $S(=O)_2$, —NHC(=O)NH, or $NR_{4b}C(=O)NR_{4b}$;

where each substituent on Y or Z is $(L_8R_8)_j$, wherein each $L_8$ is independently selected from a bond, —O—, —C(=O)—, —S—, —S(=O)—, —S(=O)$_2$—, —NHC(O)—, —C(O)NH—, S(=O)$_2$NH—, —NHS(=O)$_2$, —OC(O)NH—, —NHC(O)O—, —OC(O)O—, —NHC(O)NH—, —C(O)O—, —OC(O)—, C$_1$-C$_6$ alkyl, C$_2$-C$_6$ alkenyl, fluoroalkyl, heteroaryl, aryl, or heterocycle; and each R$_s$ is independently selected from H, halogen, —N(R$_4$)$_2$, —CN, —NO$_2$, N$_3$, —S(=O)$_2$NH$_2$, lower alkyl, lower cycloalkyl, —C$_1$-C$_6$ fluoroalkyl, heteroaryl, or heteroalkyl; where j is 0, 1, 2, 3, or 4;

each R$_3$ is independently selected from H, —S(=O)$_2$R$_8$, —S(=O)$_2$NH$_2$—C(O)R$_8$, —CN, —NO$_2$, heteroaryl, or heteroalkyl;

each R$_{3b}$ is independently selected from substituted or unsubstituted lower alkyl, substituted or unsubstituted lower cycloalkyl, substituted or unsubstituted phenyl or benzyl;

each R$_4$ is independently selected from H, substituted or unsubstituted lower alkyl, substituted or unsubstituted lower cycloalkyl, phenyl or benzyl; or two R$_4$ groups can together form a 5-, 6-, 7-, or 8-membered heterocyclic ring; or R$_{3b}$ and R$_4$ can together form a 5-, 6-, 7-, or 8-membered heterocyclic ring;

each R$_{4b}$ is independently selected from H, substituted or unsubstituted lower alkyl, substituted or unsubstituted lower cycloalkyl, substituted or unsubstituted aryl or substituted or unsubstituted benzyl; substituted or unsubstituted heteroaryl, substituted or unsubstituted heterocycle;

R$_6$ is H, L$_2$-(substituted or unsubstituted alkyl), L$_2$-(substituted or unsubstituted cycloalkyl), L$_2$-(substituted or unsubstituted alkenyl), L$_2$-(substituted or unsubstituted cycloalkenyl), L$_2$-(substituted or unsubstituted heterocycle), L$_2$-(substituted or unsubstituted heteroaryl), or L$_2$-(substituted or unsubstituted aryl), where L$_2$ is a bond, O, S, —S(=O)—, —S(=O)$_2$, C(O), —CH(OH), -(substituted or unsubstituted C$_1$-C$_6$ alkyl), or -(substituted or unsubstituted C$_2$-C$_6$ alkenyl);

R$_7$ is L$_3$-X-L$_4$-G$_1$, wherein,
L$_3$ is a bond, or substituted or unsubstituted alkyl;
X is a bond, O, —C(=O), —CR$_9$(OR$_9$), S, —S(=O), —S(=O)$_2$, —NR$_9$, —NR$_9$C(O), —C(O)NR$_9$, —NR$_9$C(O)NR$_9$—, or aryl;
L$_4$ is a bond, or substituted or unsubstituted alkyl;
G$_1$ is H, tetrazolyl, —NHS(=O)$_2$R$_8$, S(=O)$_2$N(R$_9$)$_2$, —OR$_9$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, —S(=O)$_2$R$_8$, -L$_5$-(substituted or unsubstituted alkyl), -L$_5$-(substituted or unsubstituted alkenyl), -L$_5$-(substituted or unsubstituted heteroaryl), or -L$_5$-(substituted or unsubstituted aryl), wherein L$_5$ is —OC(O)O—, —NHC(O)NH—, —NHC(O)O, —O(O)CNH—, —NHC(O), —C(O)NH, —C(O)O, or —OC(O);

or G$_1$ is W-G$_5$, where W is a substituted or unsubstituted aryl, substituted or unsubstituted heterocycle or substituted or unsubstituted heteroaryl and G$_5$ is H, tetrazolyl, —NHS(=O)$_2$R$_s$, S(=O)$_2$N(R$_9$)$_2$, OH, —OR$_8$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, or —S(=O)$_2$R$_s$;

each R$_8$ is independently selected from substituted or unsubstituted lower alkyl, substituted or unsubstituted lower cycloalkyl, phenyl or benzyl;

each R$_9$ is independently selected from H, substituted or unsubstituted lower alkyl, substituted or unsubstituted lower cycloalkyl, phenyl or benzyl; or two R$_9$ groups can together form a 5-, 6-, 7-, or 8-membered heterocyclic ring; or R$_8$ and R$_9$ can together form a 5-, 6-, 7-, or 8-membered heterocyclic ring and each R$_{10}$ is independently selected from H, —S(=O)$_2$R$_8$, —S(=O)$_2$NH$_2$—C(O)R$_8$, —CN, —NO$_2$, heteroaryl, or heteroalkyl;

R$_5$ is H, halogen, —N$_3$, —CN, —ONO$_2$, -L$_6$-(substituted or unsubstituted C$_1$-C$_6$ alkyl), -L$_6$-(substituted or unsubstituted C$_2$-C$_6$ alkenyl), -L$_6$-(substituted or unsubstituted heteroaryl), or -L$_6$-(substituted or unsubstituted aryl), wherein L$_6$ is a bond, O, S, —S(=O), S(=O)$_2$, NH, C(O), —NHC(O)O, —OC(O)NH, —NHC(O), —NHC(O)NH—, or —C(O)NH;

R$_{11}$ is L$_7$-L$_{10}$-G$_6$, wherein L$_7$ is a bond, —O, —S, —S(=O), —S(=O)$_2$, —NH, —C(O), —C(O)NH, —NHC(O), (substituted or unsubstituted C$_1$-C$_6$ alkyl), or (substituted or unsubstituted C$_2$-C$_6$ alkenyl);

L$_{10}$ is a bond, (substituted or unsubstituted alkyl), (substituted or unsubstituted cycloalkyl), (substituted or unsubstituted cycloalkenyl), (substituted or unsubstituted heteroaryl), (substituted or unsubstituted aryl), or (substituted or unsubstituted heterocycle);

G$_6$ is H, CN, SCN, N$_3$, NO$_2$, halogen, OR$_9$, —C(=O)CF$_3$, —C(=O)R$_9$, —C(=O)OR$_9$, —SR$_8$, —S(=O)R$_8$, —S(=O)$_2$R$_8$, N(R$_9$)$_2$, tetrazolyl, —NHS(=O)$_2$R$_8$, —S(=O)$_2$N(R$_9$)$_2$, —C(O)NHS(=O)$_2$R$_8$, —S(=O)$_2$NHC(O)R$_9$, —C(=O)N(R$_9$)$_2$, NR$_9$C(O)R$_9$, C(R$_9$)$_2$C(=O)N(R$_9$)$_2$—C(=NR$_{10}$)N(R$_9$)$_2$, —NR$_9$C(=NR$_{10}$)N(R$_9$)$_2$, —NR$_9$C(=CR$_{10}$)N(R$_9$)$_2$, -L$_5$-(substituted or unsubstituted alkyl), -L$_5$-(substituted or unsubstituted alkenyl), -L$_5$-(substituted or unsubstituted heteroaryl), or -L$_5$-(substituted or unsubstituted aryl), wherein L$_5$ is —NHC(O)O, —NHC(O)NH—, —OC(O)O—, —OC(O)NH—, —NHC(O), —C(O)NH, —C(O)O, or —OC(O);

or G$_6$ is W-G$_7$, wherein W is (substituted or unsubstituted heterocycle) or a (substituted or unsubstituted heteroaryl) and G$_7$ is H, halogen, CN, NO$_2$, N$_3$, CF$_3$, OCF$_3$, C$_1$-C$_6$ alkyl, C$_3$-C$_6$ cycloalkyl, —C$_1$-C$_6$ fluoroalkyl, tetrazolyl, —NHS(=O)$_2$R$_8$, S(=O)$_2$N(R$_9$)$_2$, OH, —OR$_8$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, or —S(=O)$_2$R$_8$, -L$_5$-(substituted or unsubstituted alkyl), -L$_5$-(substituted or unsubstituted alkenyl), -L$_5$-(substituted or unsubstituted heteroalkyl), -L$_5$-(substituted or unsubstituted heteroaryl), -L$_5$-(substituted or unsubstituted heterocycle), or -L$_5$-(substituted or unsubstituted aryl), wherein L$_5$ is a bond, —O—, C(=O), S, S(=O), S(=O)$_2$, —NH, —NHC(O)O, —NHC(O)NH—, —OC(O)O—, —OC(O)NH—, —NHC(O), —C(O)NH, —C(O)O, or —OC(O); provided that when L$_{10}$ is phenyl or thiophenyl, Y is -(substituted or unsubstituted heteroaryl), -(substituted or unsubstituted aryl), and Z is [C(R$_2$)$_2$]$_n$C(R$_1$)$_2$O, then G$_6$ is W-G$_7$; and R$_{12}$ is H, (substituted or unsubstituted C$_1$-C$_6$ alkyl), (substituted or unsubstituted C$_3$-C$_6$ cycloalkyl).

For any and all of the embodiments (such as, e.g. Formula (G), Formula (G-I), and Formula (G-II)), substituents are selected from among a list of alternatives. For example, in one embodiment, the non-aromatic heterocycle of Y is selected from quinolizines, dioxines, piperidines, morpholines, thiazines, tetrahydropyridines, piperazines, oxazinanones, dihydropyrroles, dihydroimidazoles, tetrahydrofurans, dihydrooxazoles, oxiranes, pyrrolidines, pyrazolidines, dihydrothiophenones, imidazolidinones, pyrrolidinones, dihydrofuranones, dioxolanones, thiazolidines, piperidinones, tetrahydronaphthalenes, tetrahydroquinolines, tetrahydrothiophenes, and thiazepanes.

In further embodiments, the non-aromatic heterocycle of Y is selected from the group consisting of the following structures:

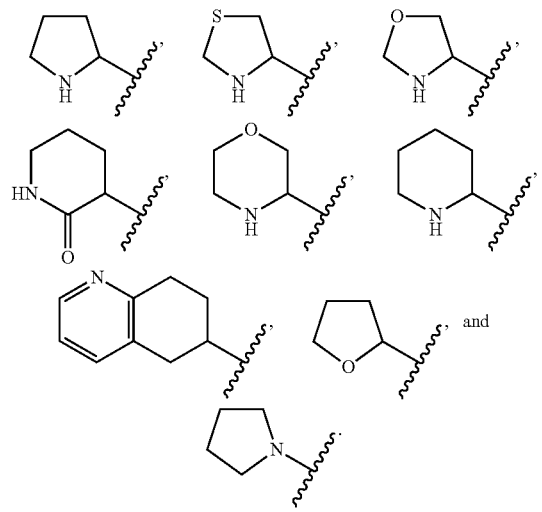

By way of example only, the non-aromatic heterocycle of Y is selected from

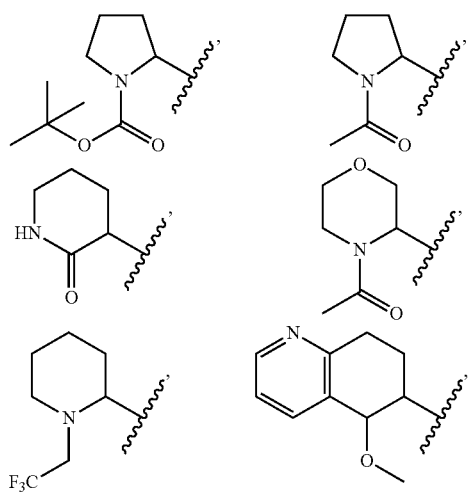

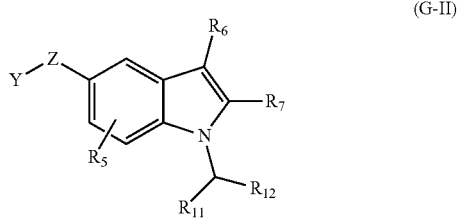

In a further or alternative embodiment, the "G" group (e.g. G$_1$, G$_5$, G$_6$, G$_7$) is any group that is used to tailor the physical and biological properties of the molecule. Such tailoring/modifications are achieved using groups which modulate acidity, basicity, lipophilicity, solubility and other physical properties of the molecule. The physical and biological properties modulated by such modifications to "G" include, by way of example only, solubility, in vivo absorption, and in vivo metabolism. In addition, in vivo metabolism may include, by way of example only, controlling in vivo PK properties, off-target activities, potential toxicities associated with cypP450 interactions, drug-drug interactions, and the like. Further, modifications to "G" allow for the tailoring of the in vivo efficacy of the compound through the modulation of, by way of example, specific and non-specific protein binding to plasma proteins and lipids and tissue distribution in vivo. Additionally, such tailoring/modifications to "G" allow for the design of compounds selective for 5-lipoxygenase-activating protein over other proteins.

In further or alternative embodiments, "G" is L$_{20}$-Q, wherein L$_{20}$ is an enzymatically cleavable linker and Q is a drug, or an affinity moiety. In further or alternative embodiments, the drug includes, by way of example only, leukotriene receptor antagonists and anti-inflammatory agents. In further or alternative embodiments, the leukotriene receptor antagonists include, but are not limited to, CysLT1/CysLT2 dual antagonists and CysLT1 antagonists. In further or alternative embodiments, the affinity moiety allow for site specific binding and include, but are not limited to, antibodies, antibody fragments, DNA, RNA, siRNA, and ligands.

Formula (G-II) is as follows:

(G-II)

wherein,

Z is selected from N(R$_1$), S(O)$_m$, CR$_1$=CR$_1$, C≡C—, C(R$_1$)$_2$[C(R$_2$)$_2$]$_n$, [C(R$_2$)$_2$]$_n$C(R$_1$)$_2$O, OC(R$_1$)$_2$[C(R$_2$)$_2$]$_n$, [C(R$_2$)$_2$]$_n$C(R$_1$)$_2$S(O)$_m$, S(O)$_m$C(R$_1$)$_2$[C(R$_2$)$_2$]$_n$, [C(R$_2$)$_2$]$_n$C(R$_1$)$_2$NR$_1$, NR$_1$C(R$_1$)$_2$[C(R$_2$)$_2$]$_n$, [C(R$_2$)$_2$]$_n$O[C(R$_1$)$_2$]$_n$, [C(R$_1$)$_2$]$_n$O[C(R$_2$)$_2$]$_n$, —C(O)NR$_2$—, —NR$_2$C(O)—, —NR$_2$C(O)O—, —OC(O)NR$_2$—, —S(O)$_2$NR$_2$—, —CR$_1$=N—N—, NR$_2$C(O)NR$_2$—, —OC(O)O—, S(O)$_2$NR$_2$, or —NR$_2$S(O)$_2$—, wherein each R$_1$ is independently H, CF$_3$, or an optionally substituted lower alkyl and two R$_1$ on the same carbon may join to form a carbonyl (=O); and each R$_2$ is independently H, OH, OMe, CF$_3$, or an optionally substituted lower alkyl and two R$_2$ on the same carbon may join to form a carbonyl (=O); m is 0, 1 or 2; each n is independently 0, 1, 2, or 3;

Y is -$L_1$-(substituted or unsubstituted aryl); -$L_1$-(substituted or unsubstituted heteroaryl); -$L_1$-(substituted or unsubstituted non-aromatic heterocycle), provided that when the heteroatom is directly bound to Z, the non-aromatic heterocycle is substituted; where $L_1$ is a bond, a substituted or unsubstituted alkyl, substituted or unsubstituted alkenyl, substituted or unsubstituted alkynyl, a substituted or unsubstituted heterocycle, a substituted or unsubstituted heteroaryl, a substituted or unsubstituted cycloalkyl, or substituted or unsubstituted aryl, —C(O), C($R_8$)(OH), C($R_8$)(OMe), C(=NOH), C(=NO$R_{4b}$), C(=O)NH, C(=O)N$R_{4b}$, —NHC(=O), N$R_{4b}$C(=O), S, S(=O), S(=O)$_2$, —NHC(=O)NH, or N$R_{4b}$C(=O)N$R_{4b}$; where each substituent on Y or Z is ($L_s R_s$)$_j$, wherein each $L_s$ is independently selected from a bond, —O—, —C(=O)—, —S—, —S(=O)—, —S(=O)$_2$—, —NHC(O)—, —C(O)NH—, S(=O)$_2$NH—, —NHS(=O)$_2$, —OC(O)NH—, —NHC(O)O—, —OC(O)O—, —NHC(O)NH—, —C(O)O—, —OC(O)—, $C_1$-$C_6$ alkyl, $C_2$-$C_6$ alkenyl, —$C_1$-$C_6$ fluoroalkyl, heteroaryl, aryl, or heterocycle; and each $R_s$ is independently selected from H, halogen, —N($R_4$)$_2$, —CN, —NO$_2$, $N_3$, —S(=O)$_2$NH$_2$, lower alkyl, lower cycloalkyl, —$C_1$-$C_6$ fluoroalkyl, heteroaryl, or heteroalkyl; where j is 0, 1, 2, 3, or 4;

each $R_3$ is independently selected from H, —S(=O)$_2$$R_8$, —S(=O)$_2$NH$_2$—C(O)$R_8$, —CN, —NO$_2$, heteroaryl, or heteroalkyl;

each $R_{3b}$ is independently selected from substituted or unsubstituted lower alkyl, substituted or unsubstituted lower cycloalkyl, substituted or unsubstituted phenyl or benzyl;

each $R_4$ is independently selected from H, substituted or unsubstituted lower alkyl, substituted or unsubstituted lower cycloalkyl, phenyl or benzyl; or two $R_4$ groups can together form a 5-, 6-, 7-, or 8-membered heterocyclic ring; or $R_{3b}$ and $R_4$ can together form a 5-, 6-, 7-, or 8-membered heterocyclic ring;

each $R_{4b}$ is independently selected from H, substituted or unsubstituted lower alkyl, substituted or unsubstituted lower cycloalkyl, substituted or unsubstituted aryl or substituted or unsubstituted benzyl; substituted or unsubstituted heteroaryl, substituted or unsubstituted heterocycle;

$R_6$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(O), —CH(OH), -(substituted or unsubstituted $C_1$-$C_6$ alkyl), or -(substituted or unsubstituted $C_2$-$C_6$ alkenyl);

$R_7$ is $L_3$-X-$L_4$-$G_1$, wherein, $L_3$ is a bond, or substituted or unsubstituted alkyl;

X is a bond, O, —C(=O), —C$R_9$(O$R_9$), S, —S(=O), —S(=O)$_2$, —N$R_9$, —N$R_9$C(O), —C(O)N$R_9$, —N$R_9$C(O)N$R_9$—, or aryl;

$L_4$ is a bond, or substituted or unsubstituted alkyl;

$G_1$ is H, tetrazolyl, —NHS(=O)$_2$$R_8$, S(=O)$_2$N($R_9$)$_2$, —O$R_9$, —C(=O)CF$_3$, —C(O)NHS(=O)$_2$$R_8$, —S(=O)$_2$NHC(O)$R_9$, CN, N($R_9$)$_2$, —N($R_9$)C(O)$R_9$, —C(=N$R_{10}$)N($R_9$)$_2$, —N$R_9$C(=N$R_{10}$)N($R_9$)$_2$, —N$R_9$C(=C$R_{10}$)N($R_9$)$_2$, —C(O)N$R_9$C(=N$R_{10}$)N($R_9$)$_2$, —C(O)N$R_9$C(=C$R_{10}$)N($R_9$)$_2$, —CO$_2$$R_9$, —C(O)$R_9$, —CON($R_9$)$_2$, —S$R_8$, —S(=O)$R_8$, —S(=O)$_2$$R_8$, -$L_5$-(substituted or unsubstituted alkyl), -$L_5$-(substituted or unsubstituted alkenyl), -$L_5$-(substituted or unsubstituted heteroaryl), or -$L_5$-(substituted or unsubstituted aryl), wherein $L_5$ is —OC(O)O—, —NHC(O)NH—, —NHC(O)O, —O(O)CNH—, —NHC(O), —C(O)NH, —C(O)O, or —OC(O);

or $G_1$ is W-$G_5$, where W is a substituted or unsubstituted aryl, substituted or unsubstituted heterocycle or substituted or unsubstituted heteroaryl and $G_5$ is H, tetrazolyl, —NHS(=O)$_2$$R_8$, S(=O)$_2$N($R_9$)$_2$, OH, —O$R_8$, —C(=O)CF$_3$, —C(O)NHS(=O)$_2$$R_8$, —S(=O)$_2$NHC(O)$R_9$, CN, N($R_9$)$_2$, —N($R_9$)C(O)$R_9$, —C(=N$R_{10}$)N($R_9$)$_2$, —N$R_9$C(=N$R_{10}$)N($R_9$)$_2$, —N$R_9$C(=C$R_{10}$)N($R_9$)$_2$, —C(O)N$R_9$C(=N$R_{10}$)N($R_9$)$_2$, —C(O)N$R_9$C(=C$R_{10}$)N($R_9$)$_2$, —CO$_2$$R_9$, —C(O)$R_9$, —CON($R_9$)$_2$, —S$R_8$, —S(=O)$R_8$, or —S(=O)$_2$$R_8$;

each $R_8$ is independently selected from substituted or unsubstituted lower alkyl, substituted or unsubstituted lower cycloalkyl, phenyl or benzyl;

each $R_9$ is independently selected from H, substituted or unsubstituted lower alkyl, substituted or unsubstituted lower cycloalkyl, phenyl or benzyl; or two $R_9$ groups can together form a 5-, 6-, 7-, or 8-membered heterocyclic ring; or $R_8$ and $R_9$ can together form a 5-, 6-, 7-, or 8-membered heterocyclic ring and each $R_{10}$ is independently selected from H, —S(=O)$_2$$R_8$, —S(=O)$_2$NH$_2$—C(O)$R_8$, —CN, —NO$_2$, heteroaryl, or heteroalkyl;

$R_5$ is H, halogen, —$N_3$, —CN, —ONO$_2$, -$L_6$-(substituted or unsubstituted $C_1$-$C_6$ alkyl), -$L_6$-(substituted or unsubstituted $C_2$-$C_6$ alkenyl), -$L_6$-(substituted or unsubstituted heteroaryl), or -$L_6$-(substituted or unsubstituted aryl), wherein $L_6$ is a bond, O, S, —S(=O), S(=O)$_2$, NH, C(O), —NHC(O)O, —OC(O)NH, —NHC(O), —NHC(O)NH—, or —C(O)NH;

$R_{11}$ is $L_7$-$L_{10}$-$G_6$, wherein $L_7$ is a bond, —O—, —S—, —S(=O), —S(=O)$_2$, —NH, —C(O), —C(O)NH, —NHC(O), (substituted or unsubstituted $C_1$-$C_6$ alkyl), or (substituted or unsubstituted $C_2$-$C_6$ alkenyl);

$L_{10}$ is a bond, (substituted or unsubstituted alkyl), (substituted or unsubstituted cycloalkyl), (substituted or unsubstituted cycloalkenyl), (substituted or unsubstituted heteroaryl), (substituted or unsubstituted aryl), or (substituted or unsubstituted heterocycle);

$G_6$ is H, CN, SCN, $N_3$, NO$_2$, halogen, O$R_9$, —C(=O)CF$_3$, —C(=O)$R_9$, —C(=O)O$R_9$, —S$R_8$, —S(=O)$R_8$, —S(=O)$_2$$R_8$, N($R_9$)$_2$, tetrazolyl, —NHS(=O)$_2$$R_8$, —S(=O)$_2$N($R_9$)$_2$, —C(O)NHS(=O)$_2$$R_8$, —S(=O)$_2$NHC(O)$R_9$, —C(=O)N($R_9$)$_2$, N$R_9$C(O)$R_9$, C($R_9$)$_2$C(=O)N($R_9$)$_2$—C(=N$R_{10}$)N($R_9$)$_2$, —N$R_9$C(=N$R_{10}$)N($R_9$)$_2$, —N$R_9$C(=C$R_{10}$)N($R_9$)$_2$, -$L_5$-(substituted or unsubstituted alkyl), -$L_5$-(substituted or unsubstituted alkenyl), -$L_5$-(substituted or unsubstituted heteroaryl), or -$L_5$-(substituted or unsubstituted aryl), wherein $L_5$ is —NHC(O)O, —NHC(O)NH—, —OC(O)O—, —OC(O)NH—, —NHC(O), —C(O)NH, —C(O)O, or —OC(O);

or $G_6$ is W-$G_7$, wherein W is (substituted or unsubstituted heterocycle) or a (substituted or unsubstituted heteroaryl) and $G_7$ is H, halogen, CN, NO$_2$, $N_3$, CF$_3$, OCF$_3$, $C_1$-$C_6$ alkyl, $C_3$-$C_6$ cycloalkyl, —$C_1$-$C_6$ fluoroalkyl, tetrazolyl, —NHS(=O)$_2$$R_8$, S(=O)$_2$N($R_9$)$_2$, OH, —O$R_8$, —C(=O)CF$_3$, —C(O)NHS(=O)$_2$$R_8$, —S(=O)$_2$NHC(O)$R_9$, CN, N($R_9$)$_2$, —N($R_9$)C(O)$R_9$, —C(=N$R_{10}$)N($R_9$)$_2$, —N$R_9$C(=N$R_{10}$)N($R_9$)$_2$, —N$R_9$C(=C$R_{10}$)N($R_9$)$_2$, —C(O)N$R_9$C(=N$R_{10}$)N($R_9$)$_2$, —C(O)N$R_9$C(=C$R_{10}$)N($R_9$)$_2$, —CO$_2$$R_9$, —C(O)$R_9$, —CON($R_9$)$_2$, —S$R_8$, —S(=O)$R_8$, or —S(=O)$_2$$R_8$, -$L_5$-(substituted or unsubstituted alkyl), -$L_5$-(substituted or unsubstituted alkenyl), -$L_5$-(substituted or unsubstituted heteroalkyl), -$L_5$-(substituted or unsubstituted heteroaryl), -$L_5$-(substituted or unsubstituted heterocycle), or -$L_5$-(substituted or unsubstituted aryl), wherein $L_5$ is a bond, —O—, C(=O), S, S(=O), S(=O)$_2$, —NH, —NHC(O)O, —NHC(O)NH—, —OC(O)O—, —OC(O)NH—, —NHC(O), —C(O)NH, —C(O)O, or —OC(O);

provided that when $L_{10}$ is phenyl or thiophenyl, Y is -(substituted or unsubstituted heteroaryl), -(substituted or unsubstituted aryl), and Z is $[C(R_2)_2]_nC(R_1)_2O$, then $G_6$ is W-$G_7$; and $R_{12}$ is H, (substituted or unsubstituted $C_1$-$C_6$ alkyl), (substituted or unsubstituted $C_3$-$C_6$ cycloalkyl).

For any and all of the embodiments (such as, e.g. Formula (G), Formula (G-I), and Formula (G-II)), substituents can be selected from among from a subset of the listed alternatives. For example, in some embodiments, Z is $[C(R_2)_2]_nC(R_1)_2O$. In further or alternative embodiments, Y is -(substituted or unsubstituted heteroaryl), -(substituted or unsubstituted aryl) and $G_6$ is W-$G_7$. In further or alternative embodiments, Y is -$L_1$-(substituted or unsubstituted alkyl), -$L_1$-(substituted or unsubstituted cycloalkyl), -$L_1$-(substituted or unsubstituted heterocycle), -$L_1$-(substituted or unsubstituted heteroaryl), -$L_1$-(substituted or unsubstituted non-aromatic heterocycle) provided that when the heteroatom is directly bound to Z, the non-aromatic heterocycle is substituted; -$L_1$-(substituted or unsubstituted aryl). In further or alternative embodiments, Y is a heteroaryl selected from the group consisting of pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

In further or alternative embodiments, $R_6$ is $L_2$-(substituted or unsubstituted alkyl), or $L_2$-(substituted or unsubstituted cycloalkyl), $L_2$-(substituted or unsubstituted aryl), where $L_2$ is a bond, O, S, —S(O)$_2$, —C(O), —CH(OH), or substituted or unsubstituted alkyl. In further or alternative embodiments, $R_7$ is $L_3$-X-$L_4$-$G_1$; wherein, $L_3$ is a bond; and X is a bond, O, —CR$_9$(OR$_9$), S, —S(=O), —S(=O)$_2$, —NR$_9$, —NR$_9$C(O), —C(O)NR$_9$. In further or alternative embodiments, $G_1$ is tetrazolyl, —NHS(=O)$_2$R$_8$, S(=O)$_2$N(R$_9$)$_2$, —OR$_9$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, —S(=O)$_2$R$_8$.

In further or alternative embodiments, the non-aromatic heterocycle of group Y can be selected from a quinolizine, a dioxine, a piperidine, a morpholine, a thiazine, a tetrahydropyridine, a piperazine, a oxazinanone, a dihydropyrrole, a dihydroimidazole, a tetrahydrofuran, a dihydrooxazole, an oxirane, a pyrrolidine, a pyrazolidine, a dihydrothiophenone, an imidazolidinone, a pyrrolidinone, a dihydrofuranone, a dioxolanone, a thiazolidine, a piperidinone, a tetrahydronaphthalene, a tetrahydroquinoline, a tetrahydrothiophene, and a thiazepane. In further or alternative embodiments, the non-aromatic heterocycle of group Y can be selected from the group consisting of:

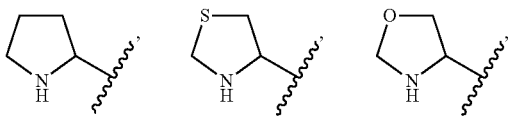

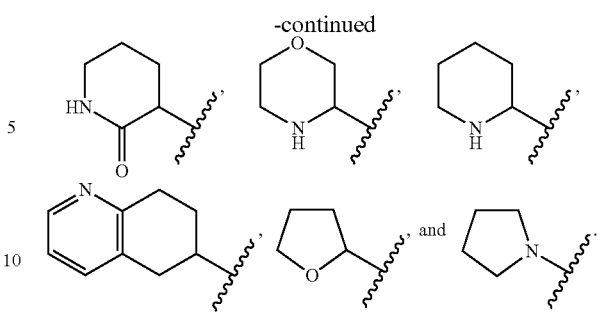

In further or alternative embodiments, "G" (e.g. $G_1$, $G_5$, $G_6$, $G_7$) is $L_{20}$-Q, wherein $L_{20}$ is an enzymatically cleavable linker and Q is a drug, or an affinity moiety. In further or alternative embodiments, the drug includes, by way of example only, leukotriene receptor antagonists and anti-inflammatory agents. In further or alternative embodiments, the leukotriene receptor antagonists include, but are not limited to, CysLT1/CysLT2 dual antagonists and CysLT1 antagonists. In further or alternative embodiments, the affinity moiety allows for site specific binding and include, but are not limited to, antibodies, antibody fragments, DNA, RNA, siRNA, and ligands.

In a further or alternative embodiment, the "G" group (e.g. $G_1$, $G_5$, $G_6$, $G_7$) of any of Formula (G), Formula (G-I), or Formula (G-II), is any group that is used to tailor the physical and biological properties of the molecule. Such tailoring/modifications are achieved using groups which modulate acidity, basicity, lipophilicity, solubility and other physical properties of the molecule. The physical and biological properties modulated by such modifications to "G" include, by way of example only, solubility, in vivo absorption, and in vivo metabolism. In addition, in vivo metabolism may include, by way of example only, controlling in vivo PK properties, off-target activities, potential toxicities associated with cypP450 interactions, drug-drug interactions, and the like. Further, modifications to "G" allow for the tailoring of the in vivo efficacy of the compound through the modulation of, by way of example, specific and non-specific protein binding to plasma proteins and lipids and tissue distribution in vivo. Additionally, such tailoring/modifications to "G" allow for the design of compounds selective for 5-lipoxygenase-activating protein over other proteins. In further or alternative embodiments, "G" is $L_{20}$-Q, wherein $L_{20}$ is an enzymatically cleavable linker and Q is a drug, or an affinity moiety. In further or alternative embodiments, the drug includes, by way of example only, leukotriene receptor antagonists and anti-inflammatory agents. In further or alternative embodiments, the leukotriene receptor antagonists include, but are not limited to, CysLT1/CysLT2 dual antagonists and CysLT1 antagonists. In further or alternative embodiments, the affinity moiety allows for site specific binding and include, but are not limited to, antibodies, antibody fragments, DNA, RNA, siRNA, and ligands.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Formula (G) is as follows:

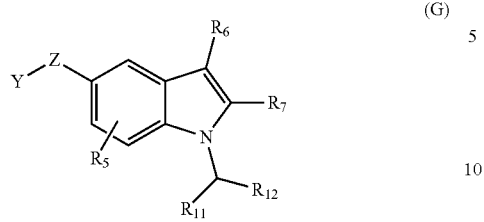

wherein,

Z is selected from [C(R$_1$)$_2$]$_m$[C(R$_2$)$_2$]$_n$, [C(R$_2$)$_2$]$_n$[C(R$_1$)]$_m$O, O[C(R$_1$)]$_m$[C(R$_2$)$_2$]$_n$, [C(R$_2$)$_2$]$_n$O[C(R$_1$)$_2$]$_n$, or [C(R$_1$)$_2$]$_n$O[C(R$_2$)$_2$]$_n$, wherein each R$_1$ is independently H, CF$_3$, or an optionally substituted lower alkyl and two R$_1$ on the same carbon may join to form a carbonyl (=O); and each R$_2$ is independently H, OH, OMe, CF$_3$, or an optionally substituted lower alkyl and two R$_2$ on the same carbon may join to form a carbonyl (=O); m is 0, 1 or 2; each n is independently 0, 1, 2, or 3;

Y is H or -(substituted or unsubstituted aryl); or -(substituted or unsubstituted heteroaryl);

where each substituent on Y or Z is (L$_s$R$_s$)$_j$, wherein each L$_s$ is independently selected from a bond, —O—, —C(=O)—, —S—, —S(=O)—, —S(=O)$_2$—, —NHC(O)—, —C(O)NH—, S(=O)$_2$NH—, —NHS(=O)$_2$—, —OC(O)NH—, —NHC(O)O—, —OC(O)O—, —NHC(O)NH—, —C(O)O—, —OC(O)—, substituted or unsubstituted C$_1$-C$_6$ alkyl, C$_2$-C$_6$ alkenyl, —C$_1$-C$_6$ fluoroalkyl, substituted or unsubstituted heteroaryl, substituted or unsubstituted aryl, or substituted or unsubstituted heterocycle; and each R$_s$ is independently selected from H, halogen, —N(R$_4$)$_2$, —CN, —NO$_2$, N$_3$, —S(=O)$_2$NH$_2$, substituted or unsubstituted lower alkyl, substituted or unsubstituted lower cycloalkyl, —C$_1$-C$_6$ fluoroalkyl, substituted or unsubstituted aryl, substituted or unsubstituted heteroaryl, or substituted or unsubstituted heteroalkyl; where j is 0, 1, 2, 3, or 4;

R$_6$ is H, L$_2$-(substituted or unsubstituted alkyl), L$_2$-(substituted or unsubstituted cycloalkyl), L$_2$-(substituted or unsubstituted alkenyl), L$_2$-(substituted or unsubstituted cycloalkenyl), L$_2$-(substituted or unsubstituted heterocycle), L$_2$-(substituted or unsubstituted heteroaryl), or L$_2$-(substituted or unsubstituted aryl), where L$_2$ is a bond, O, S, —S(=O), —S(=O)$_2$, C(O), —CH(OH), -(substituted or unsubstituted C$_1$-C$_6$ alkyl), or -(substituted or unsubstituted C$_2$-C$_6$ alkenyl);

R$_7$ is L$_3$-X-L$_4$-G$_1$, wherein,

L$_3$ is a substituted or unsubstituted alkyl;

X is a bond, O, —C(=O), —CR$_9$(OR$_9$), S, —S(=O), —S(=O)$_2$, —NR$_9$, —NR$_9$C(O), —C(O)NR$_9$, —NR$_9$C(O)NR$_9$—;

L$_4$ is a bond, or a substituted or unsubstituted alkyl;

G$_1$ is H, tetrazolyl, —NHS(=O)$_2$R$_8$, S(=O)$_2$N(R$_9$)$_2$, —OR$_9$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, —S(=O)$_2$R$_8$, -L$_5$-(substituted or unsubstituted alkyl), -L$_5$-(substituted or unsubstituted alkenyl), -L$_5$-(substituted or unsubstituted heteroaryl), or -L$_5$-(substituted or unsubstituted aryl), wherein L$_5$ is —OC(O)O—, —NHC(O)NH—, —NHC(O)O, —O(O)CNH—, —NHC(O), —C(O)NH, —C(O)O, or —OC(O);

or G$_1$ is W-G$_5$, where W is a substituted or unsubstituted aryl, substituted or unsubstituted heterocycle or substituted or unsubstituted heteroaryl and G$_5$ is H, tetrazolyl, —NHS(=O)$_2$R$_8$, S(=O)$_2$N(R$_9$)$_2$, OH, —OR$_8$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, or —S(=O)$_2$R$_8$;

each R$_8$ is independently selected from substituted or unsubstituted lower alkyl, substituted or unsubstituted lower cycloalkyl, substituted or unsubstituted phenyl or substituted or unsubstituted benzyl;

each R$_9$ is independently selected from H, substituted or unsubstituted lower alkyl, substituted or unsubstituted lower cycloalkyl, substituted or unsubstituted phenyl or substituted or unsubstituted benzyl; or two R$_9$ groups can together form a 5-, 6-, 7-, or 8-membered heterocyclic ring; or R$_8$ and R$_9$ can together form a 5-, 6-, 7-, or 8-membered heterocyclic ring and each R$_{10}$ is independently selected from H, —S(=O)$_2$R$_8$, —S(=O)$_2$NH$_2$—C(O)R$_8$, —CN, —NO$_2$, heteroaryl, or heteroalkyl;

R$_5$ is H, halogen, substituted or unsubstituted C$_1$-C$_6$ alkyl, substituted or unsubstituted O—C$_1$-C$_6$ alkyl;

R$_{11}$ is L$_7$-L$_{10}$-G$_6$, wherein L$_7$ is a bond, —C(O), —C(O)NH, —NHC(O), or (substituted or unsubstituted C$_1$-C$_6$ alkyl); L$_{10}$ is a bond, (substituted or unsubstituted alkyl), (substituted or unsubstituted cycloalkyl), (substituted or unsubstituted heteroaryl), (substituted or unsubstituted aryl), or (substituted or unsubstituted heterocycle);

G$_6$ is OR$_9$, —C(=O)R$_9$, —C(=O)OR$_9$, —SR$_8$, —S(=O)R$_8$, —S(=O)$_2$R$_8$, N(R$_9$)$_2$, tetrazolyl, —NHS(=O)$_2$R$_8$, —S(=O)$_2$N(R$_9$)$_2$, —C(O)NHS(=O)$_2$R$_8$, —S(=O)$_2$NHC(O)R$_9$, —C(=O)N(R$_9$)$_2$, NR$_9$C(O)R$_9$, C(R$_9$)$_2$C(=O)N(R$_9$)$_2$—C(=NR$_{10}$)N(R$_9$)$_2$, —NR$_9$C(=NR$_{10}$)N(R$_9$)$_2$, —NR$_9$C(=CR$_{10}$)N(R$_9$)$_2$, -L$_5$-(substituted or unsubstituted alkyl), -L$_5$-(substituted or unsubstituted alkenyl), -L$_5$-(substituted or unsubstituted heteroaryl), or -L$_5$-(substituted or unsubstituted aryl), wherein L$_5$ is —O—, C(=O), S, S(=O), S(=O)$_2$, —NH, —NHC(O)O, —NHC(O)NH—, —OC(O)O—, —OC(O)NH—, —NHC(O), —C(O)NH, —C(O)O, or —OC(O)

or G$_6$ is W-G$_7$, wherein W is (substituted or unsubstituted heterocycle), (substituted or unsubstituted aryl) or a (substituted or unsubstituted heteroaryl) and G$_7$ is H, halogen, CN, NO$_2$, N$_3$, CF$_3$, OCF$_3$, C$_1$-C$_6$ alkyl, C$_3$-C$_6$ cycloalkyl, —C$_1$-C$_6$ fluoroalkyl, tetrazolyl, —NHS(=O)$_2$R$_8$, S(=O)$_2$N(R$_9$)$_2$, OH, —OR$_8$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, or —S(=O)$_2$R$_8$, -L$_5$-(substituted or unsubstituted alkyl), -L$_5$-(substituted or unsubstituted alkenyl), -L$_5$-(substituted or unsubstituted heteroalkyl), -L$_5$-(substituted or unsubstituted heteroaryl), -L$_5$-(substituted or unsubstituted heterocycle), or -L$_5$-(substituted or unsubstituted aryl), wherein $L_5$ is a bond, —O—, C(=O), S, S(=O), S(=O)$_2$, —NH, —NHC(O)O, —NHC(O)NH—, —OC(O)O—, —OC(O)NH—, —NHC(O), —C(O)NH, —C(O)O, or —OC(O);

provided that $R_{11}$ comprises at least one (unsubstituted or substituted) aromatic moiety and at least one (unsubstituted or substituted) cyclic moiety, wherein the (unsubstituted or substituted) cyclic moiety is a (unsubstituted or substituted) heterocyclic group or a (unsubstituted or substituted) heteroaryl group and $R_{11}$ is not a thienyl-phenyl group;

$R_{12}$ is H, (substituted or unsubstituted $C_1$-$C_6$ alkyl), (substituted or unsubstituted $C_3$-$C_6$ cycloalkyl);

or active metabolite, or solvate, or pharmaceutically acceptable salt, or a pharmaceutically acceptable prodrug thereof.

For any and all of the embodiments (such as, e.g. Formula (G), Formula (G-I), and Formula (G-II)), substituents can be selected from among from a subset of the listed alternatives. For example, in some embodiments, Z is $[C(R_2)_2]_nC(R_1)_2O$.

In further or alternative embodiments, Y is -(substituted or unsubstituted heteroaryl) or -(substituted or unsubstituted aryl) and $G_6$ is W-$G_7$.

In further or alternative embodiments, Y is -(substituted or unsubstituted heteroaryl).

In further or alternative embodiments, Y is selected from the group consisting of pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, imidazo[1,2-a]pyridinyl and furopyridinyl, wherein Y is substituted or unsubstituted.

In further or alternative embodiments, Y is selected from the group consisting of pyridinyl or quinolinyl, wherein Y is substituted or unsubstituted.

In further or alternative embodiments, $R_6$ is $L_2$-(substituted or unsubstituted alkyl), or $L_2$-(substituted or unsubstituted cycloalkyl), $L_2$-(substituted or unsubstituted aryl), where $L_2$ is a bond, O, S, —S(O)$_2$, —C(O), or substituted or unsubstituted alkyl.

In further or alternative embodiments, X is a bond, O, —C(=O), —CR$_9$(OR$_9$), S, —S(=O), —S(=O)$_2$, —NR$_9$, —NR$_9$C(O), —C(O)NR$_9$.

In further or alternative embodiments, $G_1$ is tetrazolyl, —NHS(=O)$_2$R$_8$, S(=O)$_2$N(R$_9$)$_2$, —OR$_9$, —C(=O)CF$_3$, —C(O)NHS(=O)$_2$R$_8$, —S(=O)$_2$NHC(O)R$_9$, CN, N(R$_9$)$_2$, —N(R$_9$)C(O)R$_9$, —C(=NR$_{10}$)N(R$_9$)$_2$, —NR$_9$C(=NR$_{10}$)N(R$_9$)$_2$, —NR$_9$C(=CR$_{10}$)N(R$_9$)$_2$, —C(O)NR$_9$C(=NR$_{10}$)N(R$_9$)$_2$, —C(O)NR$_9$C(=CR$_{10}$)N(R$_9$)$_2$, —CO$_2$R$_9$, —C(O)R$_9$, —CON(R$_9$)$_2$, —SR$_8$, —S(=O)R$_8$, or —S(=O)$_2$R$_8$.

In further or alternative embodiments, $L_3$ is unsubstituted alkyl; X is a bond; $L_4$ is a bond; and $G_1$ is —C(O)OR$_9$.

In further or alternative embodiments, $R_9$ is H or unsubstituted alkyl.

In further or alternative embodiments, $L_{10}$ is a substituted or unsubstituted aryl substituted or unsubstituted heteroaryl and $G_6$ is W-$G_7$ wherein W is substituted or unsubstituted heteroaryl, substituted or unsubstituted heterocycle.

In further or alternative embodiments, $L_{10}$ is a substituted or unsubstituted aryl.

In further or alternative embodiments, $L_3$ is unsubstituted alkyl; X is a bond; $L_4$ is a bond; and $G_1$ is —OR$_9$.

In further or alternative embodiments, $G_1$ is W-$G_5$, where W is a substituted or unsubstituted heterocycle or substituted or unsubstituted heteroaryl.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further embodiments of Formula (G), Formula (G-I) and Formula (G-II), include, but are not limited to, compounds shown in FIGS. 8-11 and in Tables 1-4.

TABLE 1

N-(aryl-heteroaryl) indoles acid replacements

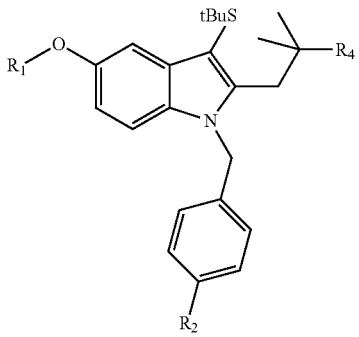

| Compound # | $R_1$ | $R_2$ | $R_4$ | M + H |
|---|---|---|---|---|
| 1-1 | Pyridine-2-ylmethyl | pyridine-2-yl | C(O)NH$_2$ | 579 |
| 1-2 | Pyridine-2-ylmethyl | 2-methoxypyridin-5-yl | CO$_2$Et | 638 |
| 1-3 | Pyridine-2-ylmethyl | 2-methoxypyridin-5-yl | C(O)(CH$_2$)$_6$OH | see Exp. |
| 1-4 | Pyridine-2-ylmethyl | pyridin-2-yl | OH | 552 |

TABLE 1-continued

N-(aryl-heteroaryl) indoles acid replacements

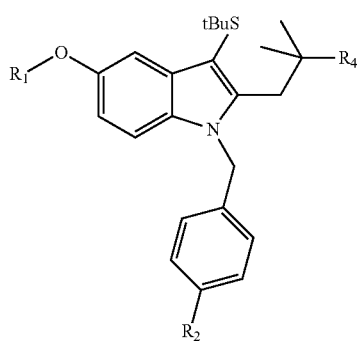

| Compound # | R₁ | R₂ | R₄ | M + H |
|---|---|---|---|---|
| 1-5 | Pyridine-2-ylmethyl | pyridin-3-yl | OH | 552 |
| 1-6 | Pyridine-2-ylmethyl | thiazol-2-yl | OH | 558 |
| 1-7 | Pyridine-2-ylmethyl | 1,3,4-oxadiazol-2-yl | OH | 543 |
| 1-8 | Pyridine-2-ylmethyl | 2-methoxypyridin-5-yl | 1,3,4-oxadiazol-2-yl | 634 |
| 1-9 | Pyridine-2-ylmethyl | 2-methoxypyridin-5-yl | 1,3,4-oxadiazol-2-ylamine | 649 |
| 1-10 | Pyridine-2-ylmethyl | 2-methoxypyridin-5-yl | N-pyrazin-2-yl-propionamide | 687 |
| 1-11 | Pyridine-2-ylmethyl | 2-methoxypyridin-5-yl | N-thiazol-2-yl-propionamide | 692 |
| 1-12 | Pyridine-2-ylmethyl | 2-methoxypyridin-5-yl | N-pyridin-3-yl-propionamide | 686 |
| 1-13 | Pyridine-2-ylmethyl | 2-methoxypyridin-5-yl | C(O)NH(CH₂CH₂NMe₂) | 680 |
| 1-14 | Pyridine-2-ylmethyl | 1,3,4-oxadiazol-2-ylamine | CH₃ | 556 |
| 1-15 | Quinolin-2-ylmethyl | 5-fluoro-pyridin-2-yl | C(O)NHC(=NH)NH₂ | 689 |

TABLE 2

N-(aryl-heteroaryl) indoles and N-(aryl-heterocycle)indoles

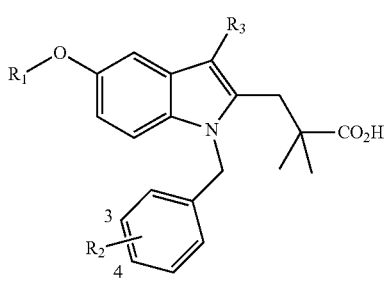

| Compound # | R₁ | position | R₂ | R₃ | M + H |
|---|---|---|---|---|---|
| 2-1 | Pyridin-2-ylmethyl | 4 | 2-thiazolyl | 2-methyl-2-propylthio | 586 |
| 2-2 | Pyridin-2-ylmethyl | 4 | 2-pyrimidinyl | 2-methyl-2-propylthio | 581 |
| 2-3 | Pyridin-2-ylmethyl | 4 | 3-pyridyl | 2-methyl-2-propylthio | 580 |
| 2-4 | Pyridin-2-ylmethyl | 4 | 4-pyrimidinyl | 2-methyl-2-propylthio | 581 |
| 2-5 | Pyridin-2-ylmethyl | 4 | 2-pyrazinyl | 2-methyl-2-propylthio | 581 |
| 2-6 | Pyridin-2-ylmethyl | 4 | 6-methoxy-3-pyridazinyl | 2-methyl-2-propylthio | 611 |

TABLE 2-continued

N-(aryl-heteroaryl) indoles and N-(aryl-heterocycle)indoles

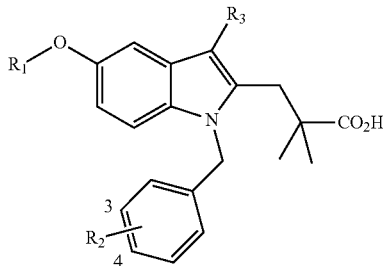

| Compound # | $R_1$ | position | $R_2$ | $R_3$ | M + H |
|---|---|---|---|---|---|
| 2-7 | Pyridin-2-ylmethyl | 4 | 2-amino-4-pyridazinyl | 2-methyl-2-propylthio | 596 |
| 2-8 | Pyridin-2-ylmethyl | 4 | 2-thiazolyl | 3,3-dimethylbutanoyl | 596 |
| 2-9 | Pyridin-2-ylmethyl | 4 | 2-thiazolyl | H | 498 |
| 2-10 | Pyridin-2-ylmethyl | 4 | 2-thiazolyl | acetyl | 501 |
| 2-11 | Pyridin-2-ylmethyl | 4 | 3 methoxy-6-pyridazinyl | H | 523 |
| 2-12 | Pyridin-2-ylmethyl | 4 | 3 methoxy-6-pyridazinyl | acetyl | 565 |
| 2-13 | Pyridin-2-ylmethyl | 4 | 3 methoxy-6-pyridazinyl | ethyl | 551 |
| 2-14 | Pyridin-2-ylmethyl | 4 | 2-thiazolyl | 3,3-dimethylbut-1-yl | 582 |
| 2-15 | Pyridin-2-ylmethyl | 4 | 2-thiazolyl | cyclopropylcarbonyl | 566 |
| 2-16 | Pyridin-2-ylmethyl | 4 | 2-thiazolyl | cyclobutylcarbonyl | 580 |
| 2-17 | Pyridin-2-ylmethyl | 4 | 3-hydroxy-6-pyridazinyl | 2-methyl-2-propylthio | 597 |
| 2-18 | Pyridin-2-ylmethyl | 4 | 4-pyridyl | 2-methyl-2-propylthio | 580 |
| 2-19 | Pyridin-2-ylmethyl | 4 | 2-methoxypyridin-5-yl | 2-methyl-2-propylthio | 610 |
| 2-20 | Pyridin-2-ylmethyl | 4 | 2-methyl-4-pyridazinyl | 2-methyl-2-propylthio | 595 |
| 2-21 | Pyridin-2-ylmethyl | 4 | 5-methyl-thiazol-2-yl | 2-methyl-2-propylthio | 600 |
| 2-22 | Pyridin-2-ylmethyl | 4 | 2-thiazolyl | cyclobutylmethyl | 566 |
| 2-23 | 2-Methylthiazol-4-yl | 4 | 2-methoxy-4-pyridazinyl | 2-methyl-2-propylthio | 631 |
| 2-24 | 2-Methylthiazol-4-yl | 4 | 2-thiazolyl | 2-methyl-2-propylthio | 606 |
| 2-25 | 2-Methylthiazol-4-yl | 4 | 2-thiazolyl | H | 518 |
| 2-26 | 2-Methylthiazol-4-yl | 4 | 2-thiazolyl | 3,3-dimethylbutanoyl | 616 |
| 2-27 | 2-Methylthiazol-4-yl | 4 | 2-methoxy-4-pyridazinyl | H | 543 |
| 2-28 | 2-Methylthiazol-4-yl | 4 | 2-methoxy-4-pyridazinyl | 3,3-dimethylbutanoyl | 641 |
| 2-29 | Pyridin-2-ylmethyl | 4 | 2-thiazolyl | ethyl | 526 |
| 2-30 | Benzothiazol-2-yl | 4 | 2-thiazolyl | 2-methyl-2-propylthio | 667 |
| 2-31 | 2-Methylthiazol-4-yl | 4 | 2-pyrimidinyl | 2-methyl-2-propylthio | 601 |
| 2-32 | Benzothiazol-2-yl | 4 | 2-pyrimidinyl | 2-methyl-2-propylthio | 637 |
| 2-33 | Pyridin-2-ylmethyl | 4 | 1-(pyridin-2-ylmethyl)-2-methyl-imidazol-4-yl | 2-methyl-2-propylthio | 674 |
| 2-34 | Pyridin-2-ylmethyl | 4 | 2,4-dimethylthiazol-5-yl | 2-methyl-2-propylthio | 614 |
| 2-35 | Pyridin-2-ylmethyl | 4 | 5-fluoro-thiazol-2-yl | 2-methyl-2-propylthio | 604 |
| 2-36 | Pyridin-2-ylmethyl | 4 | 5-trifluoromethyl-thiazol-2-yl | 2-methyl-2-propylthio | |
| 2-37 | Pyridin-2-ylmethyl | 4 | 2-methyl-thiazol-4-yl | 2-methyl-2-propylthio | |
| 2-38 | Pyridin-2-ylmethyl | 4 | 2-methyl-thiazol-5-yl | 2-methyl-2-propylthio | |
| 2-39 | Pyridin-2-ylmethyl | 4 | 4-methyl-thiazol-2-yl | 2-methyl-2-propylthio | 600 |

TABLE 2-continued

N-(aryl-heteroaryl) indoles and N-(aryl-heterocycle)indoles

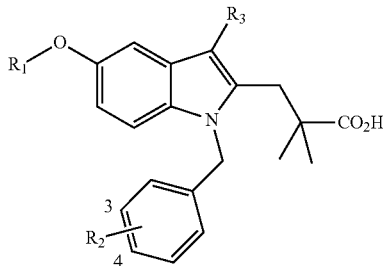

| Compound # | R₁ | position | R₂ | R₃ | M + H |
|---|---|---|---|---|---|
| 2-40 | Pyridin-2-ylmethyl | 4 | isoxazol-4-yl | 2-methyl-2-propylthio | |
| 2-41 | Pyridin-2-ylmethyl | 4 | 3,5-dimethyl-isoxazol-4-yl | 2-methyl-2-propylthio | 600 |
| 2-42 | Pyridin-2-ylmethyl | 4 | 2-methyl-imidazol-4-yl | 2-methyl-2-propylthio | |
| 2-43 | Pyridin-2-ylmethyl | 4 | 1-methyl-imidazol-5-yl | 2-methyl-2-propylthio | 583 |
| 2-44 | Pyridin-2-ylmethyl | 4 | 1-methyl-imidazol-4-yl | 2-methyl-2-propylthio | |
| 2-45 | Pyridin-2-ylmethyl | 4 | Imidazol-4-yl | 2-methyl-2-propylthio | |
| 2-46 | Pyridin-2-ylmethyl | 4 | 4-methyl-imidazol-5-yl | 2-methyl-2-propylthio | |
| 2-47 | Pyridin-2-ylmethyl | 4 | 5-methoxypyridin-2-yl | 2-methyl-2-propylthio | 610 |
| 2-48 | Pyridin-2-ylmethyl | 4 | pyridine-2-yl | 2-methyl-2-propylthio | |
| 2-49 | Pyridin-2-ylmethyl | 4 | pyrazol-4-yl | 2-methyl-2-propylthio | |
| 2-50 | Pyridin-2-ylmethyl | 4 | 1-methyl-pyrazol-4-yl | 2-methyl-2-propylthio | |
| 2-51 | Pyridin-2-ylmethyl | 4 | 3-methyl-pyrazol-4-yl | 2-methyl-2-propylthio | |
| 2-52 | Pyridin-2-ylmethyl | 4 | 5-methyl-1 2 4 -oxadiazol-3-yl | 2-methyl-2-propylthio | |
| 2-53 | Pyridin-2-ylmethyl | 4 | 2-methyl-1,3,4-oxadiazol-5-yl | 2-methyl-2-propylthio | |
| 2-54 | Pyridin-2-ylmethyl | 4 | 1,3,4-oxadiazol-2-yl | 2-methyl-2-propylthio | |
| 2-55 | Pyridin-2-ylmethyl | 4 | 1,3,4-thiadiazol-2-yl | 2-methyl-2-propylthio | 587 |
| 2-56 | Pyridin-2-ylmethyl | 4 | 3-methyl-pyrazol-5-yl | 2-methyl-2-propylthio | |
| 2-57 | Pyridin-2-ylmethyl | 4 | 1,2,3-thiadiazol-4-yl | 2-methyl-2-propylthio | |
| 2-58 | Pyridin-2-ylmethyl | 4 | 1-tetrazolyl | 2-methyl-2-propylthio | |
| 2-59 | Pyridin-2-ylmethyl | 4 | 2-tetrazolyl | 2-methyl-2-propylthio | |
| 2-60 | Pyridin-2-ylmethyl | 4 | 1-methyl-tetrazol-5-yl | 2-methyl-2-propylthio | |
| 2-61 | Pyridin-2-ylmethyl | 4 | 2-methyl-tetrazol-5-yl | 2-methyl-2-propylthio | |
| 2-62 | Pyridin-2-ylmethyl | 4 | 2-pyridone-5-yl | 2-methyl-2-propylthio | 596 |
| 2-63 | Pyridin-2-ylmethyl | 4 | pyridin-3-yl | 2-methyl-2-propylthio | |
| 2-64 | Pyridin-2-ylmethyl | 4 | 2-cyanopyridin-5-yl | 2-methyl-2-propylthio | 606 |
| 2-65 | Pyridin-2-ylmethyl | 4 | 2-trifluoromethylpyridin-5-yl | 2-methyl-2-propylthio | 648 |
| 2-66 | Pyridin-2-ylmethyl | 4 | 2-acetylaminopyridin-5-yl | 2-methyl-2-propylthio | |
| 2-67 | Pyridin-2-ylmethyl | 4 | 2-methoxypyrimidin-5-yl | 2-methyl-2-propylthio | 611 |
| 2-68 | Pyridin-2-ylmethyl | 4 | 2-methoxythiazol-4-yl | 2-methyl-2-propylthio | 616 |
| 2-69 | 3-fluoro-pyridin-2-ylmethyl | 4 | 2-methoxypyridin-5-yl | 2-methyl-2-propylthio | |

TABLE 2-continued

N-(aryl-heteroaryl) indoles and N-(aryl-heterocycle)indoles

| Compound # | R₁ | position | R₂ | R₃ | M + H |
|---|---|---|---|---|---|
| 2-70 | 3-fluoro-pyridin-2-ylmethyl | 4 | 2-methoxypyridin-5-yl | 2-methyl-2-propylthio | |
| 2-71 | 4-fluoro-pyridin-2-ylmethyl | 4 | 2-methoxypyridin-5-yl | 2-methyl-2-propylthio | |
| 2-72 | 5-fluoro-pyridin-2-ylmethyl | 4 | 2-methoxypyridin-5-yl | 2-methyl-2-propylthio | |
| 2-73 | 5-methyl-pyridin-2-ylmethyl | 4 | 2-methoxypyridin-5-yl | 2-methyl-2-propylthio | 625 |
| 2-74 | 5-cyano-pyridin-2-ylmethyl | 4 | 2-methoxypyridin-5-yl | 2-methyl-2-propylthio | |
| 2-75 | 5-methoxy-pyridin-2-ylmethyl | 4 | 2-methoxypyridin-5-yl | 2-methyl-2-propylthio | |
| 2-76 | 5-ethyl-pyridin-2-ylmethyl | 4 | 4-methoxypyridin-2-yl | 2-methyl-2-propylthio | 638 |
| 2-77 | Quinolin-2-ylmethyl | 4 | 4-methoxypyridin-2-yl | 2-methyl-2-propylthio | 660 |
| 2-78 | 6-fluoroquinolin-2-ylmethyl | 4 | 4-methoxypyridin-2-yl | 2-methyl-2-propylthio | 678 |
| 2-79 | Quinolin-2-ylmethyl | 3 | 5-fluoropyridin-2-yl | 2-methyl-2-propylthio | |
| 2-80 | Quinolin-2-ylmethyl | 3 | 2-methoxypyridin-5-yl | 2-methyl-2-propylthio | |
| 2-81 | Quinolin-2-ylmethyl | 3 | 5-trifluoromethylpyridin-2-yl | 2-methyl-2-propylthio | |
| 2-82 | 5-methyl-pyridin-2-ylmethyl | 4 | 3-fluoropyridin-2-yl | 2-methyl-2-propylthio | 612 |
| 2-83 | Quinolin-2-ylmethyl | 3 | 2-trifluoromethylpyridin-5-yl | 2-methyl-2-propylthio | |
| 2-84 | 5-ethyl-pyridin-2-ylmethyl | 4 | 3-fluoropyridin-2-yl | 2-methyl-2-propylthio | 627 |
| 2-85 | Quinolin-2-ylmethyl | 4 | 3-fluoropyridin-2-yl | 2-methyl-2-propylthio | 648 |
| 2-86 | Quinolin-2-ylmethyl | 3 | 2-ethoxypyridin-5-yl | 2-methyl-2-propylthio | |
| 2-87 | Pyridin-2-ylmethyl | 4 | 5-carboxamido-pyridin-2-yl | 2-methyl-2-propylthio | 623 |
| 2-88 | Pyridin-2-ylmethyl | 4 | 5-cyanopyridin-2-yl | 2-methyl-2-propylthio | 605 |
| 2-89 | Pyridin-2-ylmethyl | 4 | 5-methoxythiazol-2-yl | 2-methyl-2-propylthio | 616 |
| 2-90 | Pyridin-2-ylmethyl | 4 | 2-methyl-pyridin-5-yl | 2-methyl-2-propylthio | 594 |
| 2-91 | Pyridin-2-ylmethyl | 4 | 5-trifluoromethyl-pyridin-2-yl | 2-methyl-2-propylthio | 670 |
| 2-92 | Pyridin-2-ylmethyl | 4 | 2-ethoxythiazol-4-yl | 2-methyl-2-propylthio | 631 |
| 2-93 | Pyridin-2-ylmethyl | 4 | 4-methyl-imidazol-2-yl | 2-methyl-2-propylthio | 583 |
| 2-94 | Pyridin-2-ylmethyl | 4 | 2-ethoxypyridin-5-yl | 2-methyl-2-propylthio | 624 |
| 2-95 | Pyridin-2-ylmethyl | 4 | 6-methoxypyridin-2-yl | 2-methyl-2-propylthio | 610 |
| 2-96 | Pyridin-2-ylmethyl | 4 | 5-methoxypyridin-3-yl | 2-methyl-2-propylthio | 610 |
| 2-97 | Pyridin-2-ylmethyl | 4 | 2-carboxamido-pyridin-5-yl | 2-methyl-2-propylthio | 624 |
| 2-98 | Pyridin-2-ylmethyl | 4 | 5-methyl-pyridin-2-yl | 2-methyl-2-propylthio | 594 |

TABLE 2-continued

N-(aryl-heteroaryl) indoles and N-(aryl-heterocycle)indoles

| Compound # | R₁ | position | R₂ | R₃ | M + H |
|---|---|---|---|---|---|
| 2-99 | 6-Fluoro-pyridin-2-ylmethyl | 4 | 2-methoxypyridin-5-yl | 2-methyl-2-propylthio | 628 |
| 2-100 | 6-Methoxy-pyridin-2-ylmethyl | 4 | 2-methoxypyridin-5-yl | 2-methyl-2-propylthio | 640 |
| 2-101 | 6-Methyl-pyridin-2-ylmethyl | 4 | 2-methoxypyridin-5-yl | 2-methyl-2-propylthio | 624 |
| 2-102 | 5-Methyl-pyridin-2-ylmethyl | 4 | 2-trifluoromethyl-pyridin-5-yl | 2-methyl-2-propylthio | 662 |
| 2-103 | 5-Methyl-pyridin-2-ylmethyl | 4 | 5-trifluoromethyl-pyridin-2-yl | 2-methyl-2-propylthio | 662 |
| 2-104 | 6-cyclopropyl-pyridin-2-ylmethyl | 4 | 2-methoxypyridin-5-yl | 2-methyl-2-propylthio | 650 |
| 2-105 | 5-Methyl-pyridin-2-ylmethyl | 4 | 5-methyl-pyridin-2-yl | 2-methyl-2-propylthio | 608 |
| 2-106 | 5-Methyl-pyridin-2-ylmethyl | 4 | 6-methoxy-pyridazin-3-yl | 2-methyl-2-propylthio | 625 |
| 2-107 | 5-Methyl-pyridin-2-ylmethyl | 4 | 2-ethoxypyridin-5-yl | 2-methyl-2-propylthio | 639 |
| 2-108 | 5-Chloro-pyridin-2-ylmethyl | 4 | 2-methoxypyridin-5-yl | 2-methyl-2-propylthio | 644 |
| 2-109 | S-1-(pyridin-2-yl)-1-ethyl | 4 | 5-trifluoromethyl-pyridin-2-yl | 2-methyl-2-propylthio | 684 (M + Na) |
| 2-110 | R-1-(pyridin-2-yl)-1-ethyl | 4 | 5-trifluoromethyl-pyridin-2-yl | 2-methyl-2-propylthio | 663 |
| 2-111 | S-1-(pyridin-2-yl)-1-ethyl | 4 | 2-methoxypyridin-5-yl | 2-methyl-2-propylthio | 624 |
| 2-112 | R-1-(pyridin-2-yl)-1-ethyl | 4 | 2-methoxypyridin-5-yl | 2-methyl-2-propylthio | 624 |
| 2-113 | S-1-(pyridin-2-yl)-1-ethyl | 4 | 6-methoxypyridin-2-yl | 2-methyl-2-propylthio | 625 |
| 2-114 | R-1-(pyridin-2-yl)-1-ethyl | 4 | 6-methoxypyridin-2-yl | 2-methyl-2-propylthio | 624 |
| 2-115 | S-1-(pyridin-2-yl)-1-ethyl | 4 | 2-ethoxythiazol-4-yl | 2-methyl-2-propylthio | 644 |
| 2-116 | R-1-(pyridin-2-yl)-1-ethyl | 4 | 2-ethoxythiazol-4-yl | 2-methyl-2-propylthio | 644 |
| 2-117 | 3-Methyl-pyridin-2-ylmethyl | 4 | 2-methoxypyridin-5-yl | 2-methyl-2-propylthio | 624 |
| 2-118 | 3-Methyl-pyridin-2-ylmethyl | 4 | 5-trifluoromethyl-pyridin-2-yl | 2-methyl-2-propylthio | 662 |
| 2-119 | 3,5-dimethylpyridin-2-ylmethyl | 4 | 2-methoxypyridin-5-yl | 2-methyl-2-propylthio | 638 |
| 2-120 | 3,5-dimethylpyridin-2-ylmethyl | 4 | 5-trifluoromethyl-pyridin-2-yl | 2-methyl-2-propylthio | 676 |
| 2-121 | Benzothiazol-2ylmethyl | 4 | 2-methoxypyridin-5-yl | 2-methyl-2-propylthio | 666 |
| 2-122 | Benzothiazol-2ylmethyl | 4 | 5-trifluoromethyl-pyridin-2-yl | 2-methyl-2-propylthio | 666 |
| 2-123 | Benzothiazol-2ylmethyl | 4 | 2-methoxypyridin-5-yl | cyclobutylcarbonyl | 660 |
| 2-124 | Benzothiazol-2ylmethyl | 4 | 5-trifluoromethyl-pyridin-2-yl | cyclobutylmethyl | 646 |
| 2-125 | 5-Ethylpyridin-2-ylmethyl | 4 | 2-methoxypyridin-5-yl | 2-methyl-2-propylthio | 638 |
| 2-126 | 5-Ethylpyridin-2-ylmethyl | 4 | 2-ethoxypyridin-5-yl | 2-methyl-2-propylthio | 652 |
| 2-127 | 5-Ethylpyridin-2-ylmethyl | 4 | 2-trifluoromethyl-pyridin-5-yl | 2-methyl-2-propylthio | 676 |

TABLE 2-continued

N-(aryl-heteroaryl) indoles and N-(aryl-heterocycle)indoles

| Compound # | R₁ | position | R₂ | R₃ | M + H |
|---|---|---|---|---|---|
| 2-128 | 5-Ethylpyridin-2-ylmethyl | 4 | 5-trifluoromethyl-pyridin-2-yl | 2-methyl-2-propylthio | 677 |
| 2-129 | 5-Methylpyridin-2-ylmethyl | 4 | 2-ethoxythiazol-4-yl | 2-methyl-2-propylthio | 644 |
| 2-130 | 5-Methylpyridin-2-ylmethyl | 4 | 2-methoxythiazol-4-yl | 2-methyl-2-propylthio | 630 |
| 2-131 | 5-Methylpyridin-2-ylmethyl | 4 | 6-methoxypyridin-2-yl | 2-methyl-2-propylthio | 624 |
| 2-132 | Pyridin-2-ylmethyl | 4 | 2-methoxypyridin-5-yl | cyclobutylmethyl | 590 |
| 2-133 | 5-Methylpyridin-2-ylmethyl | 4 | 2-methoxypyridin-5-yl | cyclobutylmethyl | 604 |
| 2-134 | 5-Methylpyridin-2-ylmethyl | 4 | 2-methoxypyridin-5-yl | 2-methyl-prop-1-yl | 592 |
| 2-135 | Quinolin-2-ylmethyl | 4 | 2-methoxypyridin-5-yl | 2-methyl-2-propylthio | 660 |
| 2-136 | Quinolin-2-ylmethyl | 4 | 2-trifluoromethyl-pyridin-5-yl | 2-methyl-2-propylthio | 936 |
| 2-137 | Quinolin-2-ylmethyl | 4 | 5-trifluoromethyl-pyridin-2-yl | 2-methyl-2-propylthio | 698 |
| 2-138 | Quinolin-2-ylmethyl | 4 | 6-methoxy-pyridazin-3-yl | 2-methyl-2-propylthio | 661 |
| 2-139 | Quinolin-2-ylmethyl | 4 | 2-ethoxypyridin-5-yl | 2-methyl-2-propylthio | 674 |
| 2-140 | 6-fluoroquinolin-2-ylmethyl | 4 | 6-methoxypyridin-2-yl | 2-methyl-2-propylthio | 678 |
| 2-141 | 6-fluoroquinolin-2-ylmethyl | 4 | 2-methoxypyridin-5-yl | 2-methyl-2-propylthio | 678 |
| 2-142 | 6-fluoroquinolin-2-ylmethyl | 4 | 2-ethoxythiazol-4-yl | 2-methyl-2-propylthio | 698 |
| 2-143 | 6-fluoroquinolin-2-ylmethyl | 4 | 5-trifluoromethyl-pyridin-2-yl | 2-methyl-2-propylthio | 716 |
| 2-144 | 7-fluoroquinolin-2-ylmethyl | 4 | 2-trifluoromethyl-pyridin-5-yl | 2-methyl-2-propylthio | 716 |
| 2-145 | 7-fluoroquinolin-2-ylmethyl | 4 | 5-trifluoromethyl-pyridin-2-yl | 2-methyl-2-propylthio | 716 |
| 2-146 | 7-fluoroquinolin-2-ylmethyl | 4 | 2-methoxypyridin-5-yl | 2-methyl-2-propylthio | 678 |
| 2-147 | 7-fluoroquinolin-2-ylmethyl | 4 | 2-ethoxypyridin-5-yl | 2-methyl-2-propylthio | 692 |
| 2-148 | 6-fluoroquinolin-2-ylmethyl | 4 | 3-fluoropyridin-2-yl | 2-methyl-2-propylthio | 666 |
| 2-149 | 5-methyl-pyridin-2-ylmethyl | 4 | 3-trifluoromethylpyridin-2-yl | 2-methyl-2-propylthio | 662 |
| 2-150 | 5-ethyl-pyridin-2-ylmethyl | 4 | 3-trifluoromethylpyridin-2-yl | 2-methyl-2-propylthio | 676 |
| 2-151 | Quinolin-2-ylmethyl | 4 | 3-trifluoromethylpyridin-2-yl | 2-methyl-2-propylthio | 698 |
| 2-152 | Quinolin-2-ylmethyl | 3 | 5-methoxythiazol-2-yl | 2-methyl-2-propylthio | |
| 2-153 | Quinolin-2-ylmethyl | 3 | 3-methoxy-6-pyridazinyl | 2-methyl-2-propylthio | |
| 2-154 | Quinolin-2-ylmethyl | 3 | 5-fluoro-thiazol-2-yl | 2-methyl-2-propylthio | |
| 2-155 | Quinolin-2-ylmethyl | 3 | pyridin-2-yl | 2-methyl-2-propylthio | |
| 2-156 | 6-fluoroquinolin-2-ylmethyl | 4 | 3-trifluoromethylpyridin-2-yl | 2-methyl-2-propylthio | 716 |

TABLE 2-continued

N-(aryl-heteroaryl) indoles and N-(aryl-heterocycle)indoles

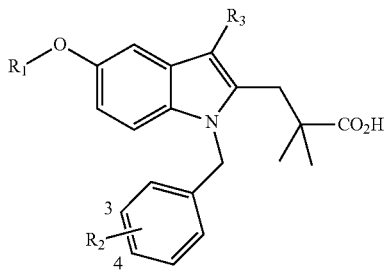

| Compound # | R₁ | position | R₂ | R₃ | M + H |
|---|---|---|---|---|---|
| 2-157 | 3-methylpyridin-2-ylmethyl | 4 | 2-ethoxypyridin-5-yl | 2-methyl-2-propylthio | 638 |
| 2-158 | 3-methylpyridin-2-ylmethyl | 4 | 2-trifluoromethylpyridin-5-yl | 2-methyl-2-propylthio | 662 |
| 2-159 | 3,5-dimethylpyridin-2-ylmethyl | 4 | 2-ethoxypyridin-5-yl | 2-methyl-2-propylthio | 652 |
| 2-160 | 4-methylpyridin-2-ylmethyl | 4 | 2-methoxypyridin-5-yl | 2-methyl-2-propylthio | 624 |
| 2-161 | 4-methylpyridin-2-ylmethyl | 4 | 2-ethoxypyridin-5-yl | 2-methyl-2-propylthio | 638 |
| 2-162 | 4-methylpyridin-2-ylmethyl | 4 | 2-trifluoromethylpyridin-5-yl | 2-methyl-2-propylthio | 662 |
| 2-163 | 5-methylpyridin-2-ylmethyl | 4 | 5-trifluoromethylpyridin-2-yl | cyclobutylmethyl | 642 |
| 2-164 | 6-fluoroquinolin-2-ylmethyl | 4 | 2-ethoxypyridin-5-yl | 2-methyl-2-propylthio | 692 |
| 2-165 | 6-fluoroquinolin-2-ylmethyl | 4 | 2-trifluoromethylpyridin-5-yl | 2-methyl-2-propylthio | 716 |
| 2-166 | 6-methylquinolin-2-ylmethyl | 4 | 2-methoxypyridin-5-yl | 2-methyl-2-propylthio | 674 |
| 2-167 | 6-methylquinolin-2-ylmethyl | 4 | 5-trifluoromethylpyridin-2-yl | 2-methyl-2-propylthio | 712 |
| 2-168 | quinolin-2-ylmethyl | 4 | 3-methylpyridazin-6-yl | 2-methyl-2-propylthio | 645 |
| 2-169 | quinolin-2-ylmethyl | 4 | 3-ethoxypyridazin-6-yl | 2-methyl-2-propylthio | 675 |
| 2-170 | quinolin-2-ylmethyl | 4 | 2-methoxypyridin-5-yl | 2-methyl-1-propyl | 628 |
| 2-171 | 6-fluoroquinolin-2-ylmethyl | 4 | 3-methoxypyridazin-6-yl | 2-methyl-2-propylthio | 679 |
| 2-172 | Pyridine-2-ylmethyl | 4 | 2-methoxypyridin-5-yl | 2-methyl-2-propylthio-S,S-dioxide | 642 |
| 2-173 | Pyridine-2-ylmethyl | 4 | 2-methoxypyridin-5-yl | 2-methyl-2-propylthio-S-oxide | 626 |
| 2-174 | N-oxido-pyridine-2-ylmethyl | 4 | 2-methoxypyridin-5-yl | 2-methyl-2-propylthio | 626 |
| 2-175 | Imidazo[1,2-a]pyridine-2-ylmethyl | 4 | 2-methoxypyridin-5-yl | 2-methyl-2-propylthio | 649 |
| 2-176 | Imidazo[1,2-a]pyridine-2-ylmethyl | 4 | 2-ethoxypyridin-5-yl | 2-methyl-2-propylthio | 663 |
| 2-177 | Imidazo[1,2-a]pyridine-2-ylmethyl | 4 | 5-trifluoromethylpyridin-2-yl | 2-methyl-2-propylthio | 687 |
| 2-178 | R-1-(pyridin-2-yl)-1-ethyl | 4 | 2-ethoxypyridin-5-yl | 2-methyl-2-propylthio | 638 |
| 2-179 | 6-fluoroquinolin-2-ylmethyl | 4 | 3-methylpyridazin-6-yl | 2-methyl-2-propylthio | 663 |
| 2-180 | 5-methylisoxazol-3-ylmethyl | 4 | 2-methoxypyridin-5-yl | 2-methyl-2-propylthio | 614 |
| 2-181 | 5-methylisoxazol-3-ylmethyl | 4 | 2-ethoxypyridin-5-yl | 2-methyl-2-propylthio | 628 |

TABLE 2-continued

N-(aryl-heteroaryl) indoles and N-(aryl-heterocycle)indoles

| Compound # | R$_1$ | position | R$_2$ | R$_3$ | M + H |
|---|---|---|---|---|---|
| 2-182 | 5-methylisoxazol-3-ylmethyl | 4 | 5-trifluoromethylpyridin-2-yl | 2-methyl-2-propylthio | 652 |
| 2-183 | 1,3-dimethylpyrazol-5-ylmethyl | 4 | 2-methoxypyridin-5-yl | 2-methyl-2-propylthio | 627 |
| 2-184 | 1,5-dimethylpyrazol-3-ylmethyl | 4 | 2-methoxypyridin-5-yl | 2-methyl-2-propylthio | 627 |
| 2-185 | 6-fluoroquinolin-2-ylmethyl | 4 | 3-ethoxypyridazin-6-yl | 2-methyl-2-propylthio | 693 |
| 2-186 | 5-ethylpyridin-2-ylmethyl | 4 | 3-ethoxypyridazin-6-yl | 2-methyl-2-propylthio | 653 |
| 2-187 | 5-ethylpyridin-2-ylmethyl | 4 | 3-methoxypyridazin-6-yl | 2-methyl-2-propylthio | 639 |
| 2-188 | 6-fluoroquinolin-2-ylmethyl | 4 | 5-fluoropyridin-2-yl | 2-methyl-2-propylthio | 666 |
| 2-189 | R-1-(pyridin-2-yl)-1-ethyl | 4 | 5-fluoropyridin-2-yl | 2-methyl-2-propylthio | 612 |
| 2-190 | 6-fluoroquinolin-2-ylmethyl | 4 | 2-ethoxypyridin-6-yl | 2-methyl-2-propylthio | 692 |
| 2-191 | R-1-(pyridin-2-yl)-1-ethyl | 4 | 2-ethoxypyridin-6-yl | 2-methyl-2-propylthio | 638 |
| 2-192 | 5-methylpyridin-2-ylmethyl | 4 | 5-fluoropyridin-2-yl | 2-methyl-2-propylthio | 612 |
| 2-193 | 5-methylpyridin-2-ylmethyl | 4 | 2-ethoxypyridin-6-yl | 2-methyl-2-propylthio | 638 |
| 2-194 | 6-fluoroquinolin-2-ylmethyl | 4 | 2-trifluoromethylpyridin-5-yl | 2-methylprop-1-yl | 684 |
| 2-195 | Pyridin-2-ylmethyl | 3 | 5-trifluoromethylpyridin-2-yl | 2-methyl-2-propylthio | 648 |
| 2-196 | Pyridin-2-ylmethyl | 3 | 2-methoxypyridin-5-yl | 2-methyl-2-propylthio | 610 |
| 2-197 | Quinolin-2-ylmethyl | 4 | 5-fluoropyridin-2-yl | 2-methyl-2-propylthio | 648 |
| 2-198 | Quinolin-2-ylmethyl | 4 | 2-ethoxypyridin-6-yl | 2-methyl-2-propylthio | 674 |
| 2-199 | Pyridin-2-ylmethyl | 4 | 2-ethoxypyridin-6-yl | 2-methyl-2-propylthio | 624 |
| 2-200 | 6-fluoroquinolin-2-ylmethyl | 4 | 2-trifluoromethylpyridin-6-yl | 2-methyl-2-propylthio | 716 |
| 2-201 | Pyridine-2-ylmethyl | 4 | 5-fluoropyridin-2-yl | 2-methyl-2-propylthio | 598 |
| 2-202 | 5-methylpyridin-2-ylmethyl | 4 | 2-trifluoromethylpyridin-6-yl | 2-methyl-2-propylthio | 662 |
| 2-203 | Quinolin-2-ylmethyl | 4 | 2-trifluoromethylpyridin-6-yl | 2-methyl-2-propylthio | 698 |
| 2-204 | Pyridin-2-ylmethyl | 4 | 2-trifluoromethylpyridin-6-yl | 2-methyl-2-propylthio | 648 |
| 2-205 | Quinolin-2-ylmethyl | 4 | 2-thiazolyl | 2-methyl-2-propylthio | 636 |
| 2-206 | Pyridin-2-ylmethyl | 3 | 4-methoxytetrahydropyran-4-yl | 2-methyl-2-propylthio | 617 |

TABLE 2-continued

N-(aryl-heteroaryl) indoles and N-(aryl-heterocycle)indoles

| Compound # | R₁ | position | R₂ | R₃ | M + H |
|---|---|---|---|---|---|
| 2-207 | 6-fluoroquinolin-2-ylmethyl | 4 | Pyridin-2-yl | 2-methyl-2-propylthio | 648 |
| 2-208 | 5-Ethylpyridin-2-ylmethyl | 4 | Pyridin-3-yl | 2-methyl-2-propylthio | 608 |
| 2-209 | Quinolin-2-ylmethyl | 4 | Pyridin-3-yl | 2-methyl-2-propylthio | 630 |
| 2-210 | 6-fluoroquinolin-2-ylmethyl | 4 | Pyridin-3-yl | 2-methyl-2-propylthio | 648 |
| 2-211 | 5-methylpyridin-2-ylmethyl | 4 | Pyridin-2-yl | 2-methyl-2-propylthio | 594 |
| 2-212 | 5-Ethylpyridin-2-ylmethyl | 4 | Pyridin-2-ylmethyl | 2-methyl-2-propylthio | 608 |
| 2-213 | Quinolin-2-ylmethyl | 4 | Pyridin-2-yl | 2-methyl-2-propylthio | 630 |
| 2-214 | 5-methylpyridin-2-ylmethyl | 4 | Pyridin-3-yl | 2-methyl-2-propylthio | 594 |
| 2-215 | 5-methylpyridin-2-ylmethyl | 4 | 4-methoxypyridin-2-yl | 2-methyl-2-propylthio | 624 |
| 2-216 | Quinolin-2-ylmethyl | 4 | 3-methoxypyridin-2-yl | 2-methyl-2-propylthio | 660 |
| 2-217 | 5-methylpyridin-2-ylmethyl | 4 | 3-methoxypyridin-2-yl | 2-methyl-2-propylthio | 624 |
| 2-218 | 5-ethylpyridin-2-ylmethyl | 4 | 3-methoxypyridin-2-yl | 2-methyl-2-propylthio | 638 |
| 2-219 | 5-methylpyridin-2-ylmethyl | 4 | 4-trifluoromethyl pyridin-2-yl | 2-methyl-2-propylthio | 663 |
| 2-220 | 5-ethylpyridin-2-ylmethyl | 4 | 4-trifluoromethyl pyridin-2-yl | 2-methyl-2-propylthio | 677 |
| 2-221 | Quinolin-2-ylmethyl | 4 | 4-trifluoromethyl pyridin-2-yl | 2-methyl-2-propylthio | 698 |
| 2-222 | 5-methylpyridin-2-ylmethyl | 4 | 5-fluoropyridin-3-yl | 2-methyl-2-propylthio | 613 |
| 2-223 | 5-ethylpyridin-2-ylmethyl | 4 | 5-fluoropyridin-3-yl | 2-methyl-2-propylthio | 626 |
| 2-224 | Quinolin-2-ylmethyl | 4 | 5-fluoropyridin-3-yl | 2-methyl-2-propylthio | 649 |
| 2-225 | 2,3-dimethyl pyridin-6-yl | 4 | 2-methoxypyridin-5-yl | 2-methyl-2-propylthio | |
| 2-226 | 2,3-dimethyl pyridin-6-yl | 4 | 3-trifluoromethyl pyridin-2-yl | 2-methyl-2-propylthio | |
| 2-227 | 2,3-dimethyl pyridin-6-yl | 4 | 4-trifluoromethyl pyridin-2-yl | 2-methyl-2-propylthio | |
| 2-228 | 2,3-dimethyl pyridin-6-yl | 4 | 3-fluoropyridin-2-yl | 2-methyl-2-propylthio | |
| 2-229 | 2,3-dimethyl pyridin-6-yl | 4 | 5-fluoropyridin-3-yl | 2-methyl-2-propylthio | |
| 2-230 | 2,3-dimethyl pyridin-6-yl | 4 | 4-methoxypyridin-2-yl | 2-methyl-2-propylthio | |
| 2-231 | 2,3-dimethyl pyridin-6-yl | 4 | Pyridine-3-yl | 2-methyl-2-propylthio | |
| 2-232 | 5-methylpyridin-2-ylmethyl | 4 | 2-methoxypyridin-3-yl | 2-methyl-2-propylthio | |
| 2-233 | 5-ethylpyridin-2-ylmethyl | 4 | 2-methoxypyridin-3-yl | 2-methyl-2-propylthio | |
| 2-234 | Quinolin-2-ylmethyl | 4 | 2-methoxypyridin-3-yl | 2-methyl-2-propylthio | |

TABLE 3

N-(heteroaryl-aryl) and N-(heteroaryl-heteroaryl) indoles

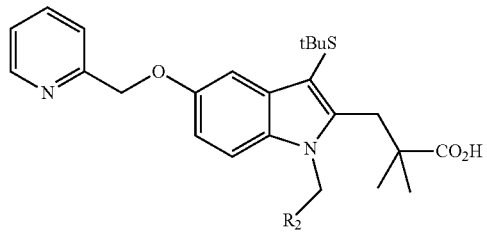

| Compound # | R₂ | M + H |
|---|---|---|
| 3-1 | 2-(2-methoxy pyrid-5-yl)-pyrid-5-yl | 611 |
| 3-2 | 2-(4-methoxy phenyl)-pyrid-5-yl | 610 |
| 3-3 | 2-(4-trifluoromethoxy phenyl)-pyrid-5-yl | 664 |
| 3-4 | 5-(4-methoxy phenyl)-pyrid-2-yl | 610 |
| 3-5 | 5-(4-trifluoromethoxyphenyl)-pyrid-2-yl | 664 |

TABLE 4

N-(aryl-heteroaryl) indoles with non-aryl C5 substituents

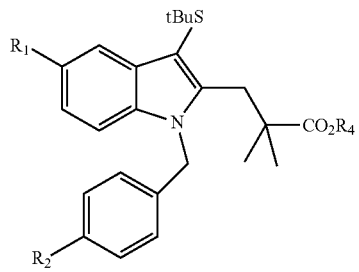

| Compound # | R₁ | R₂ | R₄ | M + H |
|---|---|---|---|---|
| 4-1 | OH | 2-methoxypyridin-5-yl | H | 519 |
| 4-2 | isopropyl | 2-methoxypyridin-5-yl | H | 545 |

Synthesis of Compounds

Compounds of Formula (G), Formula (G-I), and Formula (G-II), described in the prior section may be synthesized using standard synthetic techniques known to those of skill in the art or using methods known in the art in combination with methods described herein. In additions, solvents, temperatures and other reaction conditions presented herein may vary according to those of skill in the art.

The starting material used for the synthesis of the compounds of Formula (G), Formula (G-I), and Formula (G-II), described in the prior section may be synthesized or can be obtained from commercial sources, such as, but not limited to, Aldrich Chemical Co. (Milwaukee, Wis.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. Table 5 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 5

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd_0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

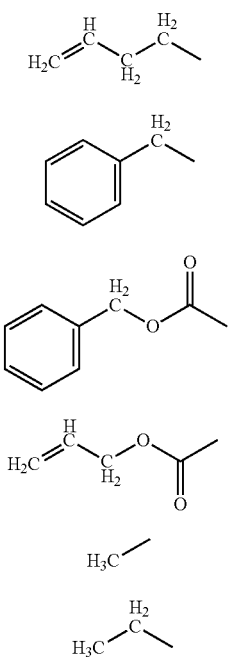

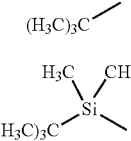
t-butyl

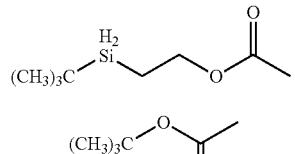
TBDMS

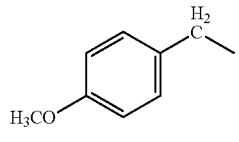
Teoc

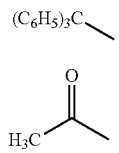
Boc

pMBn

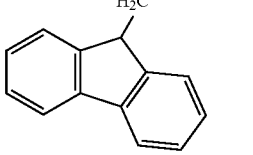
trityl acetyl

Fmoc

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Indole containing compounds can be prepared using standard literature procedures such as those found in Katritzky, "Handbook of Heterocyclic Chemistry" Pergamon Press, Oxford, 1986; Pindur et al, *J. Heterocyclic Chem.*, vol 25, 1, 1987, and Robinson "The Fisher Indole Synthesis", John Wiley & Sons, Chichester, N.Y. , 1982, each of which is herein incorporated by reference in their entirety.

A non-limiting example of the synthetic approach toward indole compounds of Formula (G), Formula (G-I) and Formula (G-II), is shown according to reaction Scheme I shown in FIG. 1, wherein a 4-substituted anilines (I-1) can be converted to the corresponding hydrazine (I-2) using standard methodology. Reaction of hydrazine (I-2) with an appropriately substituted ketone (I-3) under standard Fisher-indolization conditions yields the indole (I-4). Indole (I-6) results from the N-alkylation of (I-4) with a benzyl halide (I-5) (or tosylate (OTs) or mesylate (OMs)) in a solvent such as tetrahydrofuran (THF) or dimethylformamide (DMF) in the presence of a base such as NaH. In the case where the 5-substituent on the indole ring is methoxy (i.e. Z is MeO) the methyl group can be removed under standard conditions, for example using $BBr_3$, in a solvent such as $CH_2Cl_2$ to afford the phenol (I-7). This phenol can be alkylated using an electrophile (YX) to provide the alkylated product (I-8). Alternatively, in the case when the 5-substituent on the indole ring is, for example, a halide or triflate (OTf; 1-7) it can be coupled with a wide variety of reagents using standard metal mediated coupling reactions well known to those skilled in the art of organic synthesis to afford alternate compounds of structure (I-6). Such chemistry is described in Comprehensive Organometallic Chemistry II, vol 12, Pergamon, edited by Abel, Stone and Wilkinson. The Z substitutent of the indole (I-6) can be further modified using standard chemical procedures. In addition, when $R_7$ or $R_6$ is a bromo or iodine, standard cross coupling reactions allow the introduction of a variety of functional groups using procedures well known to those practiced in the art of organic synthesis. Furthermore, when $R_7$ is H, it is possible, under certain conditions, to regioselectively lithiate using a strong base such as nBuLi and then condense the anion with an electrophile to introduce substituents at C-2 (see Hasan et al, *J. Org. Chem.*, 46, 157-164, 1981).

Figure 2:
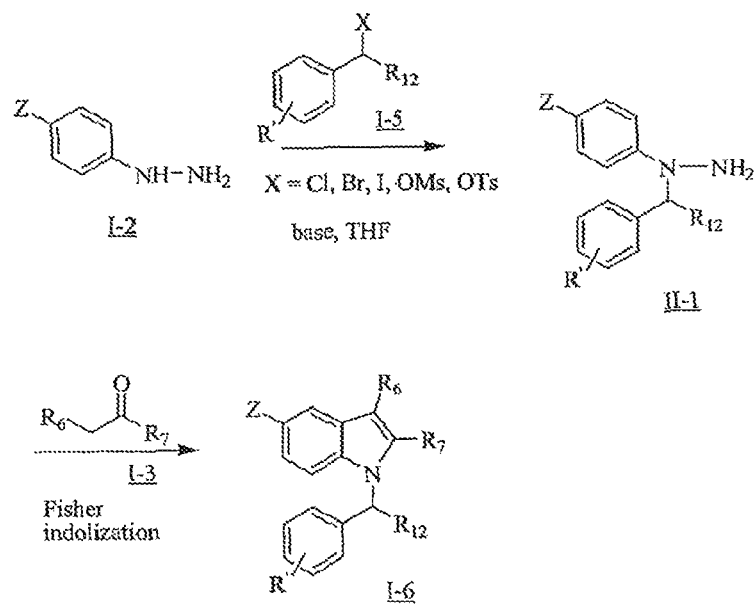
FIG. 2 presents illustrative schemes for the syntheses of compounds described herein.
Figure 2:
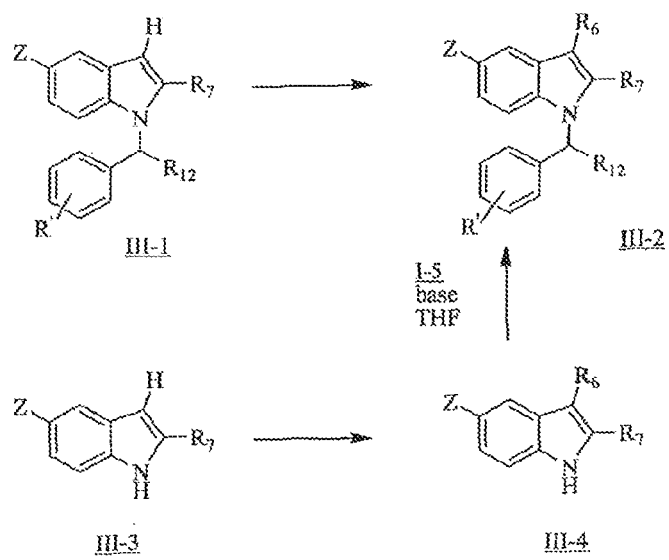
Figure 3:
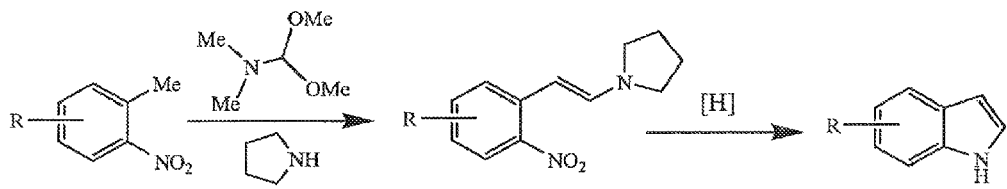
FIG. 3 presents illustrative schemes for the syntheses of compounds described herein.
Figure 3:
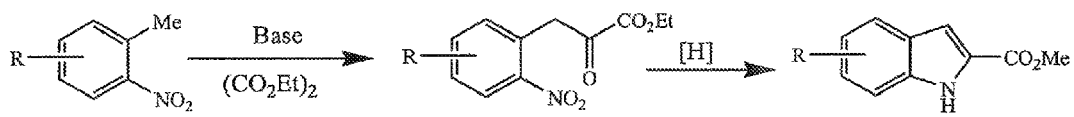
Figure 3:
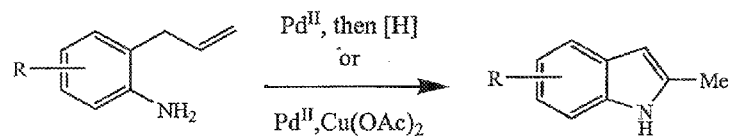
Figure 3:
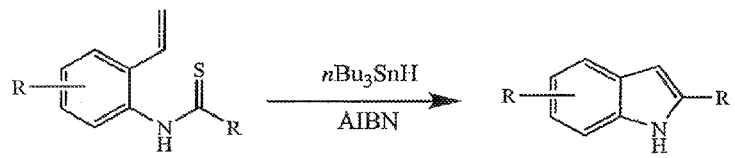
Figure 3:
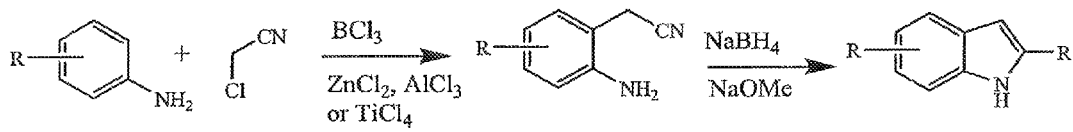
Figure 4:
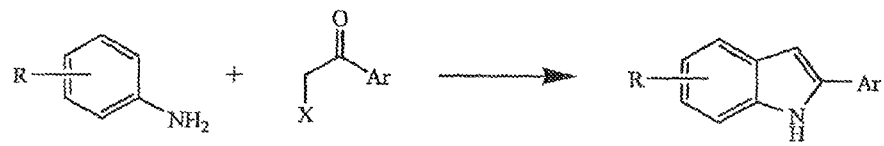
FIG. 4 presents illustrative schemes for the syntheses of compounds described herein.
Figure 4:
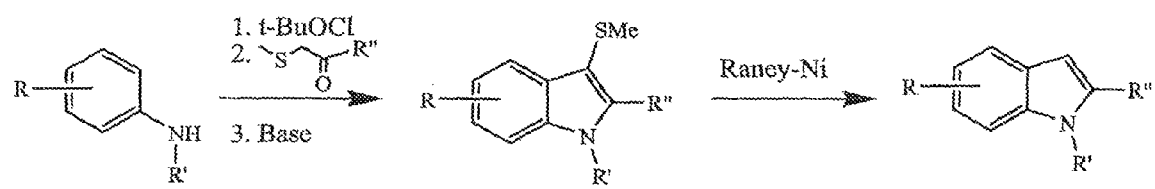
Figure 4:
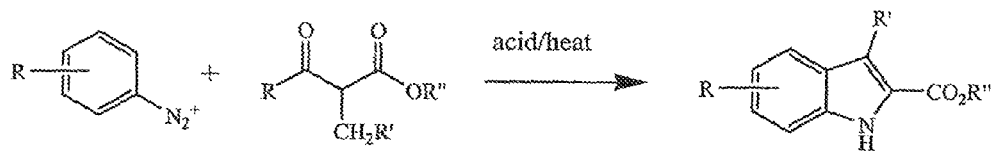
Figure 4:
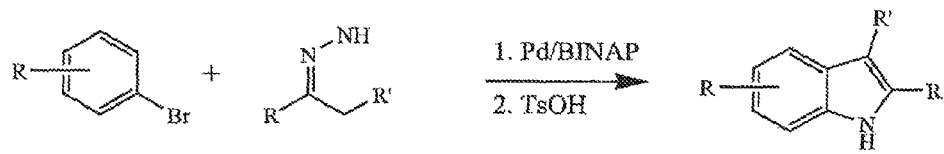
Figure 4:
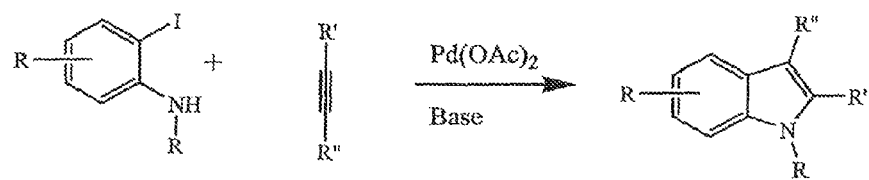
Figure 5:
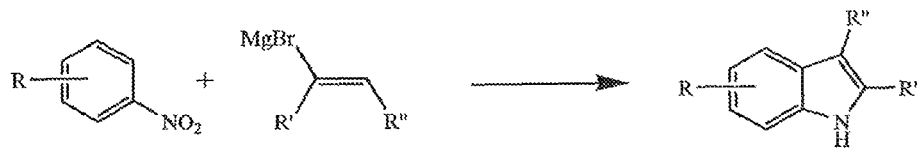
FIG. 5 presents illustrative schemes for the syntheses of compounds described herein.
Figure 5:
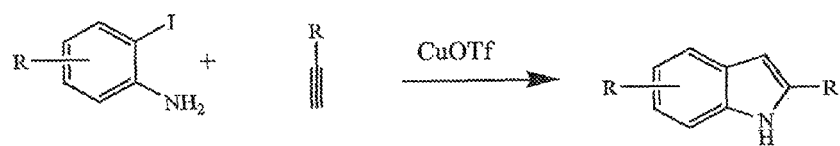
Figure 5:
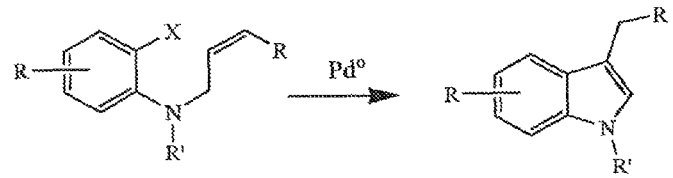
Figure 5:
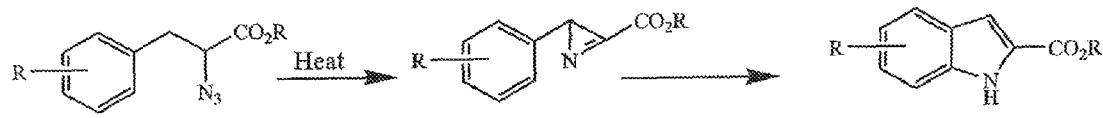
Figure 5:
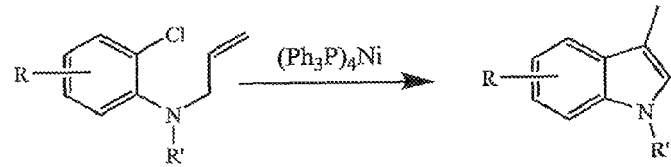
Figure 6:
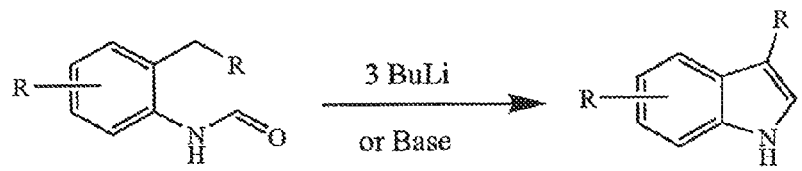
FIG. 6 presents illustrative schemes for the syntheses of compounds described herein.
Figure 6:
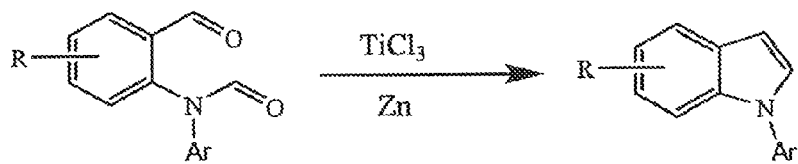
Figure 6:
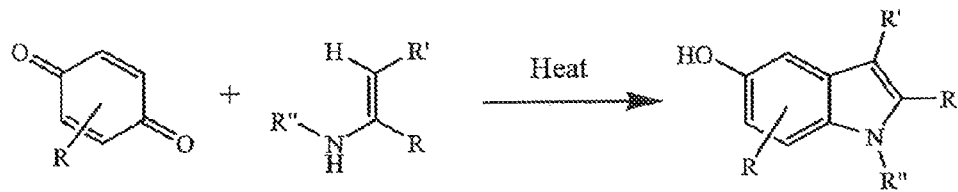
Figure 6:
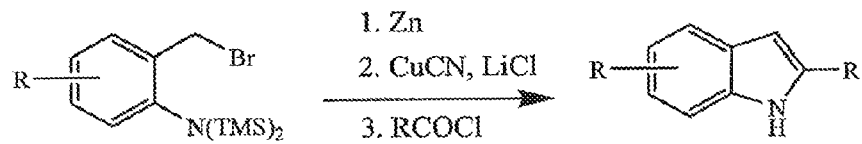
Figure 6:
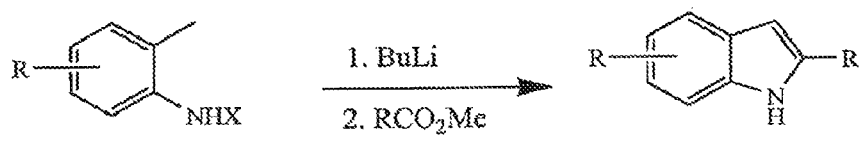
Figure 7:
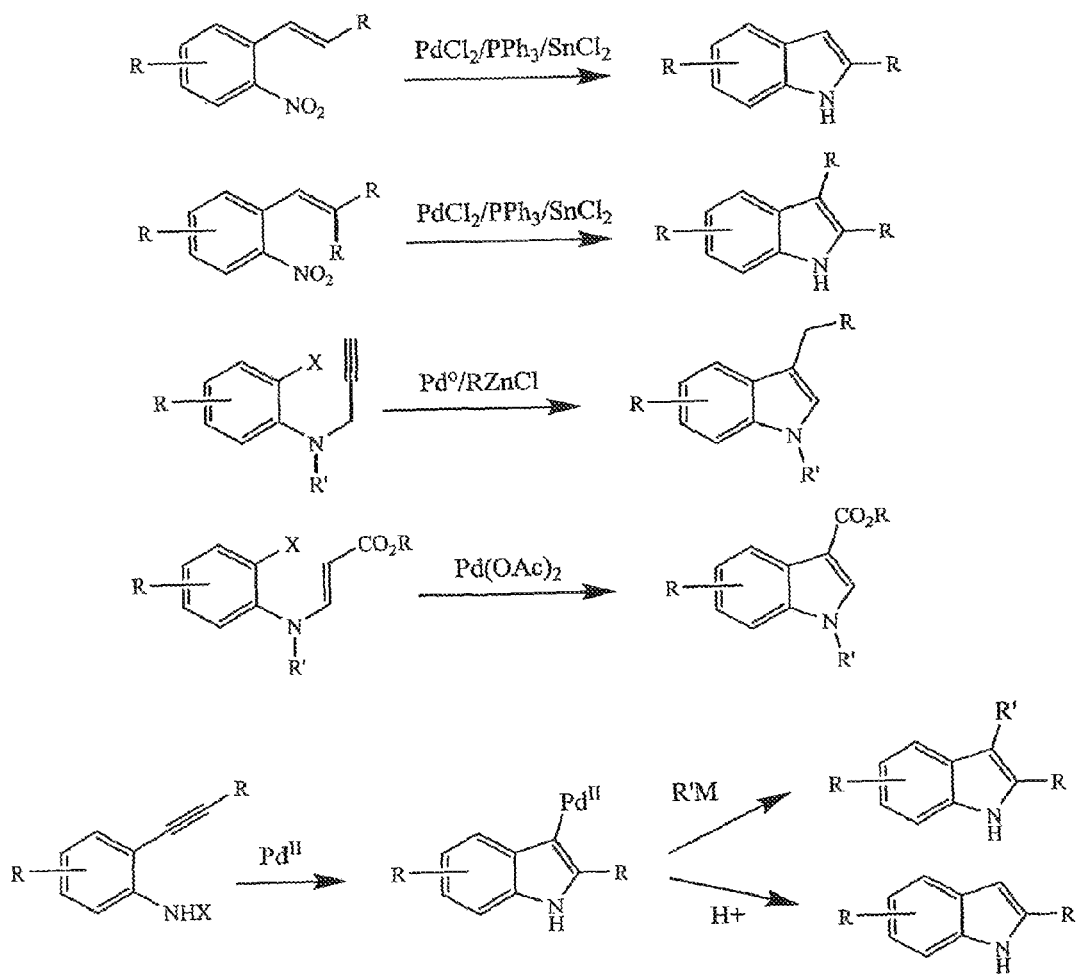
FIG. 7 presents illustrative schemes for the syntheses of compounds described herein.
Figure 7:
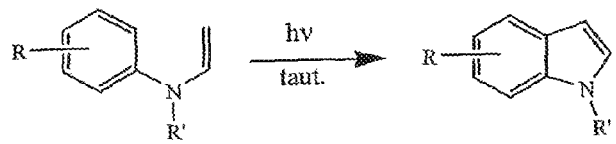
Figure 7:
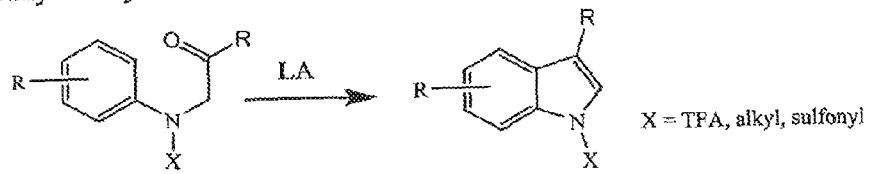
Figure 8:
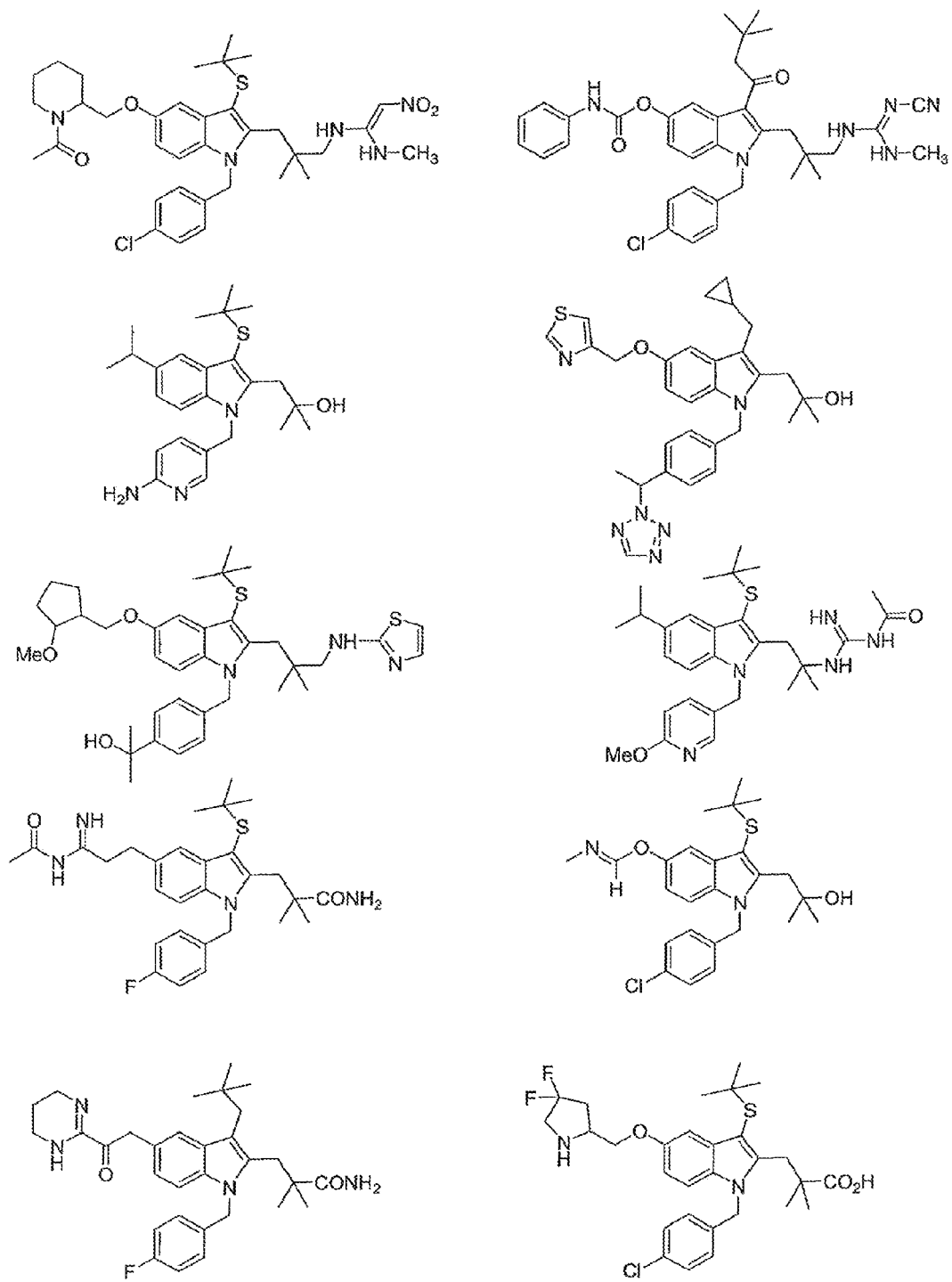
FIG. 8 presents illustrative examples of compounds described herein.
Figure 9:
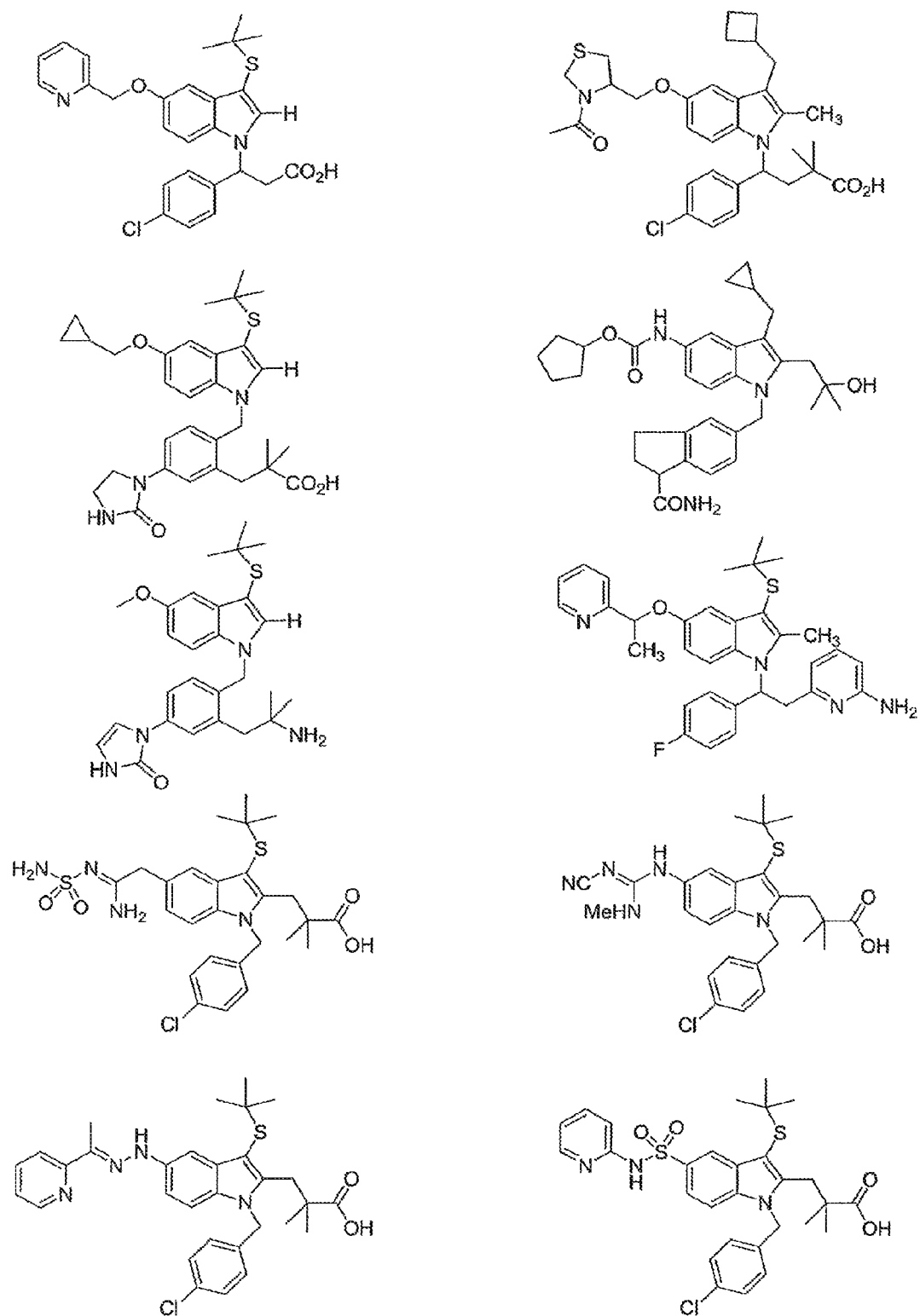
FIG. 9 presents illustrative examples of compounds described herein.
Figure 10:
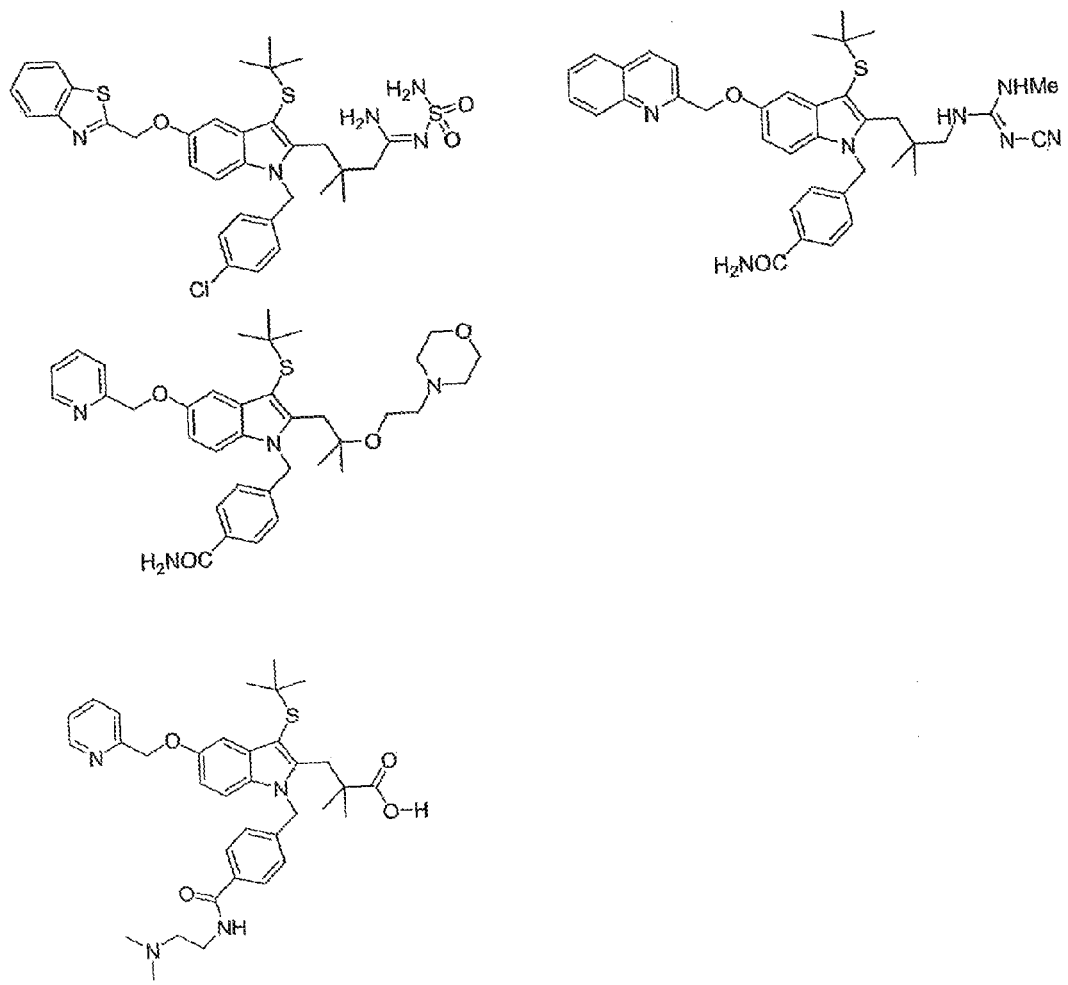
FIG. 10 presents illustrative examples of compounds described herein.
Figure 11:
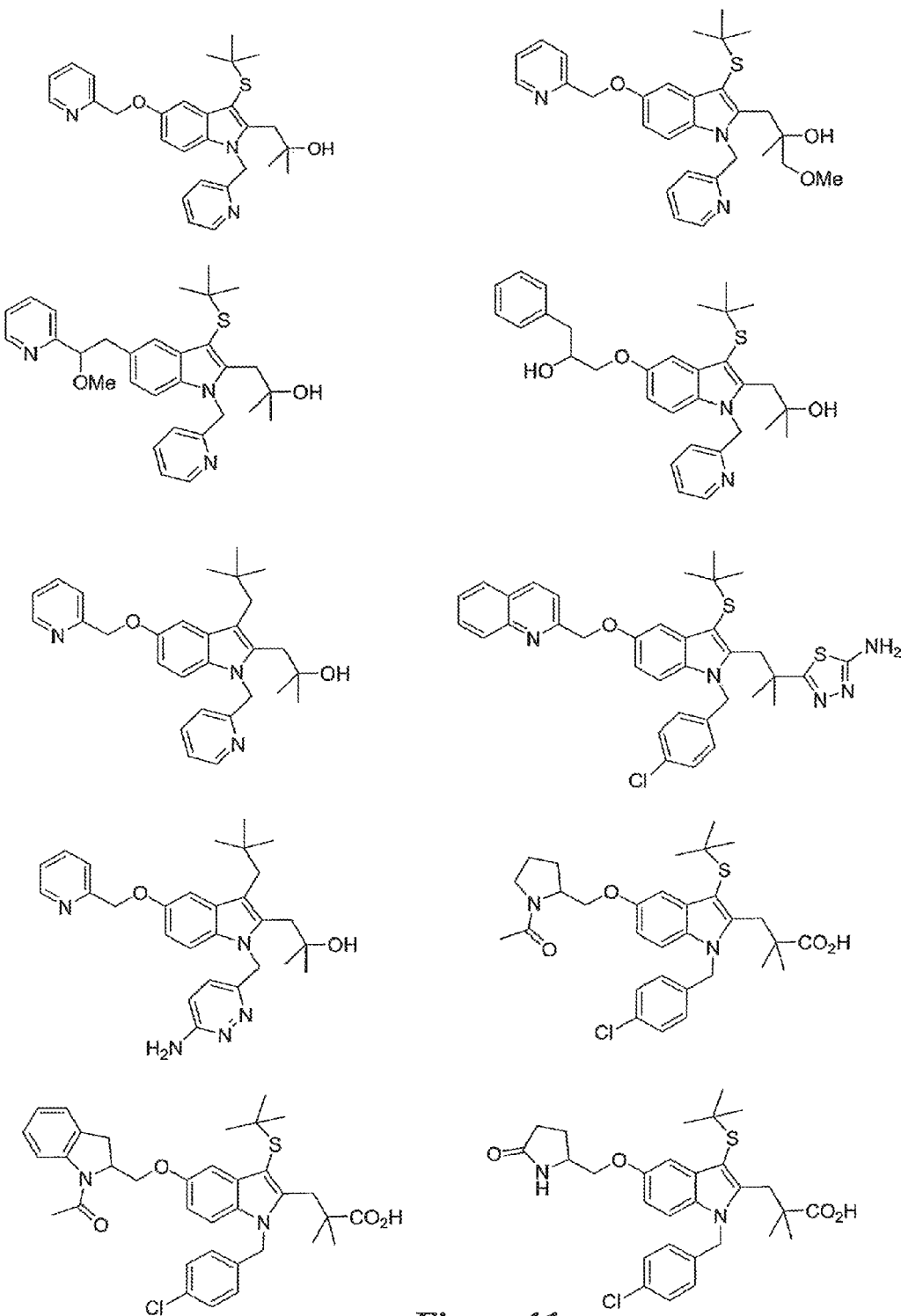
FIG. 11 presents illustrative examples of compounds described herein.

Another non-limiting example of the synthetic approach toward compounds of Formula (G), Formula (G-I) and Formula (G-II) is shown according to reaction Scheme II in FIG. 2. Commencing with the hydrazine I-2, N-alkylation with a benzyl halide (or tosylate or mesylate; I-5) using the conditions described above, provides the hydrazine derivative (II-1). Reaction with an appropriately substituted ketone (I-3) using standard Fisher indolization conditions provides the indole (I-6).

Another non-limiting example of the synthetic approach toward compounds of Formula (G), Formula (G-I) and Formula (G-II) is shown according to reaction Scheme III in FIG. 2, wherein 3-H-indoles (III-1) can be prepared directly using the procedures described above or, alternatively, they can be prepared from 3-thioindoles by treatment with moist $AlCl_3$ in a solvent such as $CH_2Cl_2$. Functionalzation at the 3-position can be achieved using a variety of reactions and procedures to allow the introduction of a wide range of substituents. By way of example only, acylation using an acid chloride (or anhydride) in the presence of a Lewis acid such as $AlCl_3$, allows for the introduction of acyl groups (I-6; $R_6$=C(O)R') see Murakami et al. *Heterocycles*, v14, 1939-1941, 1980 and references cited therein. Commencing with (III-1), and using, by way of example only, sulfenic chlorides in a suitable solvent, compounds of general structure (III-2) wherein $R_6$ is SR" can be prepared (Raban, *J. Org. Chem.*, v45, 1688, 1980). Similar chemistry using indole (III-3) can be performed or, alternatively, diarlydisulfides in the presence of a base such as NaH in DMF can be used to generate (III-4) (Atkinson et al, *Synthesis,* 480-481, 1988). The reaction of electron deficient olefins with 3-H indoles (III-1) or (III-3) in the presence of a Lewis acid (such as $Yb(OTf)_3.3H_2O$) allows the installation of 3-alkyl substituents of general structure (III-2) or (III-4) (where $R_6$ is a substituted alkyl group; see Harrington and Kerr, *Synlett,* 1047-1048, 1996). Alternatively, indole (III-3) can be reacted with benzyl derivatives (I-5) in warm DMF to yield (III-4) where $R_6$ is a substituted benzyl group (Jacobs et al, *J. Med. Chem.,* v36, 394-409, 1993).

Further Synthesis of Indole and Indole-Type Compounds

Additional non-limiting examples of the synthetic strategy toward indole or indole-like scaffolds for compounds of Formula (G), Formula (G-I) and Formula (G-II), include modifications to various syntheses of indoles, including, but not limited to; Batcho-Leimgruber Indole Synthesis, Reissert Indole Synthesis, Hegedus Indole Synthesis, Fukuyama Indole Synthesis, Sugasawa Indole Synthesis, Bischler Indole Synthesis, Gassman Indole Synthesis, Fischer Indole Synthesis, Japp-Klingemann Indole Synthesis, Buchwald Indole Synthesis, Larock Indole Synthesis, Bartoli Indole Synthesis, Castro Indole Synthesis, Hemetsberger Indole Synthesis, Mori-Ban Indole Synthesis, Madelung Indole Synthesis, Nenitzescu Indole Synthesis, and other unnamed reactions. Non-limiting examples of such synthetic methods are shown in FIGS. 3-7.

Further Forms of Compounds

Compounds of Formula (G), Formula (G-I) and Formula (G-II), can be prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Alternatively, compounds of Formula (G), Formula (G-I) and Formula (G-II), can be prepared as a pharmaceutically acceptable base addition salts (which is a type of a pharmaceutically acceptable salt) by reacting the free acid form of the compound with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like.

Compounds of Formula (G), Formula (G-I) and Formula (G-II), can be prepared as a pharmaceutically acceptable salts formed when an acidic proton present in the parent compound either is replaced by a metal ion, for example an alkali metal ion, an alkaline earth ion, or an aluminum ion; or coordinates with an organic base. In addition, the salt forms of the disclosed compounds can be prepared using salts of the starting materials or intermediates.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds of Formula (G), Formula (G-I) and Formula (G-II), can be conveniently prepared or formed during the processes described herein. By way of example only, hydrates of compounds of Formula (G), Formula (G-I) and Formula (G-II), can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Compounds of Formula (G), Formula (G-I) and Formula (G-II), may be in various forms, including but not limited to, amorphous forms, milled forms and nano-particulate forms. In addition, compounds of Formula (G), Formula (G-I) and Formula (G-II), include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds of Formula (G), Formula (G-I) and Formula (G-II), in unoxidized form can be prepared from N-oxides of compounds of Formula (G), Formula (G-I) and/or Formula (G-II), by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

Compounds of Formula (G), Formula (G-I) and Formula (G-II), can be prepared as prodrugs. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.,* 269:G210-218 (1995); McLoed et al., *Gastroenterol,* 106:405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems,* Vol. 14 of the A.C.S. Symposium Series; and Edward B. Roche, *Bioreversible Carriers in Drug Design,* American Pharmaceutical Association and Pergamon Press, 1987, all incorporated herein in their entirety.

Additionally, prodrug derivatives of compounds of Formula (G), Formula (G-I) and Formula (G-II), can be prepared by methods known to those of ordinary skill in the art (e.g., for further details see Saulnier et al., (1994), *Bioorganic and Medicinal Chemistry Letters,* Vol. 4, p. 1985). By way of example only, appropriate prodrugs can be prepared by reacting a non-derivatized compound of any of Formula (G), Formula (G-I), or Formula (G-II), with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

Sites on the aromatic ring portion of compounds of Formula (G), Formula (G-I) and Formula (G-II), can be susceptible to various metabolic reactions, therefore incorporation of appropriate substituents on the aromatic ring structures, such as, by way of example only, halogens can reduce, minimize or eliminate this metabolic pathway.

The compounds described herein may be labeled isotopically (e.g. with a radioisotope) or by another other means, including, but not limited to, the use of chromophores or fluorescent moieties, bioluminescent labels, or chemiluminescent labels. The compounds of Formula (G), Formula (G-I) and Formula (G-II), may possess one or more stereocenters and each center may exist in the R or S configuration. The compounds presented herein include all diastereomeric, enantiomeric, and epimeric forms as well as the appropriate mixtures thereof. Compounds of Formula (G), Formula (G-I) and Formula (G-II), can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981, herein incorporated by reference in its entirety.

Additionally, the compounds and methods provided herein may exist as geometric isomers. The compounds and methods provided herein include all cis, trans, syn, anti, entgegen (E), and zusammen (Z) isomers as well as the appropriate mixtures thereof. In some situations, compounds may exist as tautomers. All tautomers are included within the formulas described herein are provided by compounds and methods herein. In additional embodiments of the compounds and methods provided herein, mixtures of enantiomers and/or diastereoisomers, resulting from a single preparative step, combination, or interconversion may also be useful for the applications described herein.

Routes of Administration

Suitable routes of administration include, but are not limited to, intravenous, oral, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

Alternately, one may administer the compound in a local rather than systemic manner, for example, via injection of the compound directly into an organ, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical Composition/Formulation

Pharmaceutical compositions may be formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999), herein incorporated by reference in their entirety.

Provided herein are pharmaceutical compositions comprising a compound of any of Formula (G), Formula (G-I), or Formula (G-II), and a pharmaceutically acceptable diluent(s), excipient(s), or carrier(s). In addition, the compounds described herein can be administered as pharmaceutical compositions in which compounds of any of Formula (G), Formula (G-I), or Formula (G-II), are mixed with other active ingredients, as in combination therapy.

A pharmaceutical composition, as used herein, refers to a mixture of a compound of any of Formula (G), Formula (G-I), or Formula (G-II), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds of any of Formula (G), Formula (G-I), or Formula (G-II), provided herein are administered in a pharmaceutical composition to a mammal having a disease or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

For intravenous injections, compounds of any of Formula (G), Formula (G-I), or Formula (G-II), may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

For oral administration, compounds of any of Formula (G), Formula (G-I), or Formula (G-II), can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in a conventional manner Parental injections may involve bolus injection or continuous infusion. Formulations for injection may be presented in unit dosage form, e.g., in ampoules or in multi-dose containers, with an added preservative. The pharmaceutical composition of any of Formula (G), Formula (G-I), or Formula (G-II), may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds of any of Formula (G), Formula (G-I), or Formula (G-II), can be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Formulations suitable for transdermal administration of compounds having the structure of any of Formula (G), Formula (G-I), or Formula (G-II), may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds of any of Formula (G), Formula (G-I), or Formula (G-II), can be accomplished by means of iontophoretic patches and the like. Additionally, transdermal patches can provide controlled delivery of the compounds any of Formula (G), Formula (G-I), or Formula (G-II). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, the compounds of any of Formula (G), Formula (G-I), or Formula (G-II), maybe in a form as an aerosol, a mist or a powder. Pharmaceutical compositions of any of Formula (G), Formula (G-I), or Formula (G-II), are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

The compounds of any of Formula (G), Formula (G-I), or Formula (G-II), may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions comprising a compound of any of Formula (G), Formula (G-I), or Formula (G-II), may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent or excipient and a compound of any of Formula (G), Formula (G-I), or Formula (G-II), described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A composition comprising a compound of any of Formula (G), Formula (G-I), or Formula (G-II), can illustratively take the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition may include a gel formulation. In other embodiments, the liquid composition is aqueous.

Useful aqueous suspension can also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions can also comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful compositions may also include solubilizing agents to aid in the solubility of a compound of any of Formula (G), Formula (G-I), or Formula (G-II). The term "solubilizing agent" generally includes agents that result in formation of a micellar solution or a true solution of the agent. Certain acceptable nonionic surfactants, for example polysorbate 80, can be useful as solubilizing agents, as can ophthalmically acceptable glycols, polyglycols, e.g., polyethylene glycol 400, and glycol ethers.

Useful compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful compositions may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions may include one or more antioxidants to enhance chemical stability where required. Suitable antioxidants include, by way of example only, ascorbic acid and sodium metabisulfite.

Aqueous suspension compositions can be packaged in single-dose non-reclosable containers. Alternatively, multiple-dose reclosable containers can be used, in which case it is typical to include a preservative in the composition.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

All of the formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

The compounds of Formula (G), Formula (G-I), and Formula (G-II), can be used in the preparation of medicaments for the treatment of leukotriene-dependent or leukotriene mediated diseases or conditions. In addition, a method for treating any of the diseases or conditions described herein in a subject in need of such treatment, involves administration of pharmaceutical compositions containing at least one compound of any of Formula (G), Formula (G-I), or Formula (G-II), or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds of Formula (G), Formula (G-I), and Formula (G-II), described herein are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration comprise from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Use of FLAP Modulators to Prevent and/or Treat Leukotriene-Dependent or Leukotriene Mediated Diseases or Conditions The therapy of leukotriene-dependent or leukotriene mediated diseases or conditions is designed to modulate the activity of FLAP. Such modulation may include, by way of example only, inhibiting or antagonizing FLAP activity. For example, a FLAP inhibitor can be administered in order to decrease synthesis of leukotrienes within the individual, or possibly to downregulate or decrease the expression or availability of the FLAP mRNA or specific splicing variants of the FLAP mRNA. Downregulation or decreasing expression or availability of a native FLAP mRNA or of a particular splicing variant could minimize the expression or activity of a defective nucleic acid or the particular splicing variant and thereby minimize the impact of the defective nucleic acid or the particular splicing variant.

In accordance with one aspect, compositions and methods described herein include compositions and methods for treating, preventing, reversing, halting or slowing the progression of leukotriene-dependent or leukotriene mediated diseases or conditions once it becomes clinically evident, or treating the symptoms associated with or related to leukotriene-dependent or leukotriene mediated diseases or conditions, by administering to the subject a compound of any of Formula (G), Formula (G-I), or Formula (G-II), or pharmaceutical composition or medicament which includes a compound of any of Formula (G), Formula (G-I), or Formula (G-II). The subject may already have a leukotriene-dependent or leukotriene mediated disease or condition at the time of administration, or be at risk of developing a leukotriene-dependent or leukotriene mediated disease or condition. The symptoms of leukotriene-dependent or leukotriene mediated diseases or conditions in a subject can be determined by one skilled in the art and are described in standard textbooks.

The activity of 5-lipoxygenase activating protein in a mammal may be directly or indirectly modulated by the administration of (at least once) an effective amount of at least one compound of any of Formula (G), Formula (G-I), or Formula (G-II), or pharmaceutical composition or medicament which includes a compound of any of Formula (G), Formula (G-I), or Formula (G-II), to a mammal Such modulation includes, but is not limited to, reducing and/or inhibiting the activity of 5-lipoxygenase activating protein. In addition, the activity of leukotrienes in a mammal may be directly or indirectly modulated, including reducing and/or inhibiting, by the administration of (at least once) an effective amount of at least one compound of any of Formula (G), Formula (G-I), or Formula (G-II), or pharmaceutical composition or medicament which includes a compound of any of Formula (G), Formula (G-I), or Formula (G-II), to a mammal Such modulation includes, but is not limited to, reducing and/or inhibiting the activity of 5-lipoxygenase activating protein.

Prevention and/or treatment leukotriene-dependent or leukotriene mediated diseases or conditions may comprise administering to a mammal at least once an effective amount of at least one compound of any of Formula (G), Formula (G-I), or Formula (G-II), or pharmaceutical composition or medicament which includes a compound of any of Formula (G), Formula (G-I), or Formula (G-II). By way of example, the prevention and/or treatment of inflammation diseases or conditions may comprise administering to a mammal at least once an effective amount of at least one compound of any of Formula (G), Formula (G-I), or Formula (G-II), or pharmaceutical composition or medicament which includes a compound of any of Formula (G), Formula (G-I), or Formula (G-II). Leukotriene-dependent or leukotriene mediated diseases or conditions that may be treated by a method comprising administering to a mammal at least once an effective amount of at least one compound of any of Formula (G), Formula (G-I), or Formula (G-II), or pharmaceutical composition or medicament which includes a compound of any of Formula (G), Formula (G-I), or Formula (G-II), include, but are not limited to, bone diseases and disorder, cardiovascular diseases and disorders, inflammatory diseases and disorders, dermatological diseases and disorders, ocular diseases and disorders, cancer and other proliferative diseases and disorders, respiratory diseases and disorder, and non-cancerous disorders.

By way of example only, included in the prevention/treatment methods described herein are methods for treating respiratory diseases comprising administering to the mammal at least once an effective amount of at least one compound of any of Formula (G), Formula (G-I), or Formula (G-II), or pharmaceutical composition or medicament which includes a compound of any of Formula (G), Formula (G-I), or Formula (G-II). By way of example the respiratory disease may be asthma; see Riccioni et al, *Ann. Clin. Lab. Sci.*, v34, 379-387 (2004). In addition, the respiratory disease may include, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, allergic rhinitis, vascular responses, endotoxin shock, fibrogenesis, pulmonary fibrosis, allergic diseases, chronic inflammation, and adult respiratory distress syndrome.

By way of example only, included in such treatment methods are methods for preventing chronic obstructive pulmonary disease comprising administering to the mammal at least once an effective amount of at least one compound of any of Formula (G), Formula (G-I), or Formula (G-II), or pharmaceutical composition or medicament which includes a compound of any of Formula (G), Formula (G-I), or Formula (G-II). In addition, chronic obstructive pulmonary disease includes, but is not limited to, chronic bronchitis or emphysema, pulmonary hypertension, interstitial lung fibrosis and/or airway inflammation and cystic fibrosis.

By way of example only, included in such treatment methods are methods for preventing increased mucosal secretion and/or edema in a disease or condition comprising administering to the mammal at least once an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II); see Jala et al, *Trends in Immunol.*, v25, 315-322 (2004) and Mehrabian et al, *Curr. Opin. Lipidol.*, v14, 447-457 (2003).

By way of example only, included in the prevention/treatment methods described herein are methods for reducing cardiac reperfusion injury following myocardial ischemia and/or endotoxic shock comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for reducing the constriction of blood vessels in a mammal comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for lowering or preventing an increase in blood pressure of a mammal comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for preventing eosinophil and/or basophil and/or dendritic cell and/or neutrophil and/or monocyte recruitment comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for the prevention or treatment of abnormal bone remodeling, loss or gain, including diseases or conditions as, by way of example, osteopenia, osteoporosis, Paget's disease, cancer and other diseases comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for preventing ocular inflammation and allergic conjunctivitis, vernal keratoconjunctivitis, and papillary conjunctivitis comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II); see Lambiase et al, *Arch. Opthalmol.*, v121, 615-620 (2003).

By way of example only, included in the prevention/treatment methods described herein are methods for preventing CNS disorders comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II). CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

By way of example only, included in the prevention/treatment methods described herein are methods for the treatment of cancer comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II). The type of cancer may include, but is not limited to, pancreatic cancer and other solid or hematological tumors, see Poff and Balazy, *Curr. Drug Targets Inflamm. Allergy*, v3, 19-33 (2004) and Steele et al, *Cancer Epidemiology & Prevention*, v8, 467-483 (1999).

By way of example only, included in the prevention/treatment methods described herein are methods for preventing endotoxic shock and septic shock comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein methods for preventing rheumatoid arthritis and osteoarthritis comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for preventing increased GI diseases comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II). Such GI diseases include, by way of example only, inflammatory bowel disease (IBD), colitis and Crohn's disease.

By way of example only, included in the prevention/treatment methods described herein are methods for the reduction of inflammation while also preventing transplant rejection or preventing or treating tumors or acclerating the healing of wounds comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for the prevention or treatment of rejection or dysfunction in a transplanted organ or tissue comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for treating type II diabetes comprising administering to at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for treating inflammatory responses of the skin comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II). Such inflammatory responses of the skin include, by way of example, psoriasis, dermatitis, contact dermatitis, eczema, urticaria, rosacea, wound healing and scarring. In another aspect are methods for reducing psoriatic lesions in the skin, joints, or other tissues or organs, comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for the treatment of cystitis, including, by way of example only, interstitial cystitis, comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

By way of example only, included in the prevention/treatment methods described herein are methods for the treatment of metabolic syndromes such as Familial Mediterranean Fever comprising administering at least once to the mammal an effective amount of at least one compound of any of Formula (G), Formula (G-I), or Formula (G-II), or pharmaceutical composition or medicament which includes a compound of any of Formula (G), Formula (G-I), or Formula (G-II).

Combination Treatments

In certain instances, it may be appropriate to administer at least one compound of any of Formula (G), Formula (G-I), or Formula (G-II), in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for asthma involving administration of one of the compounds described herein, increased therapeutic benefit may result by also providing the patient with other therapeutic agents or therapies for asthma. In any case, regardless of the disease, disorder or condition being treated, the overall benefit experienced by the patient may simply be additive of the two therapeutic agents or the patient may experience a synergistic benefit.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. A combination treatment regimen may encompasses treatment regimens in which administration of a FLAP or 5-LO inhibitor described herein is initiated prior to, during, or after treatment with a second agent described above, and continues until any time during treatment with the second agent or after termination of treatment with the second agent. It also includes treatments in which a FLAP or 5-LO inhibitor described herein and the second agent being used in combination are administered simultaneously or at different times and/or at decreasing or increasing intervals during the treatment period. Combination treatment further includes periodic treatments that start and stop at various times to assist with the clinical management of the patient. For example, a FLAP or 5-LO inhibitor described herein in the combination treatment can be administered weekly at the onset of treatment, decreasing to biweekly, and decreasing further as appropriate.

Compositions and methods for combination therapy are provided herein. In accordance with one aspect, the pharmaceutical compositions disclosed herein are used to treat leukotriene-dependent or leukotriene mediated conditions. In accordance with another aspect, the pharmaceutical compositions disclosed herein are used to treat respiratory diseases, where treatment with a FLAP inhibitor is indicated, in particular asthma, and to induce bronchodilation in a subject. In one embodiment, pharmaceutical compositions disclosed herein are used to treat a subject suffering from a vascular inflammation-driven disorder. In one embodiment, the pharmaceutical compositions disclosed herein are used to treat a subject susceptible to myocardial infarction (MI).

Combination therapies described herein can be used as part of a specific treatment regimen intended to provide a beneficial effect from the co-action of a FLAP inhibitors described herein and a concurrent treatment. It is understood that the dosage regimen to treat, prevent, or ameliorate the condition(s) for which relief is sought, can be modified in accordance with a variety of factors. These factors include the type of respiratory disorder and the type of bronchodilation from which the subject suffers, as well as the age, weight, sex, diet, and medical condition of the subject. Thus, the dosage regimen actually employed can vary widely and therefore can deviate from the dosage regimens set forth herein.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is one of the compounds described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

In addition, the compounds of any of Formula (G), Formula (G-I), or Formula (G-II), may also be used in combination with procedures that may provide additional or synergistic benefit to the patient. By way of example only, patients are expected to find therapeutic and/or prophylactic benefit in the methods described herein, wherein pharmaceutical composition of any of Formula (G), Formula (G-I), or Formula (G-II), and/or combinations with other therapeutics are combined with genetic testing to determine whether that individual is a carrier of a mutant gene that is known to be correlated with certain diseases or conditions.

The compounds of any of Formula (G), Formula (G-I), or Formula (G-II), and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, preferably about 1 month to about 5 years, and more preferably from about 1 month to about 3 years.

By way of example, therapies which combine compounds of any of Formula (G), Formula (G-I), or Formula (G-II), with inhibitors of leukotriene synthesis or leukotriene receptor antagonists, either acting at the same or other points in the leukotriene synthesis pathway, could prove to be particularly useful for treating leukotriene-dependent or leukotriene mediated diseases or conditions. In addition, by way of example, therapies which combine compounds of any of Formula (G), Formula (G-I), or Formula (G-II), with inhibitors of inflammation could prove to be particularly useful for treating leukotriene-dependent or leukotriene mediated diseases or conditions.

Anti-Inflammatory Agents

In another embodiment described herein, methods for treatment of leukotriene-dependent or leukotriene mediated conditions or diseases includes administered to a patient compounds, pharmaceutical compositions, or medicaments described herein in combination with an anti-inflammatory agent including, but not limited to, arthrotec, asacol, auralglan, azulfidine, daypro, etodolac, ponstan, salofalk, and solumedrol; non-steroidal anti-inflammatory agents, by way of example, aspirin (Bayer™, Bufferin™), indomethacin (Indocin™), rofecoxib (Vioxx™), celecoxib (Celebrex™), valdecoxib (Bextra™), diclofenac, etodolac, ketoprofen, Iodine, mobic, nabumetone, naproxen, piroxicam; and corticosteroids, by way of example, celestone, prednisone, and deltasone. Corticosteroids do not directly inhibit leukotriene production, therefore co-dosing with steroids could provide additional anti-inflammatory benefit.

By way of example, asthma is a chronic inflammatory disease characterized by pulmonary eosinophilia and airway hyperresponsiveness. Zhao et al., *Proteomics*, Jul. 4, 2005. In patients with asthma, leukotrienes may be released from mast cells, eosinophils, and basophils. The leukotrienes are involved in contraction of airway smooth muscle, an increase in vascular permeability and mucus secretions, and have been reported to attract and activate inflammatory cells in the airways of asthmatics (Siegel et al., ed., Basic Neurochemistry, Molecular, Cellular and Medical Aspects, Sixth Ed., Lippincott Williams & Wilkins, 1999). Thus, in another embodiment described herein, the methods for treatment of respiratory diseases includes administration to a patient compounds, pharmaceutical compositions, or medicaments described herein in combination with an anti-inflammatory agent.

Leukotriene Receptor Antagonists

In another embodiment described herein, methods for treatment of leukotriene-dependent or leukotriene mediated conditions or diseases includes administered to a patient compounds, pharmaceutical compositions, or medicaments described herein in combination with leukotriene receptor antagonists including, but are not limited to, $CysLT_1/CysLT_2$ dual receptor antagonists and $CysLT_1$ receptor antagonists. In another embodiment described herein, methods for treatment of leukotriene-dependent or leukotriene mediated conditions or diseases includes administered to a patient compounds, pharmaceutical compositions, or medicaments described herein in combination with a $CysLT_1/CysLT_2$ dual receptor antagonist. $CysLT_1/CysLT_2$ dual receptor antagonists include, but are not limited to, BAY u9773, Cuthbert et al EP 00791576 (published 27 Aug. 1997), DUO-LT (Galczenski et al, D38, Poster F4 presented at American Thoracic Society, May 2002) and Tsuji et al, *Org. Biomol. Chem.*, 1, 3139-3141, 2003. For a particular patient, the most appropriate formulation or method of use of such combination treatments may depend on the type of leukotriene-dependent or leukotriene mediated disorder, the time period in which the FLAP inhibitor acts to treat the disorder and the time period in which the $CysLT_1/CysLT_2$ dual receptor antagonist acts to inhibit CysLT receptor activity. By way of example only, such combination treatments may be used for treating a patient suffering from a respiratory disorders.

In another embodiment described herein, methods for treatment of leukotriene-dependent or leukotriene mediated conditions or diseases includes administered to a patient compounds, pharmaceutical compositions, or medicaments described herein in combination with a $CysLT_1$ receptor antagonist. $CysLT_1$ receptor antagonists include, but are not limited to, Zafirlukast ("Accolate™"), Montelukast ("Singulair™"), Prankulast ("Onon™"), and derivatives or analogs thereof. Such combinations may be used to treat leukotriene-dependent or leukotriene mediated disorder, including respiratory disorders.

The co-administration of a FLAP or 5-LO inhibitor described herein with a $CysLT_1$ receptor antagonist or a dual $CysLT_1/CysLT_2$ receptor antagonist may have therapeutic benefit over and above the benefit derived from the administration of a either a FLAP or 5-LO inhibitor or a $CysLT_1R$ antagonist alone. In the case that substantial inhibition of leukotriene production has undesired effects, partial inhibition of this pathway through the amelioration of the effects of the proinflammatory $LTB_4$ and cysteinyl leukotrienes combined with the block of the $CysLT_1$ receptor and/or dual $CysLT_1/CysLT_2$ receptor block may afford substantial therapeutic benefits, particularly for respiratory diseases.

Other Combination Therapies

In another embodiment described herein, methods for treatment of leukotriene-dependent or leukotriene mediated conditions or diseases, such as proliferative disorders, including cancer, comprises administration to a patient compounds, pharmaceutical compositions, or medicaments described herein in combination with at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In another embodiment described herein, methods for treatment of leukotriene-dependent or leukotriene mediated conditions or diseases, such as the therapy of transplanted organs or tissues or cells, comprises administration to a patient compounds, pharmaceutical compositions, or medicaments described herein in combination with at least one additional agent selected from the group consisting of azathioprine, a corticosteroid, cyclophosphamide, cyclosporin, dacluzimab, mycophenolate mofetil, OKT3, rapamycin, tacrolimus, thymoglobulin.

In another embodiment described herein, methods for treatment of leukotriene-dependent or leukotriene mediated conditions or diseases, such as atherosclerosis, comprises administration to a patient compounds, pharmaceutical compositions, or medicaments described herein in combination with at least one additional agent selected from the group consisting of HMG-CoA reductase inhibitors (e.g., statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; nisvastatin, also referred to as NK-104; rosuvastatin); agents that have both lipid-altering effects and other pharmaceutical activities; HMG-CoA synthase inhibitors; cholesterol absorption inhibitors such as ezetimibe; cholesterol ester transfer protein (CETP) inhibitors, for example JTT-705 and CP529, 414; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/

IIIa fibrinogen receptor antagonists and aspirin; human peroxisome proliferator activated receptor gamma (PPARγ) agonists, including the compounds commonly referred to as glitazones, for example troglitazone, pioglitazone and rosiglitazone and including those compounds included within the structural class known as thiazolidinediones as well as those PPARγ agonists outside the thiazolidinedione structural class; PPARγ agonists such as clofibrate, fenofibrate including micronized fenofibrate, and gemfibrozil; PPAR dual α/γ agonists such as 5-[(2,4-dioxo-5-thiazolidinyl)methyl]-2-methoxy-N-[[4-(trifluoromethyl)phenyl]methyl]-benzamide, known as KRP-297; vitamin B6 (also known as pyridoxine) and the pharmaceutically acceptable salts thereof such as the HCl salt; vitamin B12 (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

In another embodiment described herein, methods for treatment of leukotriene-dependent or leukotriene mediated conditions or diseases, such as the therapy of stroke, comprises administration to a patient compounds, pharmaceutical compositions, or medicaments described herein in combination with at least one additional agent selected from COX-2 inhibitors; nitric oxide synthase inhibitors, such as N-(3-(aminomethyl)benzyl)acetamidine; Rho kinase inhibitors, such as fasudil; angiotension II type-1 receptor antagonists, including candesartan, losartan, irbesartan, eprosartan, telmisartan and valsartan; glycogen synthase kinase 3 inhibitors; sodium or calcium channel blockers, including crobenetine; p38 MAP kinase inhibitors, including SKB 239063; thromboxane AX-synthetase inhibitors, including isbogrel, ozagrel, ridogrel and dazoxiben; statins (HMG CoA reductase inhibitors), including lovastatin, simvastatin, dihydroxy open-acid simvastatin, pravastatin, fluvastatin, atorvastatin, nisvastatin, and rosuvastatin; neuroprotectants, including free radical scavengers, calcium channel blockers, excitatory amino acid antagonists, growth factors, antioxidants, such as edaravone, vitamin C, TROLOX™, citicoline and minicycline, and reactive astrocyte inhibitors, such as (2R)-2-propyloctanoic acid; beta andrenergic blockers, such as propranolol, nadolol, timolol, pindolol, labetalol, metoprolol, atenolol, esmolol and acebutolol; NMDA receptor antagonists, including memantine; NR2B antagonists, such as traxoprodil; 5-HT1A agonists; receptor platelet fibrinogen receptor antagonists, including tirofiban and lamifiban; thrombin inhibitors; antithrombotics, such as argatroban; antihypertensive agents, such as enalapril; vasodilators, such as cyclandelate; nociceptin antagonists; DPIV antagonists; GABA 5 inverse agonists; and selective androgen receptor modulators.

In another embodiment described herein, methods for treatment of leukotriene-dependent or leukotriene mediated conditions or diseases, such as the therapy of pulmonary fibrosis, comprises administration to a patient compounds, pharmaceutical compositions, or medicaments described herein in combination with at least one additional agent selected from anti-inflammatory agents, such as corticosteroids, azathioprine or cyclophosphamide.

In another embodiment described herein, methods for treatment of leukotriene-dependent or leukotriene mediated conditions or diseases, such as the therapy of interstitial cystitis, comprises administration to a patient compounds, pharmaceutical compositions, or medicaments described herein in combination with at least one additional agent selected from dimethylsulfoxide, omalizumab, and pentosan polysulfate.

In another embodiment described herein, methods for treatment of leukotriene-dependent or leukotriene mediated conditions or diseases, such as the therapy of disorders of bone, comprises administration to a patient compounds, pharmaceutical compositions, or medicaments described herein in combination with at least one additional agent selected from the group consisting of minerals, vitamins, bisphosphonates, anabolic steroids, parathyroid hormone or analogs, and cathepsin K inhibitors.

Treatment of Leukotriene Based Conditions or Diseases Using $CysLT_1$/$CysLT_2$ Receptor Antagonists In accordance with another aspect, the compositions and methods described herein are designed to deliver a $CysLT_1$/$CysLT_2$ dual receptor antagonist to block the CysLT receptor activity. The term "CysLT antagonist" or "CysLT receptor antagonist" or "leukotriene receptor antagonist" refers to a therapy that decreases the signaling of CysLTs through CysLT receptors. CysLT typically refers to either $LTC_4$, $LTD_4$ or $LTE_4$. Cysteinyl leukotrienes are potent smooth muscle constricting agents, particularly in respiratory and circulatory systems. These are mediated via at least two cell receptors, $CysLT_1$ and $CysLT_2$. The $CysLT_1$ receptor and $CysLT_2$ receptors are G-protein-coupled receptors with seven putative transmembrane regions and an intracellular domain that interacts with G-proteins, Evans et al, *Prostaglandins and Other Lipid Mediators,* 68-69, p587-597, (2002). Examples of $CysLT_1$/$CysLT_2$ dual receptor antagonists are BAY u9773, Cuthbert et al EP 00791576 (published 27 Aug. 1997), DUO-LT (Galczenski et al, D38, Poster F4 presented at American Thoracic Society, May 2002) and Tsuji et al, *Org. Biomol. Chem.,* 1, 3139-3141, 2003.

In certain embodiments, methods for treatment of leukotriene-dependent or leukotriene mediated diseases or conditions includes administering to patients compounds, pharmaceutical compositions, or medicaments comprising a $CysLT_1$/$CysLT_2$ receptor antagonist. By way of example, such compounds, pharmaceutical compositions, or medicaments may be used as treatment and/or prevention for respiratory diseases including, but not limited to, chronic stable asthma.

Diagnostic Methods for Patient Identification

The screening of "leukotriene-responsive patients" which may be selected for treatment with compounds of any of Formula (G), Formula (G-I), or Formula (G-II), or pharmaceutical compositions or medicaments described herein which include compounds of any of Formula (G), Formula (G-I), or Formula (G-II), or other FLAP modulators, may be accomplished using techniques and methods described herein. Such techniques and methods include, by way of example, evaluation of gene haplotypes (genotype analysis), monitoring/measurement of biomarkers (phenotype analysis), monitoring/measurement of functional markers (phenotype analysis), which indicate patient response to known modulators of the leukotriene pathway, or any combination thereof.

Genotype Analysis: FLAP Polymorphisms

Human FLAP has been purified and cloned and is an 18 kilodalton membrane-bound protein which is most highly expressed in human neutrophils. The FLAP gene is located at 13q12 and the gene has been linked to increased risk for both myocardial infarction and stroke in several populations. A number of polymorphisms and haplotypes in the gene encoding FLAP have been identified in individuals (U.S. Patent Application 2005113408; Sayers, *Clin. Exp. Allergy,* 33(8): 1103-10, 2003; Kedda, et al., *Clin. Exp. Allergy,* 35(3):332-8, 2005). Particular FLAP haplotypes have been linked to myocardial infarction and stroke in several populations (Helgadottir A et al. *Nature Genet.* 36:233-239 (2004); Helgadottir A et al. *Am J Hum Genet.* 76:505-509 (2004); Lohmussaar E et al. *Stroke* 36: 731-736 (2005); Kajimoto K et al. *Circ J* 69:1029-1034 (2005). Previously, polymorphisms in certain genes have been demonstrated to correlate with responsiveness to given therapies, for example, the responsiveness of cancers to particular chemotherapeutic agents (Erichsen, et al., *Br. J. Cancer,* 90(4):747-51, 2004; Sullivan, et al., *Oncogene,* 23(19):3328-37, 2004). Therefore, patients who are under consideration for treatment with the novel FLAP inhibitors described herein, or drug combinations that include such novel FLAP inhibitors, may be screened for potential responsiveness to treatment based on their FLAP polymorphisms, or haplotypes.

Additionally, polymorphisms in any of the synthetic or signaling genes dedicated to the leukotriene pathway could result in a patient who is more responsive or less responsive to leukotriene modulator therapy (either FLAP or 5-LO inhibitor or leukotriene receptor antagonists). The genes dedicated to the leukotriene pathway are 5-lipoxygenase, 5-lipoxygenase-activating protein, $LTA_4$ hydrolase, $LTC_4$ synthase, $LTB_4$ receptor 1 ($BLT_1$), $LTB_4$ receptor 2 ($BLT_2$), cysteinyl leukotriene receptor 1 ($CysLT_1R$), cysteinyl leukotriene receptor 2 ($CysLT_2R$). For example, the 5-LO gene has been linked to aspirin intolerant asthma and airway hyperresponsiveness (Choi J H et al. *Hum Genet* 114:337-344 (2004); Kim, S H et al. *Allergy* 60:760-765 (2005). Genetic variants in the promoter region of 5-LO have been shown to predict clinical responses to a 5LO inhibitor in asthmatics (Drazen et al, *Nature Genetics,* 22, p168-170, (1999). The $LTC_4$ synthase gene has been linked to atopy and asthma (Moissidis I et al. *Genet Med* 7:406-410 (2005). The $CysLT_2$ receptor has been linked to asthma and atopy (Thompson M D et al. *Pharmacogenetics* 13:641-649 (2003); Pillai S G et al. *Pharmacogenetics* 14:627-633 (2004); Park J S et al. *Pharmacogenet Genomics* 15:483-492 (2005); Fukai H et al. *Pharmacogenetics* 14:683-690 (2004). Any polymorphisms in any leukotriene pathway gene or combination of polymorphisms or haplotypes may result in altered sensitivity of the patient to therapy aimed at reducing the pathological effects of leukotrienes. Selection of patients who might best respond to the leukotriene modulator therapies described herein may include knowledge of polymorphisms in the leukotriene pathway genes and also knowledge of the expression of leukotriene-driven mediators. Patient selection could be made on the basis of leukotriene pathway genotype alone, phenotype alone (biomarkers or functional markers) or any combination of genotype and phenotype.

A "haplotype," as described herein, refers to a combination of genetic markers ("alleles"). A haplotype can comprise one or more alleles (e.g., a haplotype containing a single SNP), two or more alleles, three or more alleles, four or more alleles, or five or more alleles. The genetic markers are particular "alleles" at "polymorphic sites" associated with FLAP. A nucleotide position at which more than one sequence is possible in a population is referred to herein as a "polymorphic site." Where a polymorphic site is a single nucleotide in length, the site is referred to as a single nucleotide polymorphism ("SNP"). For example, if at a particular chromosomal location, one member of a population has an adenine and another member of the population has a thymine at the same position, then this position is a polymorphic site, and, more specifically, the polymorphic site is a SNP. Polymorphic sites can allow for differences in sequences based on substitutions, insertions or deletions. Each version of the sequence with respect to the polymorphic site is referred to herein as an "allele" of the polymorphic site. Thus, in the previous example, the SNP allows for both an adenine allele and a thymine allele.

Typically, a reference sequence is referred to for a particular sequence. Alleles that differ from the reference are referred to as "variant" alleles. The term "variant FLAP" as used herein, refers to a sequence that differs from a reference FLAP sequence, but is otherwise substantially similar. The genetic markers that make up the haplotypes described herein are FLAP variants. In certain embodiments the FLAP variants are at least about 90% similar to a reference sequence. In other embodiments the FLAP variants are at least about 91% similar to a reference sequence. In other embodiments the FLAP variants are at least about 92% similar to a reference sequence. In other embodiments the FLAP variants are at least about 93% similar to a reference sequence. In other embodiments the FLAP variants are at least about 94% similar to a reference sequence. In other embodiments the FLAP variants are at least about 95% similar to a reference sequence. In other embodiments the FLAP variants are at least about 96% similar to a reference sequence. In other embodiments the FLAP variants are at least about 97% similar to a reference sequence. In other embodiments the FLAP variants are at least about 98% similar to a reference sequence. In other embodiments the FLAP variants are at least about 99% similar to a reference sequence.

Additionally, in certain embodiments the FLAP variants differ from the reference sequence by at least one base, while in other embodiments the FLAP variants differ from the reference sequence by at least two bases. In other embodiments the FLAP variants differ from the reference sequence by at least three bases, and in still other embodiments the FLAP variants differ from the reference sequence by at least four bases.

Additional variants can include changes that affect a polypeptide, e.g., the FLAP polypeptide. The polypeptide encoded by a reference nucleotide sequence is the "reference" polypeptide with a particular reference amino acid sequence, and polypeptides encoded by variant alleles are referred to as "variant" polypeptides with variant amino acid sequences. The FLAP nucleic acid sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence; duplication of all or a part of a sequence; transposition; or a rearrangement of a nucleotide sequence, as described in detail above. Such sequence changes alter the polypeptide encoded by a FLAP nucleic acid. For example, if the change in the nucleic acid sequence causes a frame shift, the frame shift can result in a change in the encoded amino acids, and/or can result in the generation of a premature stop codon, causing generation of a truncated polypeptide.

By way of example, a polymorphism associated with a susceptibility to myocardial infarction (MI), acute coronary syndrome (ACS), stroke or peripheral arterial occlusive disease (PAOD) can be a synonymous change in one or more nucleotides (i.e., a change that does not result in a change in the amino acid sequence). Such a polymorphism can, for example, alter splice sites, decrease or increase expression levels, affect the stability or transport of mRNA, or otherwise affect the transcription or translation of the polypeptide. The haplotypes described below are found more frequently in individuals with MI, ACS, stroke or PAOD than in individuals without MI, ACS, stroke or PAOD. Therefore, these haplotypes may have predictive value for detecting a susceptibility to MI, ACS, stroke or PAOD in an individual.

Several variants of the FLAP gene have been reported to correlate with the incidence of myocardial infarction in patients (Hakonarson, *JAMA*, 293(18):2245-56, 2005), plus FLAP gene markers reportedly associated with the risk for developing asthma have been described in U.S. Pat. No. 6,531,279. Methods for identifying FLAP sequence variants are described, e.g., in U.S. Publication No. 2005/0113408, and in U.S. Pat. No. 6,531,279, incorporated herein by reference herein in their entirety.

By way of example only, a haplotype associated with a susceptibility to myocardial infarction or stroke comprises markers SG13S99, SG13S25, SG13S377, SG13S106, SG13S32 and SG13S35 at the 13q12-13 locus. Or, the presence of the alleles T, G, G, G, A and G at SG13S99, SG13S25, SG13S377, SG13S106, SG13S32 and SG13S35, respectively (the B6 haplotype), is diagnostic of susceptibility to myocardial infarction or stroke. Or, a haplotype associated with a susceptibility to myocardial infarction or stroke comprises markers SG13S99, SG13S25, SG13S106, SG13S30 and SG13S42 at the 13q12-13 locus. Or, the presence of the alleles T, G, G, G and A at SG13S99, SG13S25, SG13S106, SG13S30 and SG13S42, respectively (the B5 haplotype), is diagnostic of susceptibility to myocardial infarction or stroke Or, a haplotype associated with a susceptibility to myocardial infarction or stroke comprises markers SG13S25, SG13S106, SG13S30 and SG13S42 at the 13q12-13 locus. Or, the presence of the alleles G, G, G and A at SG13S25, SG13S106, SG13S30 and SG13S42, respectively (the B4 haplotype), is diagnostic of susceptibility to myocardial infarction or stroke. Or, a haplotype associated with a susceptibility to myocardial infarction or stroke comprises markers SG13S25, SG13S106, SG13S30 and SG13S32 at the 13q12-13 locus. Or, the presence of the alleles G, G, G and A at SG13S25, SG13S106, SG13S30 and SG13S32, respectively (the Bs4 haplotype), is diagnostic of susceptibility to myocardial infarction or stroke. In such embodiments just described, patients who are under consideration for treatment with compounds of any of Formula (G), Formula (G-I), or Formula (G-II), or drug combinations described herein that include compounds of any of Formula (G), Formula (G-I), or Formula (G-II), may be screened for potential responsiveness to treatment with compounds of any of Formula (G), Formula (G-I), or Formula (G-II), based on such haplotypes.

By way of example only, a haplotype associated with a susceptibility to myocardial infarction or stroke comprises markers SG13S99, SG13S25, SG13S114, SG13S89 and SG13S32 at the 13q12-13 locus. Or, the presence of the alleles T, G, T, G and A at SG13S99, SG13S25, SG13S114, SG13S89 and SG13S32, respectively (the AS haplotype), is diagnostic of susceptibility to myocardial infarction or stroke. Or, a haplotype associated with a susceptibility to myocardial infarction or stroke comprises markers SG13S25, SG13S114, SG13S89 and SG13S32 at the 13q12-13 locus. Or, the presence of the alleles G, T, G and A at SG13S25, SG13S114, SG13S89 and SG13S32, respectively (the A4 haplotype), is diagnostic of susceptibility to myocardial infarction or stroke. In such embodiments just described, patients who are under consideration for treatment with compounds of any of Formula (G), Formula (G-I), or Formula (G-II), or drug combinations described herein that include compounds of any of Formula (G), Formula (G-I), or Formula (G-II), may be screened for potential responsiveness to treatment with compounds of any of Formula (G), Formula (G-I), or Formula (G-II), based on such haplotypes.

Detecting haplotypes can be accomplished by methods known in the art for detecting sequences at polymorphic sites, and therefore patients may be selected using genotype selection of FLAP, 5-LO or other leukotriene pathway gene polymorphisms. The presence or absence of a leukotriene pathway gene polymorphism or haplotype can be determined by various methods, including, for example, using enzymatic amplification, restriction fragment length polymorphism analysis, nucleic acid sequencing, electrophoretic analysis of nucleic acid from the individual, or any combination thereof. In certain embodiments, determination of a SNP or haplotype may identify patients who will respond to, or gain benefit from, treatment with compounds of any of Formula (G), Formula (G-I), or Formula (G-II). By way of example, methods of diagnosing a susceptibility to myocardial infarction or stroke in an individual, comprises determining the presence or absence of certain single nucleotide polymorphisms (SNPs) or of certain haplotypes, wherein the presence of the SNP or the haplotype is diagnostic of susceptibility to myocardial infarction or stroke.

Phenotype Analysis: Biomarkers

Patients who are under consideration for treatment with compounds of any of Formula (G), Formula (G-I), or Formula (G-II), or drug combinations described herein that include compounds of any of Formula (G), Formula (G-I), or Formula (G-II), may be screened for potential responsiveness to treatment based on leukotriene-driven inflammatory biomarker phenotypes.

Patient screening based on leukotriene-driven inflammatory biomarker phenotypes may be used as an alternative to, or it may be complimentary with, patient screening by leukotriene pathway gene haplotype detection. The term "biomarker" as used herein refers to a characteristic which can be measured and evaluated as an indicator of normal biological processes, pathological processes, or pharmacological responses to therapeutic intervention. Thus a biomarker may be any substance, structure or process which can be measured in the body, or its products, and which may influence or predict the incidence of outcome or disease. Biomarkers may be classified into markers of exposure, effect, and susceptibility. Biomarkers can be physiologic endpoints, by way of example blood pressure, or they can be analytical endpoints, by way of example, blood glucose, or cholesterol concentrations. Techniques, used to monitor and/or measure biomarkers include, but are not limited to, NMR, LC-MS, LC-MS/MS, GC-MS, GC-MS/MS, HPLC-MS, HPLC-MS/MS, FT-MS, FT-MS/MS, ICP-MS, ICP-MS/MS, peptide/protein sequencing, nucleic acid sequencing, electrophoresis techniques, immuno-assays, immuno-blotting, in-situ hybridization, fluorescence in-situ hybridization, PCR, radio-immuno assays, and enzyme-immuno assays. Single nucleotide polymorphisms (SNPs) have also been useful for the identification of biomarkers for propensity to certain diseases and also susceptibility or responsiveness to drugs such as chemotherapeutic agents and antiviral agents. These techniques, or any combination thereof, may be used to screen patients for leukotriene-dependent or leukotriene mediated diseases or conditions, wherein such patients may be beneficially treated with compounds of any of Formula (G), Formula (G-I), or Formula (G-II), or drug combinations described herein that include compounds of any of Formula (G), Formula (G-I), or Formula (G-II).

By way of example only, patients may be selected for treatment with compounds of any of Formula (G), Formula (G-I), or Formula (G-II), or drug combinations described herein that include compounds of any of Formula (G), Formula (G-I), or Formula (G-II), by screening for enhanced inflammatory blood biomarkers such as, but not limited to, stimulated $LTB_4$, $LTC_4$, $LTE_4$, myeloperoxidase (MPO), eosinophil peroxidase (EPO), C-reactive protein (CRP), soluble intracellular adhesion molecule (sICAM), monocyte chemoattractant protein (MCP-1), monocyte inflammatory protein (MIP-1α), interleukin-6 (IL-6), the TH2 T cell activators interleukin 4 (IL-4), and 13 (IL-13) and other inflammatory cytokines. In certain embodiments, patients with inflammatory respiratory diseases, including but not limited to, asthma and COPD, or with cardiovascular diseases, are selected as those most likely to be responsive to leukotriene synthesis inhibition using compounds of any of Formula (G), Formula (G-I), or Formula (G-II), by using a panel of leukotriene driven inflammatory biomarkers.

Phenotype Analysis: Functional Markers

Patients who are under consideration for treatment with compounds of any of Formula (G), Formula (G-I), or Formula (G-II), or drug combinations described herein that include compounds of any of Formula (G), Formula (G-I), or Formula (G-II), may be screened for response to known modulators of the leukotriene pathway. Patient screening by evaluation of functional markers as indicators of a patient's response to known modulators of the leukotriene pathway may be used as an alternative to, or it may be complimentary with, patient screening by leukotriene pathway gene haplotype detection (genotype analysis) and/or monitoring/measurement of leukotriene-driven inflammatory biomarker phenotypes. Functional markers may include, but are not limited to, any physical characteristics associated with a leukotriene dependent condition or disease, or knowledge of current or past drug treatment regimens.

By way of example only, the evaluation of lung volume and/or function may be used as a functional marker for leukotriene-dependent or leukotriene mediated diseases or conditions, such as respiratory diseases. Lung function tests may be used to screen patients, with such leukotriene-dependent or leukotriene mediated diseases or conditions, for treatment using compounds of any of Formula (G), Formula (G-I), or Formula (G-II), or pharmaceutical compostitons or medicaments which include compounds of any of Formula (G), Formula (G-I), or Formula (G-II). Such tests include, but are not limited to, evaluation of lung volumes and capacities, such as tidal volume, inspiratory reserve volume, expiratory reserve volume, residual volume, inspiratory capacity, functional residual capacity, vital capacity, total lung capacity, respiratory minute volume, alveolar ventilation, timed vital capacity, and ventilatory capacity. Method of measurement of lung volumes and capacities include, but are not limited to, maximum expiratory flow volume curve, forced expiratory volume in 1 sec. (FEV1), peak expiratory flow rate. In addition, other lung function tests used as functional markers for patient evaluation described herein include, but are not limited to, respiratory muscle power, maximum inspiratory pressure, maximum expiratory pressure, transdiaphragmatic pressure, distribution of ventilation, single breath nitrogen test, pulmonary nitrogen washout, and gas transfer.

Additionally, the knowledge of a patients past or current treatment regimen may be used as a functional marker to assist in screening patients for treatment of leukotriene dependent conditions or diseases using compounds of any of Formula (G), Formula (G-I), or Formula (G-II), or pharmaceutical compositions or medicaments which include compounds of any of Formula (G), Formula (G-I), or Formula (G-II). By way of example only, such treatment regimens may include past or current treatment using zileuton (Zyflo™), montelukast (Singulair™), pranlukast (Onon™), zafirlukast (Accolate™).

Also, patients who are under consideration for treatment with compounds of any of Formula (G), Formula (G-I), or Formula (G-II), or drug combinations described herein that include compounds of any of Formula (G), Formula (G-I), or Formula (G-II), may be screened for functional markers which include, but are not limited to, reduced eosinophil and/or basophil, and/or neutrophil, and/or monocyte and/or dendritic cell and/or lymphocyte recruitment, decreased mucosal secretion, decreased mucosal edema, and/or increased bronchodilation.

Figure 12:
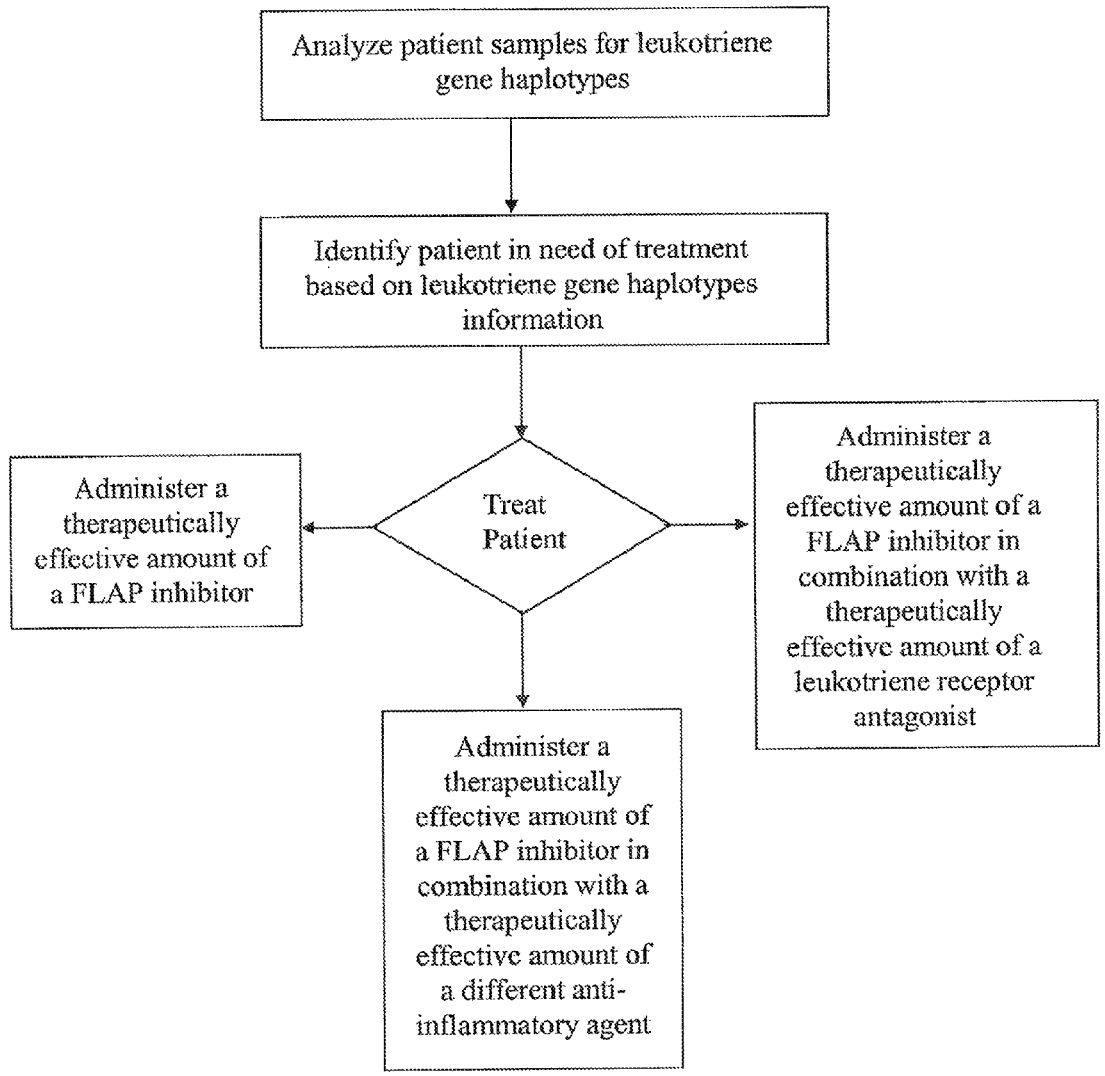
FIG. 12 present an illustrative scheme for the treatment of patients using the compounds and methods described herein.
Figure 13:
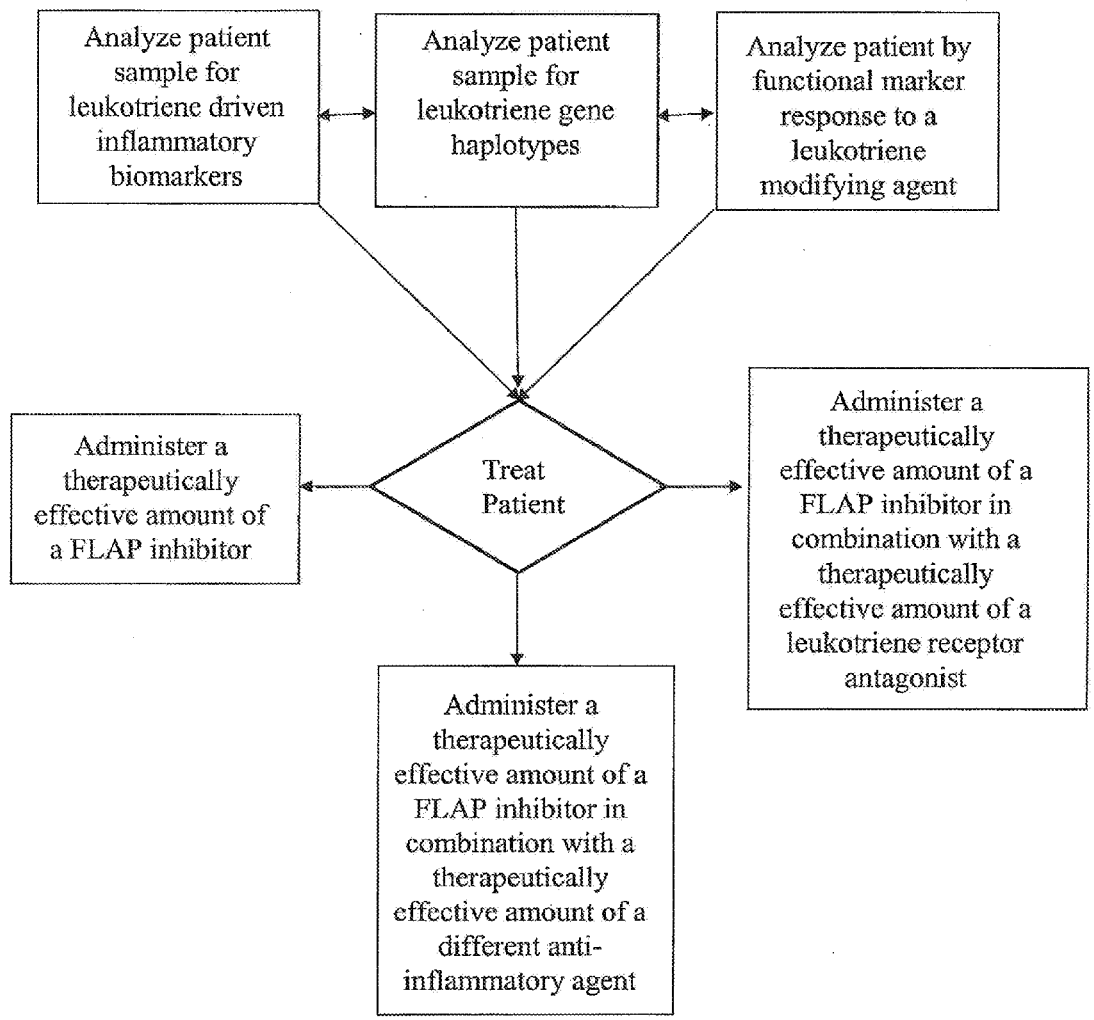
FIG. 13 present an illustrative scheme for the treatment of patients using the compounds and methods described herein.
Figure 14:
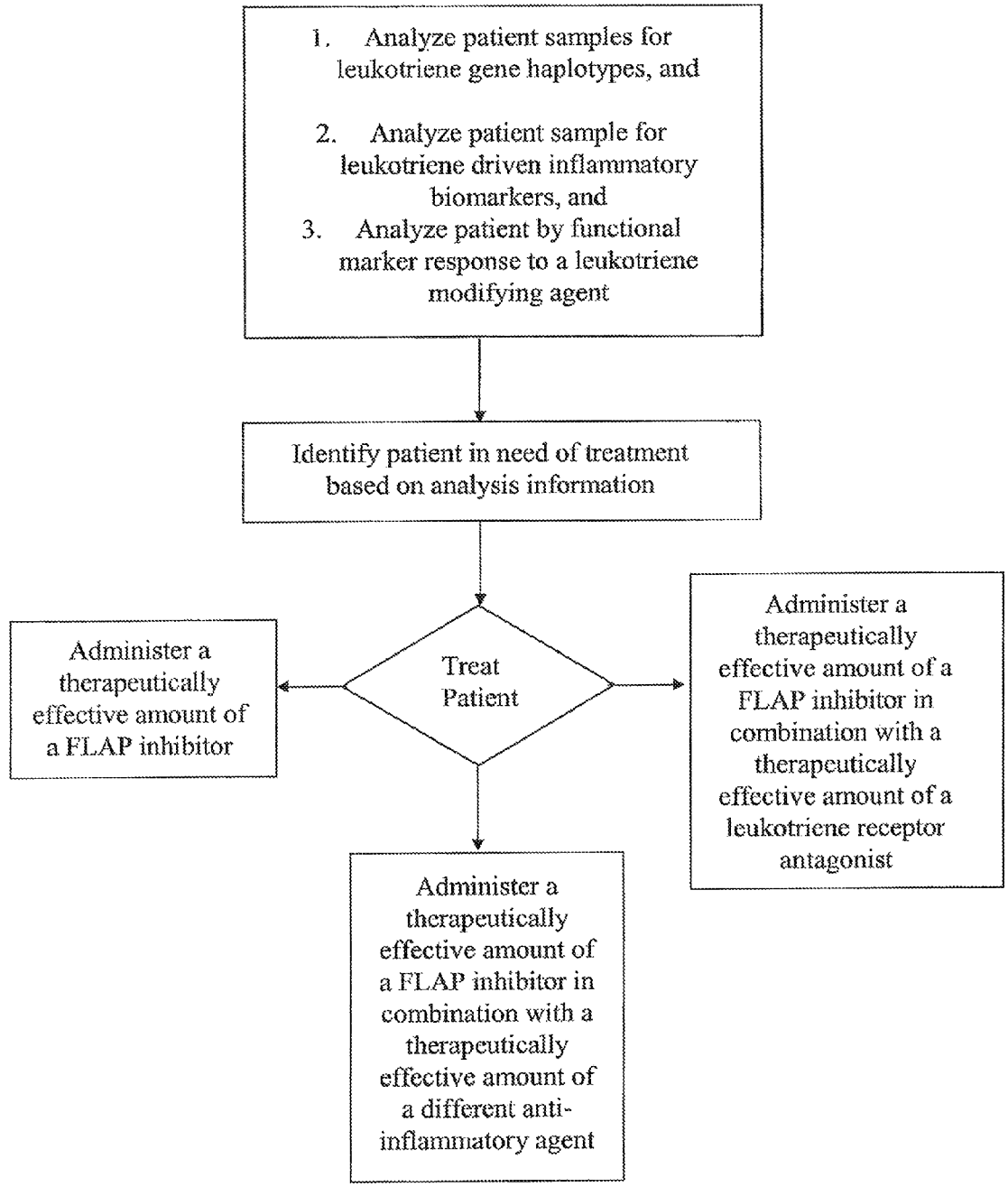
FIG. 14 present an illustrative scheme for the treatment of patients using the compounds and methods described herein.

Methods for the identification of a patient in need of treatment for leukotriene-dependent or leukotriene mediated conditions or diseases, and exemplary, non-limiting treatment methods are shown in FIG. 12, FIG. 13 and FIG. 14, wherein a patient sample is analyzed and the information obtained is used to identify possible treatment methods. It is expected that one skilled in the art will use this information in conjunction with other patient information, including, but not limited to age, weight, sex, diet, and medical condition, to choose a treatment method. It is also expected that each piece of information will be given a particular weight in the decision process. In certain embodiments, the information obtained from the diagnostic methods described above and any other patient information, including, but not limited to age, weight, sex, diet, and medical condition, are incorporated into an algorithm used to elucidate a treatment method, wherein each piece of information will be given a particular weight in the decision process.

In certain embodiments a patient sample is analyzed for leukotriene gene haplotypes, by way of example only, FLAP haplotypes, and the information obtained identifies a patient in need of treatment using various treatment methods. Such treatment methods include, but are not limited to, administering a therapeutic effective amount of a compound of any of Formula (G), Formula (G-I), or Formula (G-II), or pharmaceutical composition or medicament which includes a compound of any of Formula (G), Formula (G-I), or Formula (G-II), administering a therapeutic effective amount of a compound of any of Formula (G), Formula (G-I), or Formula (G-II), or pharmaceutical composition or medicament which includes a compound of any of Formula (G), Formula (G-I), or Formula (G-II), in combination with a therapeutic effective amount of a leukotriene receptor antagonist (by way of example, $CysLT_1$/$CysLT_2$ antagonist or $CysLT_1$ antagonist), or administering a therapeutic effective amount of a compound of any of Formula (G), Formula (G-I), or Formula (G-II), or pharmaceutical composition or medicament which includes a compound of any of Formula (G), Formula (G-I), or Formula (G-II), in combination with a therapeutic effective amount of another anti-inflammatory agent. In other embodiments a patient sample is analyzed for leukotriene gene haplotypes, by way of example only, FLAP haplotypes, and/or phenotype biomarkers, and/or phenotype functional marker responses to leukotriene modifying agents. The patient may then be treated using various treatment methods. Such treatment methods include, but are not limited to, administering a therapeutic effective amount of a compound of any of Formula (G), Formula (G-I), or Formula (G-II), or pharmaceutical composition or medicament which includes a compound of any of Formula (G), Formula (G-I), or Formula (G-II), administering a therapeutic effective amount of a compound of any of Formula (G), Formula (G-I), or Formula (G-II), or pharmaceutical composition or medicament which includes a compound of any of Formula (G), Formula (G-I), or Formula (G-II), in combination with a therapeutic effective amount of a leukotriene receptor antagonist (by way of example, CysLT$_1$/CysLT$_2$ antagonist or CysLT$_1$ antagonist), or administering a therapeutic effective amount of a compound of any of Formula (G), Formula (G-I), or Formula (G-II), or pharmaceutical composition or medicament which includes a compound of any of Formula (G), Formula (G-I), or Formula (G-II), in combination with a therapeutic effective amount of another anti-inflammatory agent. In still other embodiments a patient sample is analyzed for leukotriene gene haplotypes, by way of example only, FLAP haplotypes, and phenotype biomarkers, and phenotype functional marker responses to leukotriene modifying agents. The patient may then be treated using various treatment methods. Such treatment methods include, but are not limited to, administering a therapeutic effective amount of a FLAP inhibitor, or pharmaceutical composition or medicament which includes a FLAP inhibitor, administering a therapeutic effective amount of a FLAP inhibitor, or pharmaceutical composition or medicament which includes a FLAP inhibitor, in combination with a therapeutic effective amount of a leukotriene receptor antagonist (by way of example, CysLT$_1$/CysLT$_2$ antagonist or CysLT$_1$ antagonist), or administering a therapeutic effective amount of a FLAP inhibitor, or pharmaceutical composition or medicament which includes a FLAP inhibitor, in combination with a therapeutic effective amount of another anti-inflammatory agent.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Preparation of Intermediates Used in the Synthesis of Compounds of Formula (G), Formula (G-I), and Formula (G-II)

Starting materials and intermediates used in the synthesis of compounds of Formula (G), Formula (G-I), and Formula (G-II) are commercially available or can be synthesized by synthetic methods known in the art or described herein. The preparation of intermediates, such as, for example, those shown in Table 6, which are used herein and not commercially available is described below. Other intermediates not specifically mentioned herein and used in the synthesis of compounds of Formula (G), Formula (G-I), and Formula (G-II), can be prepared using the methods described herein or known in the art.

TABLE 6

Intermediates used in the Synthesis of Compounds of Formula (G), Formula (G-I), and Formula (G-II)

| Compound # | Structure | Compound Name | Method for Preparation |
|---|---|---|---|
| Int-5 | 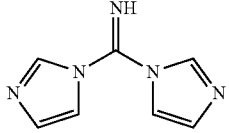 [SMILES: N=C(n1ccnc1)n1ccnc1] | C-(Di-imidazol-1-yl)-methyleneamine | Route 8, Step 1 |
| Int-10 | 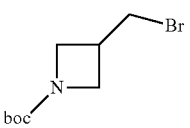 | 3-Bromomethyl-azetidine-1-carboxylic acid tert-butyl ester | Route 1, Steps 1-3a SM: 3-Azetidinecarboxylic acid (Sigma Aldrich) |

TABLE 6-continued

Intermediates used in the Synthesis of Compounds of Formula (G), Formula (G-I), and Formula (G-II)

| Compound # | Structure | Compound Name | Method for Preparation |
|---|---|---|---|
| Int-19 | 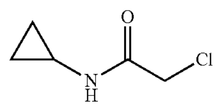 | 2-Chloro-N-cyclopropyl-acetamide | Route 2, Step 1<br>SM: Cyclopropylamine (Sigma Aldrich) |
| Int-20 | 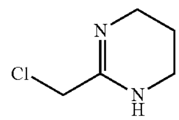 | 2-Chloromethyl-1,4,5,6-tetrahydro-pyrimidine Hydrochloride | Route 3, Steps 1-2<br>SM: Chloro-acetonitrile (Sigma Aldrich) |
| Int-21 | 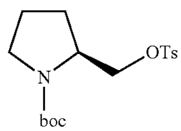 | (S)-2-(Toluene-4-sulfonyloxymethyl)-pyrrolidine-1-carboxylic acid tert-butyl ester | Route 1, Step 3c<br>SM: (S)-(−)-1-(tert-Butoxycarbonyl)-2-pyrrolidinemethanol (Sigma Aldrich) |
| Int-22 | 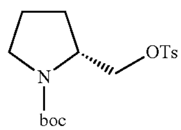 | (R)-2-(Toluene-4-sulfonyloxymethyl)-pyrrolidine-1-carboxylic acid tert-butyl ester | Route 1, Step 3c<br>SM: (R)-(+)-1-(tert-Butoxycarbonyl)-2-pyrrolidinemethanol (Sigma Aldrich) |
| Int-23 | 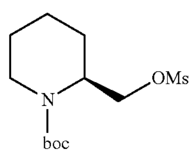 | (S)-2-Methanesulfonyloxymethyl-piperidine-1-carboxylic acid tert butyl ester | Route 1, Step 3d<br>SM: 1-Boc-(S)-2-piperidinemethanol (Chem Impex) |
| Int-24 | 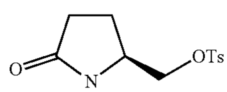 [SMILES: Cc1ccc(S(=O)(=O)OC[C@@H]2CCC(=O)N2)cc1] | Toluene-4-sulfonic acid (S)-5-oxo-pyrrolidin-2-ylmethyl ester | Route 1, Step 3c<br>SM: (S)-(+)-5-(Hydroxymethyl)-2-pyrrolidinone (Sigma Aldrich) |
| Int-25 | 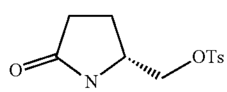 [SMILES: Cc1ccc(S(=O)(=O)OC[C@H]2CCC(=O)N2)cc1] | Toluene-4-sulfonic acid (R)-5-oxo-pyrrolidin-2-ylmethyl ester; | 6-27-Route 1, Step 3c<br>SM: (R)-(−)-5-(Hydroxymethyl)-2-pyrrolidinone (Acros Organics) |
| Int-27 | 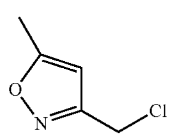 | 3-Chloromethyl-5-methyl-isoxazole Hydrochloride | Route 4, Step 4<br>SM: (5-Methylisoxazol-3-yl)methanol (Acros Organics) |
| Int-28 | 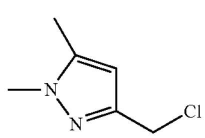 | 3-Chloromethyl-1,5-dimethy-1H-pyrazole Hydrochloride | Route 4, Step 4<br>SM: (1,5-Dimethyl-1H-pyrazol-3-yl)methanol (Acros Organics) |
| Int-29 | 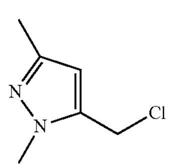 | 5-Chloromethyl-1,3-dimethyl-1H-pyrazole Hydrochloride | Route 4, Step 4<br>SM: (1,3-Dimethyl-1H-pyrazol-5-yl)methanol (Acros Organics) |
| Int-30 | 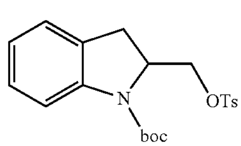 | 2-(Toluene-4-sulfonyloxymethyl)-2,3-dihydro-indole-1-carboxylic acid tert-butyl ester | Route 1, Steps 1-3c<br>SM: Indoline-2-carboxylic Acid (Sigma Aldrich) |

TABLE 6-continued

Intermediates used in the Synthesis of Compounds of Formula (G), Formula (G-I), and Formula (G-II)

| Compound # | Structure | Compound Name | Method for Preparation |
|---|---|---|---|
| Int-31 | 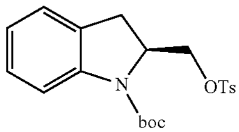 | (S)-2-(Toluene-4-sulfonyloxymethyl)-2,3-dihydro-indole-1-carboxylic acid tert-butyl ester | Route 1, Steps 1, 3c<br>SM: (S)-(+)-2-Indolinemethanol (Sigma Aldrich) |
| Int-32 | 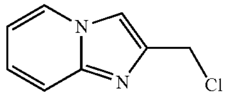 [SMILES: ClCc1cn2ccccc2n1] | 2-Chloromethyl-imidazo[1,2-a]pyridine | Route 4, Step 4<br>SM: Imidazo[1,2-a]pyridin-2-ylmethanol (Acros Organics) |
| Int-33 | 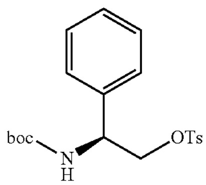 | Toluene-4-sulfonic acid (S)-2-tert-butoxycarbonylamino-2-phenyl-ethyl ester | Route 1, Steps 1, 3c<br>SM: (S)-(+)-2-Phenylglycinol (Sigma Aldrich) |
| Int-34 | 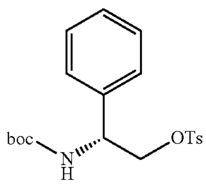 | Toluene-4-sulfonic acid (R)-2-tert-butoxycarbonylamino-2-phenyl-ethyl ester | Route 1, Step 3c<br>SM: (R)-(−)-N-(tert-Butoxycarbonyl)-2-phenylglycinol (Sigma Aldrich) |
| Int-38 | 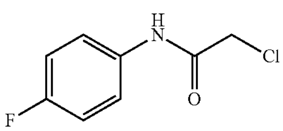 [SMILES: O=C(CCl)Nc1ccc(F)cc1] | 2-Chloro-N-(4-fluoro-phenyl)-acetamide | Route 2, Step 1<br>SM: 4-Fluoroaniline (Sigma Aldrich) |
| Int-39 | 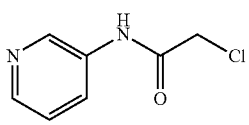 [SMILES: O=C(CCl)Nc1cccnc1] | 2-Chloro-N-pyridin-3-yl-acetamide | Route 2, Step 1<br>SM: 3-Aminopyridine (Sigma Aldrich) |
| Int-44 | 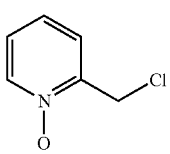 | 2-Chloromethyl-pyridin-1-ol | Route 4, Step 1<br>SM: 2-Chloromethyl-pyridine Hydrochloride (Sigma Aldrich) |
| Int-45 | 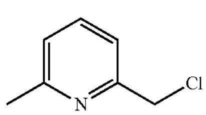 | 2-Chloromethyl-6-methyl-pyridine Hydrochloride | Route 4, Step 4<br>SM: 6-Methyl-2-pyridinemethanol (Sigma Aldrich) |
| Int-46 | 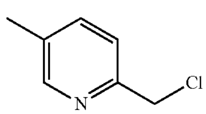 | 2-Chloromethyl-5-methyl-pyridine Hydrochloride | Route 4, Steps 1-4<br>SM: 2,5-Lutidine (Sigma Aldrich) |
| Int-47 | 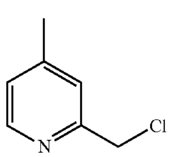 | 2-Chloromethyl-4-methyl-pyridine Hydrochloride | Route 4, Steps 1-4<br>SM: 2,4-Lutidine (Sigma Aldrich) |

TABLE 6-continued

Intermediates used in the Synthesis of Compounds of Formula (G), Formula (G-I), and Formula (G-II)

| Compound # | Structure | Compound Name | Method for Preparation |
|---|---|---|---|
| Int-48 | 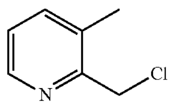 | 2-Chloromethyl-3-methyl-pyridine Hydrochloride | Route 4, Steps 1-4 SM: 2,3-Lutidine (Sigma Aldrich) |
| Int-49 | 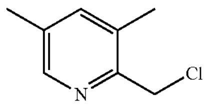 | 2-Chloromethyl-3,5-dimethyl-pyridine Hydrochloride | Route 4, Steps 1-4 SM: 2,3,5-Collidine (Sigma Aldrich) |
| Int-50 | 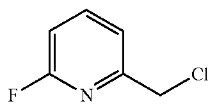 | 2-Chloromethyl-6-fluoro-pyridine Hydrochloride | Route 5, Step 3c SM: 2-Fluoro-6-methylpyridine (Oakwood Product) |
| Int-51 | 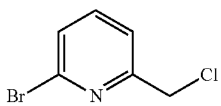 | 2-Chloromethyl-6-bromo-pyridine Hydrochloride | Route 4, Step 4 SM: (6-Bromo-pyridin-2-yl)-methanol (Sigma Alrich) |
| Int-52 | 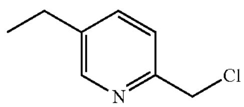 | 2-Chloromethyl-5-ethyl-pyridine | Route 4, Steps 1-4 SM: 5-Ethyl-2-mtthypyridint (Sigma Aldrich) |
| Int-53 | 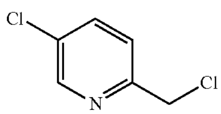 | 2-Chloromethyl-5-chloro-pyridine | Route 1, Step 2; Route 4, Step 4 SM: 5-Chloropyridine-2-carboxylic Acid (Matrix Scientific) |
| Int-54 | 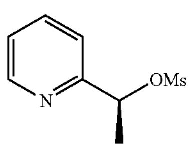 | Methanesulfonic acid (S)-1-pyridin-2-yl-ethyl ester | Route 1, Step 3 SM: (R)-alpha-Methyl-2-pyridinemethanol (Sigma Aldrich) |
| Int-55 | 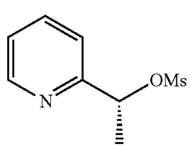 | Methanesulfonic acid (R)-1-pyridin-2-yl-ethyl ester | Route 1, Step 3 SM: (S)-alpha-Methyl-2-pyridinemethanol (Sigma Aldrich) |
| Int-57 | 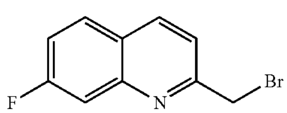 | 2-Bromomethyl-7-fluoro-quinoline | Route 5, Step 3a SM: 7-Fluoro-2-methylquinoline (Sigma Aldrich) |
| Int-58 | 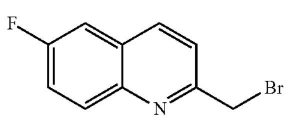 | 2-Bromomethyl-6-fluoro-quinoline | Route 5, Step 3a SM: 6-Fluoro-2-methylquinoline (Sigma Aldrich) |
| Int-59 | 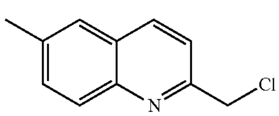 | 2-Chloromethyl-6-methyl-quinoline | Route 4, Steps 1-4 SM: 2,6-Dimethylquinoline (Sigma Aldrich) |
| Int-60 | 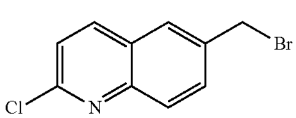 [SMILES: Clc1ccc2cc(CBr)ccc2n1] | 2-Chloro-6-bromomethyl-quinoline | Route 5, Steps 1-3a SM: Cinnamoyl chloride (Sigma Aldrich) and p-toluidine (Sigma Aldrich) |

TABLE 6-continued

Intermediates used in the Synthesis of Compounds of Formula (G), Formula (G-I), and Formula (G-II)

| Compound # | Structure | Compound Name | Method for Preparation |
|---|---|---|---|
| Int-71 | 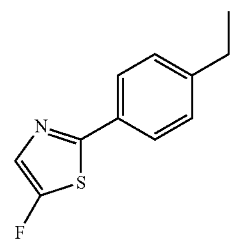 | 5-Fluoro-2-(4-iodomethyl-phenyl)-thiazole | Route 6, Step 1-2a; Route 1, Step 3b |
| Int-72 | 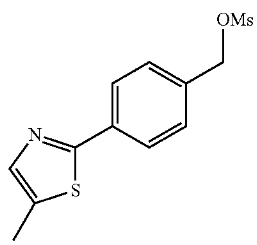 [SMILES: Cc1cnc(-c2ccc(COS(C)(=O)=O)cc2)s1] | Methanesulfonic acid 4-(5-methyl-thiazol-2-yl)-benzyl ester | Route 6, Step 1-2b; Route 1, Step 3d |
| Int-73 | 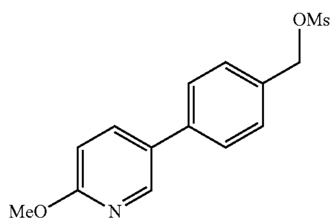 [SMILES: COc1ccc(-c2ccc(COS(C)(=O)=O)cc2)cn1] | Methanesulfonic acid 4-(6-methoxy-pyridin-3-yl)-benzyl ester | Route 6, Step 1; Route 1, Step 3d |
| Int-74 | 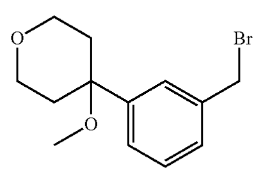 [SMILES: COC1(c2cccc(CBr)c2)CCOCC1] | 4-(3-Bromomethyl-phenyl)-4-methoxy-tetrahydro-pyran | Route 9, Step 1; Route 5, Step 3a |
| Int-75 | 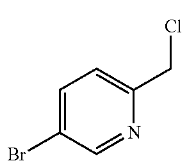 | 5-Bromo-2-chloromethyl-pyridine | Route 4, Step 4 (5-Bromo-pyridin-2-yl)-methanol (Biofine International) |
| Int-76 | 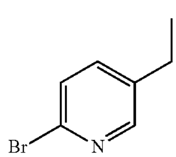 | 2-Bromo-5-iodomethyl-pyridine | Route 1, Step 3b (6-Bromo-pyridin-3-yl)-methanol (Biofine International) |
| Int-118 | 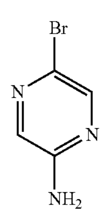 | 5-Bromo-pyrazin-2-ylamine | Route 5, Step 3b SM: Aminopyrazine (Lancaster) |

TABLE 6-continued

Intermediates used in the Synthesis of Compounds of Formula (G), Formula (G-I), and Formula (G-II)

| Compound # | Structure | Compound Name | Method for Preparation |
|---|---|---|---|
| Int-135 | 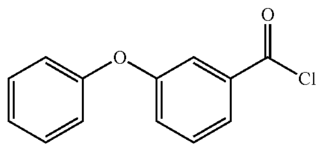 [SMILES: O=C(Cl)c1cccc(Oc2ccccc2)c1] | 3-Phenoxy-benzoyl chloride | Route 7, Step 1 SM: 3-Phenoxy-benzoic acid (Sigma Aldrich) |
| Int-136 | 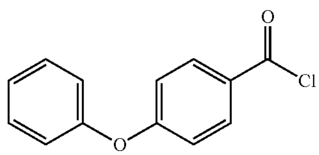 [SMILES: O=C(Cl)c1ccc(Oc2ccccc2)cc1] | 4-Phenoxy-benzoyl chloride | Route 7, Step 1 SM: 4-Phenoxy-benzoic acid (Sigma Aldrich) |
| Int-140 | 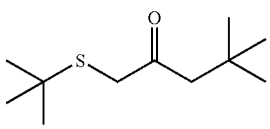 | 1-tert-Butylsulfanyl-4,4-dimethyl-pentan-2-one | Route 10, Steps 1-2 |

Route 1:

Step 1: BOC Protection (Int-10)

3-Azetidinecarboxylic acid (Sigma Aldrich, 0.25 g, 2.5 mmol) was dissolved in tBuOH (5 mL) and 1N NaOH (2.7 mL, 2.7 mmol). Di-tert-butyl dicarbonate (0.59 g, 2.7 mmol) was added, and the reaction was stirred overnight at room temperature. The reaction was diluted with water, acidified slowly to pH 4 with 1N HCl, and the mixture was extracted with EtOAc until all product was removed from the aqueous layer by ninhydrin stain. The combined organic layers were dried, filtered, and concentrated to give the desired product.

Step 2: Borane Reduction (Int-10)

Acid from Step 1 (0.7 g, 3.5 mmol) was dissolved in THF and cooled to 0° C. under $N_2$. Borane-THF complex was added to the solution, and the reaction was stirred at room temperature overnight. The reaction was cooled to 0° C. and quenched with water. The mixture was extracted 3 times with EtOAc, the combined organic layers were dried over $MgSO_4$, filtered, and concentrated. The crude material was filtered through a plug of silica gel and eluted with EtOAc to give the desired compound.

Step 3a: $Br_2$ Bromide Formation (Int-10)

Triphenylphosphine (1.7 g, 6.5 mmol) was dissolved in DMF and cooled to 0° C. Bromine (0.31 mL, 5.9 mmol) as added slowly, and the solution was stirred for 30 minutes. Alcohol from Step 2 (0.32 g, 2.0 mmol) was added in DMF and the reaction was stirred at room temperature overnight. The mixture was diluted with water, extracted 3 times with EtOAc, and the combined organic layers were dried over $MgSO_4$, filtered, and concentrated. The crude material was filtered through a plug of silica gel and eluted with EtOAc to give the desired compound.

Step 3b: $I_2$ Iodide Formation (Int-73)

(6-Bromo-pyridin-3-yl)-methanol (0.5 g, 2.7 mmol) was dissolved in toluene (20 mL). Triphenylphosphine (0.9 g, 3.5 mmol) and imidazole (0.4 g, 6.0 mmol) were added, followed by a solution of iodine (0.88 g, 3.5 mmol) in toluene dropwise. The reaction was stirred at room temperature for 15 minutes, and then poured into saturated aq. $Na_2CO_3$. The organic layer was washed with aq. sodium thiosulfate, water, then dried over $MgSO_4$, filtered, and concentrated. The crude material was purified on silica gel (EtOAc:hexanes gradient) to give the desired product.

Step 3c: Tosylation (Int-21)

(S)-(−)-1-(tert-Butoxycarbonyl)-2-pyrrolidinemethanol (1.0 g, 5.0 mmol) was dissolved in pyridine (3 mL), and toluenesulfonyl chloride (1.0 g, 5.5 mmol) was added. The reaction was stirred overnight at room temperature, and diluted with water and extracted with EtOAc. The combined organic layers were washed with water, dried over $MgSO_4$, filtered, and concentrated. The residue was purified on silica gel (0 to 10% EtOAc in hexanes) to give the desired product.

Step 3d: Mesylation (Int-55)

(R)-alpha-Methyl-2-pyridinemethanol (1.0 g, 8.1 mmol) was dissolved in $CH_2Cl_2$ (20 mL) and cooled to 0° C. Triethylamine (1.7 mL, 12.2 mmol) was added, followed by methanesulfonyl chloride (0.66 mL, 8.4 mmol) dropwise. The reaction was stirred for 30 minutes, and then diluted with $CH_2Cl_2$, washed with water, dried over $MgSO_4$, filtered, and concentrated to obtain the desired product.

Route 2:

Step 1: Amide Formation (Int-19)

Cyclopropylamine (0.35 mL, 5.0 mmol) and triethylamine (0.7 mL, 5.1 mmol) were dissolved in $CH_2Cl_2$ (10 mL). The reaction was cooled to −10° C. and chloroacetyl chloride (0.4 mL, 5.0 mmol) was added dropwise. The reaction was stirred at −10° C. for 1 hour, then at room temperature for 2 hours, followed by a quench with water. The aqueous layer was extracted with $CH_2Cl_2$, and the organic layers were dried, filtered, and concentrated to give the desired product.

Route 3:

Step 1: Imine Formation (Int-20)

Chloroacetonitrile (0.5 g, 6.6 mmol) was dissolved in $Et_2O$ (10 mL) and cooled to 0° C. EtOH (0.43 mL, 7.3 mmol) was added, followed by 4N HCl in 1,4-dioxane (15 mL, 59.6 mmol). The reaction was stirred at 0° C. for 4 days, and then concentrated to give the desired product as a white solid.

Step 2: Cyclization (Int-20)

Imine from Step 1 (0.3 g, 2.0 mmol) was dissolved in EtOH (4 mL) and cooled to 0° C. 1,3-Diaminopropane (0.17 mL, 2.0 mmol) was added, followed by $iPr_2NEt$ (0.35 mL, 2.0 mmol). The reaction was stirred at 0° C. for 2 hours, and then 4N HCl in 1,4-dioxane (0.5 mL, 2 mmol) was added. The mixture was filtered, and the filtrate was concentrated to give the desired product.

Route 4:

Step 1: mCPBA Oxidation (Int-46)

2,5-Lutidine (5.0 g, 46.7 mmol) was dissolved in $CHCl_3$ (125 mL) and cooled to 0° C. m-Chloroperoxybenzoic acid (70%; 13.9 g, 55.2 mmol) was added, and the reaction was stirred overnight at room temperature. The mixture was washed with saturated aq. $Na_2CO_3$, dried over $Na_2SO_4$, filtered, and concentrated to give the desired product.

Step 2: Acetylation (Int-46)

The N-oxide from Step 1 (46.7 mmol) was dissolved in acetic anhydride (25 mL) and heated to reflux at 100° C. for one hour. The mixture was cooled to room temperature, and ethanol (46.7 mmol) was slowly added to quench the reaction. The solution was evaporated to dryness and purified on silica gel to give the desired product.

Step 3: Hydrolysis (Int-46)

Acetate from Step 2 (46.7 mmol) was dissolved in concentrated HCl (20 mL) and refluxed for 1 hour. The reaction was cooled and evaporated to dryness to give an orange solid, which was used directly in the next reaction.

Step 4: $SOCl_2$ Chloride Formation (Int-46)

Alcohol from Step 3 (1.0 g, 8.1 mmol) was dissolved in thionyl chloride (3 mL) and stirred at room temperature for 30 minutes under $N_2$. The mixture was evaporated to dryness to give the desired product as a hydrochloride salt, which was used directly in subsequent reactions.

Route 5:

Step 1: Condensation (Int-60)

p-Toluidine (10 g, 60.0 mmol) and triethylamine (8.4 mL, 60.3 mmol) were dissolved in $CH_2Cl_2$ (200 mL) at room temperature. Cinnamoyl chloride (6.5 g, 60.7 mmol) was added, and the reaction was stirred for 1 hour. The reaction was washed with water, dried, filtered, and concentrated. To the residue was added aluminum chloride (5 g, 37.5 mmol), which was heated neat. After 45 minutes, ice was added to form a precipitate. The mixture was stirred overnight at room temperature. The precipitate was then filtered and dissolved in $CH_2Cl_2$, washed with 1N HCl, brine, dried over $MgSO_4$, filtered, and concentrated. The residue was recrystallized from ethanol to give the desired quinolinone product.

Step 2: $POCl_3$ Chloride Formation (Int-60)

Quinolinone from Step 1 (3.12 g, 19.6 mmol) was heated to 90° C. in $POCl_3$ (10 mL). Once no starting material remained, the reaction was cooled and concentrated. The residue was diluted with EtOAc and saturated aq. $NaHCO_3$, and the aqueous layer was extracted with EtOAc. The combined organics were dried, filtered, and concentrated to give the chloroquinoline product.

Step 3a: NBS Bromide Formation (Alkyl) (Int-60)

Quinoline from Step 2 (19.6 mmol) was heated to 80° C. for 1 hour in benzene (200 mL) with NBS (3.6 g, 20.2 mmol) and catalytic benzoyl peroxide. The reaction mixture was concentrated and purified on silica gel to give the desired product.

Step 3b: NBS Bromide Formation (Aryl) (Int-118)

2-Aminopyrazine (4 g, 42 mmol) was dissolved in water (2 mL) and DMSO (70 mL), and NBS (7.5 g, 42 mmol) was added over 1 hour at 0° C. The reaction was warmed to room temperature and stirred overnight. The mixture was poured onto ice and extracted 4 times with EtOAc. The combined organic layers were washed with 5% $Na_2CO_3$, water, and brine, dried over $MgSO_4$, filtered, and concentrated. The residue was purified on silica gel to give the desired product.

Step 3c: NCS Chloride Formation (Int-50)

2-Fluoro-6-methylpyridine (1.11 g, 10 mmol), NCS (2.0 g, 15 mmol), and catalytic benzoyl peroxide were dissolved in benzene and heated to reflux overnight. The reaction was concentrated and diluted with water and EtOAc. The organic layer was washed with saturated aq. $NaHCO_3$, dried, filtered, and concentrated. The residue was purified on silica gel to give the desired product.

Route 6:

Step 1: Suzuki Coupling (Int-71)

To (4-Hydroxymethylphenyl)boronic acid (CombiBlocks; 1.0 g, 6.6 mmol) in $DME/H_2O$ (16 mL, 2:1) was added 2-bromothiazole (1.2 g, 7.2 mmol) and $K_2CO_3$ (2.7 g, 19.7 mmol). The reaction was degassed with $N_2$ for 20 minutes. $Pd(PPh_3)_4$ (0.76 g, 0.7 mmol) was added and the reaction was further degassed for 10 minutes. The reaction was then heated to 90° C. overnight under $N_2$. LCMS confirmed the formation of the product. The reaction was partitioned between water and EtOAc and the aqueous layer was extracted twice with EtOAc. The combined organic layers were dried over $MgSO_4$, filtered, concentrated, and purified on silica gel (EtOAc:hexanes gradient) to give the desired product.

Step 2a: F-Alkylation (Int-71)

Thiazole from Step 1 (0.35 g, 1.8 mmol) was dissolved in THF (15 mL) and cooled to −78° C. under $N_2$. n-Butyllithium (1.6M; 4.6 mL, 7.3 mmol) was added dropwise, followed by NFSi (1.2 g, 3.7 mmol). The reaction was quenched at −78° C. with saturated aq. $NH_4Cl$, and diluted with EtOAc and water. The aqueous layer was extracted twice with EtOAc, and the combined organics were dried over MgSO$_4$, filtered, and concentrated. The residue was purified on silica gel to give the desired compound.

Step 2b: Me-Alkylation (Int-72)

Thiazole from Step 1 (0.33 g, 1.7 mmol) was dissolved in THF (15 mL) and cooled to −78° C. under N$_2$. n-Butyllithium (1.6M; 4.3 mL, 6.7 mmol) was added dropwise, followed by iodomethane (0.16, 2.6 mmol). The reaction was quenched at −78° C. with saturated aq. NH$_4$Cl, and diluted with EtOAc and water. The aqueous layer was extracted twice with EtOAc, and the combined organics were dried over MgSO$_4$, filtered, and concentrated. The residue was purified on silica gel to give the desired compound.
Route 7:

Step 1: Acid Chloride Formation (Int 135)

3-Phenoxy-benzoic acid (0.50 g, 0.23 mmol) was dissolved in CH$_2$Cl$_2$. Oxalyl chloride (0.32 g, 0.25 mmol) was added, followed by 1-2 drops of DMF. The reaction was stirred at room temperature, and then concentrated to give the desired acid chloride.
Route 8:

Step 1: Alkylation (Int-5)

To imidazole (0.41 g, 6.0 mmol) in CH$_2$Cl$_2$ was added bromoacetonitrile (0.21 g, 2.0 mmol), and the reaction was refluxed for 30 minutes. The mixture was cooled to room temperature and filtered, and the filtrate was concentrated to give the desired product.
Route 9:

Step 1: Methylation (Int-74)

To 4-m-Tolyl-tetrahydro-pyran-4-ol (2.5 g, 13.0 mmol) in THF (50 mL) was added sodium hydride (60%; 0.8 g, 20.0 mmol) at room temperature. Iodomethane (1.25 mL, 20 mmol) was added, and the reaction was stirred for 1 hour. The mixture was quenched with water, and the aqueous layer was extracted with EtOAc. The combined organic layers were washed with water, dried over MgSO$_4$, filtered, and concentrated. The residue was purified on silica gel to give the desired compound.
Route 10:

Step 1: Bromination

To 4,4-Dimethyl-pentan-2-one (3.7 mL, 26.3 mmol) in MeOH (2.8 mL) at 0° C. was added bromine (1.34 mL, 26.3 mmol) in a single stream. The reaction was warmed slowly to 10° C. for 30 minutes to initiate the reaction, and then stirred at room temperature for an additional 15 minutes. The reaction was diluted with water and diethyl ether, and the aqueous layer was extracted with diethyl ether three times. The combined organic layers were dried over MgSO$_4$, filtered, and concentrated to give the desired product as a colourless liquid.

Step 2: Thiol Addition

Bromide from Step 1 (26.3 mmol) was dissolved in THF (50 mL), and the mixture was cooled to 0° C. 2-Methyl-2-propanethiol (2.45 mL, 21.6 mmol) was added, followed by triethylamine (7.9 mL, 56.8 mmol). The reaction was stirred at room temperature for 18 hours, then diluted with water. The aqueous layer was extracted with diethyl ether, and the combined organic layers were dried over MgSO4, filtered, and concentrated to give the desired product.

Synthesis of Compounds of Formula (G), Formula (G-I) and Formula (G-II)

Scheme A:

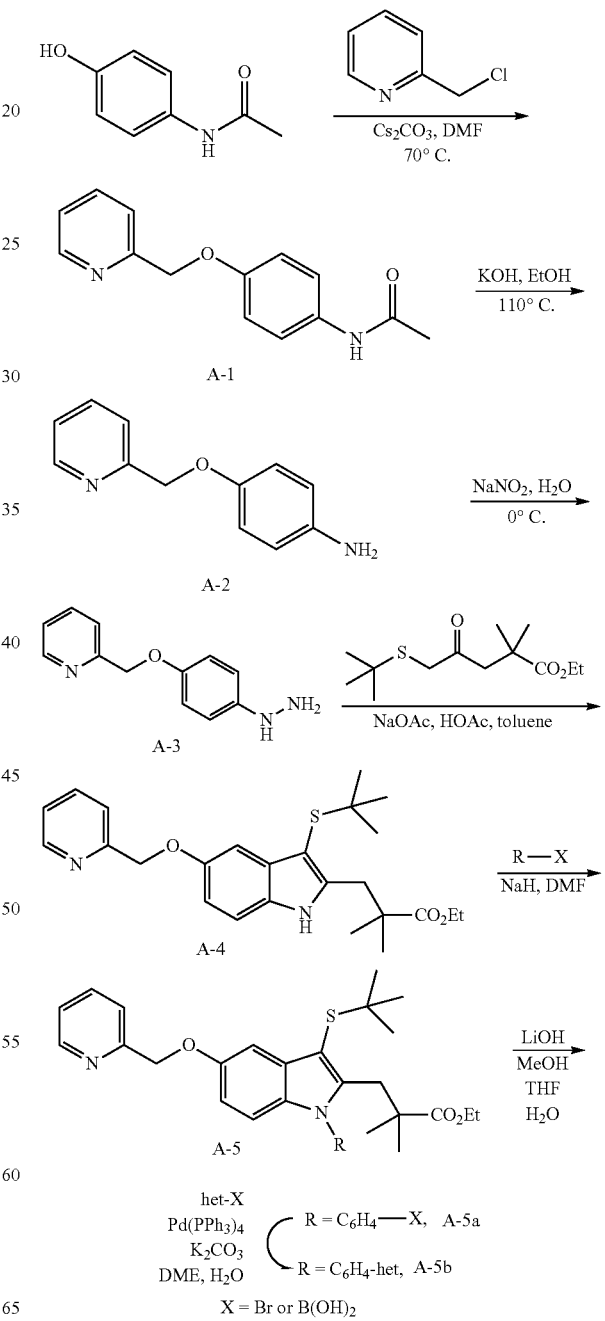

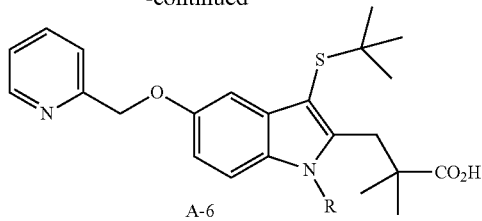

A-6

Example 1

Preparation of Compound 1-2, Compound 2-19, Compound 2-21, Compound 2-35, Compound 2-62, Compound 2-89, Compound 2-195, Compound 2-196, Compound 2-206, Compound 3-1, Compound 3-2, Compound 3-3, Compound 3-4, Compound 3-5, and Compound 4-1

Compound 1-2, Compound 2-19, Compound 2-21, Compound 2-35, Compound 2-62, Compound 2-89, Compound 2-195, Compound 2-196, Compound 2-206, Compound 3-1, Compound 3-2, Compound 3-3, Compound 3-4, Compound 3-5, and Compound 4-1, were prepared as outlined in Scheme A. A detailed illustrative example of the reaction conditions shown in Scheme A is described for the synthesis of 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid (Compound 2-19).

Step 1: N-[4-(Pyridin-2-ylmethoxy)-phenyl]-acetamide

A mixture of 4-acetamidophenol (Sigma-Aldrich; 73.6 g), 2-chloromethylpyridine hydrochloride (80 g) and cesium carbonate (320 g) in DMF (1 L) was stirred at 70° C. for 2 days. The mixture was cooled, poured into water (2 L) and extracted with EtOAC (×6). The organic layers were washed with brine, dried (MgSO₄) and filtered to give a tan solid (A-1, 114 g) which was used as such in the next step.

Step 2: 4-(Pyridin-2-ylmethoxy)-phenylamine hydrochloride

A-1 (114 g) was dissolved in EtOH (1 L) and to this was added KOH (50 g) in water (200 mL). The solution was heated to 110° C. for 2 days, KOH (20 g in 100 mL water) was added and heating continued for a further 2 days. The solution was cooled, the EtOH was removed in vacuo and the residue partitioned between EtOAc and water. After extraction of the water with EtOAc (×3), the organic layers were washed with brine, dried (MgSO₄) and filtered. To this solution was added saturated HCl in EtOAc and a precipitated formed immediately. Collection of the solids by filtration followed by drying under vacuum provided the title compound (A-2, 95 g) as a pink solid.

Step 3: [4-(Pyridin-2-ylmethoxy)-phenyl]-hydrazine dihydrochloride

A-2 (95 g) was dissolved in water (1 L) at 0° C. and to this was added NaNO₂ (26 g) in water (100 mL). The diazonium salt was allowed to form over 45 minutes and then it was poured slowly over 15 minutes into a rapidly stirred mixture of Na₂S₂O₄ (350 g) in water (1 L) and ether (1 L) at 0° C. Stirring continued for 40 minutes then mixture was made basic using conc. KOH. After extraction using EtOAc (×2) the organic layers were washed with water, then brine, dried (MgSO₄) and filtered. To this solution was added saturated HCl in EtOAc and a precipitated formed immediately. Collection of the solids by filtration followed by drying under vacuum provided the title compound as a tan solid (A-3, 75 g).

Step 4: 3-[3-tert-Butylsulfanyl-5-(pyridin-2-ylmethoxy)-1H-indol-2-yl]-2,2-dimethyl-propionic acid ethyl ester A-3 (75 g), ethyl 5-(t-butylthio)-2,2-dimethyl-4-oxo-pentanoate (prepared according to the procedures described in U.S. Pat. No. 5,288,743 issued Feb. 22, 1994; 64 g), NaOAc (40 g) in toluene (800 mL) and HOAc (400 mL) was stirred at room temperature for 3 days. The mixture was poured into water and made basic with solid Na₂CO₃. The mixture was extracted with EtOAc (×3), then washed with water (×2), brine, dried (MgSO₄), filtered and concentrated to give a dark red-black oil. Column chromatography of the mother liquor (silica gel packed in hexanes; eluting with hexane then hexane-EtOAc 9:1 rising to 4:1) afforded 68 g of the title compound (A-4), as a yellow solid.

Step 5: 3-[3-tert-Butylsulfanyl-1-[4-(6-methoxy-pyridin-3-yl)-benzyl]-5-(pyridin-2-ylmethoxy)-1H-indol-2-yl]-2,2-dimethyl-propionic acid ethyl ester 3-[3-tert-Butylsulfanyl-5-(pyridin-2-ylmethoxy)-1H-indol-2-yl]-2,2-dimethyl-propionic acid ethyl ester (A-4; 20.0 g, 45.4 mmol) was dissolved in DMF (150 mL) and cooled to −10° C. under N₂. Sodium hydride (60% dispersion in mineral oil; 2.0 g, 50.0 mmol) was added portionwise, and the reaction was stirred at −10° C. for 45 minutes until the foam had disappeared. To this dark brown-reddish solution was added methanesulfonic acid 4-(6-methoxy-pyridin-3-yl)-benzyl ester (Int-72; 16.0 g, 54.5 mmol) in DMF dropwise. The reaction was then stirred at −10° C. for 1 hour and allowed to warm to room temperature slowly. After 16 hours, LCMS confirmed the formation of the product. The reaction was quenched with saturated NH₄Cl and diluted with methyl tert-butyl ether (MTBE) and water. The aqueous phase was extracted twice with MTBE. The combined organic layers were dried over MgSO₄, filtered, and concentrated, and the crude product was purified by column chromatography to give the desired product (A-5).

Step 6: 3-[3-tert-Butylsulfanyl-1-[4-(6-methoxy-pyridin-3-yl)-benzyl]-5-(pyridin-2-ylmethoxy)-1H-indol-2-yl]-2,2-dimethyl-propionic acid A-5 (21.5 g, 33.7 mmol) was dissolved in THF (100 mL) and MeOH (100 mL) and stirred until it became a clear solution. 3N LiOH aqueous solution (56 mL, 168.5 mmol) was added and the reaction was refluxed at 80° C. for 2 hours. LCMS confirmed the formation of the product, so the reaction was cooled to room temperature and partitioned between EtOAc and water. The pH of the aqueous solution was adjusted to pH 1 with 10% HCl, and the aqueous phase was extracted three times with EtOAc. The combined organic layers were washed with water, dried over MgSO₄, filtered, and concentrated to give the desired free acid (A-6).

Mass spectrometry data of Compound 1-2, Compound 2-19, Compound 2-21, Compound 2-35, Compound 2-62, Compound 2-89, Compound 2-195, Compound 2-196, Compound 2-206, Compound 3-1, Compound 3-2, Compound 3-3, Compound 3-4, Compound 3-5, and Compound 4-1 is shown in Tables 1-4.

Notes:

For Compound 1-2, step 6 was not performed.
For Compound 2-62, after Step 6, the 6-methoxy-pyridin-3-yl in the precursor was hydrolyzed with potassium hydroxide to give the 6-hydroxy-pyridin-3-yl in the final product.
For Compound 2-89, during Step 6, the 5-fluorothiazoyl in the precursor was also hydrolyzed to give the 5-methoxythiazolyl in the final product.
For Compound 2-195, after Step 5, a Suzuki cross-coupling reaction was performed to give compound A-5b, as described in Example 5, Step 2.
For Compound 2-196, after Step 5, a Suzuki cross-coupling reaction was performed to give compound A-5b, as described in Example 5, Step 2.
For Compound 3-1, after Step 5, a Suzuki cross-coupling reaction was performed to give compound A-5b, as described in Example 5, Step 2.
For Compound 3-2, after Step 5, a Suzuki cross-coupling reaction was performed to give compound A-5b, as described in Example 5, Step 2.
For Compound 3-3, after Step 5, a Suzuki cross-coupling reaction was performed to give compound A-5b, as described in Example 5, Step 2.
For Compound 3-4, after Step 5, a Suzuki cross-coupling reaction was performed to give compound A-5b, as described in Example 5, Step 2.
For Compound 3-5, after Step 5, a Suzuki cross-coupling reaction was performed to give compound A-5b, as described in Example 5, Step 2.
For Compound 4-1, i) during Step 1,1-(4-isopropylphenyl) hydrazine was used in place of 4-methoxyphenylhydrazine, and 1-iodo-4-bromomethylbenzene was used in place of 4-chlorobenzylchloride, ii) Steps 3 and 4 were not performed; the product from Step 2 (C-2) was used directly in Step 5, iii) after the hydrolysis in Step 5, a Suzuki cross-coupling reaction was performed to give the final compound, as described in Example 5, Step 2.

Scheme B:

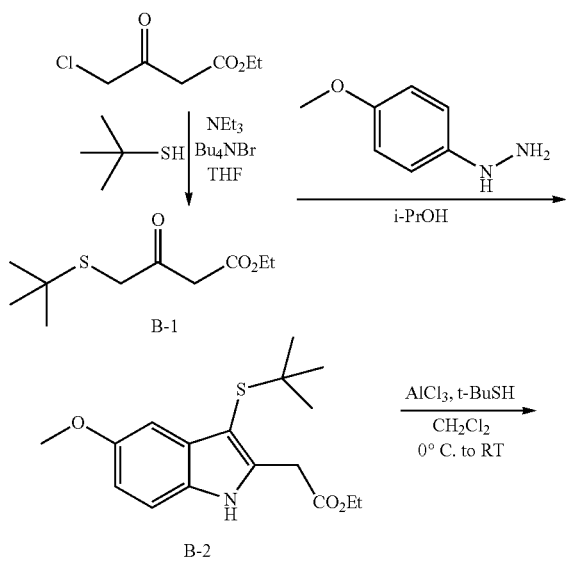

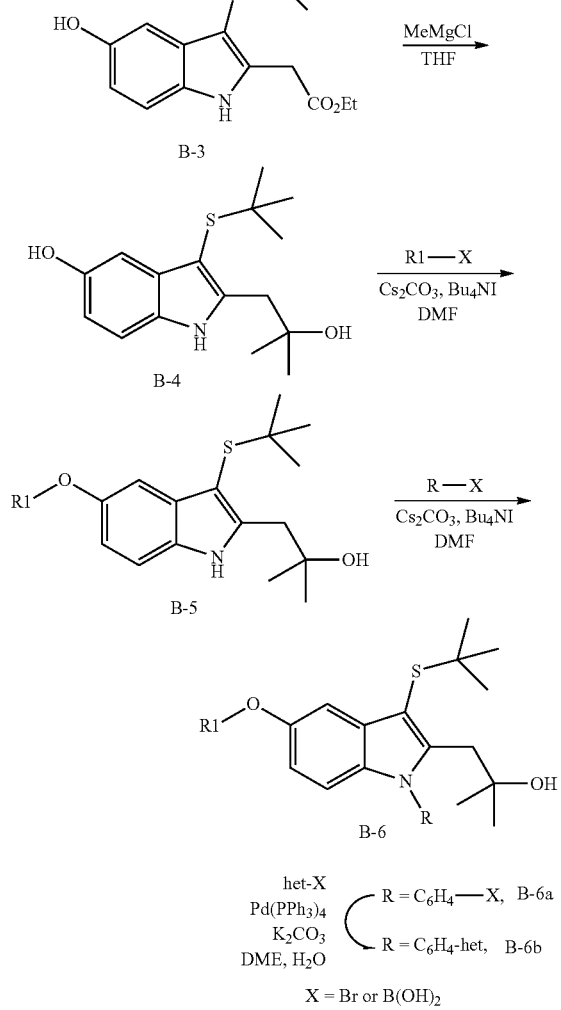

Example 2

Preparation of Compound 1-4, Compound 1-5, and Compound 1-6

Compound 1-4, Compound 1-5, and Compound 1-6 were prepared as outlined in Scheme B. A detailed illustrative example of the reaction conditions shown in Scheme B is described for the synthesis of 1-[3-tert-butylsulfanyl-1-(4-chloro-benzyl)-5-(pyridin-2-ylmethoxy)-1H-indol-2-yl]-2-methyl-propan-2-ol.

Step 1: 4-tert-Butylsulfanyl-3-oxo-butyric acid ethyl ester

Ethyl 4-chloroacetoacetate (7.5 mL, 51.9 mmol), 2-methyl-2-propanethiol (5.6 mL, 49.7 mmol), triethylamine (10.8 mL, 77.4 mmol), and catalytic tetrabutylammonium bromide were dissolved in THF (250 mL) and stirred at room temperature overnight. Silica gel was added, and the mixture was concentrated and filtered over a plug of silica gel to obtain the desired product (B-1), which was used without further purification.

Step 2: (3-tert-Butylsulfanyl-5-methoxy-1H-indol-2-yl)-acetic acid ethyl ester 4-Methoxyphenylhydrazine hydrochloride (7.7 g, 44.1 mmol) and B-1 (7.4 g, 33.9 mmol) were dissolved in 2-propanol (150 mL) and heated to reflux for 24 hours. The reaction mixture was concentrated and partitioned between EtOAc and saturated aq. NaHCO$_3$. The aqueous layer was extracted with EtOAc, and the combined organic layers were washed with brine, dried over MgSO$_4$, filtered, and concentrated. The residue was purified on silica gel (0 to 30% EtOAc in hexanes) to give the desired product (B-2).

Step 3: (3-tert-Butylsulfanyl-5-hydroxy-1H-indol-2-yl)-acetic acid ethyl ester Aluminum chloride (7.5 g 56.0 mmol) was suspended in tert-butylthiol (21 mL, 186.7 mmol) at 0° C. B-2 (6.0 g, 18.7 mmol) was added in CH$_2$Cl$_2$ (21 mL), and the reaction was allowed to warm to room temperature. After 2 hours, the reaction was complete by TLC analysis, so the solution poured into ice and acidified with 10% HCl aqueous solution. The aqueous layer was extracted three times with EtOAc, the combined organics were dried over MgSO$_4$, filtered, and concentrated to give the desired product (B-3).

Step 4: 3-tert-Butylsulfanyl-2-(2-hydroxy-2-methyl-propyl)-1H-indol-5-ol

B-3 (2.2 g, 7.0 mmol) was dissolved in THF (70 mL) and cooled to 0° C. Methylmagnesium chloride (3M; 14 mL, 42.0 mmol) was added dropwise, and the reaction was stirred for 1 hour at room temperature. The reaction was quenched with aq. NH$_4$Cl and extracted with EtOAc. The combined organic layers were dried over MgSO$_4$, filtered, concentrated, and purified on silica gel to give the desired product (B-4).

Step 5: 1-[3-tert-Butylsulfanyl-5-(pyridin-2-yl-methoxy)-1H-indol-2-yl]-2-methyl-propan-2-ol To B-4 (0.18 g, 0.61 mmol) in DMF (6 mL) was added cesium carbonate (1.0 g, 3.1 mmol). The reaction was stirred at room temperature for 30 minutes, and then 2-chloromethylpyridine hydrochloride (0.11 g, 0.67 mmol) and tetrabutylammonium iodide (0.05 g, 0.13 mmol) were added, and the reaction was stirred at room temperature for an additional 16 hours. The reaction was partitioned between water and diethyl ether, and the aqueous layer was extracted with diethyl ether. The combined organic layers were washed with water, dried over MgSO$_4$, filtered, and concentrated. The residue was purified on silica gel to give the desired product (B-5).

Step 6: 1-[3-tert-Butylsulfanyl-1-(4-chloro-benzyl)-5-(pyridin-2-ylmethoxy)-1H-indol-2-yl]-2-methyl-propan-2-ol To B-5 (0.05 g, 0.13 mmol) in DMF (3 mL) was added cesium carbonate (0.21 g, 0.65 mmol). The reaction was stirred at room temperature for 30 minutes, and then 1-chloro-4-chloromethylbenzene (0.03 g, 0.20 mmol) and tetrabutylammonium iodide (0.05 g, 0.13 mmol) were added, and the reaction was stirred at room temperature overnight. The reaction was partitioned between water and EtOAc, and the aqueous layer was extracted with EtOAc. The combined organics were washed with water, dried over MgSO$_4$, filtered, concentrated, and purified on silica gel (EtOAc:hexanes gradient) to give the desired compound (B-6).

Mass spectrometry data of Compound 1-4, Compound 1-5, and Compound 1-6, is shown in Tables 1-4.

Notes:
For Compound 1-4, Compound 1-5, and Compound 1-6, after Step 6, a Suzuki cross-coupling reaction was performed to give compound B-6b, as described in Example 5, Step 2.

Scheme C:

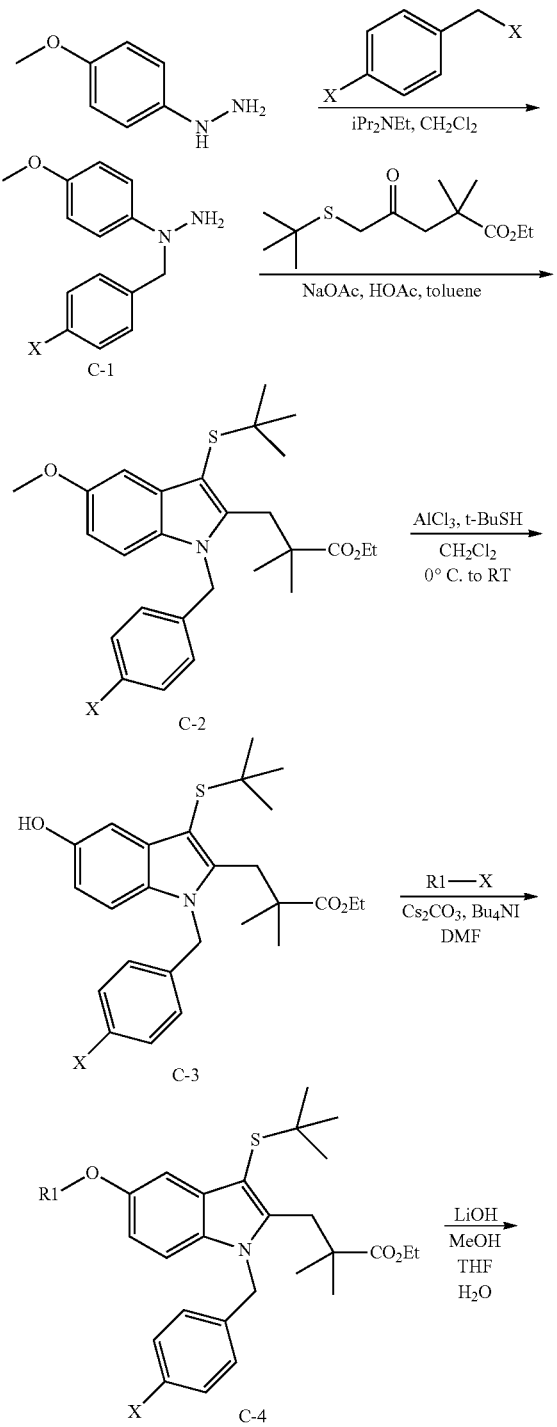

-continued

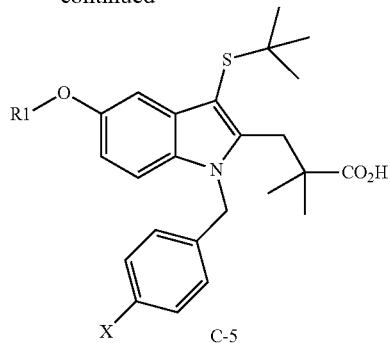

Example 3 (X=Cl)

(S)-2-[3-tert-Butylsulfanyl-2-(2-carboxy-2-methyl-propyl)-1-(4-chloro-benzyl)-1H-indol-5-yloxymethyl]-pyrrolidine-1-carboxylic acid tert-butyl ester

Step 1: N-(4-Chloro-benzyl)-N-(4-methoxy-phenyl)-hydrazine Hydrochloride

A solution of 4-Methoxyphenylhydrazine hydrochloride (10.0 g, 57.3 mmol), 4-chlorobenzylchloride (9.2 g, 57.2 mmol), tetrabutylammonium bromide (3.7 g, 11.5 mmol), and diisopropylethylamine (20 mL, 115 mmol) in $CH_2Cl_2$ (250 mL) was stirred at room temperature for several days. The reaction mixture was diluted with water and the organic layer was dried over $MgSO_4$, filtered, and concentrated. The residue was taken up in toluene (200 mL) and diethyl ether (100 mL), and 1 equivalent of 4N HCl in dioxane was added at 0° C. The mixture was stirred at room temperature for 2 hours, and then evaporated to dryness to give the desired product (C-1; X=Cl) as a purple solid.

Step 2: 3-[1-(4-Chloro-benzyl)-3-tert-butylsulfanyl-5-methoxy-1H-indol-2-yl]-2,2-dimethyl-propionic acid ethyl ester C-1 (~16 g, 57.3 mmol), ethyl 5-(t-butylthio)-2,2-dimethyl-4-oxo-pentanoate (prepared according to the procedures described in U.S. Pat. No. 5,288,743 issued Feb. 22, 1994; 14.8 g, 57.3 mmol), NaOAc (5.2 g) in toluene (120 mL) and HOAc (66 mL) was stirred at room temperature in the dark for 5 days. The mixture was partitioned between EtOAc and water, and the organic layer was stirred with solid $NaHCO_3$, filtered, and evaporated. The residue was purified on silica gel (0 to 55% $CH_2Cl_2$ in hexanes), and the isolated product was recrystallized from hexanes to give the desired product (C-2; X=Cl).

Step 3: 3-[1-(4-Chloro-benzyl)-3-tert-butylsulfanyl-5-hydroxy-1H-indol-2-yl]-2,2-dimethyl-propionic acid ethyl ester Aluminum chloride (0.820 g 6.15 mmol) was suspended in tert-butylthiol (1.8 mL, 16 mmol) and cooled to 0° C. C-2 (1.0 g, 2.0 mmol) was added in $CH_2Cl_2$ (2.4 mL), and the reaction was allowed to warm to room temperature. After 3 hours, the reaction was complete by TLC analysis, so the solution was diluted with $CH_2Cl_2$ and washed with 10% ice-cooled HCl aqueous solution. The aqueous layer was extracted three times with $CH_2Cl_2$, the combined organics were dried over $MgSO_4$, filtered, and concentrated to give the desired product (C-3; X=Cl) as a colourless foam.

Step 4: (S)-2-[3-tert-Butylsulfanyl-1-(4-chloro-benzyl)-2-(2-ethoxycarbonyl-2-methyl-propyl)-1H-indol-5-yloxymethyl]-pyrrolidine-1-carboxylic acid tert-butyl ester To 3-[1-(4-Chloro-benzyl)-3-tert-butylsulfanyl-5-hydroxy-1H-indol-2-yl]-2,2-dimethyl-propionic acid ethyl ester (C-3; 0.5 g, 1.05 mmol) in DMF (2.5 mL) was added N-BOC-(S)-2-(toluene-4-sulfonyloxymethyl)pyrrolidine (0.39 g, 1.10 mmol), and $Cs_2CO_3$ (0.69 g, 2.1 mmol). The reaction was stirred at 45° C. for 2 hours, and then catalytic potassium iodide was added and the reaction was heated to 60° C. overnight. The reaction mixture was diluted with EtOAc, washed with water, dried over $Na_2SO_4$, filtered, and concentrated. The residue was purified on silica get (0 to 15% EtOAc in hexanes) to give the desired product (C-4; X=Cl).

Step 5: (S)-2-[3-tert-Butylsulfanyl-2-(2-carboxy-2-methyl-propyl)-1-(4-chloro-benzyl)-1H-indol-5-yloxymethyl]-pyrrolidine-1-carboxylic acid tert-butyl ester (1-1)

The ester from Step 4 (0.16 g, 0.26 mmol) was dissolved in MeOH (1 mL), THF (1 mL), and water (1 mL). Lithium hydroxide (0.6 g, 1.43 mmol) was added, and the reaction was heated for 12 hours until no starting material was seen by TLC analysis. The reaction was diluted with water, acidified to pH 5 with citric acid, and extracted with EtOAc. The combined organic layers were washed with water, dried over $MgSO_4$, filtered, and concentrated. The residue was purified on silica gel (0 to 40% EtOAc in hexanes) to give the desired product (C-5; X=Cl).

Scheme D:

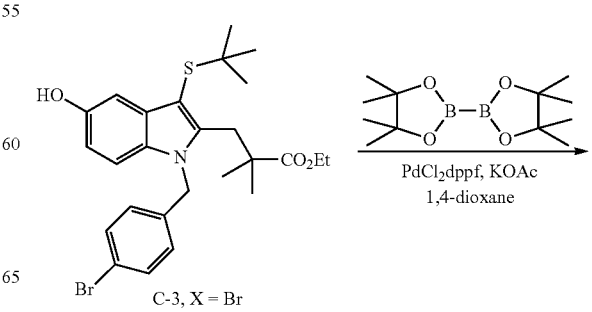

-continued

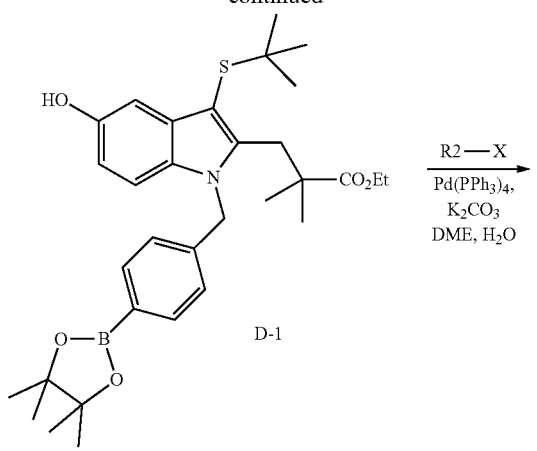

D-1

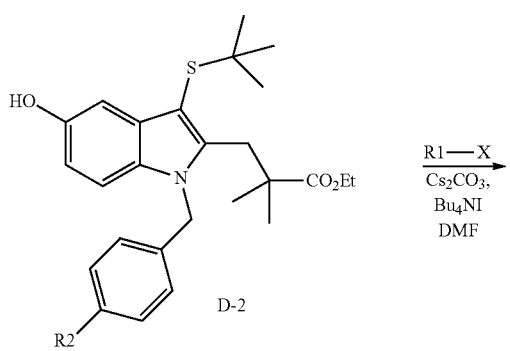

D-2

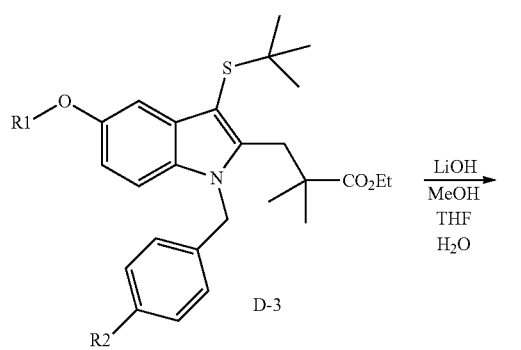

D-3

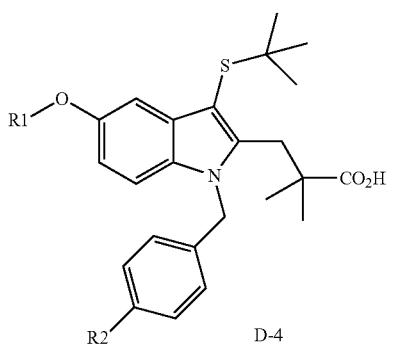

D-4

Example 4

Preparation of Compound 2-23, Compound 2-24, Compound 2-31, Compound 2-32, Compound 2-33, Compound 2-76, Compound 2-77, Compound 2-78, Compound 2-79, Compound 2-80, Compound 2-81, Compound 2-82, Compound 2-84, Compound 2-85, Compound 2-99, Compound 2-100, Compound 2-101, Compound 2-104, Compound 2-108, Compound 2-122, Compound 2-135, Compound 2-141, Compound 2-148, Compound 2-149, Compound 2-150, Compound 2-151, Compound 2-156, Compound 2-183, Compound 2-184, Compound 2-188, Compound 2-189, Compound 2-190, Compound 2-191, Compound 2-192, Compound 2-193, Compound 2-197, Compound 2-198, Compound 2-199, Compound 2-200, Compound 2-201, Compound 2-202, Compound 2-203, Compound 2-204, Compound 2-205; Compound 2-207, Compound 2-208, Compound 2-209, Compound 2-210, Compound 2-211, Compound 2-212, Compound 2-213, Compound 2-214, Compound 2-215, Compound 2-216, Compound 2-217, Compound 2-218, Compound 2-219, Compound 2-220, Compound 2-221, Compound 2-222, Compound 2-223, Compound 2-224, Compound 2-225, Compound 2-226, Compound 2-227, Compound 2-228, Compound 2-229, Compound 2-230, Compound 2-231, Compound 2-232, Compound 2-233, Compound 2-234, and Compound 4-2

Compound 2-23, Compound 2-24, Compound 2-31, Compound 2-32, Compound 2-33, Compound 2-76, Compound 2-77, Compound 2-78, Compound 2-79, Compound 2-80, Compound 2-81, Compound 2-82, Compound 2-84, Compound 2-85, Compound 2-99, Compound 2-100, Compound 2-101, Compound 2-104, Compound 2-108, Compound 2-122, Compound 2-135, Compound 2-141, Compound 2-148, Compound 2-149, Compound 2-150, Compound 2-151, Compound 2-156, Compound 2-183, Compound 2-184, Compound 2-188, Compound 2-189, Compound 2-190, Compound 2-191, Compound 2-192, Compound 2-193, Compound 2-197, Compound 2-198, Compound 2-199, Compound 2-200, Compound 2-201, Compound 2-202, Compound 2-203, Compound 2-204, Compound 2-205; Compound 2-207, Compound 2-208, Compound 2-209, Compound 2-210, Compound 2-211, Compound 2-212, Compound 2-213, Compound 2-214, Compound 2-215, Compound 2-216, Compound 2-217, Compound 2-218, Compound 2-219, Compound 2-220, Compound 2-221, Compound 2-222, Compound 2-223, Compound 2-224, Compound 2-225, Compound 2-226, Compound 2-227, Compound 2-228, Compound 2-229, Compound 2-230, Compound 2-231, Compound 2-232, Compound 2-233, Compound 2-234, and Compound 4-2, were prepared as shown in Scheme D. A detailed illustrative example of the reaction conditions shown in Scheme D is described for the synthesis of 3-{3-tert-Butylsulfanyl-5-(6-fluoro-quinolin-2-ylmethoxy)-1-[4-(6-methoxy-pyridin-3-yl)-benzyl]-1H-indol-2-yl}-2,2-dimethyl-propionic acid (Compound 2-141).

Step 1: 3-{3-tert-Butylsulfanyl-5-hydroxy-1-[4-(4,4,5,5-tetramethyl-[1,3,2]dioxaborolan-2-yl)-benzyl]-1H-indol-2-yl}-2,2-dimethyl-propionic acid ethyl ester The phenol from Example 3, Step 3 (C-3, X=Br; 35.0 g, 67.5 mmol), bis(pinacolato)diboron (Combi-Blocks; 25.0 g, 98.4 mmol), and KOAc (19.9 g, 209.1 mmol) was dissolved in 1,4-dioxane (350 mL) and degassed with $N_2$ for 30 minutes. $PdCl_2dppf$ (2.5 g, 3.1 mmol) was added, and the reaction mixture was degassed an additional 30 minutes with $N_2$. The reaction was heated at 85° C. overnight. The reaction mixture was partitioned between water and EtOAc, the aqueous layer was extracted three times with EtOAc, the combined organic layers were washed with water, brine, dried over $MgSO_4$, filtered, and concentrated. The crude material was purified on silica gel (15% EtOAc in hexanes) to give the desired product (D-1, 33.5 g).

Step 2: 3-{3-tert-Butylsulfanyl-5-hydroxy-1-[4-(6-methoxy-pyridin-3-yl)-benzyl]-1H-indol-2-yl}-2,2-dimethyl-propionic acid ethyl ester D-1 (25.34 g, 44.8 mmol), 5-bromo-2-methoxypyridine (Combi-blocks; 10.9 g, 70.3 mmol), and $K_2CO_3$ (15.5 g, 112.1 mmol) were dissolved in DME (300 mL) and water (150 mL) and degassed with $N_2$ for 30 minutes. $Pd(PPh_3)_4$ (1.6 g, 1.4 mmol) was added, and the reaction mixture was degassed with $N_2$ for an additional 15 minutes. The solution was heated to 80° C. overnight, and then cooled to room temperature and diluted with EtOAc and water. The aqueous layer was extracted 3 times with EtOAc, the combined organic layers were washed with water, brine, dried over $MgSO_4$, filtered, and concentrated. The crude material was purified on silica gel (0 to 8% EtOAc in hexanes) to give the desired product (D-2, 23.7 g).

Step 3: 3-{3-tert-Butylsulfanyl-5-(6-fluoro-quinolin-2-ylmethoxy)-1-[4-(6-methoxy-pyridin-3-yl)-benzyl]-1H-indol-2-yl}-2,2-dimethyl-propionic acid ethyl ester To 3-{3-tert-Butylsulfanyl-5-hydroxy-1-[4-(6-methoxy-pyridin-3-yl)-benzyl]-1H-indol-2-yl}-2,2-dimethyl-propionic acid ethyl ester (D-2; 6.5 g, 11.9 mmol) in MeCN (75 mL) was added 2-bromomethyl-6-fluoro-quinoline (3.14 g, 13.1 mmol), and $Cs_2CO_3$ (9.7 g, 29.8 mmol). The reaction was stirred at room temperature overnight, after which LCMS showed the reaction was complete. The reaction mixture was partitioned between EtOAc and water, the aqueous layer was extracted with EtOAc, and the combined organic layers were dried over $MgSO_4$, filtered, and concentrated. The residue was purified on silica gel (0 to 25% EtOAc in hexanes) to give the desired product (D-3, 7.6 g).

Step 4: 3-{3-tert-Butylsulfanyl-5-(6-fluoro-quinolin-2-ylmethoxy)-1-[4-(6-methoxy-pyridin-3-yl)-benzyl]-1H-indol-2-yl}-2,2-dimethyl-propionic acid D-3 (6.58 g, 9.3 mmol) was dissolved in MeOH (36 mL), THF (75 mL), and water (36 mL). Lithium hydroxide (2.42 g, 57.7 mmol) was added, and the reaction was heated at 60° C. for 6 hours until no starting material was seen by TLC analysis. The reaction was diluted with water, acidified to pH 5 with citric acid, and extracted with EtOAc. The combined organic layers were washed with water, dried over $MgSO_4$, filtered, and concentrated. The residue was triturated with hexane:EtOAc (9:1) overnight, and filtered to give the desired product (D-4, 5.9 g).

Mass spectrometry data for Compound 2-23, Compound 2-24, Compound 2-31, Compound 2-32, Compound 2-33, Compound 2-76, Compound 2-77, Compound 2-78, Compound 2-79, Compound 2-80, Compound 2-81, Compound 2-82, Compound 2-84, Compound 2-85, Compound 2-99, Compound 2-100, Compound 2-101, Compound 2-104, Compound 2-108, Compound 2-122, Compound 2-135, Compound 2-141, Compound 2-148, Compound 2-149, Compound 2-150, Compound 2-151, Compound 2-156, Compound 2-183, Compound 2-184, Compound 2-188, Compound 2-189, Compound 2-190, Compound 2-191, Compound 2-192, Compound 2-193, Compound 2-197, Compound 2-198, Compound 2-199, Compound 2-200, Compound 2-201, Compound 2-202, Compound 2-203, Compound 2-204, Compound 2-205; Compound 2-207, Compound 2-208, Compound 2-209, Compound 2-210, Compound 2-211, Compound 2-212, Compound 2-213, Compound 2-214, Compound 2-215, and Compound 4-2, is shown in Tables 1-4.

Notes:

For Compound 2-33, during Step 3, the imidazole was also alkylated to give the final product.

For Compound 2-79, during Step 4, the ethyl ester of the precursor was also hydrolyzed to give the acid in the final product.

For Compound 2-80, after Step 3, the ketone in the precursor was reduced with sodium borohydride to give the alcohol in the final product.

For Compound 2-100, during Step 4, the 6-fluoropyridinyl in the precursor was also hydrolyzed to give the 6-methoxypyridinyl in the final product.

For Compound 2-104, after Step 3, a Suzuki cross-coupling reaction was performed on the 6-bromopyridinyl in the precursor to give the 6-cyclopropylpyridinyl in the final product, as described in Example 5, Step 2.

For Compound 4-2, Step 3 was not performed.

Scheme E:

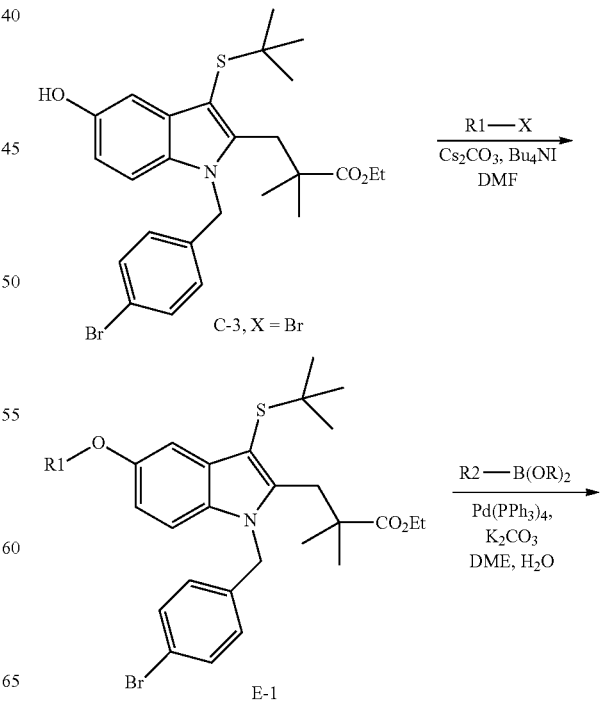

-continued

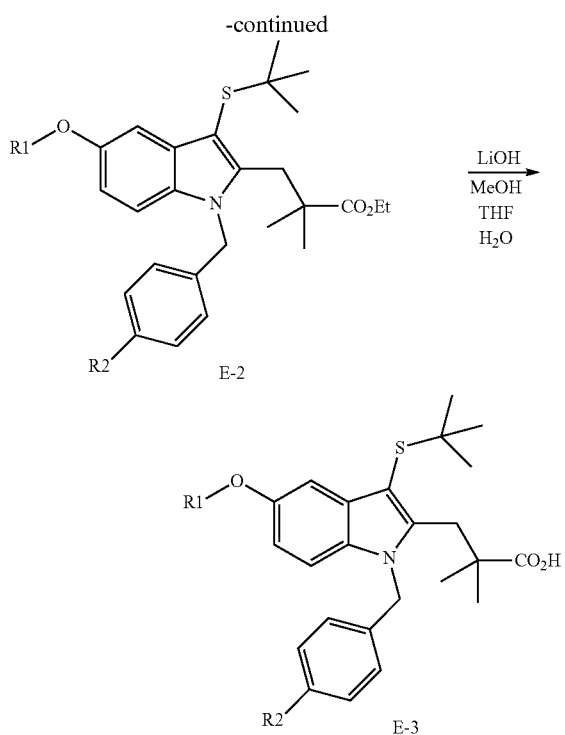

Example 5

Preparation of Compound 2-30, Compound 2-64, Compound 2-73, Compound 2-87, Compound 2-88, Compound 2-97, Compound 2-107, and Compound 2-121

Compound 2-30, Compound 2-64, Compound 2-73, Compound 2-87, Compound 2-88, Compound 2-97, Compound 2-107, and Compound 2-121, were prepared as shown in Scheme E. A detailed illustrative example of the reaction conditions shown in Scheme E is described for the synthesis of 3-[3-tert-butylsulfanyl-1-[4-(6-methoxy-pyridin-3-yl)-benzyl]-5-(5-methyl-pyridin-2-ylmethoxy)-1H-indol-2-yl]-2,2-dimethyl-propionic acid (Compound 2-73).

Step 1: 3-[1-(4-Bromo-benzyl)-3-tert-butylsulfanyl-5-(6-fluoro-quinolin-2-ylmethoxy)-1H-indol-2-yl]-2,2-dimethyl-propionic acid ethyl ester To 3-[1-(4-Bromo-benzyl)-3-tert-butylsulfanyl-5-hydroxy-1H-indol-2-yl]-2,2-dimethyl-propionic acid ethyl ester (C-3; 0.25 g, 0.48 mmol) in DMF (2 mL) was added 2-chloromethyl-5-methyl-pyridine hydrochloride (0.13 g, 0.72 mmol), $Cs_2CO_3$ (0.39 g, 1.21 mmol), and catalytic tetrabutylammonium iodide. The reaction was stirred at room temperature overnight, after which LCMS showed the reaction was complete. The reaction mixture was partitioned between EtOAc and water, the aqueous layer was extracted with EtOAc, and the combined organic layers were dried over $MgSO_4$, filtered, and concentrated. The crude material was purified on silica gel (0 to 15% EtOAc in hexanes) to give an additional the desired product (E-1, 0.30 g).

Step 2: 3-{3-tert-Butylsulfanyl-5-(6-fluoro-quinolin-2-ylmethoxy)-1-[4-(6-methoxy-pyridin-2-yl)-benzyl]-1H-indol-2-yl}-2,2-dimethyl-propionic acid ethyl ester E-1 (0.06 g, 0.10 mmol), 2-methoxy-pyridine-5-boronic acid (0.02 g, 0.14 mmol), and $K_2CO_3$ (0.03 g, 0.24 mmol) were dissolved in DME (1 mL) and water (0.5 mL) and degassed with $N_2$ for 10 minutes. $Pd(PPh_3)_4$ (0.01 g, 0.01 mmol) was added, and the reaction mixture was degassed with $N_2$ for an additional 10 minutes. The solution was heated to 80° C. for 4 hours, and then cooled to room temperature and diluted with EtOAc and water. The aqueous layer was extracted 3 times with EtOAc, the combined organic layers were washed with water, brine, dried over $MgSO_4$, filtered, and concentrated. The crude material was purified on silica gel (0 to 50% EtOAc in hexanes) to give the desired product (E-2).

Step 3: 3-{3-tert-Butylsulfanyl-5-(6-fluoro-quinolin-2-ylmethoxy)-1-[4-(6-methoxy-pyridin-2-yl)-benzyl]-1H-indol-2-yl}-2,2-dimethyl-propionic acid E-2 (0.22 g, 0.3 mmol) was dissolved in MeOH (0.1 mL), THF (0.1 mL), and water (0.1 mL). Lithium hydroxide, 1N aqueous solution (0.1 mL) was added, and the reaction was heated at 60° C. for 4 hours until no starting material was seen by LCMS. The reaction was diluted with water and EtOAc, acidified to pH 5 with citric acid, and extracted with EtOAc. The combined organic layers were washed with water, dried over $MgSO_4$, filtered, and concentrated to give the desired product (F-4).

Mass spectrometry data for Compound 2-30, Compound 2-64, Compound 2-73, Compound 2-87, Compound 2-88, Compound 2-97, Compound 2-107, and Compound 2-121, is shown in Table 1-4.

Notes:
For Compound 2-64, Steps 2 and 3 were performed in the reverse order.
For Compound 2-87, during Step 3, the 5-cyanopyridyl in the precursor was also hydrolyzed to give the 5-carbamoylpyridyl in the final product.
For Compound 2-88, Steps 2 and 3 were performed in the reverse order.
For Compound 2-97, during Step 3, the 6-cyanopyridyl in the precursor was also hydrolyzed to give the 6-carbamoylpyridyl in the final product.

Scheme F:

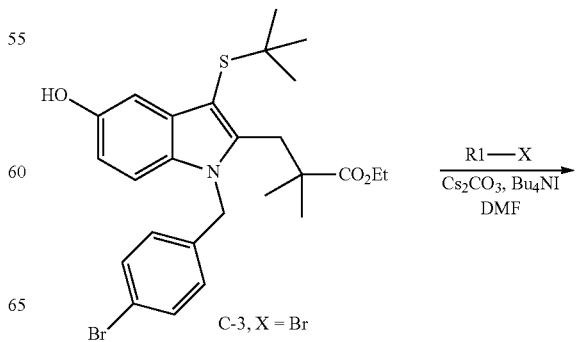

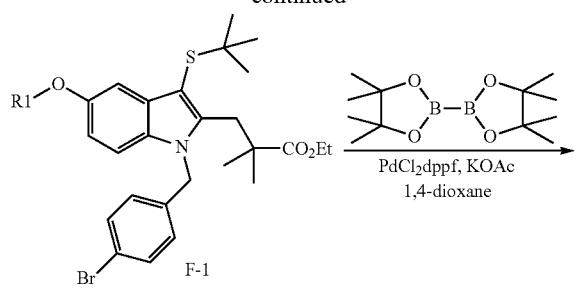
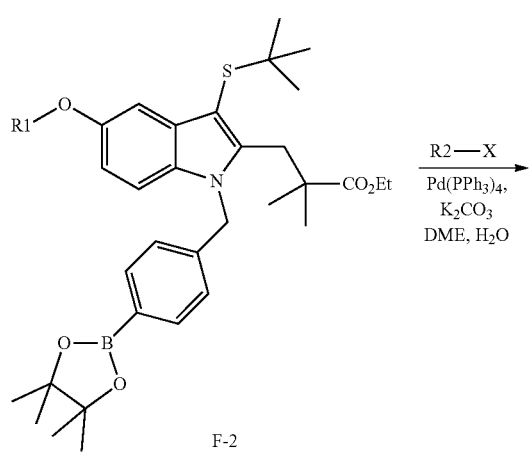
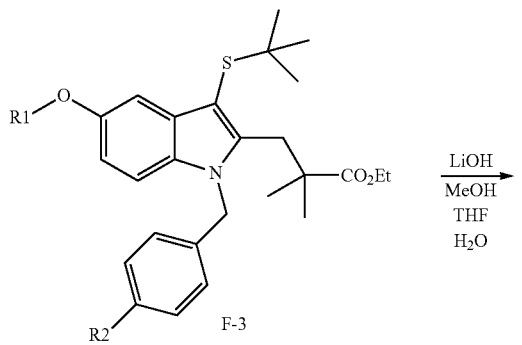
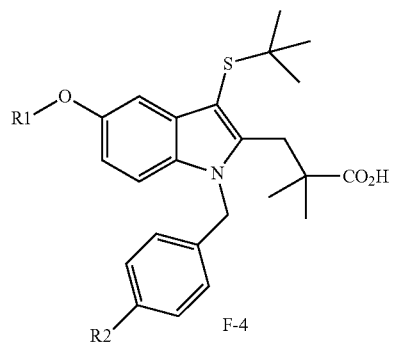

Example 6

Preparation of Compound 2-1, Compound 2-2, Compound 2-3, Compound 2-4, Compound 2-5, Compound 2-6, Compound 2-7, Compound 2-17, Compound 2-18, Compound 2-20, Compound 2-34, Compound 2-39, Compound 2-41, Compound 2-43, Compound 2-47, Compound 2-55, Compound 2-65, Compound 2-67, Compound 2-68, Compound 2-90, Compound 2-91, Compound 2-92, Compound 2-93, Compound 2-94, Compound 2-95, Compound 2-96, Compound 2-98, Compound 2-102, Compound 2-103, Compound 2-105, Compound 2-106, Compound 2-109, Compound 2-110, Compound 2-111, Compound 2-112, Compound 2-113, Compound 2-114, Compound 2-115, Compound 2-116, Compound 2-117, Compound 2-118, Compound 2-119, Compound 2-120, Compound 2-125, Compound 2-126, Compound 2-127, Compound 2-128, Compound 2-129, Compound 2-130, Compound 2-131, Compound 2-136, Compound 2-137, Compound 2-138, Compound 2-139, Compound 2-140, Compound 2-142, Compound 2-143, Compound 2-144, Compound 2-145, Compound 2-146, Compound 2-147, Compound 2-157, Compound 2-158, Compound 2-159, Compound 2-160, Compound 2-161, Compound 2-162, Compound 2-164, Compound 2-165, Compound 2-166, Compound 2-167, Compound 2-168, Compound 2-169, Compound 2-171, Compound 2-172, Compound 2-173, Compound 2-174, Compound 2-175, Compound 2-176, Compound 2-177, Compound 2-178, Compound 2-179, Compound 2-180, Compound 2-181, Compound 2-182, Compound 2-185, Compound 2-186, and Compound 2-187

Compound 2-1, Compound 2-2, Compound 2-3, Compound 2-4, Compound 2-5, Compound 2-6, Compound 2-7, Compound 2-17, Compound 2-18, Compound 2-20, Compound 2-34, Compound 2-39, Compound 2-41, Compound 2-43, Compound 2-47, Compound 2-55, Compound 2-65, Compound 2-67, Compound 2-68, Compound 2-90, Compound 2-91, Compound 2-92, Compound 2-93, Compound 2-94, Compound 2-95, Compound 2-96, Compound 2-98, Compound 2-102, Compound 2-103, Compound 2-105, Compound 2-106, Compound 2-109, Compound 2-110, Compound 2-111, Compound 2-112, Compound 2-113, Compound 2-114, Compound 2-115, Compound 2-116, Compound 2-117, Compound 2-118, Compound 2-119, Compound 2-120, Compound 2-125, Compound 2-126, Compound 2-127, Compound 2-128, Compound 2-129, Compound 2-130, Compound 2-131, Compound 2-136, Compound 2-137, Compound 2-138, Compound 2-139, Compound 2-140, Compound 2-142, Compound 2-143, Compound 2-144, Compound 2-145, Compound 2-146, Compound 2-147, Compound 2-157, Compound 2-158, Compound 2-159, Compound 2-160, Compound 2-161, Compound 2-162, Compound 2-164, Compound 2-165, Compound 2-166, Compound 2-167, Compound 2-168, Compound 2-169, Compound 2-171, Compound 2-172, Compound 2-173, Compound 2-174, Compound 2-175, Compound 2-176, Compound 2-177, Compound 2-178, Compound 2-179, Compound 2-180, Compound 2-181, Compound 2-182, Compound 2-185, Compound 2-186, and Compound 2-187, were prepared as shown in Scheme F. A detailed illustrative example of the reaction conditions shown in Scheme F is described for the synthesis of 3-{3-tert-butylsulfanyl-5-(6-fluoro-quinolin-2-ylmethoxy)-1-[4-(6-methoxy-pyridin-2-yl)-benzyl]-1H-indol-2-yl}-2,2-dimethyl-propionic acid (Compound 2-140).

Step 1: 3-[1-(4-Bromo-benzyl)-3-tert-butylsulfanyl-5-(6-fluoro-quinolin-2-ylmethoxy)-1H-indol-2-yl]-2,2-dimethyl-propionic acid ethyl ester To 3-[1-(4-Bromo-benzyl)-3-tert-butylsulfanyl-5-hydroxy-1H-indol-2-yl]-2,2-dimethyl-propionic acid ethyl ester (C-3; 2.0 g, 3.9 mmol) in MeCN (25 mL) was added 2-bromomethyl-6-fluoro-quinoline (1.0 g, 4.2 mmol), and $Cs_2CO_3$ (2.5 g, 7.7 mmol). The reaction was stirred at room temperature overnight, after which LCMS showed the reaction was complete. The reaction mixture was partitioned between EtOAc and water, the aqueous layer was extracted with EtOAc, and the combined organic layers were dried over $MgSO_4$, filtered, and concentrated. The residue was recrystallized in EtOAc:hexane to give the desired product (F-1, 1.9 g). The filtrate was concentrated and purified on silica gel (0 to 15% EtOAc in hexanes) to give an additional 1 g of F-1.

Step 2: 3-{3-tert-Butylsulfanyl-5-(6-fluoro-quinolin-2-ylmethoxy)-1-[4-(4,4,5,5-tetramethyl-[1,3,2]dioxaborolan-2-yl)-benzyl]-1H-indol-2-yl}-2,2-dimethyl-propionic acid ethyl ester F-1 (1.0 g, 1.5 mmol), bis(pinacolato)diboron (CombiBlocks; 1.1 g, 4.3 mmol), and KOAc (0.44 g, 4.5 mmol) was dissolved in 1,4-dioxane (15 mL) and degassed with $N_2$ for 10 minutes in a sealed vessel. $PdCl_2dppf$ (0.13 g, 0.16 mmol) was added, and the reaction mixture was degassed an additional 10 minutes with $N_2$. The vessel was sealed and the reaction was heated at 95° C. overnight. The reaction mixture was partitioned between water and EtOAc, the aqueous layer was extracted three times with EtOAc, the combined organic layers were washed with water, brine, dried over $MgSO_4$, filtered, and concentrated. The crude material was purified on silica gel (0 to 20% EtOAc in hexanes) to give the desired product (F-2).

Step 3: 3-{3-tert-Butylsulfanyl-5-(6-fluoro-quinolin-2-ylmethoxy)-1-[4-(6-methoxy-pyridin-2-yl)-benzyl]-1H-indol-2-yl}-2,2-dimethyl-propionic acid ethyl ester F-2 (0.25 g, 0.35 mmol), 2-bromo-6-methoxypyridine (0.09 g, 0.48 mmol), and $K_2CO_3$ (0.15 g, 1.05 mmol) were dissolved in DME (3.5 mL) and water (1.8 mL) and degassed with $N_2$ for 10 minutes. $Pd(PPh_3)_4$ (0.06 g, 0.05 mmol) was added, and the reaction mixture was degassed with $N_2$ for an additional 10 minutes. The solution was heated to 85° C. for 4 hours, and then cooled to room temperature and diluted with EtOAc and water. The aqueous layer was extracted 3 times with EtOAc, the combined organic layers were washed with water, brine, dried over $MgSO_4$, filtered, and concentrated. The crude material was purified on silica gel (0 to 25% EtOAc in hexanes) to give the desired product (F-3).

Step 4: 3-{3-tert-Butylsulfanyl-5-(6-fluoro-quinolin-2-ylmethoxy)-1-[4-(6-methoxy-pyridin-2-yl)-benzyl]-1H-indol-2-yl}-2,2-dimethyl-propionic acid F-3 (0.22 g, 0.3 mmol) was dissolved in MeOH (1.5 mL), THF (3 mL), and water (1.5 mL). Lithium hydroxide (0.08 g, 1.9 mmol) was added, and the reaction was heated at 60° C. for 3.5 hours until no starting material was seen by TLC analysis. The reaction was diluted with water, acidified to pH 5 with citric acid, and extracted with EtOAc. The combined organic layers were washed with water, dried over $MgSO_4$, filtered, and concentrated to give the desired product (F-4).

Mass spectrometry data for Compound 2-1, Compound 2-2, Compound 2-3, Compound 2-4, Compound 2-5, Compound 2-6, Compound 2-7, Compound 2-17, Compound 2-18, Compound 2-20, Compound 2-34, Compound 2-39, Compound 2-41, Compound 2-43, Compound 2-47, Compound 2-55, Compound 2-65, Compound 2-67, Compound 2-68, Compound 2-90, Compound 2-91, Compound 2-92, Compound 2-93, Compound 2-94, Compound 2-95, Compound 2-96, Compound 2-98, Compound 2-102, Compound 2-103, Compound 2-105, Compound 2-106, Compound 2-109, Compound 2-110, Compound 2-111, Compound 2-112, Compound 2-113, Compound 2-114, Compound 2-115, Compound 2-116, Compound 2-117, Compound 2-118, Compound 2-119, Compound 2-120, Compound 2-125, Compound 2-126, Compound 2-127, Compound 2-128, Compound 2-129, Compound 2-130, Compound 2-131, Compound 2-136, Compound 2-137, Compound 2-138, Compound 2-139, Compound 2-140, Compound 2-142, Compound 2-143, Compound 2-144, Compound 2-145, Compound 2-146, Compound 2-147, Compound 2-157, Compound 2-158, Compound 2-159, Compound 2-160, Compound 2-161, Compound 2-162, Compound 2-164, Compound 2-165, Compound 2-166, Compound 2-167, Compound 2-168, Compound 2-169, Compound 2-171, Compound 2-172, Compound 2-173, Compound 2-174, Compound 2-175, Compound 2-176, Compound 2-177, Compound 2-178, Compound 2-179, Compound 2-180, Compound 2-181, Compound 2-182, Compound 2-185, Compound 2-186, and Compound 2-187, is shown in Tables 1-4.

Notes:

For Compound 2-17, during Step 4, the 6-methoxypyridazinyl in the precursor was also hydrolyzed to give the 6-hydroxypyridazinyl in the final product.

For Compound 2-172, after Step 2, the 3-tert-butylsulfanyl in the precursor was oxidized with m-chloroperoxybenzoic acid to give the 2-methylpropane-2-sulfonyl in the final product.

For Compound 2-173, after Step 2, the 3-tert-butylsulfanyl moiety in the precursor was oxidized with m-chloroperoxybenzoic acid to give the 2-methylpropane-2-sulfinyl moiety in the final product.

Scheme G:

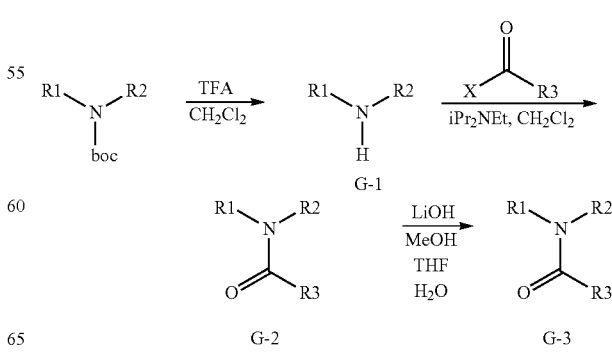

Example 7

3-{5-((S)-1-Acetyl-2,3-dihydro-1H-indol-2-yl-methoxy)-3-tert-butylsulfanyl-1-[4-(6-methoxy-pyridazin-3-yl)-benzyl]-1H-indol-2-yl}-2,2-dimethyl-propionic acid

Step 1: 3-{3-tert-Butylsulfanyl-5-[(S)-1-(2,3-dihydro-1H-indol-2-yl)methoxy]-1-[4-(6-methoxy-pyridazin-3-yl)-benzyl]-1H-indol-2-yl}-2,2-dimethyl-propionic acid ethyl ester (S)-2-{3-tert-Butylsulfanyl-2-(2-ethoxycarbonyl-2-methyl-propyl)-1-[4-(6-methoxy-pyridazin-3-yl)-benzyl]-1H-indol-5-yloxymethyl}-2,3-dihydro-indole-1-carboxylic acid tert-butyl ester (0.23 g, 0.30 mmol) was dissolved in CH₂Cl₂ (1.5 mL). TFA (1.5 mL) was added and the reaction was stirred at room temperature for 10 minutes until no starting material was seen by TLC analysis. The solution was concentrated in vacuo, and the crude product (G-1) was used without further purification.

Step 2: 3-{5-((S)-1-Acetyl-2,3-dihydro-1H-indol-2-ylmethoxy)-3-tert-butylsulfanyl-1-[4-(6-methoxy-pyridazin-3-yl)-benzyl]-1H-indol-2-yl}-2,2-dimethyl-propionic acid ethyl ester G-1 (0.30 mmol) was dissolved in CH₂Cl₂ (1 mL). Diisopropylethylamine (0.5 mL) was added, followed by acetic anhydride (33 uL, 0.35 mmol), and the reaction was stirred at room temperature until no starting material was seen by LCMS. The reaction was diluted with CH₂Cl₂ and MeOH, concentrated, redissolved in CH₂Cl₂ and washed with water, dried over Na₂SO₄, filtered, and concentrated. The residue was purified on silica gel to give the desired product (G-2).

Step 3: 3-{5-((S)-1-Acetyl-2,3-dihydro-1H-indol-2-ylmethoxy)-3-tert-butylsulfanyl-1-[4-(6-methoxy-pyridazin-3-yl)-benzyl]-1H-indol-2-yl}-2,2-dimethyl-propionic acid G-2 (0.05 g, 0.07 mmol) was dissolved in MeOH (0.5 mL), THF (0.5 mL), and water (0.5 mL). Lithium hydroxide (0.03 g, 0.7 mmol) was added, and the reaction was heated at 60° C. for 6 hours until no starting material was seen by TLC analysis. The reaction was diluted with water, acidified to pH 5 with citric acid, and extracted with EtOAc. The combined organic layers were washed with water, dried over MgSO₄, filtered, and concentrated. The residue was purified on silica gel to give the desired product (G-3).

Scheme H:

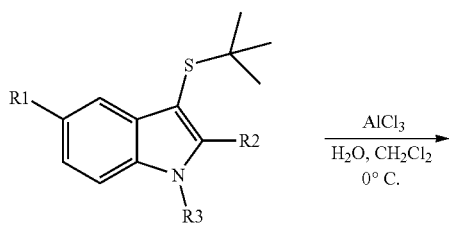

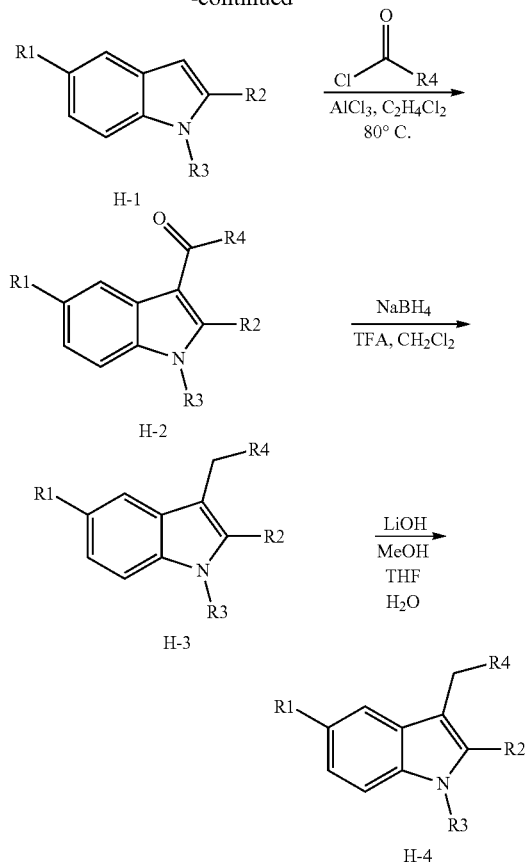

Example 8

Preparation of Compound 2-8, Compound 2-9, Compound 2-10, Compound 2-11, Compound 2-12, Compound 2-13, Compound 2-14, Compound 2-15, Compound 2-16, Compound 2-22, Compound 2-25, Compound 2-26, Compound 2-27, Compound 2-28, Compound 2-29, Compound 2-123, Compound 2-124; Compound 2-132, Compound 2-133, Compound 2-134; Compound 2-163, Compound 2-170, and Compound 2-194

Compound 2-8, Compound 2-9, Compound 2-10, Compound 2-11, Compound 2-12, Compound 2-13, Compound 2-14, Compound 2-15, Compound 2-16, Compound 2-22, Compound 2-25, Compound 2-26, Compound 2-27, Compound 2-28, Compound 2-29, Compound 2-123, Compound 2-124; Compound 2-132, Compound 2-133, Compound 2-134; Compound 2-163, Compound 2-170, and Compound 2-194, were prepared as shown in Scheme H. A detailed illustrative example of the reaction conditions shown in Scheme H is described for the synthesis of 3-{5-(benzothiazol-2-ylmethoxy)-3-cyclobutylmethyl-1-[4-(6-methoxy-pyridin-3-yl)-benzyl]-1H-indol-2-yl}-2,2-dimethyl-propionic acid (Compound 2-124).

Step 1: 3-{5-(Benzothiazol-2-ylmethoxy)-1-[4-(6-methoxy-pyridin-3-yl)-benzyl]-1H-indol-2-yl}-2,2-dimethyl-propionic acid ethyl ester Aluminum chloride (0.18 g, 1.37 mmol) was suspended in CH₂Cl₂ (1 mL), and water (19 uL, 1.0 mmol) was added slowly at room temperature. The mixture was stirred for 5 minutes, and then cooled to 0° C. 3-{5-(Benzothiazol-2-yl-methoxy)-3-tert-butylsulfanyl-1-[4-(6-methoxy-pyridin-3-yl)-benzyl]-1H-indol-2-yl}-2,2-dimethyl-propionic acid ethyl ester (0.12 g, 0.17 mmol) was added in CH$_2$Cl$_2$ (1 mL), and the reaction was stirred at room temperature for 2 hours. Once no starting material was observed by tlc, water was added and the mixture was extracted with CH$_2$Cl$_2$. The combined organic layers were washed with water, dried over MgSO$_4$, filtered, and concentrated. The residue was purified to give the desired product (H-1).

Step 2: 3-{5-(Benzothiazol-2-ylmethoxy)-3-cyclobutanecarbonyl-1-[4-(6-methoxy-pyridin-3-yl)-benzyl]-1H-indol-2-yl}-2,2-dimethyl-propionic acid ethyl ester To H-1 (0.10 g, 0.17 mmol) in dichloroethane (5 mL) was added cyclobutanecarbonyl chloride (57 uL, 0.50 mmol) and aluminum chloride (0.09 g, 0.66 mmol). The reaction was heated under N$_2$ for 1.5 hours, and then cooled to room temperature and quenched with saturated aq. potassium sodium tartrate. The mixture was extracted with EtOAc, and the combined organic layers were dried over MgSO$_4$, filtered, concentrated, and purified on silica gel to give the desired product (H-2).

Step 3: 3-{5-(Benzothiazol-2-ylmethoxy)-3-cyclobutylmethyl-1-[4-(6-methoxy-pyridin-3-yl)-benzyl]-1H-indol-2-yl}-2,2-dimethyl-propionic acid ethyl ester H-2 (0.05 g, 0.08 mmol) was suspended in CH$_2$Cl$_2$, and sodium borohydride (0.03 g, 0.8 mmol) was added dropwise in TFA (1 mL) and CH$_2$Cl$_2$ (1 mL). The mixture was stirred at room temperature for 4 hours, and then quenched with water and basified with solid NaOH pellets. The mixture was extracted with CH$_2$Cl$_2$, and the combined organics were dried over MgSO$_4$, filtered, and concentrated. The residue was purified on silica gel to give the desired product (H-3).

Step 4: 3-{5-(Benzothiazol-2-ylmethoxy)-3-cyclobutylmethyl-1-[4-(6-methoxy-pyridin-3-yl)-benzyl]-1H-indol-2-yl}-2,2-dimethyl-propionic acid H-3 (0.03 g, 0.04 mmol) was dissolved in MeOH (0.5 mL) and THF (0.5 mL). Aq. lithium hydroxide (1N, 0.5 mL) was added, and the reaction was heated at 60° C. for 4 hours until no starting material was seen by LCMS. The reaction was diluted with water, acidified to pH 5 with citric acid, and extracted with EtOAc. The combined organic layers were washed with water, dried over MgSO$_4$, filtered, and concentrated to give the desired product (H-4).

Mass spectrometry data for Compound 2-8, Compound 2-9, Compound 2-10, Compound 2-11, Compound 2-12, Compound 2-13, Compound 2-14, Compound 2-15, Compound 2-16, Compound 2-22, Compound 2-25, Compound 2-26, Compound 2-27, Compound 2-28, Compound 2-29, Compound 2-123, Compound 2-124; Compound 2-132, Compound 2-133, Compound 2-134; Compound 2-163, Compound 2-170, and Compound 2-194, is shown in Tables 1-4.

Notes:
For Compound 2-8, only Steps 1, 2, and 4 were performed.
For Compound 2-9, only Steps 1 and 4 were performed.
For Compound 2-10, only Steps 1, 2, and 4 were performed.
For Compound 2-11, only Steps 1 and 4 were performed.
For Compound 2-12, only Steps 1, 2, and 4 were performed.
For Compound 2-15, only Steps 1, 2, and 4 were performed.
For Compound 2-16, only Steps 1, 2, and 4 were performed.
For Compound 2-25, only Steps 1 and 4 were performed.
For Compound 2-26, only Steps 1, 2, and 4 were performed.
For Compound 2-27, only Steps 1 and 4 were performed.
For Compound 2-28, only Steps 1, 2, and 4 were performed.
For Compound 2-123, only Steps 1, 2, and 4 were performed.

Scheme I:

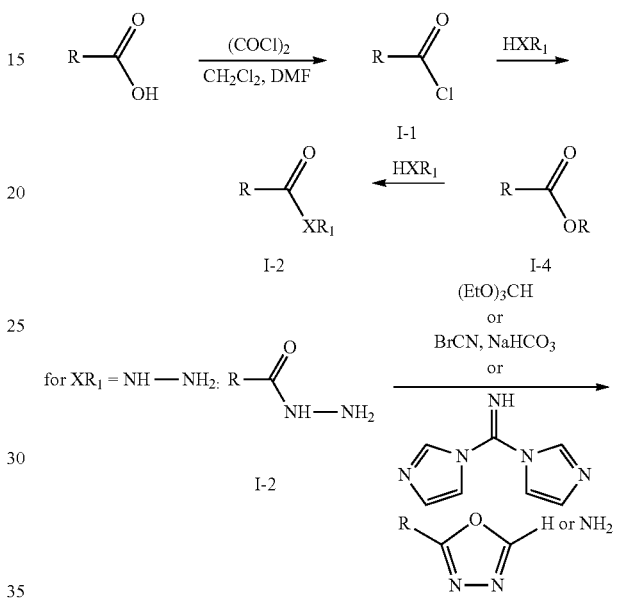

Example 9

Preparation of Compound 1-1, Compound 1-3, Compound 1-7, Compound 1-8, Compound 1-9, Compound 1-10, Compound 1-11, Compound 1-12, Compound 1-13, Compound 1-14 and Compound 1-15

Compound 1-1, Compound 1-3, Compound 1-7, Compound 1-8, Compound 1-9, Compound 1-10, Compound 1-11, Compound 1-12, Compound 1-13, Compound 1-14 and Compound 1-15., were prepared as outlined in Scheme I. A detailed illustrative example of the reaction conditions shown in Scheme H is described for the synthesis of 3-[3-tert-butyl-sulfanyl-1-(4-chloro-benzyl)-5-isopropyl-1H-indol-2-yl]-N-(2-hydroxy-ethyl)-2,2-dimethyl-propionamide.

Step 1: 3-[3-tert-Butylsulfanyl-1-(4-chloro-benzyl)-5-isopropyl-1H-indol-2-yl]-2,2-dimethyl-propionyl chloride To 3-[3-tert-butylsulfanyl-1-(4-chloro-benzyl)-5-isopropyl-1H-indol-2-yl]-2,2-dimethyl-propionic acid (prepared according to the procedures described in U.S. Pat. No. 5,081,138 issued Jan. 14, 1992; 0.25 g, 0.53 mmol) suspended in CH$_2$Cl$_2$ (5 mL) was added oxalyl chloride (48 uL, 0.56 mmol) and catalytic DMF. The reaction was stirred at room temperature for 3 hours, and then concentrated to give I-1, which was used without further purification.

Step 2: 3-[3-tert-Butylsulfanyl-1-(4-chloro-benzyl)-5-isopropyl-1H-indol-2-yl]-N-(2-hydroxy-ethyl)-2,2-dimethyl-propionamide To I-1 (0.18 mmol) in $CH_2Cl_2$ was added triethylamine (0.1 mL, 0.70 mmol) and 2-aminoethanol (10 uL, 0.19 mmol). The reaction was stirred for 2 days at room temperature, and then concentrated and purified on silica gel (EtOAc:hexanes gradient) to give the desired product (I-2).

Step 3: 5-{4-[3-tert-Butylsulfanyl-2-(2,2-dimethyl-propyl)-5-(pyridin-2-ylmethoxy)-indol-1-ylmethyl]-phenyl}-[1,3,4]oxadiazol-2-ylamine To 4-[3-tert-Butylsulfanyl-2-(2,2-dimethyl-propyl)-5-(pyridin-2-ylmethoxy)-indol-1-ylmethyl]-benzoic acid hydrazide (0.05 g, 0.10 mmol) in DMF (1 mL) was added C-(Di-imidazol-1-yl)-methyleneamine (0.08 g, 0.50 mmol), and the reaction was heated at 85° C. for 3 hours. The mixture was cooled to room temperature and partitioned between water and EtOAc. The aqueous layer was extracted with EtOAc, and the combined organic layers were dried over $MgSO_4$, filtered, and concentrated. The residue was purified on silica gel (EtOAc:hexane gradient) to give the desired product.

Mass spectrometry data for Compound 1-1, Compound 1-7, Compound 1-8, Compound 1-9, Compound 1-10, Compound 1-11, Compound 1-12, Compound 1-13, and Compound 1-14, is shown in Tables 1-4. NMR data for Compound 1-3 is shown below.

Notes:
For Compound 1-3, $^1H$ NMR ($CDCl_3$) δ 8.6 (d, 1H), 8.31 (d, 1H), 7.70 (m, 2H), 7.57 (d, 1H), 7.38 (d, 2H), 7.32 (d, 1H), 7.20 (m, 1H), 7.08 (d, 1H), 6.80 (m, 4H), 5.41 (s, 2H), 5.27 (s, 2H), 3.96 (t, 5H), 3.57 (t, 2H), 3.27 (s, 2H), 1.57-1.20 (m, 23H).

For Compound 1-7, during Step 3, hydrazide I-2 was converted to 1,3,4-oxadiazol-2-yl I-3 using triethyl orthoformate.

For Compound 1-8, i) hydrazide I-2 was made directly from ester I-4, ii) during Step 3, hydrazide I-2 was converted to 1,3,4-oxadiazol-2-yl I-3 using triethyl orthoformate.

For Compound 1-9, i) hydrazide I-2 was made directly from ester I-4, ii) during Step 3, hydrazide I-2 was converted to 1,3,4-oxadiazol-2-ylamine I-3 using cyanogen bromide and sodium bicarbonate.

For Compound 1-14, during Step 3, hydrazide I-2 was converted to 1,3,4-oxadiazol-2-ylamine I-3 using C-(di-imidazol-1-yl)-methyleneamine

Example 10

FLAP Binding Assays

A non-limiting example of such a FLAP binding assay is as follows:

Packed human polymorphonuclear cell pellets ($1.8 \times 10^9$ cells) (Biological Speciality Corporation) were resuspended, lysed and 100,000 g membranes prepared as described (Charleson et al. Mol. Pharmacol, 41, 873-879, 1992). 100,000×g pelleted membranes were resuspended in Tris-Tween assay buffer (100 mM Tris HCl pH 7.4, 140 mM NaCl, 2 mM EDTA, 0.5 mM DTT, 5% glycerol, 0.05% Tween 20) to yield a protein concentration of 50-100 ug/mL. 10 uL membrane suspension was added to 96 well Millipore plate, 78 µL Tris-Tween buffer, 10 µL $^3H$ MK886 or $^3H$ 3-[5-(pyrid-2-ylmethoxy)-3-tert-butylthio-1-benzyl-indol-2-yl]-2,2-dimethylpropionic acid (or $^{125}I$ MK591 derivative Eggler et al, J. Labelled Compounds and Radiopharmaceuticals, 1994, vXXXIV, 1147)) to ~30,000 cpm, 2 µL inhibitor and incubated for 30 minutes at room temperature. 100 µL ice-cold washed buffer was added to the incubation mixture. Plates were then filtered and washed 3× with 200 µL ice cold Tris-Tween buffer, scintillation bottoms sealed, 100 µL scintillant added, shaken for 15 minutes then counted in a TopCount. Specific binding was determined as defined as total radioactive binding minus non-specific binding in the presence of 10 µM MK886. IC50s were determined using Graphpad prism analysis of drug titration curves.

Example 11

Human Blood $LTB_4$ Inhibition Assay

A non-limiting example of such a human blood $LTB_4$ inhibition assay is as follows:

Blood was drawn from consenting human volunteers into heparinized tubes and 125 µL aliquots added to wells containing 2.5 µL 50% DMSO (vehicle) or 2.5 µL drug in 50% DMSO. Samples were incubated for 15 minutes at 37° C. 2 µL calcium ionophore A23817 (from a 50 mM DMSO stock diluted just prior to the assay in Hanks balanced salt solution (Invitrogen)) to 1.25 mM) was added, solutions mixed and incubated for 30 minutes at 37° C. Samples were centrifuged at 1,000 rpm (~200×g) for 10 minutes at 4° C., plasma removed and a 1:100 dilution assayed for $LTB_4$ concentration using ELISA (Assay Designs). Drug concentrations to achieve 50% inhibition (IC50's) of vehicle $LTB_4$ were determined by nonlinear regression (Graphpad Prism) of % inhibition versus log drug concentration.

Example 12

Rat peritoneal Inflammation and Edema Assay

A non-limiting example of such a rat peritoneal inflammation and edema assay is as follows:

The in vivo efficacy of leukotriene biosynthesis inhibitors was assessed using a rat model of peritoneal inflammation. Male Sprague-Dawley rats (weighing 200-300 grams) received a single intraperitoneal (i.p.) injection of 3 mL saline containing zymosan (5 mg/mL) followed immediately by an intravenous (i.v.) injection of Evans blue dye (2 mL of 1.5% solution). Compounds were administered orally (3 mL/kg in 0.5% methylcellulose vehicle) 2 to 4 hours prior to zymosan injection. One to two hours after zymosan injection, rats were euthanized, and the peritoneal cavity was flushed with 10 mL phosphate buffered saline solution (PBS). The resulting fluid was centrifuged at 1,200 rpm for 10 minutes. Vascular edema was assesses by quantifying the amount of Evans blue dye in the supernatant using a spectrophotometer (Absorbance 610 nm). $LTB_4$ and cysteinyl leukotriene concentrations in the supernatant were determined by ELISA. Drug concentrations to achieve 50% inhibition of plasma leakage (Evans blue dye) and inhibition of peritoneal $LTB_4$ and cysteinyl leukotrienes could be calculated by nonlinear regression (Graphpad Prism) of % inhibition versus log drug concentration.

Example 13

Human Leukocyte Inhibition Assay

A non-limiting example of a human leukocyte inhibition assay is as follows:

Blood was drawn from consenting human volunteers into heparanized tubes and 3% dextran, 0.9% saline equal volume added. After sedimentation of red blood cells a hypotonic lysis of remaining red blood cells was performed and leukocytes sedimented at 1000 rpm. The pellet was resuspended at $1.25 \times 10^5$ cells/mL and aliquoted into wells containing 2.5 µL 20% DMSO (vehicle) or 2.5 µL drug in 20% DMSO. Samples were incubated for 5 minutes at 37° C. and 2 µL calcium ionophore A23817 (from a 50 mM DMSO stock diluted just prior to the assay in Hanks balanced salt solution (Invitrogen)) to 1.25 mM) was added, solutions mixed and incubated for 30 minutes at 37° C. Samples were centrifuged at 1,000 rpm (~200×g) for 10 minutes at 4° C., plasma removed and a 1:4 dilution assayed for $LTB_4$ concentration using ELISA (Assay Designs). Drug concentrations to achieve 50% inhibition (IC50's) of vehicle $LTB_4$ were determined by nonlinear regression (Graphpad Prism) of % inhibition versus log drug concentration. The compounds presented in Tables 1-4 had assays of 1 nM to 5 µM with this assay.

Example 14

Pharmaceutical Compositions

Example 14a

Parenteral Composition

To prepare a parenteral pharmaceutical composition suitable for administration by injection, 100 mg of a water-soluble salt of a compound of any of Formula (G), Formula (G-I), or Formula (G-II), is dissolved in DMSO and then mixed with 10 mL of 0.9% sterile saline. The mixture is incorporated into a dosage unit form suitable for administration by injection.

Example 14b

Oral Composition

To prepare a pharmaceutical composition for oral delivery, 100 mg of a compound of any of Formula (G), Formula (G-I), or Formula (G-II), is mixed with 750 mg of starch. The mixture is incorporated into an oral dosage unit for, such as a hard gelatin capsule, which is suitable for oral administration.

Example 14c

Sublingual (Hard Lozenge) Composition

To prepare a pharmaceutical composition for buccal delivery, such as a hard lozenge, mix 100 mg of a compound of any of Formula (G), Formula (G-I), or Formula (G-II), with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 14d

Inhalation Composition

To prepare a pharmaceutical composition for inhalation delivery, 20 mg of a compound of any of Formula (G), Formula (G-I), or Formula (G-II), is mixed with 50 mg of anhydrous citric acid and 100 mL of 0.9% sodium chloride solution. The mixture is incorporated into an inhalation delivery unit, such as a nebulizer, which is suitable for inhalation administration.

Example 14e

Rectal Gel Composition

To prepare a pharmaceutical composition for rectal delivery, 100 mg of a compound of any of Formula (G), Formula (G-I), or Formula (G-II), is mixed with 2.5 g of methylcellulose (1500 mPa), 100 mg of methylparapen, 5 g of glycerin and 100 mL of purified water. The resulting gel mixture is then incorporated into rectal delivery units, such as syringes, which are suitable for rectal administration.

Example 14f

Topical Gel Composition

To prepare a pharmaceutical topical gel composition, 100 mg of a compound of any of Formula (G), Formula (G-I), or Formula (G-II), is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 14 g

Ophthalmic Solution Composition

To prepare a pharmaceutical opthalmic solution composition, 100 mg of a compound of any of Formula (G), Formula (G-I), or Formula (G-II), is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and various modifications or changes suggested to persons skilled in the art are to be included within the spirit and purview of this application and scope of the appended claims. All publications, patents, and patent applications cited herein are hereby incorporated by reference for all purposes.

We claim:

1. A method for treating inflammation in a human comprising administering a therapeutically effective amount of 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid or a pharmaceutically acceptable salt or a pharmaceutically acceptable N-oxide thereof, to the human in need.

2. The method according to claim 1, wherein 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid is present in the form of a sodium salt.

3. A method for treating respiratory disease in a human comprising administering a therapeutically effective amount of 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid or a pharmaceutically acceptable salt or a pharmaceutically acceptable N-oxide thereof, to the human in need.

4. The method according to claim 3, wherein the respiratory disease is asthma.

5. The method according to claim 3, wherein the respiratory disease is chronic obstructive pulmonary disease.

6. The method according to claim 3, wherein the respiratory disease is rhinitis.

7. The method according to claim 3, wherein 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid is present in the form of a sodium salt.

8. The method according to claim 7, wherein the respiratory disease is asthma.

9. The method according to claim 7, wherein the respiratory disease is chronic obstructive pulmonary disease.

10. The method according to claim 7, wherein the respiratory disease is rhinitis.

11. A method for treating inflammation in a human comprising administering a therapeutically effective amount of 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid or a pharmaceutically acceptable salt thereof to the human in need.

12. A method for treating respiratory disease in a human comprising administering a therapeutically effective amount of 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid or a pharmaceutically acceptable salt thereof to the human in need.

13. The method according to claim 12, wherein the respiratory disease is asthma.

14. The method according to claim 12, wherein the respiratory disease is chronic obstructive pulmonary disease.

15. The method according to claim 12, wherein the respiratory disease is rhinitis.

* * * * *